US009550815B2

(12) United States Patent
Breuil et al.

(10) Patent No.: US 9,550,815 B2
(45) Date of Patent: Jan. 24, 2017

(54) ABC TERPENOID TRANSPORTERS AND METHODS OF USING THE SAME

(71) Applicant: The University of British Columbia, Vancouver (CA)

(72) Inventors: Colette Breuil, Vancouver (CA); Joerg Bohlmann, Vancouver (CA); Ye Wang, Vancouver (CA); Scott DiGuistini, Courtenay (CA); Sajeet Haridas, Walnut Creek, CA (US)

(73) Assignee: University of British Columbia, Vancouver, British Columbia (CA)

( * ) Notice: Subject to any disclaimer, the term of this patent is extended or adjusted under 35 U.S.C. 154(b) by 0 days.

(21) Appl. No.: 13/694,985

(22) Filed: Jan. 23, 2013

(65) Prior Publication Data

US 2013/0189677 A1    Jul. 25, 2013

Related U.S. Application Data

(60) Provisional application No. 61/797,936, filed on Dec. 17, 2012, provisional application No. 61/589,679, filed on Jan. 23, 2012.

(51) Int. Cl.
*C07K 14/37* (2006.01)

(52) U.S. Cl.
CPC .................................. *C07K 14/37* (2013.01)

(58) Field of Classification Search
USPC ........................................................ 800/278
See application file for complete search history.

(56) References Cited

U.S. PATENT DOCUMENTS

| | | | |
|---|---|---|---|
| 4,952,496 A | 8/1990 | Studier et al. | 435/91 |
| 5,824,774 A | 10/1998 | Chappell | 530/350 |
| 6,072,045 A | 6/2000 | Chappell | 536/23.1 |
| 6,265,639 B1 | 7/2001 | Croteau et al. | 800/298 |
| 6,468,772 B1 | 10/2002 | Chappell et al. | 435/183 |
| 6,495,354 B2 | 12/2002 | Chappell et al. | 435/183 |
| 6,531,303 B1 | 3/2003 | Millis et al. | 435/155 |
| 6,559,297 B2 | 5/2003 | Chappell et al. | 536/23.1 |
| 6,569,656 B2 | 5/2003 | Chappell et al. | 435/183 |
| 6,645,762 B2 | 11/2003 | Chappell et al. | 435/325 |
| 6,689,593 B2 | 2/2004 | Millis et al. | 435/155 |
| 6,890,752 B2 | 5/2005 | Chappell et al. | 435/325 |
| 7,186,891 B1 | 3/2007 | Chappell | 800/298 |
| 7,405,057 B2 | 7/2008 | Chappell | 435/69.1 |
| 7,442,785 B2 | 10/2008 | Chappell | 536/23.6 |
| 7,622,634 B2 * | 11/2009 | Goossens et al. | 800/288 |
| 7,838,279 B2 | 11/2010 | Millis et al. | 435/254.2 |
| 7,842,497 B2 | 11/2010 | Millis et al. | 435/254.2 |
| 8,106,260 B2 | 1/2012 | Chappell | 800/298 |
| 8,192,950 B2 | 6/2012 | Chappell | 435/41 |
| 8,263,362 B2 | 9/2012 | Chappell | 435/69.1 |
| 8,354,504 B2 | 1/2013 | Chappell | 530/379 |
| 8,569,025 B2 | 10/2013 | Zulak et al. | 435/157 |
| 8,889,381 B2 | 11/2014 | Bohlmann et al. | 435/127 |
| 2004/0249219 A1 | 12/2004 | Saucy | 568/388 |
| 2008/0178354 A1 | 7/2008 | Chappell | 800/298 |
| 2010/0151519 A1 | 6/2010 | Julien | 435/69.1 |
| 2010/0151555 A1 | 6/2010 | Julien | 435/193 |
| 2011/0189717 A1 | 8/2011 | Ajikumar et al. | 435/29 |
| 2011/0318797 A1 | 12/2011 | Chappell | 435/155 |
| 2012/0196340 A1 | 8/2012 | Chappell | 435/148 |
| 2012/0208173 A1 | 8/2012 | Zulak et al. | 435/4 |
| 2012/0246767 A1 | 9/2012 | Amick et al. | 800/316 |
| 2013/0224809 A1 | 8/2013 | Bohlmann et al. | 435/127 |
| 2013/0330793 A1 | 12/2013 | Chappell | 435/155 |

FOREIGN PATENT DOCUMENTS

| | | |
|---|---|---|
| EP | 2 363 458 | 9/2011 |
| WO | WO 99/02030 | 1/1999 |
| WO | WO 99/15624 | 4/1999 |
| WO | WO 02/083888 | 10/2002 |
| WO | WO 2004/031376 | 4/2004 |
| WO | WO 2005/056803 | 6/2005 |
| WO | WO 2006/134523 | 12/2006 |
| WO | WO 2009/044336 | 4/2009 |
| WO | WO 2009/095366 | 8/2009 |
| WO | WO 2009/101126 | 8/2009 |
| WO | WO 2010/067309 | 6/2010 |
| WO | WO 2011/000026 | 1/2011 |
| WO | WO 2013/075239 | 5/2013 |
| WO | WO 2013/110191 | 8/2013 |

OTHER PUBLICATIONS

Eichhorn et al. (Isolation of a novel ABC-transporter gene from soybean induced by salicylic acid, 57 J of Exp Botany No. 10, 2193-2201 (2006)).*
Kovalchuk and Driessen, Phylogenetic analysis of fungal ABC transporters, 11 BMC Genomics No. 177, 1-21 at 4 (2010)).*
Whisstock et al, 2003, Quart. Rev. Biophysics, 36:307-340.*
Ikram et al, 2015, Frontiers in Plant Sci., 6:1-10.*
Fischer et al, 2011, Biotech. & Bioengineering, 108:1883-1892.*
Letter/Written Disclosure of the Supplemental Information Disclosure Statement for the above-referenced application, mailed on the same day herewith, 2 pages, Jan. 23, 2013.
International Search Report and Written Opinion, issued Apr. 29, 2013, in connection with corresponding International Patent Application No. PCT/CA2013/05044, 14 pages.
Response to International Search Report and Written Opinion, submitted Nov. 22, 2013, in connection with corresponding International Patent Application No. PCT/CA2013/05044, 30 pages.

(Continued)

*Primary Examiner* — Jason Deveau Rosen

(74) *Attorney, Agent, or Firm* — McDonnell Boehnen Hulbert & Berghoff LLP

(57) ABSTRACT

Provided are ATP-binding cassette transporters (ABC transporters). More specifically, the present disclosure relates to ABC terpenoid transporters, nucleic acid sequences, amino acids, proteins, vectors, cells, transgenic organisms, uses, compositions, methods, processes, and kits thereof.

46 Claims, 13 Drawing Sheets

(56) References Cited

OTHER PUBLICATIONS

Bohlmann et al., "Terpenoid-based defenses in conifers: cDNA cloning, characterization, and functional expression of wound-inducible (E)-α-bisabolene synthase from grand fir (*Abies grandis*)," Proc. Natl. Acad. Sci. U.S.A. 95:6756-6761 (1993).

Bohlmann et al., "Monoterpene synthases from grand fir (*Abies grandis*)," J. Biol. Chem. 272:21784-21792 (1997).

Bohlmann et al., "Plant terpenoid synthases: molecular biology and phylogenetic analysis," Proc. Natl. Acad. Sci. U.S.A. 95:4126-4133 (1998).

Bohlmann et al., "cDNA cloning, characterization, and functional expression of four new monoterpene synthase members of the Tpsd gene family from Grand Fir (*Abies grandis*)," Arch. Biochem. Biophys. 368(2):232-243 (1999).

Bohlmann, "Terpenoid synthases—from chemical ecology and forest fires to biofuels and bioproducts," Structure 19(12):1730-1731 (2011).

Chen et al., "The family of terpene synthases in plants: a mid-size family of genes for specialized metabolism that is highly diversified throughout the kingdom," Plant J. 66:212-229 (2011).

Connolly et al., "Heterologous expression of a pleiotropic drug resistance transporter from Phytophthora sojae in yeast transporter mutant," Curr. Genet. 48:356-365 (2005).

Gambliel and Croteau, "Pinene cyclases I and II. Two enzymes from sage (*Salvia officinalis*) which catalyze sterospecific cyclizations of geranyl pyrophosphate to monoterpene olefins of opposite configuration," J. Biol. Chem. 259:740-748 (1984).

Genbank Accession No. EFX06115, ABC transporter [Grosmannia clavigera kw1407], Published on Jan. 31, 2011 [online][retrieved on Jan. 14, 2014] Retrieved from:<URL:ncbi.nlm.nih.gov/protein/EFX06115, 2 pages.

Genbank Accession No. EFX00255.1, "ABC transporter [Grosmannia clavigera kw1407]," Published on Jan. 31, 2011 [online][retrieved on Jan. 14, 2014] Retrieved from:<URL:ncbi.nlm.nih.gov/protein/EFX00255.1, 2 pages.

Genbank Accession No. EFX03218.1, "ABC transporter [Grosmannia clavigera kw1407]," Published on Jan. 31, 2011 [online][retrieved on Jan. 14, 2014] Retrieved from:<URL:ncbi.nlm.nih.gov/protein/EFX03218.1, 2 pages.

Hamberger et al., "Cytochrome P450 mono-oxygenases in conifer genomes: discovery of members of the terpenoid oxygenase superfamily in spruce and pine," Biochem. Soc. Trans. 34(6):1209-1214 (2006).

Hamberger et al., "Evolution of diterpene metabolism: Sitka spruce CYP720B4 catalyzes multiple oxidations in resin acid biosynthesis of conifer defense against insects," Plant Physiol. 157:1677-1695 (2011).

Haridas et al., "The genome and transcriptome of the pine saprophyte *Ophiostoma piceae*, and a comparison with the bark beetle-associated pine pathogen *Grosmannia clavigera*," BMC Genomics 14:373, 15 pages (2013).

Holben et al., "DNA probe method for the detection of specific microorganisms in the soil bacterial community," Appl. Environ. Microbiol. 54(3):703-711 (1988).

Keeling et al., "Functional plasticity of paralogous diterpene synthases involved in conifer defense," Proc. Natl. Acad. Sci. U.S.A. 105(3):1085-1090 (2008).

Keeling et al., "Transcriptome mining, functional characterization, and phylogeny of a large terpene synthase gene family in spruce (*Picea* spp.)," BMC Plant Biol. 11:43, 14 pages (2011).

Keeling et al., "The primary diterpene synthase products of Picea abies levopimaradiene/abietadiene synthase (PaLAS) are epimers of a thermally unstable diterpenol," J. Biol. Chem. 286(24):21145-21153 (2011).

Khadempour et al., "Target-specific PCR primers can detect and differentiate ophiostomatoid fungi from microbial communities associated with the mountain pine beetle *Dendroctonus ponderosae*," Fungal Biol. 114:825-833 (2010).

Ralph et al., "A conifer genomics resource of 200,000 spruce (*Picea* spp.) ESTs and 6,464 high-quality, sequence-finished full-length cDNAs for Sitka spruce (*Picea sitchensis*)," BMC Genomics 9:484, 17 pages (2008).

Ro et al., "Diterpene resin acid biosynthesis in loblolly pine (*Pinus taeda*): functional characterization of abietadiene/levopimaradiene synthase (PtTPS-LAS) cDNA and subcellular targeting of PtTPS-LAS and abietadienol/abietadienal oxidase (PtAO, CYP720B1)," Phytochem. 67:1572-1578 (2006).

Zulak et al., "Terpenoid biosynthesis and specialized vascular cells of conifer defense," J. Integr. Plant Biol. 52(1):86-97 (2010).

Alamouti et al., "Gene genealogies reveal cryptic species and host preferences for the pine fungal pathogen *Grosmannia clavigera*," Mol Ecol 20(12): 2581-2602 (2011).

Alamouti et al., "Multigene phylogeny of filamentous ambrosia fungi associated with ambrosia and bark beetles," 113(8): 822-835 (2009).

Altschul et al., "Basic local alignment search tool," J. Molec. Biol. 215(3):403-410 (1990).

Altschul et al., "Gapped BLAST and PSI-BLAST: a new generation of protein database search programs," Nucleic Acids Res. 25:3389-3402 (1997).

Asch et al., "Comparative studies of the quinic acid (qa) cluster in several *Neurospora* species with special emphasis on the qa-x-qa-2 intergenic region," Mol Gen Genet. 230(3):337-344 (1991).

Bakkali et al., "Biological effects of essential oils—a review," Food Chem Toxicol 46(2): 446-475 (2008).

Beier, D. and E. Young, "Characterization of a regulatory region upstream of the ADR2 locus of S. cerevisiae," Nature 300:724-728 (1982).

Bencurova et al., "Expression of eukaryotic glycosyltransferases in the yeast *Pichia pastoris*," Biochimie 85(3-4):413-422 (2003).

Bohlmann, J., "Pine terpenoid defences in the mountain pine beetle epidemic and in other conifer pest interactions: specialized enemies are eating holes into a diverse, dynamic and durable defence system," Tree Physiology, 943-945 (2012).

Bohlmann et al., "Terpenoid biomaterials," Plant J. 54(4):656-669 (2008).

Boone et al., "Efficacy of tree defense physiology varies with bark beetle population density: a basis for positive feedback in eru ptive species," Canadian Journal of Forest Research 41(6):1174-1188 (2011).

Butler, M. and A. Day, "Fungal melanins: a review," Canadian Journal of Microbiology 44(12):1115-1136 (1998).

Campbell et al., "Patho gen-responsive expression of a putative ATP-binding cassette transporter gene conferring resistance to the diterpenoid sclareol is regulated by multiple defense signaling pathways in Arabidopsis," Plant Physiology 133:1272-1284 (2003).

Carrillo et al., "The multiple sequence alignment problem in biology," SIAM J. Appl. Math. 48(5):1073-1082 (1988).

Chung et al., "*Ophiostoma breviusculum* sp. nov. (Ophiostomatales, Ascomycota) is a new species in the Ophiostoma piceaecomplex associated with bark beetles infesting larch in Japan," Mycologia 98(5): 801-814 (2006).

Clark et al., "Differences in the constitutive terpene profile of lodgepole pine across a geographical range in British Columbia, and correlation with historical attack by mountain pine beetle," Can Entomol 142(6):557-573 (2010).

Coleman et al., "An ABC transporter and a cytochrome P450 of Nectria haematococca MPVI are virulence factors on pea and are the major tolerance mechanisms to the phytoalexin pistatin," Mol Plant-Microbe Interact 24: 368-376 (2011).

Coleman, J. and E. Mylonakis, "Efflux in fungi: la piece de resistance," PLoS Pathogens 5(6):1000486, 7 pages (2009).

Conesa et al., "Blast2GO: a universal tool for annotation, visualization and analysis in functional genomics research," Bioinformatics 21(18):3674-3676 (2005).

Crouzet et al., "Organization and function of the plant pleiotropic drug resistance ABC transporter family," FEBS Lett 580(4):1123-1130 (2006).

Dean, M. and R. Allikmets, "Complete characterization of the human ABC gene family," J. Bionerg Biomembr 33(6): 475-479, (2001).

(56) References Cited

OTHER PUBLICATIONS

De Boer et al., "The tac promoter: a functional hybrid derived from the trp and lac promoters," Proc. Natl. Acad. Sci. U.S.A. 80:21-25 (1983).
Devereux et al., "A comprehensive set of sequence analysis programs for the V AX," Nucleic Acids Res. 12(1):387-395 (1984).
De Waard et al., "Impact of fungal drug transporters on fungicide sensitivity, multidrug resistance and virulence," Pest Manag Sci 62(3):195-207 (2006).
DiGuistini et al., "Genome and transcriptome analyses of the mountain pine beetle-fungal symbiont *Grosmannia clavigera*, a lodgepole pine pathogen," Proc. Natl. Acad. Sci., 108(6): 2504-2509 (2011).
DiGuistini et al., "Generation and annotation of lodgepole pine and oleoresin-induced expressed sequences from the blue-stain fungus *Ophiostoma clavigerum*, a mountain pine beetle-associated pathogen," FEMS Microbiol Lett 267:151-158, (2007).
Dunlop et al., "Engineering microbial biofuel tolerance and export using efflux pumps," 7:487, 7 pages (2011).
Eberhardt et al., "Monoterpene persistence in the sapwood and heartwood of longleaf pine stumps: assessment of differences in composition and stability under field conditions," Can. J. For. Res. 39:1357-1365 (2009).
Emanuelsson et al., "Predicting subcellular localization of proteins based on their N-terminal amino acid sequence," J. Mol. Biol. 300(4):1005-1016 (2000).
Fischer et al., "Metabolic engineering of monoterpene synthesis in yeast," Biotechnology and Bioengineering 108(8):1883-1892 (2011).
Fleer et al., "High-level secretion of correctly processed recombinant human interleukin-1β in Kluyveromyces lactis," Gene 107:285-295 (1991).
Fleissner et al., "An ATP-binding cassette multidrug-resistance trans porter is necessary for tolerance of Gibberella pulicaris to phytoalexins and virulence on potato tubers," Mol Plant-Microbe Interact 15: 102-108 (2002).
Franceschi et al., "Anatomical and chemical defenses of conifer bark against bark beetles and other pests," New Phytologist 167:353-375 (2005).
Galagan et al., "The genome sequence of the filamentous fungus *Neurospora crassa*," Nature 422: 859-868, (2003).
Gershenzon, J. and N. Dudareva, "The function of terpene natural products in the natural world," Nat Chem Biol 3(7):408-414 (2007).
Gilbert et al., "Useful proteins from recombinant bacteria," Sci. Am. 242(3):74-94 (1980).
Giles et al., "Organization and regulation of the Qa (Quinic Acid) genes in neurospora crassa and other fungi," J Hered 82(1):1-7 (1991).
Grabherr et al., "Full-length transcriptome assembly from RNA-Seq data without a reference genome," Nature Biotechnology 29(7): 644-652 (2011).
Gribskov et al., "Sigma factors from *E. coli*, B.subtilis, phage SP01, and phage T4 are homologous proteins," Nucleic Acids Res. 14(16):6745-6763 (1986).
Haridas and Gantt, "The mitochondrial genome of the wood-degrading basidiomycete *Trametes cingulata*," FEMS Microbiol Lett 308:29-34 (2010).
Hess et al., "Cooperation of glycolytic enzymes," Adv. Enzyme Reg. 7:149-167 (1969).
Hess-Orce et al., "Gene discovery for the bark beetle-vectored fungal tree pathogen *Grosmannia clavigera*," BMC Genomics 11:536, 11 pages (2010).
Hitzem an et al., "Isolation and characterization of the yeast 3-phosphoglycerokinase gene (PGK) by an immunological screening technique," J. Biol. Chem. 255:12073-12080 (1980).
Hofstetter et al., "Effects of tree phytochemistry on the interactions among endophloedic fungi associated with the southern pine beetle," J. Chem Ecol, 31(3):539-560 (2005).

Holland, M. and J. Holland, "Isolation and identification of yeast messenger ribonucleic acids coding for enolase, glyceraldehyde-3-phosphate dehydrogenase, and phosphoglycerate kinase," Biochem. 17:4900-4907 (1978).
Holt and Yandell,"MAKER2: an annotation pipeline and genome-database management tool for second-generation genome projects," BMC Bioinformatics 12(491):1-14 (2011).
Ignea et al., "Improving yeast strains using recyclable integration cassettes, for the production of plant terpenoids," Microbial Cell Factories 10:4, 18 pages (2011).
IUPAC-IUB Commission on Biochemical Nomenclature, "A one-letter notation for amino acid sequences. Tentative rules," J. Biol. Chem. 243(13):3557-3559 (1968).
Jay et al., "Construction of a general vector for efficient expression of mammalian proteins in bacteria: use of a synthetic ribosome binding site," Proc. Natl. Acad. Sci. U.S.A. 78(9):5543-5548 (1981).
Kall et al., "Advantages of combined transmembrane topology and signal peptide prediction—the Phobius web server," Nucleic Acids Research 35: W429-W432 (2007).
Keeling et al., "Diterpene resin acids in conifers," Phytochem. 67:2415-2423 (2006).
Keeling et al., "Genes, enzymes and chemicals of terpenoid diversity in the constitutive and induced defence of conifers against insects and pathogens," New Phytol. 170:657-675 (2006).
Khaldi et al., "SMURF: genomic mapping of fungal secondary metabolite clusters," Fungal Genet Biol. 47(9):736-741 (2010).
Kirby, J. and J. Keasling, "Biosynthesis of plant isoprenoids: perspectives for microbial engineering," Annu Rev. Plant Biol 60:335-355 (2009).
Kopper et al., "Effects of diterpene acids on components of a conifer bark beetle-fungal interaction: tolerance by *Ips pini* and sensitivity by its associate *Ophiostoma ips*," Environ. Entomol. 34(2):486-493 (2005).
Korf, I., "Gene finding in novel genomes," BMC Bioinformatics 5:1-9 (2004).
Kovalchuk, A. and A. Driessen,"Phylogenetic analysis of fungal ABC transporters," BMC Genomics 11(177):1-21 (2010).
Krokene, P. and H. Solheim, "Pathogenicity of four blue-stain fungi associated with aggressive and nonaggressive bark beetles," Ecology and Population Biology, 88(1): 39-44 (1998).
Kurz et al., "Mountain pine beetle and forest carbon feedback to climate change," Nature 452: 987-990 (2008).
Lah et al., "The cytochromes P450 of Grosmannia clavigera: Genome organization, phylogeny, and expression in response to pine host chemicals," Fungal Genet Biol 50:72-81 (2013).
Lamping et al., "Fungal PDR transporters: phylogeny, topology, motifs and function," Fungal Genet Biol 47(2):127-142 (2010).
Lee et al., "Pathogenicity of Leptographium longiclavatum associated with Dendroctonus ponderosae to Pinus contorta ," Canadian Journal of Forest Research 36(11):2864-2872 (2006).
Lee et al., "*Leptographium longiclavatum* sp. nov., a new species associated with the mountain pine beetle, *Dendroctonus ponderosae*," Mycol Res 109(10):1162-1170 (2005).
Li et al., "First cloning and characterization of two functional aquaporin genes from an arbuscular mycorrhizal fungus *Glomus intraradices*," New Phytologist 197(2):617-630 (2013).
Loppnau et al., "Isolation and disruption of the melanin pathway polyketide synthase gene of the softwood deep stain fungus *Ceratocystis resinifera*," Fungal Genet Biol 41(1):33-41 (2004).
MacPherson et al., "A Fungal family of transcriptional regulators: the zinc cluster proteins," Microbiol Mol Biol Rev 70(3):583-604 (2006).
Malissard et al., "Expression of functional soluble forms of human beta-1, 4-galactosyltransferase 1, alpha-2,6-sialyltransferase, and alpha-1, 3-fucosyltransferase VI in the methylotrophic yeast *Pichia pastoris*," Biochem Biophys Res Commun 267(1):169-173 (2000).
Martin et al., "Engineering a mevalonate pathway in *Escherichia coli* for production of terpenoids," Nat Biotechnol 21(7): 796-802 (2003). and Corrigenda, Nat Biotechnol. 26(10):1193 (2008).

(56) References Cited

OTHER PUBLICATIONS

Martinez et al., "Genome sequencing and analysis of the biomass-degrading fungus *Trichoderma reesei* (syn. *Hypocrea jecorina*)." Nat. Biotechnol. 26(5):553-560 (2008) and Corrigenda, Nat. Biotechnol. 26(10):1193 (2008).
Mayfield et al., "Expression and assembly of a fully active antibody in algae," Proc. Natl. Acad. Sci. U.S.A. 100(2):438-442 (2003).
McInerney et al., "GCUA: General codon usage analysis," Bioinformatics 14(4):372-373 (1998).
Miller et al., "Insect-induced conifer defense. White pine weevil and methyl jasmonate induce traumatic resinosis, de novo formed volatile emissions, and accumulation of terpenoid synthase and putative octadecanoid pathway transcripts in Sitka spruce," Plant Physiol. 137:369-382 (2005).
Miroux et al., "Over-production of proteins in *Escherichia coli*: mutant hosts that allow synthesis of some membrane proteins and globular proteins at high levels," J. Mol. Biol. 260(3):289-298 (1996).
Muneta et al., "Large-scale production of porcine mature interleukin-18 (IL-18) in silkworms using a hybrid baculovirus expression system," J. Vet. Med. Sci. 65(2):219-223 (2003).
Myers et al., "Optimal alignments in linear space," Comput Appl Biosci 4(1): 11-17 (1988).
Needleman, S. and C. Wunsch, "A general method applicable to the search for similarities in the amino acid sequence of two proteins," J. Mol. Biol. 48:443-453 (1970).
Oswald et al., "Monoterpenoid biosynthesis in *Saccharomyces cerevisiae*," FEMS Yeast Res 7: 413-421 (2007).
Parra et al., "CEGMA: a pipeline to accurately annotate core genes in eukaryotic genomes," Bioinformatics 23(9):1061-1067 (2007).
Parveen et al., "Response of *Saccharomyces cerevisiae* to a monoterpene: evaluation of antifungal potential by DNA microarray analysis," J. Antimicrob Chemother 54:46-55 (2004).
Paumi et al., "ABC transporters in *Saccharomyces cerevisiae* and their interactors: new technology advances the biology of the ABCC (MRP) subfamily," Microbiology and Molecular Biology Reviews 73(4):577-593 (2009).
Pavesi et al., "Identification of new eukaryotic tRNA genes in genomic DNA databases by a multistep weight matrix analysis of transcriptional control regions," Nucleic Acid Res. 22(7):1247-1256 (1994).
Pearson et al., "Improved tools for biological sequence comparison," Proc. Natl. Acad. Sci. U.S.A. 85(8):2444-2448 (1988).
Peralta-Yahya et al., "Identification and microbial production of a terpene-based advanced biofuel," Nature Comm. 2:483, 8 pages (2011).
Pham et al., "Large-scale transient transfection of serum-free suspension-growing HEK293 EBNA1 cells: peptone additives improve cell growth and transfection efficiency," Biotechnol. Bioeng. 84(3):332-342 (2003).
Pompon et al., "Genetically engineered yeast cells and their applications," Toxicol. Lett. 82-83: 815-822 (1995).
Ro et al., "Loblolly pine abietadienol/abietadienal oxidase PtAO (CYP720B1) is a multifunctional, multisubstrate cytochrome P450 monooxygenase," Proc. Natl. Acad. Sci. U.S.A. 102(22):8060-8065 (2005).
Ro et al., "Production of the antimalarial drug precursor artemisinic acid in engineered yeast," Nature 440:940-943 (2006).
Rogers et al., "The pleitropic drug ABC transporters from *Saccharomyces cerevisiae*," J Mol Microbiol Biotechnol 3(2):207-214, (2001).
Russell et al., "Nucleotide sequence of the yeast alcohol dehydrogenase II gene," J. Biol. Chem. 258:2674-2682 (1982).
Safranyik et al., "Potential for range expansion of mountain pine beetle into the Boreal Forest of North America," Can Entomol 142(5): 415-442 (2010).
Sambrook et al., "Chapter 11: Synthetic Oligonucleotide Probes," in "*Molecular Cloning: A Laboratory Manual*," 2nd Ed., Cold Spring Harbor Laboratory Press, Cold Spring Harbor, New York, 61 pages (1989).
Schardl et al., "Design and construction of a versatile system for the expression of foreign genes in plants," Gene 61(1):1-11 (1987).
Schmieder and Edwards, "Quality control and preprocessing of metagenomic datasets," Bioinformatics 27(6): 863-864 (2011).
Schwartz, R. and M. Dayhoff, eds., "Atlas of Protein Sequence and Structure," National Biomedical Research Foundation, pp. 353-358 (1979).
Shilo, B. and R. Weinberg, "DNA sequences homologous to vertebrate oncogenes are conserved in *Drosophila melanogaster*," Proc. Natl. Acad. Sci. 78(11):6789-6792 (1981).
Simpson et al., "ABySS: A parallel assembler for short read sequence data," Genome Res 19(6):1 117-1123 (2009).
Sipos, G. and K. Kuchler, "Fungal ATP-binding cassette (ABC) transporters in drug resistance & detoxification," Current Drug Targets 7:471-481 (2006).
Slater, G. and E. Birney, "Automated generation of heuristics for biological sequence comparison," BMC Bioinformatics 15(6):31, 11 pages (2005).
Smith, T. and M. Waterman, "Comparison in biosequences," Adv. Appl. Math. 2(4):482-489 (1981).
Soylu et al., "Antimicrobial activities of the essential oils of various plants against tomato late blight disease agent Phytophthora infestans," Mycopathologia 161(2):119-128 (2006).
Stanke, M. and S. Waack, "Gene prediction with a hidden Markov model and a new intron submodel," Bioinformatics 19(20):215-225 (2003).
Stefanato et al., "The ABC transporter BcatrB from Botrytis cinerea exports camalexin and is a virulence factor on Arabidopsis thaliana," Plant Journal 58: 499-510 (2009).
Takahashi et al., "Metabolic engineering of sesquiterpene metabolism in yeast," Biotechnol. Bioeng. 97:170-181 (2007).
Ter-Hovhannisyan et al., "Gene prediction in novel fungal genomes using an ab initio algorithm with unsupervised training," Genome Research 18:1979-1990 (2008).
Trapnell et al., "Differential gene and transcript expression analysis of RNA-seq experiments with TopHat and Cufflinks," Nat. Protoc. 7(3):562-578 (2012).
Turtola et al., "Secondary metabolite concentrations and terpene emissions of scots pine xylem after long-term forest fertilization," J. Environ. Qual. 31:1694-1701 (2002).
Univertisty of Alberta Microfungus Collection and Herbarium (UAMH Catalogue # 11150) Grossmannia clavigera, strain KW1407, Sender: Breuil, C., [online][retrieved on Feb. 8, 2013] Retrieved from:URL:secure.devonian.ualberta.ca/uamh/details.php?id=11150, 2 pages.
Univertisty of Alberta Microfungus Collection and Herbarium (UAMH Catalogue # 11346 Ophiostoma piceae Sender: Breuil, C., [online][retrieved on Feb. 8, 2013] Retrieved from:URL:secure.devonian.ualberta.ca/uamh/details.php?id=11346>, 1 page.
Urban et al., "An ATP-driven efflux pump is a novel pathogenicity factor in rice blast disease," EMBO J, 18:512-521, (1999).
Uzunovic et al., "Fungi that cause sapstain in Canadian softwoods," Can. J. Microbiol 45(11): 914-922, (1999).
Van den Berg et al., "Kluyveromyces as a host for heterologous gene expression: expression and secretion of prochymosin," Biotechnol. 8:135-139 (1990).
Verrier et al., "Plant ABC proteins—a unified nomenclature and updated inventory," Trends in Plant Sci 13(4): 151-159, (2008).
Wang et al., "*Agrobacterium*-meditated gene disruption using split-marker in *Grosmannia clavigera*, a mountain pine beetle associated pathogen," Current Genetics 56(3):297-307 (2010).
Wang, H. and C. Breuil, "A second reductase gene involved in melanin biosynthesis in the sap-staining fungus *Ophiostoma floccosum*," Molecular Genetics and Genomics 267(5): 557-563 (2002).
Watson et al., *Molecular Biology of the Gene*, 4th Edition, Benjamin/Cummings, p. 224 (1987).
Yamaoka et al., "The Ability of Ophiostoma clavigerum to kill mature lodgepolepine trees," 25(6-7): 401-404 (1995).
Zipfel et al., "Multi-gene phylogenies define Ceratocystiopsis and Grosmannia distinct from Ophiostoma," Studies in Mycology, 55:75-97 (2006).

(56) References Cited

OTHER PUBLICATIONS

Letter/Written Disclosure of the Supplemental Information Disclosure Statement for the above-referenced application, submitted on the same day herewith Feb. 19, 2015, 2 pages.
Fleet et al. "Nutrient composition and pigmentation of deep and surface colonizing sapstaining fungi in Pinus contorta," Holzforschung, 55:340-346 (2001).
Harrington, T., "Diseases of conifers caused by species of *Ophiostoma* and *Leptographium*," In *Ceratocystis and Ophiostoma: taxonomy, ecology, and pathogenicity*. Wingfield et al., (eds.), St Paul, Minnesota: APS Press; pp. 161-172 (1993).
Scheffer, T., "Microbiological degradation," In *Wood Deterioration and its Prevention by Preservative Treatments*. Nicholas, D., (ed.), N.Y:Syracuse University Press, 31-106 (1973).
Schirp et al., "Advances in understanding the ability of sapstaining fungi to produce cell wall degrading enzymes," Wood Fiber Sci., 35(3):434-444 (2003).
Seifert, K., "Sapstain of commercial lumber by species of *Ophiostoma* and *Ceratocystis*," In *Ceratocystis and Ophiostoma: taxonomy, ecology, and pathogenicity*. Wingfield et al., (eds.), St Paul, Minnesota: APS Press; 141-151 (1993).
Upadhyay H., "Classification of the Ophiostomatoid fungi," In *Ceratocystis and Ophiostoma: taxonomy, ecology, and pathogenicity*. Wingfield et al., (eds.), St Paul, Minnesota: APS Press; 7-13 (1993).
Uzunovic et al., "Microbial Discolorations," In *Wood Discolorations and their Preventions; with Emphasis on Bluestain*. Uzunovic et al., (eds.), Fp Innovations, pp. 16-41 (2008).

\* cited by examiner

SEQUENCE LISTING

```
<160> NUMBER OF SEQ ID NOS: 52

<210> SEQ ID NO 1
<211> LENGTH: 1459
<212> TYPE: PRT
<213> ORGANISM: Grosmannia clavigera
<220> FEATURE:
<223> OTHER INFORMATION: ABC terpenoid transporter GcABC-G1
<220> FEATURE:
<221> NAME/KEY: DOMAIN
<222> LOCATION: (133)...(363)
<223> OTHER INFORMATION: NBF; PDR Domain 1
<220> FEATURE:
<221> NAME/KEY: DOMAIN
<222> LOCATION: (473)...(683)
<223> OTHER INFORMATION: TMD 1
<220> FEATURE:
<221> NAME/KEY: DOMAIN
<222> LOCATION: (804)...(1032)
<223> OTHER INFORMATION: NBF; PDR Domain 2
<220> FEATURE:
<221> NAME/KEY: DOMAIN
<222> LOCATION: (1127)...(1342)
<223> OTHER INFORMATION: TMD 2

<400> SEQUENCE: 1

Met Glu Thr Asp Ser Lys Ser Val Glu Ser Gly Glu Thr Ala Ala Met
1               5                   10                  15

Pro Gly Gln Gln Gln Ile Ser Ser Asn Ala Gln Gly Leu Ile His Ala
            20                  25                  30

Tyr Ser Met Glu Leu Val Arg Ser Ser Arg Ala Thr Gly Gly Gly
        35                  40                  45

Gly Ala Pro Gly Arg Asn Pro Phe Thr Gly Thr Ser Asn Asp Pro Ala
    50                  55                  60

Leu Asp Pro His Ser Lys Ala Phe Asp Ala Arg Arg Trp Ala Gln Ala
65                  70                  75                  80

Val Leu His Ser Thr Gly Glu Gly Pro Asp His Cys Pro Arg Pro Thr
                85                  90                  95

Ala Gly Val Ala Tyr Arg Asn Leu Arg Val His Gly Tyr Gly Ser Pro
            100                 105                 110

Thr Asp Tyr Gln Lys Asp Val Phe Asn Val Leu Leu Gln Ala Pro Leu
        115                 120                 125

Glu Ala Ala Gln Tyr Phe Met Ser Ser Arg Arg Gly Arg Glu Val Pro
    130                 135                 140

Ile Leu Arg Asp Gly Phe Asp Gly Leu Val Arg Ser Gly Glu Met Leu
145                 150                 155                 160

Leu Val Leu Gly Arg Pro Gly Ser Gly Val Thr Thr Leu Leu Lys Thr
                165                 170                 175

Val Ala Gly Glu Thr Asn Gly Leu Gln Val Asp Ala Glu Ala Phe Ile
            180                 185                 190
```

-continued

```
Ser Tyr Gln Gly Ile Pro Met Gln Ala Ile Gln Lys Arg Phe Arg Gly
        195                 200                 205

Glu Val Val Tyr Gln Ala Glu Thr Asp Val His Phe Pro Gln Leu Thr
    210                 215                 220

Val Gly Gln Thr Leu Leu Phe Ala Ala Lys Ala Arg Thr Pro Gln Met
225                 230                 235                 240

Arg Pro Asp Gly Val Thr Arg Ala Gln Tyr Ala Lys His Ile Arg Asp
                245                 250                 255

Val Val Met Ala Val Phe Gly Ile Ser His Thr Val Asn Thr Arg Val
            260                 265                 270

Gly Ser Asp Leu Val Arg Gly Val Ser Gly Glu Arg Lys Arg Val
        275                 280                 285

Ser Ile Ala Glu Val Ala Leu Ser Gly Ser Ala Leu Gln Cys Trp Asp
    290                 295                 300

Asn Ser Thr Arg Gly Leu Asp Ser Ala Ser Ala Leu Ser Phe Ala Asn
305                 310                 315                 320

Thr Leu Arg Leu Ser Thr Glu Leu Ala Gly Thr Thr Ala Leu Val Ala
                325                 330                 335

Met Tyr Gln Ala Ser Glu Ala Ala Tyr Glu Thr Phe Gly Lys Val Cys
            340                 345                 350

Leu Leu Tyr Glu Gly Arg Gln Ile Phe Phe Gly Pro Ala Asn Glu Ala
        355                 360                 365

Lys Ala Phe Phe Val Asp Met Gly Tyr Glu Cys Pro Asp Arg Gln Thr
    370                 375                 380

Thr Ala Asp Phe Leu Thr Ser Leu Thr Asn Pro Gly Glu Arg Val Val
385                 390                 395                 400

Arg Pro Gly Phe Glu Asn Arg Val Pro Arg Thr Pro Asp Asp Phe Val
                405                 410                 415

Ala Tyr Trp Lys Ala Ser Ala Thr Arg Ala Ser Leu Leu Gln Asp Ile
            420                 425                 430

Ala Glu Phe Asp Gln Glu His Pro Met Asp Gly Thr Pro Ile Glu Ala
        435                 440                 445

Met Ala Thr Val Arg Lys Ala His Gln Ala Pro Leu Thr Pro Asn Lys
    450                 455                 460

Ser Pro Phe Thr Leu Ser Phe Pro Gln Gln Val Ala Leu Cys Met Thr
465                 470                 475                 480

Arg Gly Tyr Glu Arg Thr Met Gly Asp Lys Thr Phe Ile Val Thr
                485                 490                 495

Val Gly Gly Asn Leu Val Ile Ser Leu Val Leu Gly Ser Val Phe Tyr
            500                 505                 510

Gln Leu Ser Pro Asp Ala Ser Ser Ile Thr Ser Arg Cys Ile Leu Leu
        515                 520                 525

Phe Phe Ala Ile Leu Phe Asn Ala Leu Ser Ser Ser Leu Glu Ile Leu
    530                 535                 540

Ser Leu Tyr Ala Gln Arg Pro Ile Val Glu Lys His Ala Arg Tyr Ala
545                 550                 555                 560

Leu Tyr Thr Pro Ser Ala Glu Ala Val Ser Ser Ala Phe Cys Glu Leu
                565                 570                 575

Pro Ser Lys Ile Phe Ser Ala Ile Ala Phe Asn Ile Pro Leu Tyr Phe
            580                 585                 590

Met Ala Asp Leu Arg His Gly Ala Gly His Phe Phe Phe Leu Leu
        595                 600                 605
```

```
Phe Ala Phe Thr Cys Thr Leu Thr Met Ser Phe Ile Leu Arg Thr Ile
610                 615                 620

Gly Gln Ala Ser Arg Thr Val Gln Glu Ala Leu Thr Pro Ala Ala Val
625                 630                 635                 640

Phe Ile Ile Ser Leu Val Ile Tyr Thr Gly Phe Val Ile Pro Val Lys
                645                 650                 655

Ser Met Gln Gly Trp Met Arg Trp Ile Asn Tyr Leu Asn Pro Ile Ala
            660                 665                 670

Tyr Ala Tyr Glu Ser Leu Leu Val Asn Glu Leu Ser Gly Arg Asn Phe
        675                 680                 685

Pro Cys Ala Ser Phe Val Pro Ala Tyr Pro Asn Leu Ser Ser Ser Glu
690                 695                 700

His Thr Cys Ser Thr Ala Gly Ala Ala Pro Gly Ala Asp Phe Val Val
705                 710                 715                 720

Gly Asp Thr Ile Leu Asn Ser Ser Tyr Glu Tyr Tyr His Ala His Lys
                725                 730                 735

Trp Arg Asn Leu Gly Ile Leu Ile Gly Phe Leu Ile Ala Phe Phe Phe
            740                 745                 750

Ala Tyr Leu Val Ala Ser Glu Tyr Ile Thr Ala Glu Gln Ser Lys Gly
        755                 760                 765

Glu Val Leu Val Phe Arg Arg Gly His Lys Glu Ser Ala Val Val Glu
770                 775                 780

Arg Lys Thr Ala Thr Ser Asp Asp Ser Asp Gly Glu Lys Gly His Gln
785                 790                 795                 800

Thr Glu Gln Lys Asp Ile Cys His Trp Arg Asn Val Cys Tyr Asp Ile
                805                 810                 815

Thr Ile Lys Gly Gln Gly Arg Arg Leu Leu Asp His Val Asp Gly Trp
            820                 825                 830

Val Lys Pro Gly Thr Leu Thr Cys Leu Met Gly Val Ser Gly Ala Gly
        835                 840                 845

Lys Thr Thr Leu Leu Asp Val Leu Ala Asn Arg Val Thr Met Gly Val
850                 855                 860

Val Thr Gly Asp Met Leu Val Asn Gly Ser Pro Arg Asp Ser Ser Phe
865                 870                 875                 880

Gln Arg Lys Thr Gly Tyr Val Gln Gln Asp Val His Leu Glu Thr
                885                 890                 895

Ser Thr Val Arg Glu Ala Leu Arg Phe Ser Ala Gln Leu Arg Gln Pro
            900                 905                 910

Thr Thr Val Ser Thr Gln Asp Lys Tyr Ile Phe Val Glu Glu Val Ile
        915                 920                 925

Glu Leu Leu Glu Met Asp Glu Tyr Ala Asp Ala Ile Val Gly Val Pro
930                 935                 940

Gly Thr Gly Leu Asn Val Glu Gln Arg Lys Arg Leu Thr Ile Gly Val
945                 950                 955                 960

Glu Leu Ala Ala Lys Pro Asp Leu Leu Leu Phe Leu Asp Glu Pro Thr
                965                 970                 975

Ser Gly Leu Asp Ser Gln Thr Ala Trp Ser Val Ala Ala Leu Ile Arg
            980                 985                 990

Lys Leu Ser Ala Arg Gly Gln Ala Val Leu Cys Thr Ile His Gln Pro
        995                 1000                1005

Ser Ala Leu Leu Tyr Gln Gln Phe Asp Arg Ile Leu Leu Leu Ala Ala
1010                1015                1020

Gly Gly Arg Thr Val Tyr Phe Gly Asp Ile Gly Pro Asn Ala Glu Thr
```

-continued

```
1025                1030                1035                1040

Ile Ile Ser Tyr Phe Glu Arg Asn Gly Ala Glu Pro Cys Gly Gln Asp
                    1045                1050                1055

Glu Asn Pro Ala Glu Trp Met Leu Ser Val Ile Gly Ala Gly Pro Gly
                    1060                1065                1070

Gly Val Ala Lys Gln Asp Trp Val Ser Ile Trp Arg Asn Ser Asp Glu
                    1075                1080                1085

Tyr Ser Ala Val Gln Ala Glu Leu Asp Asn Leu Ala Lys Arg Lys Asp
                    1090                1095                1100

Thr Met Ala Ser Ser Gly Ala Thr Asp Ala Ala Ala Val Thr Thr Tyr
    1105                1110                1115                1120

Ala Thr Pro Phe Phe Phe Gln Leu Tyr Met Cys Ser Lys Arg Val Phe
                    1125                1130                1135

Glu Gln Tyr Trp Arg Thr Pro Ser Tyr Ile Tyr Ala Lys Met Ile Leu
                    1140                1145                1150

Cys Phe Ala Val Ser Leu Phe Ile Gly Leu Ser Phe Arg Lys Ala Pro
                    1155                1160                1165

Leu Ser Glu Gln Gly Leu Gln Asn Gln Met Phe Ser Ile Phe Met Leu
                    1170                1175                1180

Leu Val Ile Phe Ala Phe Leu Ala Tyr Gln Thr Met Pro His Phe Ile
    1185                1190                1195                1200

Arg Gln Arg Glu Leu Tyr Glu Ile Arg Glu Arg Ala Ser Arg Thr Tyr
                    1205                1210                1215

Ser Trp Tyr Val Phe Met Leu Ala Asn Ile Ile Val Glu Leu Pro Trp
                    1220                1225                1230

Asn Thr Ile Ala Ser Leu Leu Val Phe Leu Pro Phe Tyr Tyr Ile Val
                    1235                1240                1245

Gly Met Asn His Asn Ala Glu Ala Thr His Ser Val Ser Glu Arg Gly
                    1250                1255                1260

Gly Leu Met Phe Leu Leu Val Trp Val Phe Leu Val Phe Glu Ser Thr
    1265                1270                1275                1280

Phe Thr Asp Met Val Val Ala Gly Ser Pro Thr Ala Glu Leu Gly Ala
                    1285                1290                1295

Thr Met Ala Leu Leu Leu Phe Ala Phe Thr Leu Ile Phe Cys Gly Val
                    1300                1305                1310

Met Val Gly Lys Asp Gln Leu Pro Gly Phe Trp Ile Phe Met Tyr Arg
                    1315                1320                1325

Val Ser Pro Leu Thr Tyr Leu Val Gly Gly Leu Leu Ala Thr Gly Val
                    1330                1335                1340

Gly His His Glu Val Thr Cys Thr Ala Arg Glu Leu Leu Ser Phe Gln
    1345                1350                1355                1360

Pro Val Gly Asn Gln Thr Cys Leu Glu Tyr Met Thr Pro Tyr Met Lys
                    1365                1370                1375

Leu Ala Gly Gly Lys Val Ile Asn Pro Asn Ala Val Ala Pro Ala Ser
                    1380                1385                1390

Cys Glu Phe Cys Thr Leu Ala Asn Thr Asp Ala Phe Leu Ala Ser Ile
                    1395                1400                1405

Asn Val Ser Tyr Asp Gln Arg Trp Arg Asp Phe Gly Leu Met Trp Ala
                    1410                1415                1420

Tyr Val Val Phe Asn Val Phe Gly Ala Leu Phe Met Tyr Trp Leu Val
    1425                1430                1435                1440

Arg Ala Pro Lys Gly Asp Leu Lys Ala Arg Leu Phe Lys Leu Val Gly
                    1445                1450                1455
```

Lys Thr Ala

<210> SEQ ID NO 2
<211> LENGTH: 4380
<212> TYPE: DNA
<213> ORGANISM: Grosmannia clavigera
<220> FEATURE:
<223> OTHER INFORMATION: ABC terpenoid transporter GcABC-G1

<400> SEQUENCE: 2

| | | | | | |
|---|---|---|---|---|---|
| atggagaccg | actcgaaatc | tgtcgagtcc | ggggagaccg | cagcgatgcc | gggccagcag | 60 |
| cagatctcga | gcaacgccca | gggcctgatc | cacgcctaca | gcatggagct | ggtgcggtcg | 120 |
| agctcgcggg | ccaccggcgg | cggcggtgca | ccgggacgga | acccgttcac | cggcacgagc | 180 |
| aacgacccgg | cactcgaccc | acactccaag | gcctttgacg | cccggcgatg | ggcccaggcc | 240 |
| gtgctgcact | cgacgggcga | gggcccggat | cactgcccac | gcccgacggc | cggcgttgcc | 300 |
| taccgcaatt | gcgcgtcca | cggctacggc | agcccgaccg | actaccagaa | ggacgtcttc | 360 |
| aacgtcctgc | tgcaggcccc | gctcgaggcc | gctcagtact | ttatgagcag | ccggcgcgga | 420 |
| cgcgaggtgc | ccatcctgcg | cgacggcttt | gacgggctcg | tgcgcagcgg | tgagatgctg | 480 |
| ctcgtgctcg | gtcgtcccgg | cagtggtgtc | accaccctcc | tcaagaccgt | tgccggcgag | 540 |
| accaatggcc | tccaggtcga | cgccgaggcc | tttatctcgt | accagggcat | ccccatgcag | 600 |
| gccatccaga | aacgcttccg | cggcgaggtc | gtctaccagg | ccgagaccga | cgtccacttt | 660 |
| ccccagctca | ccgtcggcca | gaccctgctc | ttcgctgcca | aggcacgcac | tcctcagatg | 720 |
| cgtcccgatg | gcgtcacccg | tgctcaatac | gccaaacaca | tccgcgacgt | cgtcatggct | 780 |
| gtctttggca | tctctcatac | cgtcaacact | cgcgtcggct | ccgatctcgt | ccgtggtgtc | 840 |
| agcggtggtg | agcgcaagcg | tgtcagtatc | gccgaggtcg | cccttagcgg | cagcgccctc | 900 |
| cagtgctggg | acaacagcac | ccgtggtctc | gacagtgcct | ctgccctgtc | ttttgccaac | 960 |
| actcttcgcc | tctcgaccga | gctcgccggc | accactgctc | tcgtcgccat | gtaccaggct | 1020 |
| tctgaggctg | cctacgagac | ttttggcaag | gtctgccttc | tctacgaggg | ccgccagatc | 1080 |
| ttcttcggtc | ccgccaacga | ggccaaggct | ttcttcgtcg | acatgggcta | cgagtgccct | 1140 |
| gatcgccaga | ccacggccga | tttcctcacc | tcgcttacca | accctggcga | gcgtgtcgtc | 1200 |
| cgccccggct | cgagaaccg | cgtccctcgc | accctgacg | actttgtcgc | ctactggaag | 1260 |
| gccagtgcca | ctcgtgctag | cctgttgcag | gacattgccg | agttcgacca | ggagcatcct | 1320 |
| atggacggaa | ccccatcga | agctatggcc | accgtgcgga | aggcacacca | ggccccgctg | 1380 |
| actcccaaca | gtctcccctt | taccctctcg | ttccccagc | aggtcgctct | ctgcatgacc | 1440 |
| cgcggctatg | agcggactat | gggcgacaag | accttttca | tcgtcaccgt | cggcggcaac | 1500 |
| ctcgttatct | cccttgtgct | tggcagtgtc | ttctaccagc | tgtctcccga | tgcctctagc | 1560 |
| atcacgtcgc | gctgcatctt | gctcttcttc | gccattctgt | tcaatgccct | cagcagctcc | 1620 |
| ctggaaattc | tctctctgta | tgcccaacgt | ccgatcgtcg | agaagcacgc | ccgctatgca | 1680 |
| ctctatacac | cctcggccga | agctgtctcg | tctgccttct | gcgaactgcc | ctccaagatc | 1740 |
| ttctccgcta | tcgctttcaa | cattccgcta | tacttcatgg | ccgatcttcg | acatggcgcc | 1800 |
| gggcacttct | tcttcttctt | gctgttcgcc | tttacgtgta | ccttgaccat | gtccttcatc | 1860 |
| ctgcgcacca | tcgccaggc | ttctcgcacc | gttcaagagg | ctctgactcc | ggctgccgtg | 1920 |
| ttcatcatat | ctctcgtcat | ctacactggc | tttgtcattc | ccgtcaaatc | catgcagggc | 1980 |

```
tggatgcgct ggatcaacta cctcaacccc attgcctatg cctacgagag tctgctggtg    2040
aacgagctta gcggccgcaa cttcccctgc gcctcgttcg tgccggcgta cccgaacctc    2100
tccagttctg agcatacctg ctctactgct ggcgctgccc cgggtgccga ctttgtcgtt    2160
ggtgacacca ttctgaacag cagctacgag tactaccacg ctcacaagtg gcggaacctg    2220
ggcattctca tcggtttcct gatcgccttt ttcttcgcct acctcgtggc ctctgagtac    2280
atcacggccg agcagtccaa gggcgaagtc ctcgtcttcc gccgtggcca caaggagtct    2340
gccgtagtcg agaggaagac tgcgacctcg gacgacagcg atggcgagaa gggccaccag    2400
accgaacaga aggacatctg ccattggcgc aatgtgtgct acgacatcac catcaagggc    2460
cagggcagac gtctgctgga ccacgttgac ggctgggtca agcccggaac tctgacctgt    2520
cttatgggtg tctctggggc tggaaagacc actctgctcg atgtcctcgc aaaccgcgtc    2580
accatgggtg ttgtcacagg cgacatgttg gttaacggaa gccccgtga cagctccttc    2640 cagcgcaaga ccggctatgt tcagcagcag gacgtccacc tcgagacctc gactgtgcgc    2700
gaagcccttc gcttcagcgc acagctgcgg cagccaacaa ctgtcagcac ccaggacaag    2760
tacatctttg tcgaagaggt tattgagctg ctcgagatgg acgagtatgc tgacgccatt    2820
gtcggcgttc ctggtaccgg tctgaacgtc gaacagcgca agcgcctgac cattggtgtg    2880
gagcttgctg ccaagcccga tcttctgctc ttcctcgacg agcccacgtc tggcctcgac    2940
agtcagactg cctggtccgt tgccgcgctc attcgcaagc tctctgcccg cggccaggcc    3000
gttctgtgta ccatccacca gccgtccgcc ctgctgtacc agcagtttga ccgcattctc    3060
ctgctggctg ccggtggtcg caccgtgtac tttggcgaca ttggcccgaa cgcagagaca    3120
atcatcagct actttgagcg gaacggcgcc gagccctgcg acaggacga gaacccggcc    3180 gagtggatgc tctctgtcat tggtgctgga ccgggtggtg tagcaaagca ggactgggtc    3240
agtatctggc gcaacagcga cgagtacagt gccgttcagg ccgagctgga taacctggcc    3300
aagcgcaagg acactatggc ttctagcggc gcaactgacg ccgctgctgt caccacttat    3360
gccacgccct tcttcttcca gctgtacatg tgctccaagc gcgtctttga gcagtactgg    3420
cgcactccgt catacatcta cgccaagatg atcctgtgtt tcgcggtctc tctcttcatc    3480
ggtctctctt tccgcaaggc tcccttgtcc gaacagggcc tgcagaacca atgttctcc    3540 atcttcatgc tgcttgtcat cttcgccttc ctcgcctacc agacgatgcc ccatttcatc    3600
cgccagcgcg agctctacga gatccgtgaa cgtgcctcgc gcacgtactc gtggtatgtc    3660
tttatgctgg ccaacatcat cgtggagctt ccctggaaca ccatcgcctc gctgctcgtc    3720
ttcctgccgt tctactacat cgtcggcatg aaccacaacg cagaggcgac gcattcggtg    3780
tctgagcgtg gcggcctcat gttcctgctt gtctgggtct cctcgtcttc cgagtctacc    3840
tttaccgaca tggttgtggc tggctcgccc acggccgagc tgggtgccac catggccctg    3900
ctgctgtttg cctttacact gatcttctgc ggtgtcatgg ttggaaagga ccaacttcct    3960
ggcttctgga tcttcatgta ccgcgtctca cccttgacgt atctagtcgg tggcctcttg    4020
gctactggcg tcggccatca cgaagttact tgcaccgctc gggagctgct cagcttttcag    4080 ccggtcggca accagacctg cctcgagtac atgaccccgt acatgaagct cgccggtggc    4140
aaggtgatca acccgaacgc cgtggcccct gctagctgcg agttctgtac tcttgccaac    4200
accgacgcct tcctggcctc gatcaatgtc agctacgacc aacggtggcg cgactttggc    4260
ctgatgtggg cgtacgttgt cttcaacgtg ttcggtgctc tgtttatgta ctggcttgtt    4320 cgggcccca agggcgacct gaaggcacgc ctgttcaagc tggttggcaa gactgcgtaa    4380
```

<210> SEQ ID NO 3
<211> LENGTH: 1539
<212> TYPE: PRT
<213> ORGANISM: Grosmannia clavigera
<220> FEATURE:
<223> OTHER INFORMATION: ABC terpenoid transporter GcABC-G2
<220> FEATURE:
<221> NAME/KEY: DOMAIN
<222> LOCATION: (196)...(426)
<223> OTHER INFORMATION: NBF; PDR Domain 1
<220> FEATURE:
<221> NAME/KEY: DOMAIN
<222> LOCATION: (536)...(746)
<223> OTHER INFORMATION: TMD 1
<220> FEATURE:
<221> NAME/KEY: DOMAIN
<222> LOCATION: (890)...(1117)
<223> OTHER INFORMATION: NBF; PDR Domain 2
<220> FEATURE:
<221> NAME/KEY: DOMAIN
<222> LOCATION: (1209)...(1422)
<223> OTHER INFORMATION: TMD 2

<400> SEQUENCE: 3

```
Met Ser Phe Leu Ala Ser Gly Val Phe Gly Asn Tyr Asp His Thr Gly
 1               5                  10                  15

Gln Thr Ala Gly Val Pro Pro Asp Gly His Ala Arg Arg Leu Asp Tyr
             20                  25                  30

Thr Asp Glu Glu Ile Val Ser Pro Ala Gly His Thr Ala Asp Gly Ala
         35                  40                  45

Asn Thr Arg Thr Thr Ser Leu Thr Glu Thr Gly Ser Ala Pro Asp Gly
     50                  55                  60

Ile Ser Arg Gly Glu Lys Val Ala Pro Ser Gly Asn Asn Gly Ser
 65                  70                  75                  80

Ser Asp Asp Glu Asp Asp Gln Gly Thr Asp Met Gln Arg Arg Thr
                 85                  90                  95

Ser Arg Val Gln Glu Leu Ala Arg His Tyr Thr Asn Val Ser Met Ala
             100                 105                 110

Ser Gly Val Val Pro Pro Gly Ser Asn Pro Phe Thr Glu Leu Ser Asn
         115                 120                 125

Ala Asp Ser Pro Leu Asn Pro Asn Gly Glu Lys Phe Ser Ala Arg Ala
     130                 135                 140

Trp Ala Lys Ala Val Val Gln Met Ile Gln Ser Glu Gly His His Phe
145                 150                 155                 160

Arg Thr Ser Gly Val Ala Phe Gln Asn Leu Asn Val Phe Gly His Gly
                 165                 170                 175

Glu Ala Thr Asp Tyr Gln Lys Asp Phe Leu Asn Val Trp Leu Glu Gly
             180                 185                 190

Ala Gly Ile Val Arg Arg Met Leu Lys Ile Gly Gln Arg Gln Ile Asp
         195                 200                 205

Ile Leu Gln Asn Phe Asp Gly Val Val Arg Lys Gly Glu Met Leu Val
     210                 215                 220

Val Leu Gly Pro Pro Gly Ala Gly Cys Thr Thr Leu Leu Lys Thr Ile
225                 230                 235                 240

Ala Gly Glu Thr Asn Gly Leu Phe Val Asp Asp Lys Ser Tyr Phe Asn
                 245                 250                 255

Tyr Gln Gly Leu Ala Ala His Glu Met His Thr Arg His Arg Gly Glu
             260                 265                 270

Ala Ile Tyr Thr Ala Glu Val Asp Val His Phe Pro Gln Leu Ser Val
```

-continued

```
                275                 280                 285
Gly Asp Thr Leu Thr Phe Ala Ala Arg Ala Arg Ala Pro Arg Thr Ile
290                 295                 300
Pro Gly Gly Val Pro Arg His Glu Phe Ala His His Leu Arg Asp Val
305                 310                 315                 320
Val Met Ala Met Tyr Gly Ile Ser His Thr Val Asn Thr Arg Val Gly
                325                 330                 335
Asn Glu Tyr Val Arg Gly Val Ser Gly Gly Glu Arg Lys Arg Val Thr
                340                 345                 350
Ile Ala Glu Ala Thr Leu Ser Gly Ala Pro Leu Gln Cys Trp Asp Asn
                355                 360                 365
Ser Thr Arg Gly Leu Asp Ser Ala Asn Ala Val Glu Phe Val Lys Thr
370                 375                 380
Leu Arg Leu Gln Thr Glu Leu Phe Gly Asn Thr Ala Val Val Ser Ile
385                 390                 395                 400
Tyr Gln Ala Pro Gln Ser Ala Tyr Asp Leu Phe Asp Lys Val Leu Leu
                405                 410                 415
Ile Tyr Glu Gly Arg Gln Ile Tyr Phe Gly Pro Thr Ala Ala Ala Arg
                420                 425                 430
Gln Tyr Phe Ile Asp Leu Gly Phe Tyr Cys Ala Asp Arg Ala Thr Thr
                435                 440                 445
Pro Asp Phe Leu Thr Ser Met Thr Ser Pro Lys Glu Arg Ile Asp Arg
450                 455                 460
Lys Gly Phe Glu Gly Arg Thr Pro Arg Thr Pro Asp Glu Phe Ala Ala
465                 470                 475                 480
Ala Trp Arg Asn Ser Asp Ala Tyr Lys Ala Val Gln Ala Asp Ile Glu
                485                 490                 495
Asp Tyr Lys Gln Ala His Pro Ile Asp Gly Pro Asp Ala Val Ala Phe
                500                 505                 510
Arg Glu Leu Arg Arg Glu Gln Gln Ala Ser Ala Gln Arg Pro Lys Ser
                515                 520                 525
Pro Phe Thr Leu Ser Tyr Gly Gln Gln Ile Ser Leu Cys Leu Trp Arg
                530                 535                 540
Gly Phe Arg Arg Leu Ile Gly Asp Pro Ser Val Thr Leu Ser Met Leu
545                 550                 555                 560
Phe Gly Asn Phe Phe Met Ser Leu Ile Val Ala Ser Val Tyr Tyr Asn
                565                 570                 575
Leu Gln Pro Thr Thr Ala Ser Phe Phe Gln Arg Gly Ala Leu Leu Phe
                580                 585                 590
Phe Ala Cys Leu Met Asn Ala Phe Ser Ser Ala Leu Glu Ile Leu Thr
                595                 600                 605
Leu Tyr Ser Gln Arg Pro Ile Val Glu Lys His Ala Arg Tyr Ala Leu
                610                 615                 620
Tyr His Pro Ser Ala Glu Ala Val Ala Ser Met Leu Cys Asp Met Pro
625                 630                 635                 640
Tyr Lys Ile Gly Asn Thr Ile Met Phe Asn Leu Ala Leu Tyr Phe Met
                645                 650                 655
Thr Asn Leu Arg Arg Glu Pro Gly Pro Phe Phe Tyr Leu Leu Ile
                660                 665                 670
Ser Phe Thr Thr Val Leu Val Met Ser Met Ile Phe Arg Thr Ile Gly
                675                 680                 685
Ser Ala Ser Arg Thr Leu Ser Gln Ala Met Val Pro Ala Ala Val Ile
                690                 695                 700
```

-continued

Ile Leu Ala Leu Val Ile Phe Thr Gly Phe Val Pro Ile Asp Tyr
705                 710                 715                 720

Met His Gly Trp Cys Arg Trp Ile Asn Tyr Ile Asp Pro Leu Ala Tyr
            725                 730                 735

Ser Phe Glu Ser Leu Met Val Asn Glu Phe His Asn Arg Gln Phe Leu
        740                 745                 750

Cys Asn Val Tyr Val Pro Ser Ala Thr Val Ala Gly Tyr Glu Asn Val
    755                 760                 765

Thr Gly Val His Arg Val Cys Ser Ala Val Gly Ser Val Val Gly Ser
770                 775                 780

Asp Tyr Val Asp Gly Asp Arg Tyr Leu Asn Leu Ala Leu Arg Tyr Tyr
785                 790                 795                 800

His Ala His Lys Trp Arg Asn Phe Gly Ile Leu Cys Gly Phe Val Leu
            805                 810                 815

Phe Phe Leu Phe Thr Tyr Ile Val Ala Ala Glu Leu Val Ser Glu Lys
        820                 825                 830

Lys Ser Lys Gly Glu Val Leu Val Phe Arg Arg Gly Gln Pro Lys
    835                 840                 845

Ser Leu Thr Asn Gly Ser Lys Gly Asp Ala Glu Ser Gly Ser Arg Gly
850                 855                 860

Pro Gly Thr Ala Val Ala Ser Gly Gly Glu Ser Ser Asp Lys Glu Gly
865                 870                 875                 880

Gly Ala Gly Phe Ile Asp Ser Gln Arg Ser Val Phe His Trp Gln Asp
            885                 890                 895

Val Cys Tyr Glu Val Lys Ile Lys Ala Glu Thr Arg Arg Ile Leu Asp
        900                 905                 910

His Val Asp Gly Trp Val Lys Pro Gly Thr Leu Thr Ala Leu Met Gly
    915                 920                 925

Val Ser Gly Ala Gly Lys Thr Thr Leu Leu Asp Val Leu Ala Asp Arg
930                 935                 940

Thr Ser Met Gly Val Ile Thr Gly Asp Met Phe Val Asp Gly His Glu
945                 950                 955                 960

Arg Asp His Ser Phe Gln Arg Lys Thr Gly Tyr Val Gln Gln Asp
            965                 970                 975

Leu His Leu Glu Thr Thr Thr Val Arg Glu Ala Leu Asn Phe Ser Ala
        980                 985                 990

Leu Leu Arg Gln Pro Ala His Val Pro Arg Gln Glu Lys Leu Ala Tyr
    995                 1000                1005

Val Asp Glu Val Ile Lys Leu Leu Glu Met Asp Glu Tyr Ala Asp Ala
    1010                1015                1020

Val Val Gly Val Pro Gly Glu Gly Leu Asn Val Glu Gln Arg Lys Arg
1025                1030                1035                1040

Leu Thr Ile Gly Val Glu Leu Ala Ala Lys Pro Pro Leu Leu Leu Phe
        1045                1050                1055

Val Asp Glu Pro Thr Ser Gly Leu Asp Ser Gln Thr Ser Trp Ala Ile
    1060                1065                1070

Leu Asp Leu Leu Glu Lys Leu Thr Lys Ser Gly Gln Ala Val Leu Cys
    1075                1080                1085

Thr Ile His Gln Pro Ser Ala Met Leu Phe Gln Arg Phe Asp Arg Leu
    1090                1095                1100

Leu Phe Leu Ala Arg Gly Gly Arg Thr Val Tyr Phe Gly Glu Ile Gly
1105                1110                1115                1120

-continued

Lys Asn Ser His Thr Met Thr Ser Tyr Phe Glu Arg Asn Gly Gly His
             1125                1130                1135

Ala Cys Pro Ala Asp Ala Asn Pro Ala Glu Trp Met Leu Glu Val Ile
         1140                1145                1150

Gly Ala Ala Pro Gly Thr Ser Ser Glu Val Asp Trp Arg Gln Ala Trp
         1155                1160                1165

Leu Asp Ser Pro Glu Tyr Ala Ala Val Lys Thr Glu Leu Leu Arg Leu
         1170                1175                1180

Arg Glu His Pro Ala Glu Gln Pro Glu Ala Thr Ala Ala Asp Tyr Arg
1185                1190                1195                1200

Glu Phe Ala Ala Pro Phe Ala Val Gln Val Val Glu Val Ser His Arg
             1205                1210                1215

Val Phe Gln Gln Tyr Trp Arg Thr Pro Ser Tyr Ile Tyr Ser Lys Met
             1220                1225                1230

Ala Leu Cys Val Leu Val Ala Leu Phe Val Gly Phe Ser Phe Phe Lys
             1235                1240                1245

Ala Pro Leu Thr Ile Gln Gly Val Gln Asn Gln Met Phe Ala Leu Phe
             1250                1255                1260

Gln Leu Leu Thr Val Phe Gly Gln Met Val Gln Gln Thr Met Pro Tyr
1265                1270                1275                1280

Phe Val Ile Gln Arg Ser Leu Tyr Glu Val Arg Glu Arg Pro Ser Lys
             1285                1290                1295

Val Tyr Ser Trp Arg Val Phe Met Leu Ser Gln Ile Val Ala Glu Leu
             1300                1305                1310

Pro Trp Asn Thr Leu Met Ala Val Leu Met Phe Phe Cys Trp Tyr Tyr
             1315                1320                1325

Pro Val Gly Leu Tyr Ala Asn Ala Gly Asp Ala Leu His Glu Arg Gly
             1330                1335                1340

Val Leu Met Phe Leu Phe Leu Trp Cys Phe Leu Leu Phe Thr Ser Thr
1345                1350                1355                1360

Phe Thr Asp Met Ile Ile Ala Gly Phe Glu Thr Ala Glu Ala Gly Gly
             1365                1370                1375

Asn Ile Ala Asn Leu Leu Phe Met Met Cys Leu Ile Phe Cys Gly Val
             1380                1385                1390

Leu Ala Ser Pro Ser Glu Met Pro His Phe Trp Ile Phe Met Tyr Arg
             1395                1400                1405

Val Ser Pro Phe Asn Tyr Leu Ile Ser Gly Met Leu Val Thr Gly Ile
             1410                1415                1420

Ala Asn Ser Asn Val Thr Cys Ala Ala Asn Glu Phe Val Thr Ile Val
1425                1430                1435                1440

Pro Val Asn Asn Gln Thr Cys Leu Glu Tyr Met Gly Pro Tyr Met Gln
             1445                1450                1455

Ala Glu Gly Gly Tyr Leu Leu Asp Asn Asn Ala Arg Asp Pro Cys Gly
             1460                1465                1470

Phe Cys Lys Tyr Asp Ser Thr Asn Thr Leu Leu Ser Ala Phe Gly Ala
             1475                1480                1485

Glu Tyr Gly Asp Arg Trp Arg Asn Phe Gly Ile Leu Trp Ala Tyr Ile
             1490                1495                1500

Ile Phe Asn Ile Gly Ala Ala Leu Gly Val Tyr Trp Leu Phe Arg Val
1505                1510                1515                1520

Pro Lys His Thr Lys Thr Gly Gly Lys His Lys Ala Glu Lys Pro Lys
             1525                1530                1535

Lys Val Glu

<210> SEQ ID NO 4
<211> LENGTH: 4620
<212> TYPE: DNA
<213> ORGANISM: Grosmannia clavigera
<220> FEATURE:
<223> OTHER INFORMATION: ABC terpenoid transporter GcABC-G2

<400> SEQUENCE: 4

| | | | | | |
|---|---|---|---|---|---|
| atgtcgtttc | tggcatctgg | cgtcttcggc | aattatgacc | acaccggtca | gacggccggg | 60 |
| gtgcctccag | atggccacgc | acgtagactc | gactacactg | acgaggagat | cgtgtcgcct | 120 |
| gccggacata | ccgctgacgg | tgccaacacg | cggacgacgt | cgctgacgga | gacgggctct | 180 |
| gctcctgatg | ggatctcgcg | tggcgagaaa | gaggtcgcac | cgtcgggcaa | caacggcagc | 240 |
| tcggacgacg | aagacgatga | ccagggcacc | gacatgcagc | gccgcacgag | ccgggtgcag | 300 |
| gagctggctc | gccactacac | caacgtgtcg | atggcatcgg | gcgtcgttcc | acctggttcg | 360 |
| aacccgttca | cggagctctc | caacgcggac | tcgccgctca | atcccaacgg | cgaaaagttt | 420 |
| agcgctcgtg | cctgggccaa | ggccgtggtg | cagatgatcc | agagcgaggg | gcaccacttc | 480 |
| cggacgtcgg | gcgtggcttt | ccagaacctc | aacgtgtttg | gtcacggtga | ggctacggac | 540 |
| taccagaagg | atttcctcaa | cgtctggctg | gagggtgccg | gcattgtgcg | tcggatgctc | 600 |
| aagattggcc | agcgccagat | cgacattctg | cagaactttg | acggagtggt | gcgcaagggc | 660 |
| gaaatgttgg | tcgtgctggg | gcctcccggt | gccggctgca | cgacgcttct | caagaccatt | 720 |
| gctggcgaga | ccaacggtct | cttcgtggac | gacaagtcat | acttcaacta | ccaaggtttg | 780 |
| gcggctcacg | agatgcacac | tcgccaccgt | ggcgaggcca | tctacacggc | cgaagtcgac | 840 |
| gtgcacttcc | cgcagctgtc | agtcggtgac | acgctcacgt | tgctgctcg | tgcgcgtgcg | 900 |
| ccccggacga | ttcccggcgg | cgtgccgcgc | cacgagtttg | cccaccatct | gcgtgatgtc | 960 |
| gtcatggcca | tgtacggcat | ctcgcatacg | gtcaacacgc | gtgtcggcaa | cgagtatgtt | 1020 |
| cgtggtgtgt | cgggtggtga | gcggaagcgt | gtcaccattg | ctgaggcgac | gctctcgggc | 1080 |
| gcgccgctgc | agtgctggga | caacagtacc | cgtggtctcg | acagtgccaa | cgcggttgag | 1140 |
| ttcgtcaaga | cgctgcgcct | gcagaccgag | ctcttcggca | cacggctgt | cgtgtccatc | 1200 |
| taccaggccc | ctcagagcgc | ctacgacctc | ttcgacaagg | tgctgctcat | ctacgagggt | 1260 |
| cgccagatct | actttggtcc | tactgccgct | gcccgccagt | actttatcga | cctcggcttc | 1320 |
| tactgcgccg | accgtgccac | cacgcccgac | ttcctgacct | ccatgacgtc | tccgaaggaa | 1380 |
| cggattgacc | gcaagggctt | cgaggccgc | acgccacgca | cgcccgacga | gttcgccgcc | 1440 |
| gcatggcgca | actcggacgc | ttacaaggcc | gtgcaggccg | acattgagga | ttacaagcag | 1500 |
| gcccacccga | tcgatggtcc | cgatgccgtg | gctttccgcg | agcttaggcg | cgagcagcag | 1560 |
| gcatccgccc | agcggccaaa | gagtcccttc | acgctttcgt | acggtcagca | gatcagcctg | 1620 |
| tgtctgtggc | gtggattccg | tcgtcttatc | ggcgaccca | gtgtcacgct | ttctatgctc | 1680 |
| tttggtaact | tcttcatgtc | gctcatcgtc | gcgtcggtct | actacaatct | gcagcctact | 1740 |
| acggccagct | tcttccagcg | cggcgccctg | ctcttcttcg | cctgtcttat | gaacgccttc | 1800 |
| tccagtgccc | tcgaaattct | cacgctctac | tcgcaacggc | ctatcgtcga | aaaacacgcc | 1860 |
| cgttacgctc | tctatcatcc | gtccgccgag | gcggtggcgt | ctatgttgtg | cgacatgccg | 1920 |
| tacaaaatcg | gtaacacgat | catgtttaat | ttggcgctgt | atttcatgac | aaatctgcgg | 1980 |
| cgagaaccgg | gtccgttctt | cttttacctg | ctcatcagct | ttaccaccgt | gctggtcatg | 2040 |

```
tccatgatct tccgcaccat cggctcggca tcacgcacac tctcgcaggc catggtgccg    2100
gcagccgtga ttatcctggc tcttgtcatc tttactggtt tcgtcattcc gatcgactat    2160
atgcacggct ggtgtcgctg gatcaactac attgacccgc tggcttactc ttttgagtcg    2220
ctcatggtca acgagttcca caaccgccag ttcctgtgca acgtgtacgt gccttcggcc    2280
acggtggccg gctacgagaa tgtgacgggt gtgcaccgcg tctgttcggc cgtcggctcc    2340
gttgttggct ctgactacgt ggatggtgac cggtacctca acctggccct gcgctactac    2400
catgcgcaca agtggaggaa cttttggcatt ctgtgcggct tgttctcctt cttcctgttc    2460
```
(Note: line 2460 as printed reads `catgcgcaca agtggaggaa cttttggcatt ...` — reproducing literally)
```
acgtacattg tcgcggccga gcttgtgtcg gaaaagaagt ccaagggcga ggttctggtc    2520
ttccggcgcg gcgggcagcc caagtctctg acgaacggta gcaagggcga cgcagaatcg    2580
ggctcacgcg ggcccggcac ggcggttgcc agtggcggtg agagtagcga caaggagggc    2640
ggtgccggct tcatcgacag ccagcgcagc gtgtttcact ggcaggacgt gtgctatgag    2700
gtcaagatca aggcggaaac ccggcgcatt ctggaccatg tcgacggttg ggtcaagcca    2760
ggcacgctga cggcccttat gggtgtgtct ggtgccggta agactacgct tctggatgtt    2820
ttggctgacc ggacgtctat gggcgtgatt accggtgaca tgtttgtgga cggacacgag    2880
cgcgaccact cgttccagcg gaagaccggt tacgtgcaac aacaggatct gcatctcgag    2940
acgacaacgg tgcgcgaggc tctcaacttc agtgccctgc ttcgccagcc tgcccatgtt    3000
ccccgccagg agaagctcgc ttatgtggat gaggtgatca agctgctgga aatggacgag    3060
tacgcagacg ccgtcgtcgg tgttcctggc gaaggtctga acgtcgaaca acgcaagcgt    3120
cttacgatcg tgtcgaaact cgctgccaag cctccgttgt tgctgttcgt ggacgagccg    3180
acctctggtc tggactcgca gacgtcatgg gccatcctgg accttctgga aaagctgacc    3240
aagagcggac aagcggttct ttgcacgatt caccagccgt cggccatgct gttccagcgc    3300
ttcgaccggc tgctcttcct ggctcgcggc ggacggactg tgtactttgg cgaaatcggc    3360
aagaactccc acacaatgac cagctacttt gagcgcaacg gtggccacgc ttgccctgct    3420
gatgcgaacc cggctgagtg gatgctcgag gtgattggcg cagcgcccgg cacgtcttcc    3480
gaagtggact ggcgacaggc ctggctggac tctccggaat atgcggctgt caagactgaa    3540
ctcctgcgac tgcgcgagca cccggcagag cagccggagg cgaccgcggc cgactaccgc    3600
gagtttgcgg cgccgttcgc tgtgcaggtc gtcgaggtct cgcaccgtgt gttccagcag    3660
tactggcgga cgccgtctta catctacagc aagatggcac tctgtgttct ggtcgcgctc    3720
tttgtcggct tctctttctt caaggcgccc ctgacgattc agggcgtgca gaatcagatg    3780
tttgccctct tccaactact caccgttttc ggtcagatgg tccagcagac gatgccctac    3840
tttgtcatcc agcggtccct ctacgaagtg cgcgagcggc catccaaggt gtacagctgg    3900 cgcgtctttta tgctgtcgca gatcgtggcc gagctgccgt ggaacacgct gatggctgtg    3960
ctgatgtttt tctgctggta ctatcccgtc gggctgtacg ccaacgccgg cgacgcgctg    4020
cacgagcgtg gtgtgctcat gttcctcttc ctgtggtgct tcttgctctt tacctctacc    4080
ttcaccgaca tgatcattgc cggtttcgag acggccgagg ctggtggcaa cattgccaat    4140
ctgctcttca tgatgtgcct gatcttctgt ggtgtcctgg cctcgccctc ggagatgccg    4200
cacttctgga tcttcatgta ccgcgtctcg cccttcaact acctcatctc aggcatgttg    4260
gtgacgggca tcgccaactc caatgttacg tgtgcagcca acgagtttgt cactattgtg    4320
ccggtcaaca atcagacctg cctcgagtac atggggccct acatgcaggc agagggcggt    4380
tatctgctgg acaacaatgc gcgcgacccg tgcggattct gcaagtacga cagcaccaat    4440
```

-continued

```
accctgctgt cggcctttgg cgctgagtac ggcgaccggt ggcgcaactt tggcatcctc    4500
tgggcgtaca tcatcttcaa catcggtgct gccctcggcg tctactggct cttccgcgtg    4560
cccaagcaca ccaagacagg cggcaagcac aaggccgaga agccgaagaa ggtcgagtag    4620
```

```
<210> SEQ ID NO 5
<211> LENGTH: 1493
<212> TYPE: PRT
<213> ORGANISM: Grosmannia clavigera
<220> FEATURE:
<223> OTHER INFORMATION: ABC terpenoid transporter GcABC-G3
<220> FEATURE:
<221> NAME/KEY: DOMAIN
<222> LOCATION: (154)...(389)
<223> OTHER INFORMATION: NBF; PDR Domain 1
<220> FEATURE:
<221> NAME/KEY: DOMAIN
<222> LOCATION: (501)...(711)
<223> OTHER INFORMATION: TMD 1
<220> FEATURE:
<221> NAME/KEY: DOMAIN
<222> LOCATION: (845)...(1071)
<223> OTHER INFORMATION: NBF; PDR Domain 2
<220> FEATURE:
<221> NAME/KEY: DOMAIN
<222> LOCATION: (1165)...(1375)
<223> OTHER INFORMATION: TMD 2
```

<400> SEQUENCE: 5

Met Ala Arg Ser Ala Val Ser Gln Glu Ser Leu Arg Leu Ala Asp Ser
 1               5                  10                  15

Ser Arg Ser Ser Glu Glu Ala Gly Pro Glu Glu Phe Met Ala Ile Arg
            20                  25                  30

Thr Asn Gly Pro Glu Ala Ser Asp Ala Gly Thr Tyr Arg Pro Gln Arg
        35                  40                  45

Arg Asp Ser Thr Ala Met Ile Glu Glu Ser Asp Val Gln Glu Leu Arg
    50                  55                  60

Met Leu Ala Thr Ala Ile Ser Gln Arg Arg Arg Gln Ser His Ala Thr
65                  70                  75                  80

Gly Ser Glu Ala Gly Asn Glu Asp Phe Asp Ala Ala Asp Ser Ala Met
                85                  90                  95

Asp Pro Ser Ser Lys Ser Phe Asp Leu Gly Val Phe Leu Arg Arg Ile
           100                 105                 110

Ile Lys Asp Phe Arg Lys Glu Gly Phe Lys Glu Arg Arg Leu Gly Ile
       115                 120                 125

Ser Tyr Lys Asp Leu Thr Val Ser Gly Thr Gly Glu Ala Leu Gln Leu
   130                 135                 140

Gln Ser Thr Val Gly Thr Val Leu Gln Met Pro Leu Arg Leu Gly Glu
145                 150                 155                 160

Ser Phe Ser Phe Gly Lys Lys Ser His Lys Thr Ile Leu His Asn Phe
                165                 170                 175

Asp Gly His Val Glu Ser Gly Glu Leu Leu Ile Val Leu Gly Arg Pro
            180                 185                 190

Gly Ser Gly Cys Ser Thr Leu Leu Lys Thr Ile Thr Gly Gln Leu His
        195                 200                 205

Gly Leu Lys Ile Gly Glu Gln Ser Thr Ile Asp Tyr Asn Gly Ile Pro
    210                 215                 220

Met Lys His Met Ile Lys Val Phe Lys Gly Glu Val Leu Lys Asn Gln
225                 230                 235                 240

Glu Val Asp Lys His Phe Pro His Leu Thr Val Gly Gln Thr Leu Glu

```
                    245                 250                 255
        Phe Ala Ala Thr Arg Thr Pro Ser Lys Arg Ile His Ala Ile Thr
                260                 265                 270
        Arg Glu Glu His Ile Lys His Ala Ala Arg Ile Val Met Ala Ile Cys
                275                 280                 285
        Gly Leu Ser His Thr Tyr Asn Thr Lys Val Gly Asn Asp Phe Ile Arg
                290                 295                 300
        Gly Val Ser Gly Gly Glu Arg Lys Arg Val Ser Ile Ala Glu Met Met
        305                 310                 315                 320
        Leu Ala Gly Ser Pro Ile Ala Ala Trp Asp Asn Ser Thr Arg Gly Leu
                        325                 330                 335
        Asp Ser Ala Thr Ala Leu Lys Phe Val Gln Ser Leu Arg Leu Ala Ala
                        340                 345                 350
        Asp Phe Thr His Ser Val His Cys Val Ala Ile Tyr Gln Ala Ser Gln
                        355                 360                 365
        Ala Ile Tyr Asp Leu Phe Asp Lys Ala Val Leu Tyr Glu Gly Arg
                370                 375                 380
        Gln Ile Tyr Phe Gly Pro Ala Pro Ala Lys Ala Tyr Phe Glu Thr
        385                 390                 395                 400
        Met Gly Trp Phe Cys Pro Gln Arg Gln Thr Gly Asp Phe Leu Thr
                        405                 410                 415
        Ser Val Thr Asn Pro Gln Glu Arg Val Ala Arg Glu Gly Met Glu Asn
                        420                 425                 430
        Lys Val Pro Arg Thr Pro Glu Glu Phe Glu Ala Tyr Trp Tyr Gln Ser
                        435                 440                 445
        Pro Asp Cys Lys Ala Leu Arg Asn Ala Met Glu Lys His Glu Ala Ile
                450                 455                 460
        His Pro Ile Asp Pro His Gly Gln Thr Ala Val Asn Met Arg Glu Asn
        465                 470                 475                 480
        Lys Gln Gln Arg Gln Ala Lys His Val Arg Pro Lys Ser Pro Tyr Ile
                        485                 490                 495
        Ile Ser Val Ala Met Gln Val Arg Leu Thr Thr Lys Arg Ala Tyr Gln
                        500                 505                 510
        Arg Ile Leu Asn Asp Ile Ser Ala Thr Ala Thr Gln Ala Val Met Gln
                        515                 520                 525
        Val Val Leu Ala Leu Ile Ile Gly Ser Val Phe Tyr Gly Thr Pro Asn
                        530                 535                 540
        Ala Thr Ala Gly Phe Tyr Ala Lys Gly Ser Val Ile Phe Gln Ala Ile
        545                 550                 555                 560
        Leu Met Asn Ala Leu Thr Ala Ile Ser Glu Ile Asn Lys Leu Tyr Ala
                        565                 570                 575
        Gln Arg Pro Ile Val Glu Lys His Ala Ala Tyr Ala Phe Tyr His Pro
                        580                 585                 590
        Tyr Thr Glu Ala Leu Ala Gly Ile Met Thr Asp Ile Pro Ile Lys Phe
                        595                 600                 605
        Ile Thr Gly Thr Ile Phe Asn Leu Ile Val Tyr Phe Met Ser Gly Leu
                610                 615                 620
        Arg Arg Glu Pro Ala Gln Phe Phe Leu Phe Leu Ile Thr Tyr Thr
        625                 630                 635                 640
        Thr Thr Phe Val Met Ser Ala Ile Phe Arg Thr Leu Ala Ala Ile Thr
                        645                 650                 655
        Lys Thr Val Ser Gln Ala Met Met Leu Ala Gly Val Met Val Leu Ala
                        660                 665                 670
```

```
Leu Val Ile Tyr Thr Gly Phe Val Thr Val Pro Lys Met His Pro
        675                 680                 685

Trp Phe Ser Trp Ile Arg Trp Ile Asn Pro Val Tyr Ala Phe Glu
        690                 695                 700

Val Leu Ile Ala Asn Glu Phe His Gly Arg Ser Phe Thr Cys Ser Ser
705                 710                 715                 720

Ile Ile Pro Ala Tyr Thr Pro Leu Val Gly Asp Ser Trp Ile Cys Ser
                725                 730                 735

Val Ala Ser Ser Val Ala Gly Gln His Thr Val Ser Gly Asp Ala Phe
                740                 745                 750

Ile Gly Val His Tyr Lys Tyr Tyr Tyr Ala His Ala Trp Arg Asn Phe
                755                 760                 765

Gly Ile Leu Leu Ala Phe Leu Phe Ala Phe Met Phe Val Tyr Phe Val
770                 775                 780

Ser Thr Glu Leu Asn Ser Gln Thr Thr Ser Ala Ala Glu Val Leu Val
785                 790                 795                 800

Phe Gln Arg Gly His Val Pro Ala Tyr Leu Leu Asn Gly Gly Asn Lys
                805                 810                 815

Gly Ala Ile Thr Glu Asp Met Thr Lys Ala Ser Pro Gln Asp Gly
                820                 825                 830

Asn Glu Lys Thr Asp Ala Ile Glu Pro Gln Thr Asp Val Phe Thr Trp
                835                 840                 845

Arg Asp Val Val Tyr Asp Val Thr Ile Lys Gly Gln Asp Arg Arg Leu
850                 855                 860

Leu Asn His Val Ser Gly Trp Val Lys Pro Gly Thr Leu Thr Ala Leu
865                 870                 875                 880

Met Gly Val Ser Gly Ala Gly Lys Thr Thr Leu Leu Asp Ala Leu Ala
                885                 890                 895

Gln Arg Thr Thr Met Gly Val Ile Thr Gly Asp Met Phe Val Asn Gly
                900                 905                 910

Lys His Ile Asp Ala Ser Phe Gln Arg Asn Thr Gly Tyr Val Gln Gln
        915                 920                 925

Gln Asp Leu His Leu Ser Thr Ala Thr Val Arg Glu Ser Leu Arg Phe
        930                 935                 940

Ser Ala Met Leu Arg Gln Pro Gln Ser Val Ser Lys Glu Glu Lys Phe
945                 950                 955                 960

Thr Phe Val Glu Glu Val Ile Asp Met Leu Asp Met Arg Asp Phe Ala
                965                 970                 975

Asn Ala Val Val Gly Val Pro Gly Gln Gly Leu Asn Val Glu Gln Arg
                980                 985                 990

Lys Leu Leu Thr Ile Gly Val Glu Leu Ala Ala Lys Pro Lys Leu Leu
                995                 1000                1005

Leu Phe Leu Asp Glu Pro Thr Ser Gly Leu Asp Ser Gln Ser Ser Trp
        1010                1015                1020

Ala Ile Cys Ala Phe Leu Arg Lys Leu Ala Asp His Gly Gln Ala Val
1025                1030                1035                1040

Leu Cys Thr Ile His Gln Pro Ser Ala Val Leu Phe Gln Gln Phe Asp
                1045                1050                1055

Arg Leu Leu Phe Leu Ala Ala Gly Gly Lys Thr Val Tyr Phe Gly Asp
                1060                1065                1070

Ile Gly Glu Asn Ser Arg Thr Leu Leu Glu Tyr Phe Glu Thr His Gly
                1075                1080                1085
```

```
Ala Glu Lys Cys Gly Asp Glu Glu Asn Pro Ala Glu Tyr Met Leu Asn
    1090                1095                1100

Ile Val Asn Arg Gly Ser Asn Ser Gln Gly Glu Asp Trp His Asp Val
1105                1110                1115                1120

Trp Asn Ser Arg Glu Arg Gln Asp Val Met Ala Glu Ile Asn Arg
        1125                1130                1135

Ile His Val Asp Arg Ala Ala Gln Pro Leu Ala Thr His Glu Asp Pro
    1140                1145                1150

His Ser Arg Asp Glu Phe Ala Met Pro Phe Gly Ala Gln Leu Ala Arg
        1155                1160                1165

Val Ala Thr Arg Val Cys Gln Gln Tyr Trp Arg Ser Pro Thr Tyr Val
    1170                1175                1180

Phe Ser Lys Phe Ile Leu Gly Thr Val Ala Gly Leu Phe Ile Gly Phe
1185                1190                1195                1200

Ser Phe Phe Gly Ala Asp Gly Thr Leu Ala Gly Met Gln Asn Val Ile
        1205                1210                1215

Phe Ala Val Phe Met Val Ile Thr Ile Phe Ser Thr Leu Val Gln Gln
    1220                1225                1230

Ile Gln Pro His Phe Ile Thr Gln Arg Asp Leu Tyr Glu Val Arg Glu
    1235                1240                1245

Arg Pro Ser Lys Ala Tyr Ser Trp Lys Ala Phe Met Ile Ala Asn Val
    1250                1255                1260

Ile Val Glu Ile Pro Tyr Gln Ile Leu Thr Gly Ile Leu Ile Tyr Ala
1265                1270                1275                1280

Ser Phe Tyr Tyr Ala Val Ile Gly Ile Gln Ser Ser Ala Arg Gln Gly
        1285                1290                1295

Leu Ile Leu Leu Phe Cys Ile Gln Phe Met Leu Tyr Ala Ser Ser Phe
    1300                1305                1310

Ala Gln Met Thr Ile Ala Ser Met Pro Val Ala Glu Thr Ala Ala Ser
        1315                1320                1325

Ile Val Thr Leu Leu Leu Leu Phe Ser Leu Thr Phe Cys Gly Val Leu
    1330                1335                1340

Gln Thr Pro Ser Ala Leu Pro Gly Phe Trp Ile Phe Met His Arg Val
1345                1350                1355                1360

Ser Pro Phe Thr Tyr Trp Val Ala Gly Ile Val Ser Thr Gln Leu His
        1365                1370                1375

Gly Arg Ala Val Asp Cys Ser Lys Ser Glu Thr Ser Ile Phe Ser Pro
        1380                1385                1390

Pro Ala Gly Met Thr Cys Gly Glu Tyr Met Ala Pro Tyr Leu Thr Gln
        1395                1400                1405

Ala Pro Gly Asn Leu Gln Asn Pro Asn Asp Thr Glu Asn Cys Arg Tyr
    1410                1415                1420

Cys Ser Leu Lys Val Ala Val Gln Tyr Leu Ala Gln Ser Ser Ile Phe
1425                1430                1435                1440

Tyr Ser Gln Arg Trp Arg Asn Phe Gly Ile Met Trp Ala Tyr Ile Ala
        1445                1450                1455

Phe Asn Ile Phe Ile Ala Val Ile Ser Tyr Trp Ala Phe Arg Val Lys
        1460                1465                1470

Lys Trp Asn Arg Gly Gly Lys Ser Ala Lys Lys Thr Ser Glu Lys Asn
        1475                1480                1485

Lys Thr Glu Lys Ala
    1490
```

```
<210> SEQ ID NO 6
<211> LENGTH: 4482
<212> TYPE: DNA
<213> ORGANISM: Grosmannia clavigera
<220> FEATURE:
<223> OTHER INFORMATION: ABC terpenoid transporter GcABC-G3

<400> SEQUENCE: 6
atggcaaggt cggcagtatc gcaggagagc ctgcgtttgg cagattcctc tcggtcatct      60
gaggaggcag gccctgaaga gtttatggcc attcgaacaa acggcccga agcatctgat     120 gcgggaacgt atcgccccca gcgacgggat tcgacggcca tgatagaaga gagtgatgtg     180
caggagctgc ggatgcttgc cacgccacta tcgcaaagac gtcgccagag ccacgccacc     240
ggctccgagg ctggcaacga ggactttgat gctgccgatt ctgccatgga tccctctagc     300
aagtcattcg atctcggggt tttcctgcgt cgcatcatca aagattttcg caaggaaggt     360
ttcaaagagc ggcgtctggg gatttcctac aaagacctta ccgtgtccgg cacgggagag     420
gccttgcaac tgcagagcac ggtgggaacc gttctccaaa tgccattaag gcttggcgag     480
tccttcagtt tcggcaagaa gagtcacaag accattctcc acaactttga cggtcatgtc     540
gagagcggcg agctgttgat tgtgctcgga cgaccaggat cggggtgtag caccctgctc     600
aaaaccatca ccggacaatt gcatgggctg aaaatcggcg agcagtcgac aattgattac     660
aacggcatcc ccatgaaaca catgatcaag gtattcaaag gagaagtatt aaagaaccaa     720
gaggtcgaca agcatttccc ccacctcacc gtcggtcaaa cgctggaatt tgcagctgca     780
acacgtacgc catcgaagcg aatccatgcc ataacgcgcg aagagcacat caagcatgcc     840
gccaggatcg tcatggccat ctgtggcttg agccatacgt acaaccaccaa agtgggcaat     900 gacttcatcc ggggtgtctc tggtggtgag agaaagcgtg tgagcattgc cgaaatgatg     960
ctggcaggat cgcccattgc ggcttgggat aacagcaccc gcggcctaga ttccgccact    1020
gcgctgaagt ttgtccagtc tttgcggctg gctgccgatt tcacccacag tgttcattgc    1080
gtcgctattt accaggccag ccaggccatc tatgacctct ttgacaaagc tgtcgtgctt    1140
tatgaaggcc gccagatcta ctttggtcca gcacccgctg ccaaggccta ctttgaaacc    1200
atgggatggt tttgccctca gcggcagacc acgggtgatt ttcttacatc tgtcaccaac    1260
ccgcaggaaa gggtcgcgcg tgaggggatg gaaaacaagg ttccacggac accagaggaa    1320
ttcgaagcat actggtacca gtcgcccgac tgcaaggctc ttcgaaatgc catggagaag    1380
cacgaggcca tacatcccat cgatcctcac ggccagacgg ccgtaaatat gcgcgaaaac    1440
aagcagcaac gccaggcaaa gcacgtgcgg ccaaaatcgc catatatcat cagtgtagcc    1500
atgcaggtgc gcctcaccac caagcgggca taccaacgca tcctaaacga catttcggct    1560
actgcgacac aagctgtgat gcaggtcgtt ttggcgctca tcatcggctc cgtcttctac    1620
ggcactccca acgcgacagc cggcttttac gccaaaggct ccgtgatctt ccaggccatt    1680
cttatgaacg ccttgacggc aatctccgaa attaacaaac tgtatgcaca acgtcccatc    1740
gtcgagaaac atgccgccta cgccttttat catccctata cagaagcgct ggctggaatc    1800
atgactgata tccccatcaa gtttatcacg ggaaccattt tcaacctcat cgtctactttt   1860 atgtcggggc ttcgacgcga accggctcag ttcttcttgt ttttcctcat tacgtatacc    1920
acaacgtttg tcatgagtgc catcttccgt accctggctg ccatcacaaa aaccgtgtct    1980
caggcgatga tgttggccgg tgttatggtt ctggctcttg tcatctatac tggattcgtg    2040
gttactgtgc ccaagatgca tccgtggttt agctggatca gatggatcaa tcctgtctac    2100
```

```
tacgctttcg aagtcctcat tgcgaatgag tttcatggcc gttcgttcac ctgctcgagt    2160
attatcccg cctacacacc cttggtaggc gattcttgga tatgctcggt tgccagctcg    2220
gttgctggac agcatacagt tagcggagat gcctttatcg gtgttcacta caagtactac    2280
tacgcgcacg cctggagaaa tttcggtatt ctactcgcgt ttctgttcgc cttcatgttt    2340
gtttacttcg tctcgaccga actaaactcg cagaccacca gcgcagccga agtcctggtt    2400
ttccaacgcg gccatgttcc tgcatatctc ctaaacgggg gcaacaaagg tgcaattaca    2460
gaagacatga cgaaggcctc gccgcaacaa gacggaaacg aaaagaccga tgctatcgag    2520
ccacaaaccg atgtgtttac ctggcgcgat gtagtctatg atgttacaat caaaggacag    2580
gatcgtcggt tgcttaatca tgtctctggc tgggtaaagc ctggaacttt gacggcacta    2640
atggagtca gcggtgctgg caagacaaca ctactcgatg ccttagccca aggaccacg     2700
atgggtgtta ttacgggtga tatgtttgtc aacggaaagc atattgatgc tagcttccaa    2760
aggaataccg gttacgttca gcaacaagat ttgcatctat cgacagcaac ggttcgcgaa    2820
agtctccgtt tcagtgctat gcttcgtcag cctcaaagcg tcagcaaaga agagaagttc    2880
acctttgttg aggaagtgat cgacatgctg gacatgcggg acttcgcaaa tgccgtcgtc    2940
ggcgttcctg gccaagggct caatgtggaa caacgcaagc tacttactat tggtgtcgaa    3000
ttggccgcca aaccaaaact gctactcttc ctcgatgagc ctaccagcgg tctcgattcc    3060
cagagttcat gggctatctg tgccttcctc cgaaagctag ctgaccacgg ccaggctgtg    3120
ctctgtacca tacaccagcc cagtgcagtt ctgttccagc agttcgaccg gctactgttc    3180
ctcgctgccg gaggcaagac cgtctacttc ggcgacattg gggagaactc gcggacgttg    3240
ctcgaatact ttgaaaccca cggcgctgaa aagtgcggcg acgaggaaaa tccagccgag    3300
tacatgctca acattgtcaa ccgcggcagc aattcacagg gtgaggattg gcacgacgtc    3360
tggaacaaca gccgggaacg ccaggacgta atggccgaaa tcaatcgcat tcatgtggat    3420
cgcgctgcgc agccgcttgc cactcacgag gatccgcact ctcgcgatga atttgccatg    3480
ccgtttggcg cccaactagc aagggttgca acgcgcgtgt gccagcaata ctggcgcagc    3540
ccaacctatg ttttctcaaa gttcatcctt ggcactgtgg ctggcctgtt cattggcttc    3600
tcgttttcg gagccgacgg tacgctggcg ggcatgcaaa atgtcatctt tgccgtgttc    3660
atggtgatca caatattttc taccctggtc cagcaaatcc aaccacattt cattacccag    3720
cgtgacctgt atgaagtgcg agagcgtccc agcaaggcct attcctggaa ggctttcatg    3780
atcgccaacg ttatcgtcga ataccatat cagatcttaa ctggaattct tatttatgcc    3840
agcttctatt acgcagtcat tggcatccag tcgtctgccc gccagggtct catccttctt    3900
ttctgcattc agttcatgct ttatgctagt tccttcgccc agatgactat cgcttccatg    3960
cccgttgccg aaactgcagc cagtattgtc actctcctgc tcttgttcag ccttaccttc    4020
tgtggtgtcc tccagacacc ctcggctctt ccgggattct ggattttcat gcaccgtgtc    4080
agcccattca cttattgggt cgcgggcatt gtttctacgc aactccatgg ccgcgctgtg    4140
gattgctcca atctgagac gagcattttc agtccgcccg caggaatgac atgtggtgaa    4200
tatatggcgc cataccctgac ccaagctcct gggaatctgc agaacccaaa cgacaccgag    4260
aattgcagat actgttcgct gaaggtggca gtccagtatc tcgctcaaag cagcatcttc    4320
tattctcagc gctggagaaa tttcgggatc atgtgggcgt atatcgcttt caacatcttt    4380
attgctgtaa tctcgtattg ggcttttccgg gtgaagaaat ggaatcgggg gggtaagagc    4440
gcgaagaaga cttcggaaaa aaacaagacg gagaaagcat ag                      4482
```

<210> SEQ ID NO 7
<211> LENGTH: 1469
<212> TYPE: PRT
<213> ORGANISM: Ophiostoma piceae
<220> FEATURE:
<223> OTHER INFORMATION: OPP_06758-RA - Multidrug resistance protein cdr1
<220> FEATURE:
<221> NAME/KEY: DOMAIN
<222> LOCATION: (131)...(370)
<223> OTHER INFORMATION: NBF; PDR Domain 1
<220> FEATURE:
<221> NAME/KEY: DOMAIN
<222> LOCATION: (481)...(691)
<223> OTHER INFORMATION: TMD 1
<220> FEATURE:
<221> NAME/KEY: DOMAIN
<222> LOCATION: (809)...(1037)
<223> OTHER INFORMATION: NBF; PDR Domain 2
<220> FEATURE:
<221> NAME/KEY: DOMAIN
<222> LOCATION: (1139)...(1352)
<223> OTHER INFORMATION: TMD 2

<400> SEQUENCE: 7

Met Asp Asn Pro Ser Asp Glu Ser Glu Asp Thr Leu Ala Val Arg Arg
 1               5                  10                  15

Thr Gln Val Asp Asp Ser Thr His Asp Arg Ile Arg Gln Phe Ser
                20                  25                  30

Leu Asp Ile Val Arg Ser Ala Ser His Ala Thr Ala Ser His Ala Ala
            35                  40                  45

Ala His Ala Asp Leu Glu Ser Val Asn Ser Val Asp Pro His Leu Asp
        50                  55                  60

Pro Thr Ser Pro Lys Phe Asp Ala Arg Arg Trp Val Gln Glu Leu Leu
65                  70                  75                  80

His Ala Cys Ala Gln Asp Pro Glu Arg Tyr Pro Arg Pro Thr Ala Gly
                85                  90                  95

Val Ser Tyr Arg Asn Leu Lys Val His Gly Phe Gly Ser Pro Thr Asp
                100                 105                 110

Tyr Gln Lys Asp Val Phe Asn Val Leu Leu Gln Ala Pro Leu Leu Leu
            115                 120                 125

Leu Gln Thr Ile Gln Asn Arg Arg Gln Gln Val Pro Ile Leu Arg Gly
        130                 135                 140

Glu Thr Ala Asp Val Gly Phe Asp Gly Leu Val Lys Ser Gly Glu Met
145                 150                 155                 160

Leu Leu Val Leu Gly Arg Pro Gly Ser Gly Val Thr Thr Leu Leu Lys
                165                 170                 175

Thr Val Ala Gly Glu Thr Ser Gly Leu Glu Leu Asp Gly Thr Leu Ser
            180                 185                 190

Tyr Asp Gly Ile Pro Leu Lys Thr Met Gln Asp Arg Phe Arg Gly Glu
        195                 200                 205

Val Ile Tyr Gln Ala Glu Thr Asp Val His Phe Pro Gln Leu Thr Val
    210                 215                 220

Gly Gln Thr Leu Leu Phe Ala Ala Glu Ala Arg Thr Pro Arg Asn Arg
225                 230                 235                 240

Pro Ala Leu Pro Gly Ser Ser Ala Ser Ser Thr Val Ser His Gln Ala
                245                 250                 255

Tyr Ala Gln His Leu Arg Asp Val Met Met Ala Ile Phe Gly Ile Ser
            260                 265                 270

```
His Thr Ile Asn Thr Arg Val Gly Asn Asp Leu Val Arg Gly Val Ser
        275                 280                 285

Gly Gly Glu Arg Lys Arg Val Ser Ile Ala Glu Ala Ala Leu Ser Gly
290                 295                 300

Ser Ala Val Gln Cys Trp Asp Asn Ser Thr Arg Gly Leu Asp Ser Ala
305                 310                 315                 320

Thr Ala Leu Ser Phe Ala Arg Thr Leu Arg Leu Ser Thr Asp Leu Ala
                325                 330                 335

Gly Ala Thr Ala Leu Val Ala Met Tyr Gln Ala Ser Glu Pro Ser Tyr
                340                 345                 350

Ile Leu Phe Asp Lys Val Cys Leu Leu Tyr Glu Gly Arg Gln Ile Phe
                355                 360                 365

Phe Gly Arg Ala Asp Gly Ala Arg Ala Tyr Phe Glu Arg Met Gly Tyr
370                 375                 380

His Cys Pro Pro Arg Gln Thr Thr Ala Asp Phe Leu Thr Ser Leu Thr
385                 390                 395                 400

Ser Pro Asp Glu Arg Ile Val Ala Pro Asp Val Glu Pro Gly Ser Val
                405                 410                 415

Pro Arg Thr Pro Asp Glu Phe Ser Ala Ala Trp Arg Ala Ser Pro Glu
                420                 425                 430

Tyr Ala Ala Leu Gln Thr Glu Leu Asp Gln Phe Glu Ala Asp His Pro
                435                 440                 445

Met Asp Gly Thr Pro Glu Lys Ser Met Ala Val Ala Arg Arg Ala His
                450                 455                 460

Gln Ser Thr Leu Thr Pro Ser Phe Ser Pro Tyr Thr Leu Ser Leu Pro
465                 470                 475                 480

Gln Gln Ile Trp Leu Cys Met Arg Arg Gly Gly His Arg Leu Arg Gly
                485                 490                 495

Asp Val Thr Phe Phe Val Val Thr Val Leu Gly Asn Leu Val Ile Ser
                500                 505                 510

Leu Val Leu Gly Ser Val Phe Tyr Asn Leu Pro Asp Asp Ala Ser Ser
                515                 520                 525

Ile Asn Ser Arg Cys Ile Leu Leu Phe Phe Ala Ile Leu Phe Asn Ala
530                 535                 540

Leu Ser Ser Ala Leu Glu Ile Leu Ser Leu Tyr Ala Gln Arg Pro Ile
545                 550                 555                 560

Val Glu Lys His Ala Arg Tyr Ala Leu Tyr Gln Pro Ala Ala Glu Ala
                565                 570                 575

Val Ala Ser Ala Leu Cys Glu Met Pro Ser Lys Ile Leu Ser Ala Leu
                580                 585                 590

Ala Phe Asn Ile Pro Leu Tyr Phe Met Ala Asn Leu Arg Ser Gly Ala
                595                 600                 605

Asp His Phe Ile Phe Leu Leu Phe Gly Phe Thr Cys Thr Leu Thr
                610                 615                 620

Met Ser Thr Phe Ile Arg Thr Ile Gly Gln Ser Ser Lys Ser Val His
625                 630                 635                 640

Gln Ala Leu Thr Pro Ala Ala Ile Phe Ile Ala Leu Val Ile Tyr
                645                 650                 655

Thr Gly Phe Val Leu Pro Lys Ala Ala Met Gln Gly Trp Leu Lys Trp
                660                 665                 670

Ile Ser Tyr Ile Asn Pro Ile Ala Tyr Ala Tyr Glu Ser Leu Leu Ile
                675                 680                 685

Asn Glu Leu Gly Arg Gly Arg Val Phe Ala Cys Ser Asn Phe Val Pro
```

-continued

```
            690             695             700
Ser Tyr Ala Thr Asp Ala Leu Glu Arg Ala Cys Ala Thr Ala Gly Ala
705             710             715             720

Pro Val Gly Ala Asp Tyr Val Asp Gly Asn Thr Val Leu Val Gly Ser
            725             730             735

Tyr Ser Tyr Lys Asp Ser His Leu Trp Arg Asn Leu Gly Ile Leu Val
            740             745             750

Ala Phe Leu Val Phe Phe Phe Cys Ser Tyr Val Ala Ala Glu Tyr
            755             760             765

Val Arg Ala Asp Lys Ser Lys Gly Glu Val Leu Val Phe Arg Arg Gly
            770             775             780

His Glu Ala Ala Val Asp Gln Glu Ile Asp Asn Lys Asp Asn Ala Lys
785             790             795             800

Lys Thr Ser Ile Lys His Lys Glu Gly Val Phe His Trp Arg Asp
            805             810             815

Val Cys Tyr Asp Ile Thr Leu Ala Gly Lys Asp Arg Arg Leu Leu Asp
            820             825             830

His Val Asp Gly Trp Val Lys Pro Gly Thr Leu Thr Val Leu Met Gly
            835             840             845

Val Ser Gly Ala Gly Lys Thr Thr Leu Leu Asp Val Leu Ala Asp Arg
            850             855             860

Val Thr Met Gly Val Val Ser Gly Ala Met Arg Val Asp Gly Val Val
865             870             875             880

Arg Gly Ala Ser Phe Gln Arg Thr Thr Gly Tyr Val Gln Gln Asp
            885             890             895

Val His Leu Ala Thr Ser Thr Val Arg Glu Ala Leu Leu Phe Ser Ala
            900             905             910

Lys Leu Arg Gln Pro Ala Ser Val Thr Leu Gln Glu Lys Glu Ala Tyr
            915             920             925

Val Glu Asp Val Ile Ala Leu Leu Glu Met Glu Arg Tyr Ala Asp Ala
            930             935             940

Val Val Gly Val Pro Gly Glu Gly Leu Asn Val Glu Gln Arg Lys Arg
945             950             955             960

Leu Thr Ile Gly Val Glu Leu Ala Ala Lys Pro Asp Leu Leu Leu Phe
            965             970             975

Leu Asp Glu Pro Thr Ser Gly Leu Asp Ser Gln Thr Ala Trp Ser Val
            980             985             990

Thr Lys Leu Val Arg Lys Leu Ala Asp His Gly Gln Ala Val Leu Cys
            995             1000            1005

Thr Ile His Gln Pro Ser Ala Leu Leu Phe Gln Gln Phe Asp Arg Leu
    1010            1015            1020

Leu Leu Leu Ala Ala Gly Gly Arg Thr Val Tyr Phe Gly Asp Ile Gly
1025            1030            1035            1040

Glu Asn Ala Arg Thr Leu Ile Glu Tyr Phe Glu Asn His Arg Glu Glu
                1045            1050            1055

Gly Ser Thr Val Pro Pro Cys Pro Pro Gly Glu Asn Pro Ala Glu Trp
                1060            1065            1070

Met Leu Arg Val Ile Gly Ala Ala Pro Gly Val Gln Ala Gly Gln Asp
            1075            1080            1085

Trp Pro Ala Thr Trp Arg Ala Ser Asn Glu Tyr Thr Val Val Gln Thr
            1090            1095            1100

Glu Leu Ala Arg Leu Glu Gly Val Thr Ala Pro Ile Asp Ala Ala Asp
1105            1110            1115            1120
```

Ala Val Glu Ala Ala Asn Ala Ser Lys Leu Ser Tyr Ala Thr Pro Phe
            1125                1130                1135

Ser Tyr Gln Leu Tyr Met Cys Thr Gln Arg Val Phe Gln Tyr Trp
        1140                1145                1150

Arg Thr Pro Ser Tyr Ile Tyr Ala Lys Leu Ala Leu Cys Phe Gly Thr
            1155                1160                1165

Ser Leu Phe Ile Gly Leu Ser Phe Arg Asn Ala Pro Leu Thr Glu Ala
        1170                1175                1180

Gly Leu Gln Ser Gln Leu Phe Ser Ile Phe Leu Leu Val Ile Phe
1185                1190                1195                1200

Ala Phe Met Thr Tyr Gln Thr Met Pro His Phe Ile Ser Gln Arg Asp
            1205                1210                1215

Leu Phe Glu Val Arg Glu Arg Ala Ser Arg Thr Tyr His Trp Ala Val
            1220                1225                1230

Phe Met Leu Ala Asn Ile Ile Val Glu Ile Pro Trp Asn Thr Leu Ala
            1235                1240                1245

Ala Leu Leu Val Phe Leu Pro Phe Tyr Tyr Leu Thr Gly Met Asn Asn
        1250                1255                1260

Asn Ala Gly Asp Ser Val Ala Glu Arg Gly Ala Leu Phe Phe Leu Leu
1265                1270                1275                1280

Leu Trp Val Phe Leu Val Phe Glu Ser Thr Phe Ala Asp Met Val Val
            1285                1290                1295

Ala Gly Val Pro Thr Ala Glu Leu Gly Ala Thr Phe Ala Leu Leu Leu
            1300                1305                1310

Phe Ser Phe Cys Leu Ile Phe Cys Gly Val Met Val Pro Tyr Ser Ala
        1315                1320                1325

Leu Pro Gly Phe Trp Thr Phe Met Tyr Arg Val Ser Pro Leu Thr Tyr
        1330                1335                1340

Leu Ile Gly Ala Leu Leu Ser Thr Gly Val Ala Leu Asn Pro Val Asn
1345                1350                1355                1360

Cys Ser Ser Leu Glu Leu Leu Gln Phe Tyr Pro Pro Ala Asn Thr Thr
            1365                1370                1375

Cys Ile Asp Tyr Met Lys Pro Tyr Met Gln Leu Ala Gly Gly Ala Leu
        1380                1385                1390

Val Asp Gly Gly Ala Met Tyr Pro Asp Ala Cys Gln Phe Cys Thr Leu
        1395                1400                1405

Ala Met Thr Asp Ala Tyr Leu Ala Ser Val Ser Ile Ala Tyr Ser Gln
        1410                1415                1420

Arg Trp Arg Asn Phe Gly Leu Met Phe Val Tyr Val Gly Phe Asn Ala
1425                1430                1435                1440

Val Ala Ala Leu Gly Leu Tyr Trp Leu Ala Arg Ala Pro Lys Ala Gly
            1445                1450                1455

Phe Lys Thr Trp Leu Ser Ala Lys Ser Lys Gln Phe Phe
        1460                1465

<210> SEQ ID NO 8
<211> LENGTH: 4410
<212> TYPE: DNA
<213> ORGANISM: Ophiostoma piceae
<220> FEATURE:
<223> OTHER INFORMATION: OPP_06758-RA - Multidrug resistance protein
      cdr1

<400> SEQUENCE: 8
atggataacc cgtcggacga gtccgaggac accttggccg ttcgtcgtac tcaggtcgac        60

```
gacgacagca cccatgaccg aattcgccag ttcagcctcg acatagtccg ttcagcatcc      120
catgctactg catctcatgc tgctgctcat gccgaccttg agtccgtcaa ctcggttgat      180
ccccatctcg atccgacgtc acccaagttc gatgcccgcc gatgggtcca agaactgctt      240
cacgcctgtg cccaggatcc cgagcggtac cctcgtccaa ctgctggtgt atcctaccgc      300
aatctcaaag tgcatggctt cggcagccct acagactacc aaaaggacgt gttcaatgtc      360
ctgctgcagg ctcccctgtt gctgctccag acaatccaga acagacgcca acaagttcct      420
attctgcgtg gcgagacagc tgatgtgggc tttgatggac tggtcaagag cggcgagatg      480
ttgcttgtgc tgggccggcc gggcagtggt gtaacgaccc tcctcaagac agtggctggc      540
gagacgagcg gtctcgagct ggacggcaca ctgtcgtatg atggcattcc gctcaagacc      600
atgcaggacc gcttccgagg cgaggtcatc taccaggccg agacggatgt gcactttcca      660
cagctgaccg tcggacagac gcttctgttt gccgccgagg cccgtacgcc aagaaatcgg      720
ccggcgctgc ccggctcctc agcttccagt acagtaagcc accaagcgta tgcacagcac      780
ctgcgcgacg tcatgatggc catctttggc atctcgcaca ccatcaacac acgtgttgga      840
aacgacctgg tgcgtggtgt cagtggcggc gagcgcaagc gtgtgagcat tgccgaggcc      900
gctctcagcg gaagtgccgt gcagtgctgg gacaactcca cacgcggcct ggacagcgcg      960
acggcgctat cctttgcgcg cacgctgcgg ctgtctacgg acctcgcagg cgcgacagca     1020
ctagtggcca tgtaccaagc tcagaaccca tcatacatcc tcttcgacaa ggtgtgcctg     1080
ctatacgagg gccggcagat cttctttggc cgtgccgacg gagcgcgtgc atactttgag     1140
cgcatgggct accactgccc accgcggcag actacggcag acttcctgac ttctctgaca     1200
agcccggacg agcgcattgt tgcaccggac gttgagccgg gcagcgtacc acggacacca     1260
gacgagttct ccgctgcttg gcgcgctagc cccgaatatg cagcactgca gaccgagctg     1320
gaccagtttg aggcggacca ccctatggac ggcacgccgg aaaagagcat ggctgttgca     1380
cggcgtgccc accagtcgac gctgacaccg tcgttctcgc cttacacgct gtcgctgccg     1440
cagcagatct ggctatgcat gcgccgcggc gggcatcgtc tgagaggcga cgtgacattc     1500
tttgtcgtca cggtcttggg caaccttgtg atctcgctcg tgctcggcag tgtgttttac     1560
aatctgcccg acgatgcgtc gagcatcaac tcgcgctgca tcctgctatt ctttgccatt     1620
ctgttcaatg ctctgagcag tgctctagag atcctgtcgc tctatgcaca cgcccgatt      1680 gtcgaaaagc atgcccgcta cgcgctgtac caaccggccg cagaggctgt tgcatcggct     1740 cttttgtgaga tgccctccaa gatcttgtcg gcgcttgcct ttaacatccc gctctatttc     1800
atggccaatt tgcggtccgg cgccgaccac ttttcatct tcctgctatt tggcttcacg      1860
tgcacactca caatgtcgac ctttattcgc acgattggcc agtcctccaa gtctgtgcac     1920
caggcactga caccggcggc catcttcatc attgcgcttg tcatctacac gggttttgtg     1980
ctgcccaagg cggccatgca gggctggctt aaatggatct cgtacatcaa tcccattgcc     2040
tatgcctacg agagccttct catcaacgag ctgggccgcg gccgcgtctt tgcctgcagc     2100
aattttgtgc cttcctatgc taccgatgcg ctcgagagag cgtgcgcgac ggcaggtgcc     2160
ccggttggtg cagactatgt tgacggtaat accgttctcg tcggcagcta cagctacaag     2220
gacagccatc tgtggcgtaa cctaggcatc ctggtcgctt ttttggtctt tttcttttgt     2280
tcctatgttg ccgcagcaga gtatgtgcgc gctgacaagt ccaagggcga ggtgcttgtc     2340
ttccgtcgcg gccatgaggc ggctgtggac caggagatcg acaacaagga caatgctaag     2400
```

| | | | | |
|---|---|---|---|---|
| aaaacgagca | tcaagcacaa | agaaggcggt | gttttccact | ggcgtgatgt | gtgttacgat | 2460 |
| attactcttg | ctggcaaaga | ccgccgtctg | cttgaccatg | tcgacggctg | ggtgaagcct | 2520 |
| ggaaccctga | ctgtgctgat | gggtgtctcc | ggcgcgggta | agactacgct | gttggatgtg | 2580 |
| ctcgcagacc | gcgtgaccat | gggtgttgtt | tcgggagcta | tgcgcgtgga | tggcgtggtt | 2640 |
| cgcggtgcat | cgttccagcg | gactaccggc | tacgtccagc | agcaagatgt | gcacctggcc | 2700 |
| acttcgacag | tgcgcgaggc | gctcctcttt | agtgccaagc | tgcgccagcc | cgcatcggtt | 2760 |
| actctgcagg | agaaagaagc | gtatgtggaa | gacgttattg | ctttgctgga | gatggaacgg | 2820 |
| tatgccgatg | cggttgttgg | tgtacccggc | gagggtctca | atgtcgagca | gcgcaagagg | 2880 |
| ctcacaatcg | gtgttgagct | cgcggcgaag | ccagatctgc | tgctatttct | ggatgagccg | 2940 |
| acatcgggcc | ttgacagcca | gacggcgtgg | tcggttacga | agcttgttcg | gaagctggcg | 3000 |
| gaccacggac | aggccgttct | ctgtacgatc | caccagccgt | cggccctgtt | gttccagcag | 3060 |
| tttgaccgcc | ttttgcttct | ggctgccggt | ggccggactg | tgtactttgg | cgatattggc | 3120 |
| gagaacgcac | gtacgctgat | cgaatacttt | gaaaaccacc | gcgaagaagg | cagcactgtg | 3180 |
| ccgccgtgcc | cgcctggcga | aaaccctgcc | gagtggatgc | tgcgtgtcat | tggtgccgcc | 3240 |
| ccgggagtgc | aggctggcca | ggactggccg | gcaaacatgg | cgtgctagtaa | cgagtacacg | 3300 |
| gtggtgcaga | ctgagctggc | ccggcttgaa | ggtgtcaccg | ctccaatcga | tgccgctgac | 3360 |
| gctgtcgagg | ctgcgaacgc | cagcaaactg | tcctatgcaa | cacccttctc | gtaccagctg | 3420 |
| tatatgtgca | cacagcgtgt | gttccagcaa | tactggcgca | cgccgtcgta | catttacgca | 3480 |
| aagttggccc | tctgctttgg | aacttccctg | ttcatcggtc | tgtcattccg | caatgccccc | 3540 |
| ctgaccgagg | ctggtctcca | gagccagctc | ttcagtatct | tcctgttgct | ggtcatcttt | 3600 |
| gcctttatga | cgtaccagac | gatgccgcac | tttatcagcc | agcgcgatct | gttcgaggtc | 3660 |
| cgtgaacggg | cttcccgcac | ctaccactgg | gcggtcttta | tgctggccaa | catcattgtc | 3720 |
| gagattcctt | ggaacacgct | ggcggcactg | ctcgtctttc | tgccgttcta | ctacctcacc | 3780 |
| ggcatgaaca | acaatgcagg | cgactcggtg | gctgagcgtg | gcgcgctatt | cttcctgctg | 3840 |
| ctctgggtct | ttctcgtctt | cgagtccacg | tttgccgaca | tggtcgtcgc | cggtgtcccc | 3900 |
| acagcggagc | ttggtgccac | gtttgctctt | ctcctgtttt | cattctgtct | tatcttctgc | 3960 |
| ggcgtcatgg | tgccatactc | ggcgcttccc | ggcttctgga | cgttcatgta | ccgcgtgtct | 4020 |
| cccttgacgt | acctcattgg | tgctcttctg | tcgaccggtg | tggccctcaa | ccctgtcaat | 4080 |
| tgctcgtcgc | tcgagcttct | ccagttctac | cctccagcca | acacgacgtg | catcgactac | 4140 |
| atgaagccat | acatgcaact | tgcgggcggt | gctcttgtcg | acggcggcgc | aatgtacccc | 4200 |
| gatgcctgcc | agttctgtac | gctggccatg | accgatgcct | atctggcttc | tgtcagcatc | 4260 |
| gcctactcac | agcgctggcg | caactttggg | ctcatgtttg | tttatgtggg | cttcaatgcg | 4320 |
| gtggctgctc | tcgggctcta | ctggctagca | cgggcaccca | agccggtttt | caagacgtgg | 4380 |
| ctgtcagcaa | agtcgaagca | gttttttctag | | | | 4410 |

<210> SEQ ID NO 9
<211> LENGTH: 1660
<212> TYPE: PRT
<213> ORGANISM: Grosmannia clavigera
<220> FEATURE:
<223> OTHER INFORMATION: GcABC-A1

<400> SEQUENCE: 9

Met Ala Val Val Phe Phe Arg Gln Val Gln Thr Leu Val Ala Lys Asn

-continued

```
  1               5              10              15
Leu Arg Val Val Leu Ile Arg His Pro Phe Ala Thr Phe Ile Arg Thr
                 20              25              30

Leu Leu Ile Pro Ile Ile Leu Phe Val Phe Phe Ser Tyr Ala Lys Tyr
                 35              40              45

Ile Phe Val Pro Ala Ala Val Tyr Gly Ile Gly Thr Ser Arg Pro Leu
 50              55              60

Leu Ser Leu Ser Asp Ala Leu Ala Ile Ala Ser Thr Gly Arg His
 65              70              75              80

Lys Val Ala Phe Tyr Asn Gly Gly Leu Ser Gly Gly Ala Ile Asp Ala
                 85              90              95

Val Ile Asp Ala Leu Val Pro Val Val Glu Ala Ala Gly Ser Lys Val
                100             105             110

Val Arg Leu Thr Asp Asp Asn Gln Leu Asp Thr Ile Cys His Ser Ser
                115             120             125

Leu Arg Gly Val Thr Ser Cys Tyr Gly Ala Val Leu Phe Ala Ser Ser
                130             135             140

Pro Ser Glu Gly Asp Ala Gly Ile Trp Lys Tyr Thr Ile Arg Leu Asp
145             150             155             160

Gly Ala Leu Gly Ala Gly Lys Ile Asn Ile Asp Lys Ser Asp Asn Asp
                165             170             175

Gly Glu Val Tyr Ala Leu Pro Leu Gln His Ala Leu Asp Ser Ala Ile
                180             185             190

Val Ala Gln Gln Asn Gly Asn Ser Ser Gly Ala Asn Ala Ile Ala Asp
                195             200             205

Ala Ala Val His Glu Tyr Pro Phe Thr Ser Leu Thr Ser Glu Gln Arg
210             215             220

Arg Glu Glu Ile Arg Ile Asn Tyr Gln Ser Ala Ile Thr Arg Phe Leu
225             230             235             240

Gly Val Gly Phe Ile Ser Gly Val Ile Gly Ile Cys Tyr His Leu Ala
                245             250             255

Gly Phe Met Ala Thr Glu Arg Glu Thr Gly Met Ser Thr Leu Ile Asp
                260             265             270

Ala Met Met Thr Thr Ser Ala Ser Gly Ser Arg Trp Gly Glu Ala Gln
                275             280             285

Ile Ala Arg Leu Val Ser Tyr His Val Ser Phe Thr Met Leu Tyr Leu
                290             295             300

Pro Gly Trp Val Ile Gly Ser Ala Val Ala Ala Ser Val Phe Ser
305             310             315             320

Asn Thr Ser Ala Ala Ile Val Ile Leu Tyr His Val Leu Ala Gly Ile
                325             330             335

Ala Leu Ala Ser Met Ala Met Phe Gly Ala Ala Phe Phe Arg His Ser
                340             345             350

Gln Leu Ser Gly Val Ser Val Thr Leu Ile Tyr Leu Ile Leu Ala Ile
                355             360             365

Val Ser Gln Thr Ile Ser Ser Pro Gln Ser Gly Thr Val Ile Val Leu
                370             375             380

Cys Leu Leu Phe Ala Pro Cys Asn Tyr Val Phe Phe Met Thr Glu Ile
385             390             395             400

Ala Arg Phe Glu Arg His Arg Glu Ala Ala Asn Leu Leu His Val Pro
                405             410             415

Pro Gly Ser Pro Trp Gln Val Ser Gly Ile Val Leu Trp Val Phe Leu
                420             425             430
```

```
Ile Ile Gln Leu Phe Gly Tyr Phe Leu Leu Ala Ile Tyr Val Asp Arg
            435                 440                 445

Tyr Leu His Gly Thr Thr Thr Thr Gly Arg Thr Ile Thr Val Arg Ser
    450                 455                 460

Pro Asp Ser Asp Val Asp Thr Gly Ser Thr Pro Ala Leu Arg Leu Glu
465                 470                 475                 480

Ser Phe Ser Lys Thr Tyr Ser Pro Gly Pro Leu Arg Arg Ala Phe Gly
                485                 490                 495

Trp Ala Lys Lys Leu Pro Glu Pro Val His Ala Val Arg Glu Leu Thr
                500                 505                 510

Leu Ser Ala Gly Arg Gly Gln Ile Leu Val Leu Leu Gly Ser Asn Gly
            515                 520                 525

Ser Gly Lys Ser Thr Thr Leu Asp Ala Ile Ala Gly Thr Ser Lys Leu
530                 535                 540

Thr Ser Gly Arg Ile Ser Ile Asp Gly Thr Gly Leu Gly Ile Ala
545                 550                 555                 560

Pro Gln Lys Asn Val Met Trp Asp Asp Leu Thr Val Glu Glu His Ile
                565                 570                 575

Arg Val Phe Asn Arg Leu Lys Ser Pro Phe Ser Leu Ala Ser Arg Glu
                580                 585                 590

Glu Thr Arg Gln Leu Val Ala Ser Val Asp Leu Glu Met Lys Thr Lys
                595                 600                 605

Ala Leu Ala Lys Thr Leu Ser Gly Gln Gln Arg Lys Leu Gln Leu
            610                 615                 620

Gly Met Met Leu Thr Gly Gly Ser Ala Val Cys Cys Val Asp Glu Val
625                 630                 635                 640

Ser Ser Gly Leu Asp Pro Leu Ser Arg Arg Lys Ile Trp Asp Ile Leu
                645                 650                 655

Leu Ala Glu Arg Gly Arg Arg Thr Ile Ile Met Thr Thr His Phe Leu
                660                 665                 670

Asp Glu Ala Asp Leu Leu Ser Asp His Ile Ala Val Leu Ser Lys Gly
            675                 680                 685

Ala Leu Arg Ala Glu Gly Ser Ser Ala Ala Leu Lys Glu Arg Leu Gly
            690                 695                 700

Gly Gly Tyr Arg Ile His Val Pro Lys Thr Arg Thr Ser Lys Asn Thr
705                 710                 715                 720

Val Val Pro Val Asn Ser Ser Phe Asp Leu Pro Asp Val Asp Gly Val
                725                 730                 735

Val Lys Glu Ser Ala Phe Asp Thr Ile Ser Tyr Ile Ala Pro Ser Ser
                740                 745                 750

Ser Leu Ala Ala Arg Val Ile Arg Val Leu Glu Ala Ala Gly Val Ala
            755                 760                 765

Asp Tyr Arg Phe Ser Gly Pro Thr Leu Glu Asp Val Phe Leu Lys Leu
    770                 775                 780

Val Glu Glu Val Gln Ser Glu Lys Leu Glu Ala Asp Glu Leu Asp
785                 790                 795                 800

Ser Thr Val Thr Val Ser Glu Lys His Leu Ser Ser Asp Lys Asp Gly
                805                 810                 815

Ala Val Thr Ser Ser Glu Val Leu Val Arg Ser Asp Asp Gly Thr Asp
            820                 825                 830

Ala Ser Ser Asn Glu Gly Arg Gly Leu Lys Leu Met Ser Gly Arg Arg
            835                 840                 845
```

```
Ile Gly Tyr Trp Gln Gln Ala Arg Val Leu Phe Met Lys Arg Val Thr
    850                 855                 860

Val Leu Lys Ser Ser Trp Leu Pro Ser Leu Ala Ala Phe Ala Ile Pro
865                 870                 875                 880

Val Ile Ala Ala Gly Leu Val Met Leu Phe Val Met Asn Gln Gly Pro
                885                 890                 895

Ile Gly Cys Ser Ser Ala Asp Gln Leu Ser Asn Asp Gln Pro Glu Thr
            900                 905                 910

Leu Ala Glu Ser Gly Tyr Ser Val Leu Val Ala Gly Pro Arg Ala
        915                 920                 925

Gln Phe Thr Asp Thr Thr Ala Leu Leu Gln Leu Phe Thr Pro Leu Phe
    930                 935                 940

Ser Ser Asn Ser Ser Ser Ser Arg Ser Ser Asn Ser Ser Thr Asp Thr
945                 950                 955                 960

Ser Val Val Ala Ser Leu Leu Arg Asn Val Thr Leu Ala Asp Asn Phe
                965                 970                 975

Thr His Phe Asn Gln Leu Ile Met Lys Lys Arg Arg Ser Ile Gly Pro
            980                 985                 990

Ala Gly Leu Trp Leu Gly Asp Asp Ser Ser Pro Pro Thr Leu Ala Tyr
        995                 1000                1005

Arg Ala Asn Ser Gln Asp Gln Val Ser Ser Leu Tyr Gly Gln Asn Ile
    1010                1015                1020

Leu Asp Ala Leu Leu Ala Asn Thr Ser Ile Ser Val Ser Tyr Thr Ser
1025                1030                1035                1040

Phe Ala Ile Pro Trp Ser Pro Asp Thr Gly Lys Thr Leu Gln Leu Leu
                1045                1050                1055

Val Tyr Val Ser Leu Ala Cys Ala Ala Tyr Val Gly Phe Phe Ser Leu
            1060                1065                1070

Tyr Pro Asn Leu Glu Arg Arg Arg Asn Val Arg Gly Leu Gln Tyr Ser
        1075                1080                1085

Asn Gly Val Ser Ala Leu Pro Leu Trp Met Ala Tyr Val Ser Phe Asp
    1090                1095                1100

Leu Gly Ile Val Leu Leu Ser Ser Ala Leu Val Ala Ile Leu Phe Ala
1105                1110                1115                1120

Ala Leu Ser Ser Ile Trp Tyr His Val Gly Tyr Met Phe Ile Ile Phe
                1125                1130                1135

Thr Leu Tyr Gly Leu Ala Ser Ala Pro Leu Ala Tyr Phe Val Ser Leu
            1140                1145                1150

Phe Cys Ser Ser Gln Leu Ser Ala Tyr Ala Phe Thr Ala Ala Ile Gln
        1155                1160                1165

Ala Val Ile Phe Leu Val Tyr Met Ile Ala Tyr Leu Cys Thr Ile Thr
    1170                1175                1180

Tyr Ala Pro Val Asn His Ile Asp Ser Tyr Leu Leu Val Val His Phe
1185                1190                1195                1200

Val Val Ser Ala Val Ser Pro Ile Gly Ser Leu Val Arg Ala Leu Phe
                1205                1210                1215

Val Ser Leu Asn Leu Phe Ser Val Ser Cys Ser Gly Lys Glu Leu Ser
            1220                1225                1230

Gln His Pro Gly Ser Ile Thr Leu Tyr Gly Gly Pro Ile Leu Tyr Leu
        1235                1240                1245

Phe Val Gln Ala Phe Val Tyr Phe Gly Leu Val Leu Trp Phe Asp Ser
    1250                1255                1260

Gly Asp Val Gly Ala Thr Leu His Gln Met Ala Ile Arg Val Lys Arg
```

His Lys Ala Arg Arg Arg Glu Ala Ala Asp Val Glu Glu Glu Gly
1265                1270                1275                1280

Gln Glu Glu Glu Ala Ser Lys Lys Glu Gly Leu Gln Val Thr His Val
            1285                1290                1295

Thr Lys Thr Phe Lys Asn Asn Thr Ala Val Asp Asn Val Ser Phe Ser
        1300                1305                1310

Val Gly His Gly Glu Val Phe Ala Leu Leu Gly Pro Asn Gly Ala Gly
    1315                1320                1325

Lys Ser Thr Thr Ile Ser Met Ile Arg Gly Asp Ile Lys Pro Asp Asp
1330                1335                1340

Gly Asp Val Phe Val Glu Gly Ala Ser Val Gln Arg Gln Leu Gly Ala
1345                1350                1355                1360

Ala Arg Gly Gly Leu Gly Val Cys Pro Gln Phe Asp Ala Val Asp Gln
            1365                1370                1375

Met Thr Val Arg Glu His Leu Arg Phe Tyr Ala Gln Val Arg Gly Ile
        1380                1385                1390

Thr Asp Val Ala His Asn Val Gln Ala Val Met Gln Ala Val Gly Leu
    1395                1400                1405

Ala Ala Leu Gly Asp Arg Gln Ala Gln Ala Leu Ser Gly Gly Asn Lys
1410                1415                1420

Arg Lys Leu Ser Leu Gly Ile Ala Leu Met Gly Asn Pro Ala Val Val
1425                1430                1435                1440

Leu Leu Asp Glu Pro Ser Ser Gly Leu Asp Ala Ala Ala Lys Arg Ile
            1445                1450                1455

Met Trp Arg Thr Leu Ala Ala Thr Ser Pro Gly Arg Ser Ile Leu Leu
        1460                1465                1470

Thr Thr His Ser Met Glu Glu Ala Asp Ala Leu Ala Gly Arg Ala Gly
    1475                1480                1485

Ile Leu Ala Arg Arg Met Leu Ala Ala Gly Val Thr Glu Glu Leu Arg
1490                1495                1500

Ser Arg Phe Gly Ser Arg Leu Tyr Val His Val Val Cys Arg Gly Ala
1505                1510                1515                1520

Pro His Thr Pro Glu Ala Glu Thr Glu Arg Leu Arg Arg Trp Ala Ala
            1525                1530                1535

Ala Val Phe Pro Gly Ala Glu Val Glu Glu Gln Thr Tyr His Gly Gln
        1540                1545                1550

Met Arg Phe Ala Ile Pro Val Val Asn Gly Gln Leu Val Glu Asp Asp
    1555                1560                1565

Thr Ala Thr Glu Lys Pro Val Arg Ala Thr Ser Ala Val Gly Arg Leu
1570                1575                1580

Val Val Leu Leu Asp Glu Gln Arg Glu Ala Leu Gly Ile Asp His Phe
1585                1590                1595                1600

Ser Val Ser Pro Thr Thr Leu Asp Gln Val Phe Leu Thr Ile Val Gly
            1605                1610                1615

Arg His Asn Val Gln Glu Glu Gly Tyr Arg Gln Glu Glu Leu Ala Ala
        1620                1625                1630

Val Lys Arg Lys Trp Trp Lys Leu Gly Leu Arg Asp
    1635                1640                1645

<210> SEQ ID NO 10
<211> LENGTH: 1416
<212> TYPE: PRT
<213> ORGANISM: Grosmannia clavigera
<220> FEATURE:
<223> OTHER INFORMATION: GcABC-B1

<400> SEQUENCE: 10

```
Met Glu Pro Val Thr Glu Ser Leu Pro Leu Glu Asn Leu His Thr Thr
 1               5                  10                  15

Gly Pro Ala Gly Asp His Ala Ala Ser Val Gln His Leu Phe Val Ala
             20                  25                  30

Trp Thr Cys Gly Glu Leu Ser Ile Leu Val Pro Ala Val Ala Ala Ser
         35                  40                  45

Ala Val Val Ala Gly Ala Lys Thr Ala Tyr Ala Leu Ile Leu Gly Glu
     50                  55                  60

Ile Phe Gln Thr Ile Ser Asp Phe Gly Ser Gly Arg Val Ser Val His
 65                  70                  75                  80

Asp Thr Val Arg Thr Ile Ser Thr Trp Cys Leu Gly Leu Val Gly Leu
                 85                  90                  95

Gly Ala Gly Lys Ala Leu Ile Ser Phe Leu Met Met Val Met Trp Ile
            100                 105                 110

Thr His Gly Glu Ser Arg Ala Arg Ser Val Arg Leu Gln Leu Phe Gln
        115                 120                 125

Ser Leu Leu Glu Lys Glu Met Ala Trp Phe Asp Thr Arg Arg Gly Gly
    130                 135                 140

Met Ser Ser Leu Met Thr Glu Gln Asn Thr Gln Val Leu Ala Ser Leu
145                 150                 155                 160

Met Gly Val Leu Val Thr Asp Cys Val Cys Val Ala Cys Leu Val
                165                 170                 175

Val Ala Leu Val Lys Ser Trp Lys Leu Thr Leu Gly Leu Leu Ala Ser
                180                 185                 190

Val Pro Ile Ala Val Phe Val Leu Ser Phe Leu Gly Arg Gly Leu Asn
            195                 200                 205

Pro Ala Ala Glu Lys Gln Arg Glu Met Leu Asn Gln Ala Ala Lys His
        210                 215                 220

Ala Thr Ala Ala Leu Val Ala Ile Asp Leu Val Lys Val Tyr Asp Gly
225                 230                 235                 240

His Asp Thr Val Met Trp Gln Tyr Leu Ser Ser Ile Arg Leu Ala Ala
                245                 250                 255

His Phe Tyr Ile Lys Gln Ala Leu Ser Ala Cys Phe Gln Met Gly Phe
            260                 265                 270

Val Lys Leu Trp Met Val Asn Leu Phe Val Ile Gly Phe Trp Phe Gly
        275                 280                 285

Met Ile Leu Val Gly Lys Gly Gln Ala Thr Ala Gly Asn Val Leu Thr
    290                 295                 300

Ala Phe Tyr Ala Val Leu Ile Ala Phe Gln Ser Ile Glu Ala Leu Gly
305                 310                 315                 320

Thr Gln Trp Val Ser Val Leu Lys Gly Thr Val Ser Gly Lys Ala Leu
                325                 330                 335

Glu Asp Met Ile Phe Ser Gly Ser Gln Ser Ala Leu Leu Phe Ser Lys
            340                 345                 350

Ser Gln Pro Ser Arg Ala Pro Gly Gly Ile Glu Leu Ser Asn Val Ser
        355                 360                 365

Phe Ala Tyr Pro Ser Asn Pro Asn Lys Thr Val Leu Lys Asp Cys Ser
    370                 375                 380

Met Leu Phe Pro Ser Gly Gln Val Ser Phe Val Val Gly Arg Ser Gly
385                 390                 395                 400
```

-continued

```
Ser Gly Lys Ser Thr Ile Ala Asp Leu Leu Val Arg Phe Tyr His Pro
            405                 410                 415
Thr Ala Gly Arg Ile Leu Val Asp Lys Ser Pro Ile Glu Glu Leu Asp
            420                 425                 430
Val Arg Trp Leu Arg Glu Asn Val Ser Leu Ile Gln Gln Ser Ser Thr
            435                 440                 445
Val Phe Asn Gly Thr Phe Gly Trp Asn Val Ser Leu Gly Ser Ser Thr
            450                 455                 460
Pro Asp Ser Ile Asn Glu Ser Ser Ile Lys Thr Ala Cys Gln Thr Ala
465                 470                 475                 480
Leu Leu Gln Ser Thr Ile Ala Gly Leu Pro Gln Gly Leu Asp Thr Val
                485                 490                 495
Val Gly Pro Arg Gly Val Ala Leu Ser Gly Gly Gln Arg Gln Arg Leu
            500                 505                 510
Ala Val Ala Arg Ala Lys Ile Arg Asp Pro Ala Val Leu Val Leu Asp
            515                 520                 525
Glu Thr Thr Ser Gly Leu Asp Pro Lys Ser Ala Gln Met Val Leu Glu
            530                 535                 540
Ala Val Arg Ile Trp Arg Arg Glu Lys Thr Thr Val Ile Ile Thr His
545                 550                 555                 560
Asp Ile Ser Asn Ile Ala Met Glu Asp Tyr Val Tyr Val Met Asp Cys
                565                 570                 575
Gly Ser Leu Val Gln Gln Gly Pro Tyr Phe Gln Leu Ala Lys Asp Ser
            580                 585                 590
Gly Gly Met Leu Asp Thr Leu Leu Asn Ala Val Ala Val Gly Gly Ala
            595                 600                 605
Arg Asp Val Ala Thr Ala Cys Leu Ser Pro Val Glu Lys Ile Gly His
            610                 615                 620
Asp Gln Phe Gly His Gly Asn Gln Glu Asp Gly Val Asp Asp Gln Leu
625                 630                 635                 640
Ala Ala Val Gly Gly Asn Gln Ala Asp Glu Pro Ala Ile Met Ala Trp
                645                 650                 655
Pro Leu Pro Gln Thr Trp Arg Gly Ser Ser Phe Gly Ala Gly Pro Phe
                660                 665                 670
Leu Ala Ser Ser Ala Ala His Gly Asn Phe Ile His Arg Leu Ser Leu
            675                 680                 685
Gln Ser Ala Gln Ala Ser His Ala Val Asn Trp Pro Leu Pro Ala Pro
            690                 695                 700
Glu Pro Thr Leu Lys Ala Lys Glu Ser Pro Lys Ser Ile Glu Ser Arg
705                 710                 715                 720
Ser Ser Val Asp Leu Val Cys Asp Gln Gly His Gln Ala Gln Ala Asn
                725                 730                 735
Arg Gln Ser Trp Asn Glu Ser Gly Gln Arg Gln Arg Gln Ala Val Ala
            740                 745                 750
Leu Thr Arg Lys Arg Ala Leu Ser Thr Ser Cys Asp Arg Glu Thr
            755                 760                 765
Ser Pro Pro Lys Pro Lys Pro Ala Ile Pro Thr Leu Leu Thr Val Leu
770                 775                 780
Arg Thr Val Trp Pro Leu Leu Gly Lys Ala Asn Arg Ile Glu Ala Ile
785                 790                 795                 800
Leu Gly Leu Leu Cys Cys Ile Val Val Ala Gly Ser Asn Pro Gly Phe
                805                 810                 815
```

```
Ser Phe Val Phe Ala Arg Met Leu Glu Ser Phe Trp Ser Pro Lys Ala
                820                 825                 830

Asn Lys Glu Ala Val Gly Arg Pro Trp Ala Leu Ile Leu Ile Gly Leu
            835                 840                 845

Ser Ile Val Asp Gly Ser Ala Val Phe Gly Ser Phe Tyr Leu Ala Glu
        850                 855                 860

Arg Val Gly Gln Thr Trp Val Asn Ala Leu Arg Ser Glu Ala Leu Thr
865                 870                 875                 880

Arg Leu Met Arg Gln Pro Arg Ser Trp Trp Ser Ala Ser Asp Pro Glu
                885                 890                 895

Ala Gly Gln Asp Gly Glu Ser Pro Ser Pro Ser Arg Ile Val Glu Cys
            900                 905                 910

Leu Asp Arg Gly Gly Glu Glu Met Arg Lys Leu Val Ser Val Phe Val
        915                 920                 925

Pro Ile Leu Thr Met Ala Ala Gly Met Val Ile Thr Ser Val Gly Trp
    930                 935                 940

Ser Leu Ala Val Ser Trp Arg Leu Thr Leu Val Ala Leu Ala Ser Gly
945                 950                 955                 960

Pro Ile Ile Val Ser Val Thr His Leu Ala Ser Arg Val Ser Asn Lys
                965                 970                 975

Trp Glu Ser Arg Ser Asn Trp Ala Ala Glu Thr Val Ser Gly Val Phe
            980                 985                 990

Ser Glu Val Phe Pro Asp Ile Arg Val Val Arg Ala Leu Thr Leu Glu
        995                 1000                1005

Thr His Phe Ser Gly Arg Leu Ala Val Thr Val Gln Lys Ala Phe Arg
    1010                1015                1020

Thr Gly Leu Ser Arg Ala Trp Arg Thr Gly Ile Leu Tyr Gly Leu Asn
1025                1030                1035                1040

Gln Ala Leu Ser Asp Trp Leu Thr Ala Leu Val Phe Tyr Tyr Gly Val
                1045                1050                1055

Ser Leu Leu Thr Ser Gly Asp Gly Ala Arg Ile Ser Val Ser Asp Val
            1060                1065                1070

Val Gln Val Val Asn Leu Leu Leu Phe Ser Ile Gly Ser Ala Ala Ser
        1075                1080                1085

Leu Leu Ser Asn Val Pro Gln Ile Ala Ala Ser Lys Ala Val Ala Ala
    1090                1095                1100

Gln Ile Leu Glu Tyr Ala Ser Leu Ser Leu His Ala Ser His Glu His
1105                1110                1115                1120

Ser Arg Ile Val Leu Ala Arg Pro Lys Lys Leu Phe Pro Val Arg Met
                1125                1130                1135

Asp Gly Leu Val Phe Arg Tyr Pro Gly Lys Glu Ala Arg Ala Val Gly
            1140                1145                1150

Asp Ser Phe Asn Ser Leu Gln Pro Ala Ile Leu His Gly Ile Asn Leu
        1155                1160                1165

Glu Ile Arg Val Asp Asp Phe Ala Ile Val Gly Thr Ser Gly Ser
    1170                1175                1180

Gly Lys Ser Thr Ile Leu Ser Leu Leu Arg Leu Tyr Glu Ser Asp
1185                1190                1195                1200

Lys Gly Asn Gln Leu Thr Phe Asp Gly Met Pro Ala Asp Gln Leu Asp
                1205                1210                1215

Thr Lys Ala Val Arg Ser Arg Met Ala Tyr Val Pro Gln His Pro Tyr
            1220                1225                1230

Leu Phe Pro Ala Ser Val Arg Ala Asn Ile Thr Tyr Gly Leu Asp Glu
```

```
                1235                1240                1245
Ala Ser Pro Leu Cys Gln Ala Thr Cys Val Ala Asp Ala Ala Arg Ala
            1250                1255                1260

Ala Ser Ile Asp Thr Phe Val Ser Ser Leu Thr Gln Gly Tyr Asp Thr
1265                1270                1275                1280

Val Val Gly Asp Val Val Gly Glu Glu Thr Ser Gly Glu Asn Ala Gly
                1285                1290                1295

Gly Thr Gly Asn Gly Pro Cys Ser Ser Thr Asn Gly Ser Met Ser Ser
            1300                1305                1310

Leu Ser Gly Gly Gln Ala Gln Arg Val Cys Ile Ala Arg Ala Leu Leu
            1315                1320                1325

Arg Arg Pro Gln Leu Leu Val Leu Asp Glu Pro Thr Ser Ser Leu Asp
            1330                1335                1340

Ala Glu Ser Ala Gln Ile Ile Arg Thr Ala Leu Arg Gly Leu Ala Asp
1345                1350                1355                1360

Leu Gly Ser Gly Arg Ser Ile Val Val Ala Thr His Ser Lys Ala Met
                1365                1370                1375

Met Arg Leu Cys Asp Arg Val Val Val Gln Asp Gly Thr Val Val
            1380                1385                1390

Thr Ser Gly Pro Tyr Ala Glu Leu Leu Gln His Asp Glu Thr Phe Ala
            1395                1400                1405

Arg Leu Val Gly Glu Tyr Asp Asp
            1410                1415

<210> SEQ ID NO 11
<211> LENGTH: 889
<212> TYPE: PRT
<213> ORGANISM: Grosmannia clavigera
<220> FEATURE:
<223> OTHER INFORMATION: GcABC-B2

<400> SEQUENCE: 11

Met Ala Val Asp Ala Ser Asp Gln Ser Glu Ser His Asp Ser Thr Arg
  1               5                  10                  15

Phe Asn Asn Val Asp Ala Ala Ser Glu Glu Lys Ser Ile Glu Glu Gly
                 20                  25                  30

Val Met Ala Leu Thr Pro Asn His Glu Asp Val Leu Lys Asp Gln Ile
             35                  40                  45

Thr Gly Pro Val Thr Trp Gln Gly Ser Val Arg Phe Leu Leu Ser Cys
 50                  55                  60

Thr Ser Thr Ile Asp Gly Leu Val Leu Gly Ser Ser Ala Val Ala Ala
65                  70                  75                  80

Ile Ile Gly Gly Ala Ala Thr Pro Phe Ala Met Leu Leu Leu Gly Asn
                 85                  90                  95

Met Gly Gln Ser Phe Arg Gly Phe Phe Met Gly His Thr Thr Leu Asp
            100                 105                 110

Lys Phe Ser Asp Glu Val Ala Asn Ile Ser Leu Leu Tyr Val Tyr Leu
        115                 120                 125

Ala Ile Val Glu Phe Ser Ala Ile Tyr Phe Ala Thr Val Gly Phe Thr
    130                 135                 140

Met Ala Gly Asp Arg Ile Ala Gln Arg Val Arg Glu Lys Tyr Leu Ala
145                 150                 155                 160

Ala Val Leu Arg Gln Asn Ile Ala Tyr Phe Asp Gly Leu Ala Ile Gly
                165                 170                 175

Glu Val Asn Thr Leu Leu Asp Gly Val Asp Ile Ser Thr Gln Asp Val
```

```
            180                 185                 190
Ser Trp Leu Arg Gln Lys Ile Gly Leu Val Glu Gln Asp Pro Thr Leu
            195                 200                 205

Phe Ser Thr Ser Val Tyr Glu Asn Ile Arg Phe Gly Leu Val Gly Ser
210                 215                 220

Ala His Glu Asn Leu Asp Asp Ala Ala Thr Gln Lys Leu Val Glu Asp
225                 230                 235                 240

Ala Ala Arg Leu Ala Asp Ala Tyr Asp Phe Ile Met Ala Leu Pro Glu
                245                 250                 255

Gly Phe Ser Thr Asn Val Gly Asp Ser Gly Leu Ile Ser Gly Gly
                260                 265                 270

Gln Lys Gln Arg Ile Ala Ile Ala Arg Ala Val Ile Gly Asp Pro Arg
            275                 280                 285

Ile Leu Leu Leu Asp Glu Ala Thr Ser Ala Leu Asp Ala Asn Ala Glu
            290                 295                 300

Arg Arg Val Gln Arg Ala Leu Glu Asn Ala Ser Lys Gly Arg Thr Thr
305                 310                 315                 320

Ile Ser Ile Ala His Arg Leu Ser Thr Ile Thr Arg Ala Asp Asn Ile
                325                 330                 335

Leu Val Met Ser Glu Gly Arg Ile Val Glu Gln Gly Leu His Thr Thr
            340                 345                 350

Leu Met Glu Tyr Asp Gly Ile Tyr Ser Lys Leu Ile Gln His Gln Ser
            355                 360                 365

Val Gln Asp Pro Gly Arg Asn Arg Thr Glu Val Asp Val Pro Leu Gln
370                 375                 380

Glu Gly Val Asp Lys Asp Val Ser Pro Arg His Ser Glu Leu Ile Lys
385                 390                 395                 400

Gln Ser Thr Gly Ser Thr Ala Thr Ile Leu Glu Glu Lys Thr Thr Ala
                405                 410                 415

Ser Ser Ile Trp Ser Leu Ala Leu Phe Val Phe Gly Leu Asn Pro Lys
            420                 425                 430

Gly Arg Thr Leu Ile Leu Leu Gly Ala Leu Phe Ser Ile Val Ala Gly
            435                 440                 445

Ala Ser His Pro Ala Gln Ser Val Phe Leu Ala Lys Ile Ile Ala Ala
450                 455                 460

Leu Ser Gln Asn Pro Ser Glu His Lys Asn Val Arg Glu Glu Val Asp
465                 470                 475                 480

Phe Trp Ser Trp Met Tyr Phe Met Ile Gly Phe Thr Thr Val Gly Gly
                485                 490                 495

Trp Leu Gly Gln Gly Val Cys Leu Ala Tyr Tyr Ser Gln Arg Leu Thr
            500                 505                 510

His Ile Ala Arg Val Lys Gly Leu Asp Thr Val Leu His His Asp Ile
            515                 520                 525

Gly Thr Phe Ser Arg Asn Asp His Ser Thr Ala Ala Leu Thr Ser Ile
            530                 535                 540

Leu Ser Thr Ser Ala Ser Ser Leu Gln Gly Leu Ser Gly Ala Val Leu
545                 550                 555                 560

Gly Thr Leu Leu Val Val Leu Thr Val Leu Val Ala Gly Phe Ala Leu
                565                 570                 575

Ser Thr Ala Ile Gly Trp Lys Leu Ala Leu Val Cys Ala Thr Thr Thr
            580                 585                 590

Pro Ile Gln Ile Ala Cys Gly Ile Ile Arg Leu Lys Cys Val Ala Met
            595                 600                 605
```

```
Leu Glu Gly His Ser Arg Gln Val Tyr Glu Ser Ser Ala Ile Tyr Ala
            610                 615                 620

Cys Glu Tyr Gly Ser Asn Ile Arg Thr Val Ala Ala Leu Thr Leu Glu
625                 630                 635                 640

Arg Thr Ile Gln Lys Thr Tyr His Arg Leu Leu Glu Met Gln Arg Lys
                645                 650                 655

Lys Ser Leu Leu Leu Val Ser Gln Ser Ser Leu Leu Tyr Ala Ala Ser
            660                 665                 670

Gln Ser Leu Asn Phe Leu Cys Val Ser Leu Thr Phe Trp Tyr Gly Ser
            675                 680                 685

Arg Leu Val Thr Thr Glu Gly Tyr Thr Met Phe Gln Phe Phe Val Cys
            690                 695                 700

Tyr Thr Ala Ile Ile Ala Gly Ser Phe Ser Ala Gly Ala Ile Phe Ser
705                 710                 715                 720

Phe Ala Pro Asp Ile Gly Lys Ala Arg Asp Ser Ala Glu Arg Met Gln
                725                 730                 735

Ala Leu Phe Cys Glu Pro Val Asn Ile Asp Val Arg Glu Asp Gly Gly
            740                 745                 750

Ser Ser Phe Asp Asn Thr Asp Gly Thr Ile Glu Leu Lys Asn Val Ser
            755                 760                 765

Phe Arg Tyr Pro Ser Arg Pro Glu His Met Val Leu Asp Asp Ile Asn
770                 775                 780

Ile Thr Ile Leu Ser Gly Lys Tyr Ile Ala Leu Val Gly Ser Ser Gly
785                 790                 795                 800

Ser Gly Lys Ser Thr Ile Ile Ser Leu Leu Glu Arg Phe Phe Asp Pro
                805                 810                 815

Asp Asp Gly Gln Val Phe Phe Gly Ser Gln Asn Ile Lys Asp Arg Asn
            820                 825                 830

Leu Arg Asn Tyr Arg Arg Gln Leu Ala Leu Val Ser Gln Ser Ala Thr
            835                 840                 845

Leu Phe Asp Gly Thr Ile Arg Asp Asn Ile Ile Phe Gly Val Glu Asp
            850                 855                 860

Glu Asn Phe Ser Glu Glu Ala Val Met Gln Ala Cys Lys Asp Ala Asn
865                 870                 875                 880

Ile Leu Asp Phe Ile Ser Ser Leu Pro
                885

<210> SEQ ID NO 12
<211> LENGTH: 1359
<212> TYPE: PRT
<213> ORGANISM: Grosmannia clavigera
<220> FEATURE:
<223> OTHER INFORMATION: GcABC-B3

<400> SEQUENCE: 12

Met Ala Lys Asp Asn Arg Leu Ser Glu Lys Asp Ala Val Ala Thr Ala
 1               5                  10                  15

Ile Met Pro Pro Lys Ser Ala Ser Ser Arg Glu Asp Thr Gly Asp Glu
                20                  25                  30

Lys Ala Ala Ser Ser Leu Val Lys Ile Asp Ser Lys Pro Val Gln Leu
            35                  40                  45

Pro Asp Gln Lys Asn Ala Val Asp Pro Phe Gln His Leu Pro Pro Asp
        50                  55                  60

Glu Ala Ser Val Leu Arg Arg Gln Val Leu Thr Pro Glu Val Lys Val
65                  70                  75                  80
```

```
Gly Phe Arg Thr Leu Tyr Arg Tyr Ala Ser Arg Thr Asp Val Ala Ile
                85                  90                  95

Leu Val Val Ser Ala Ile Cys Gly Ala Ala Ser Gly Ala Ala Leu Pro
               100                 105                 110

Leu Met Thr Val Val Phe Gly Asn Leu Gln Gly Ser Phe Gln Lys Phe
           115                 120                 125

Phe Leu Gly Thr Leu Ser Arg His Ala Phe Met His Lys Met Ala His
    130                 135                 140

Gln Val Leu Tyr Phe Ile Tyr Leu Ala Ile Gly Glu Phe Val Thr Thr
145                 150                 155                 160

Tyr Ile Ser Thr Val Gly Phe Ile Tyr Thr Gly Glu His Ile Ser Ser
                165                 170                 175

Lys Ile Arg Glu His Tyr Leu Glu Ser Cys Met Arg Gln Asn Ile Gly
            180                 185                 190

Phe Phe Asp Lys Leu Gly Ala Gly Glu Val Thr Thr Arg Ile Thr Ala
        195                 200                 205

Asp Ala Asn Leu Val Gln Glu Gly Ile Ser Glu Lys Ile Gly Leu Thr
210                 215                 220

Leu Ala Ala Val Ala Thr Phe Phe Thr Ala Phe Val Ile Gly Phe Val
225                 230                 235                 240

Glu Tyr Trp Lys Met Thr Leu Ile Leu Leu Ser Thr Val Val Ala Leu
                245                 250                 255

Val Thr Val Met Gly Gly Gly Ser Arg Phe Ile Val Arg Tyr Ser Lys
                260                 265                 270

Leu Ser Val Ala Ala Tyr Ala Glu Gly Ser Val Ala Glu Glu Val
            275                 280                 285

Ile Ser Ser Ile Arg Asn Ser Val Ala Phe Gly Thr Gln Asp Arg Leu
            290                 295                 300

Ala Arg Arg Tyr Asp Glu Tyr Leu Thr Arg Ala Glu Gly His Gly Phe
305                 310                 315                 320

Arg Val Lys Ala Val Leu Ser Ile Met Ile Ala Cys Met Met Cys Ile
                325                 330                 335

Leu Tyr Leu Asn Tyr Gly Leu Ala Phe Tyr Val Gly Ser Asn Phe Val
            340                 345                 350

Leu Asp Asn Val Ile Pro Leu Ser Lys Val Leu Ile Ile Met Met Ser
            355                 360                 365

Val Met Met Gly Ala Phe Asn Leu Gly Asn Val Ala Pro Asn Ile Gln
370                 375                 380

Ala Phe Thr Thr Gly Leu Ala Ala Ala Lys Ile Phe Asn Thr Ile
385                 390                 395                 400

Asp Arg Ile Ser Cys Leu Asp Pro Thr Ser Asp Glu Gly Glu Lys Pro
                405                 410                 415

Ala Gly Leu Val Gly Ala Ile Arg Leu Glu His Ile Lys His Ile Tyr
            420                 425                 430

Pro Ser Arg Pro Glu Val Val Met Glu Asp Val Ser Leu Glu Ile
                435                 440                 445

Pro Ala Gly Lys Thr Thr Ala Leu Val Gly Ala Ser Gly Ser Gly Lys
450                 455                 460

Ser Thr Ile Val Gly Leu Val Glu Arg Phe Tyr His Pro Val Gln Gly
465                 470                 475                 480

Thr Val Tyr Leu Asp Gly His Asp Ile Ser Lys Leu Asn Leu Arg Trp
                485                 490                 495
```

```
Leu Arg Gln Asn Ile Ser Leu Val Gln Gln Glu Pro Ile Leu Phe Gly
                500                 505                 510

Thr Thr Ile Tyr Glu Asn Ile Ala His Gly Leu Ile Gly Ser Arg His
            515                 520                 525

Glu Gln Ala Gly Val Glu Glu Lys Leu Ala Leu Ile Glu Asp Ala Ala
        530                 535                 540

Arg Lys Ala Asn Ala His Asp Phe Ile Thr Gly Leu Pro Glu Gly Tyr
545                 550                 555                 560

Glu Thr Asn Val Gly Glu Arg Gly Phe Leu Ser Gly Gly Gln Lys
                565                 570                 575

Gln Arg Ile Ala Ile Ala Arg Ala Ile Val Ser Asp Pro Lys Ile Leu
            580                 585                 590

Leu Leu Asp Glu Ala Thr Ser Ala Leu Asp Thr Arg Ser Glu Gly Val
        595                 600                 605

Val Gln Ala Ala Leu Asp Val Ala Ala Ala Gly Arg Thr Thr Ile Thr
        610                 615                 620

Ile Ala His Arg Leu Ser Thr Ile Lys Asp Ala His Asn Ile Val Val
625                 630                 635                 640

Met Ser Ser Gly Arg Ile Val Glu Gln Gly Thr His Asn Glu Leu Ile
                645                 650                 655

Glu Arg Arg Gly Ala Tyr Tyr Asn Leu Val Ala Ala Gln Ser Ile Ala
                660                 665                 670

Thr Val Asn Ala Pro Thr Ser Glu Gln Glu Ala Leu Asp Ala Lys
            675                 680                 685

Ala Asp Ala Glu Leu Val Arg Lys Val Thr Gly Gly Ser Ser Ser Ser
690                 695                 700

Ser Ala Asp Val Glu Ala Lys Asp Gly Ser Ala Thr Glu Gly Thr Ala
705                 710                 715                 720

Thr Gly Thr Gly Asp Tyr Ser Ala Asp Pro Asp Asp Met Ala Arg
                725                 730                 735

Lys Leu Gln Arg Ser Ala Thr Gln His Ser Leu Ser Ser Leu Ala Val
                740                 745                 750

Lys Ala Arg Lys Pro Glu Ala Glu Asp Ala Ala Arg Tyr Gly Leu
            755                 760                 765

Met Thr Leu Ile Arg Leu Ile Ala Gly Phe Asn Ser Ser Glu Trp Pro
            770                 775                 780

Leu Met Cys Val Ala Leu Val Phe Ser Ile Ile Cys Gly Gly Gly Asn
785                 790                 795                 800

Pro Thr Gln Ala Val Phe Phe Ala Lys Gln Ile Ser Thr Leu Ser Val
                805                 810                 815

Val Val Thr Pro Gln Asn Arg Gly Gln Val Arg His Asp Ala His Phe
            820                 825                 830

Trp Cys Leu Met Tyr Leu Met Leu Gly Leu Val Gln Leu Leu Ala Phe
            835                 840                 845

Ser Ile Gln Gly Gly Leu Phe Ala Leu Cys Ser Glu Arg Leu Val His
            850                 855                 860

Arg Ala Arg Asp Arg Ala Phe Arg Ser Met Leu Arg Gln Asp Ile Ser
865                 870                 875                 880

Phe Phe Asp Arg Asp Glu Asn Thr Ala Gly Ala Leu Thr Ser Phe Leu
                885                 890                 895

Ser Thr Glu Val Thr His Ala Gly Leu Ser Gly Ala Thr Leu Gly
                900                 905                 910

Thr Leu Leu Thr Val Ala Thr Thr Leu Ile Ala Ala Leu Thr Leu Ser
```

```
                915                 920                 925
Ile Ala Ile Gly Trp Lys Leu Ala Leu Val Cys Thr Ser Thr Ile Pro
    930                 935                 940

Ile Leu Leu Gly Cys Gly Tyr Phe Arg Phe Trp Met Leu Ala His Tyr
945                 950                 955                 960

Gln Arg Arg Ala Lys Arg Ala Tyr Glu Gly Ser Ala Ser Tyr Ala Ser
                965                 970                 975

Glu Ala Ile Thr Ala Ile Arg Thr Val Ala Ser Leu Thr Arg Glu Asp
                980                 985                 990

Asp Val Val Gln His Tyr Arg Ala Asp Leu Ala Gln Leu Gln Thr
            995                 1000                1005

Ser Thr Val Ser Val Leu Arg Ser Ser Leu Leu Tyr Ala Ala Ser Gln
    1010                1015                1020

Ser Leu Thr Phe Leu Val Leu Ala Leu Gly Phe Trp Tyr Gly Gly Lys
1025                1030                1035                1040

Leu Leu Ser Glu Gly Ala Tyr Asp Met Phe Ser Phe Phe Val Val Phe
                1045                1050                1055

Ser Ala Val Thr Phe Gly Ala Gln Ser Ala Gly Thr Phe Phe Ser Phe
                1060                1065                1070

Ala Pro Asp Met Gly Lys Ala Arg Gln Ala Ser Ala Glu Leu Lys His
                1075                1080                1085

Leu Phe Glu Arg Pro Val Ala Ile Asp Ala Trp Ser Thr Ala Gly Arg
                1090                1095                1100

Ser Val Asp Ser Phe Asp His Pro Ile Glu Phe Arg Asp Val His Phe
1105                1110                1115                1120

Arg Tyr Pro Thr Arg Leu Glu Gln Pro Val Leu Arg Gly Leu Ser Leu
                1125                1130                1135

Thr Val His Pro Gly Gln Tyr Val Ala Leu Val Gly Ala Ser Gly Cys
                1140                1145                1150

Gly Lys Ser Thr Thr Ile Ala Leu Leu Glu Arg Phe Tyr Asp Pro Leu
                1155                1160                1165

Ala Gly Gly Ile Phe Leu Asp Gly His Asp Ile Ala Gly Leu Asn Val
                1170                1175                1180

Ser Ala Tyr Arg Arg Gly Ile Ala Leu Val Ser Gln Glu Pro Thr Leu
1185                1190                1195                1200

Tyr Met Gly Thr Ile Arg Glu Asn Ile Leu Leu Gly Ala Leu Asp Glu
                1205                1210                1215

Thr Ala Val Thr Asn Glu Ala Val Glu Phe Ala Cys Arg Glu Ala Asn
                1220                1225                1230

Ile Tyr Asp Phe Ile Val Ser Leu Pro Asp Gly Phe Asn Thr Leu Val
                1235                1240                1245

Gly Ser Lys Gly Ala Leu Leu Ser Gly Gly Gln Lys Gln Arg Ile Ala
                1250                1255                1260

Ile Ala Arg Ala Leu Ile Arg Asp Pro Lys Ile Leu Leu Leu Asp Glu
1265                1270                1275                1280

Ala Thr Ser Ala Leu Asp Ser Glu Ser Glu Lys Val Val Gln Ala Ala
                1285                1290                1295

Leu Asp Lys Ala Ala Lys Gly Arg Thr Thr Ile Ala Val Ala His Arg
                1300                1305                1310

Leu Ser Thr Ile Gln Lys Ala Asp Val Ile Tyr Val Phe Asp Gln Gly
            1315                1320                1325

Arg Ile Val Glu Gln Gly Thr His Val Glu Leu Met Gln Arg Asn Gly
                1330                1335                1340
```

```
Arg Tyr Ala Glu Leu Val Asn Leu Gln Ser Leu Glu Lys His Gln
1345                1350                1355

<210> SEQ ID NO 13
<211> LENGTH: 917
<212> TYPE: PRT
<213> ORGANISM: Grosmannia clavigera
<220> FEATURE:
<223> OTHER INFORMATION: GcABC-B4

<400> SEQUENCE: 13

Met Glu Pro His Leu Ala Gly Phe Pro Arg Cys Ser Ala Leu Leu Ala
 1               5                  10                  15

Glu Leu Arg Leu Leu Arg Val Ser Ser Val Cys Cys Pro Ala Gln Thr
             20                  25                  30

Ala Pro Cys Ser Pro Thr Ser Thr Gly Glu Cys Arg Lys Pro Ala Ala
         35                  40                  45

Pro Leu Gly Leu Ala Thr Ala Leu Glu Arg Pro Arg Gly His Gly Tyr
     50                  55                  60

Asn Gly Ala Gly His Leu Ser Ala Pro Ala His Met Pro Arg Val Leu
65                  70                  75                  80

Pro Ser Val Ala Ser Ala Val Leu Pro Val Thr Ser Ile Ser Gly Pro
                 85                  90                  95

Lys Asp Val Gly Met Ala Val Gly Tyr Arg Glu Glu Lys Asp Ile Ile
            100                 105                 110

Lys Thr Gly Ile Leu Thr Val Ile His Arg Cys Met Val Pro Ala Lys
        115                 120                 125

Ser Ser Gln Leu Leu Ser Ala Glu Arg Ser Ile Asp Gly Arg Ser Leu
    130                 135                 140

Asp Ile Thr Cys Arg Ala Ala Leu Gly Ile Ile Glu Gly His Cys Ile
145                 150                 155                 160

Ile Ala Leu Lys Ser Phe Glu His Trp Arg Glu Ile His Arg Thr Val
                165                 170                 175

Asp Ser Ser Arg Leu Ile Leu Asp Asn Ala Arg His Ala His Gly Cys
            180                 185                 190

Val Arg Ser Leu Ala Met Ile Ala Arg Gly Ile Pro Arg Ala Ala Thr
        195                 200                 205

Leu Ser Ala Gln Arg Val His Cys Gly Trp Leu Trp Ala Ala Pro Trp
    210                 215                 220

Ser Pro Gly Cys Pro Ala Ala Ala Met Leu Asp Arg Arg Arg Gly
225                 230                 235                 240

Val Phe Leu Ser Ala Ser Val Phe Ser Thr Thr Ala Ser Trp Arg Ala
                245                 250                 255

Val Asn Lys Ala Ala Gly Ser Gly Lys Val Ala Ala Ser Glu Ala
            260                 265                 270

Ala Ala Ala Asp Val Arg Ile Gln Lys Lys Ile Ala Val Pro Thr Asp
        275                 280                 285

Pro Leu Thr Gly Pro Glu Lys Ser Ala Lys Glu Gln Arg Thr Ala Asp
    290                 295                 300

Trp Ala Ile Met Lys Glu Met Ser Arg Tyr Leu Trp Pro Arg Gly Gly
305                 310                 315                 320

Ser Gly Ser Met Asp Thr Lys Leu Arg Val Ser Leu Ala Val Ser Leu
                325                 330                 335

Leu Val Gly Ala Lys Val Leu Asn Val Gln Val Pro Phe Tyr Phe Lys
            340                 345                 350
```

```
Ser Ile Val Asp Ala Met Asn Ile Asp Val Ala Ala Ala Gly Gly Thr
            355                 360                 365

Ala Ala Ala Val Ala Gly Ser Met Ile Leu Ala Tyr Gly Ala Thr Arg
        370                 375                 380

Ile Gly Ala Thr Val Leu Gln Glu Leu Arg Asn Ala Val Phe Ala Ser
385                 390                 395                 400

Val Ala Gln Lys Ala Ile Arg Asn Val Ala Arg Asn Val Phe Asp His
                405                 410                 415

Leu Leu His Leu Asp Leu Gly Phe His Leu Ala Lys Gln Thr Gly Gly
            420                 425                 430

Leu Thr Arg Ala Ile Asp Arg Gly Thr Lys Gly Ile Ser Phe Leu Leu
        435                 440                 445

Ser Ser Met Val Phe His Ile Leu Pro Thr Val Leu Glu Ile Gly Met
    450                 455                 460

Val Cys Ala Ile Leu Thr Tyr Gln Tyr Gly Ala Gln Phe Ala Ala Ile
465                 470                 475                 480

Thr Val Ala Thr Met Ala Ala Tyr Thr Gly Phe Thr Ile Thr Thr Thr
                485                 490                 495

Ala Trp Arg Thr Lys Phe Arg Arg Gln Ala Asn Ala Ala Asp Asn Arg
            500                 505                 510

Ala Ser Thr Val Ala Val Asp Ser Leu Ile Asn Tyr Glu Ser Val Lys
        515                 520                 525

Tyr Tyr Asn Asn Glu Pro Phe Glu Val Ala Arg Tyr Asp Ala Ala Leu
    530                 535                 540

Arg Gln Tyr Gln Lys Ser Ser Ile Lys Val Ala Thr Ser Leu Ala Phe
545                 550                 555                 560

Leu Asn Ser Gly Gln Asn Ile Ile Phe Ser Ser Ala Leu Thr Ala Met
                565                 570                 575

Met Tyr Leu Gly Ala Asp Gly Ile Ala Ser Asp Ser Leu Thr Val Gly
            580                 585                 590

Asp Leu Val Met Ile Asn Gln Leu Val Phe Gln Leu Ser Val Pro Leu
        595                 600                 605

Asn Phe Leu Gly Ser Val Tyr Arg Glu Leu Arg Gln Ser Leu Leu Asp
    610                 615                 620

Met Asp Thr Leu Phe Ser Leu Gln Arg Val Asn Val Ala Val Arg Asp
625                 630                 635                 640

Ala Pro Asn Ala Gln Pro Leu Leu Thr Asn Gly Gly Ala Ile Arg
                645                 650                 655

Phe Asp His Val Thr Phe Gly Tyr His Pro Asp Arg Pro Ile Met Arg
            660                 665                 670

Asp Leu Cys Leu Ala Ile Pro Ala Gly Lys Lys Val Ala Ile Val Gly
        675                 680                 685

Pro Ser Gly Cys Gly Lys Ser Thr Leu Leu Arg Leu Leu Phe Arg Phe
    690                 695                 700

Tyr Asp Val Asp Gln Gly Arg Ile Leu Ile Asp Asp Gln Asp Leu Arg
705                 710                 715                 720

His Val Thr Leu Asp Ser Leu Arg Arg Ser Ile Gly Val Val Pro Gln
                725                 730                 735

Asp Thr Ala Leu Phe Asn Asp Thr Val Glu His Asn Ile Ala Tyr Gly
            740                 745                 750

Gln Leu Asp Ala Pro His Asp Arg Val Val Ala Ala Arg Arg Ala
        755                 760                 765
```

```
Gln Val His Asp Ile Ile Gln Ser Trp Lys His Gly Tyr Gln Thr Lys
    770             775                 780

Val Gly Glu Arg Gly Leu Met Ile Ser Gly Gly Glu Lys Gln Arg Leu
785             790                 795                 800

Ala Val Ala Arg Leu Leu Leu Lys Asp Pro Pro Leu Leu Phe Phe Asp
                805                 810                 815

Glu Ala Thr Ser Ala Leu Asp Thr His Thr Glu Ala Ala Leu Met Ala
                820                 825                 830

Asn Ile Asn Ser Ile Leu Arg Glu Lys Ser Arg Thr Ser Val Phe Val
                835                 840                 845

Ala His Arg Leu Arg Thr Ile Tyr Asp Ala Asp Leu Ile Val Val Leu
        850                 855                 860

Lys Glu Gly Ser Val Ala Glu Met Gly Thr His Arg Glu Leu Ile Asp
865             870                 875                 880

Arg Asn Gly Val Tyr Ala Glu Leu Trp Ser Ala Gln Glu Thr Asn Phe
                885                 890                 895

Gln Val Glu Asp Val Glu Gly Asp Glu Ser Ile Thr Asp Asp Asp
                900                 905                 910

Asp Thr Pro Thr Lys
        915

<210> SEQ ID NO 14
<211> LENGTH: 757
<212> TYPE: PRT
<213> ORGANISM: Grosmannia clavigera
<220> FEATURE:
<223> OTHER INFORMATION: GcABC-B5

<400> SEQUENCE: 14

Met Ala Pro Thr Val Ala Glu Ser Trp Pro Glu Ala Ile Leu Gly Gln
 1               5                  10                  15

Leu Gln Leu Trp Tyr Gly Leu Val Ser Leu Val Val Phe Val Ser Ser
                20                  25                  30

Ile Ala Leu His Ser Val Trp Asp Val Arg Arg Gly Ala Glu Leu Ile
            35                  40                  45

Pro Pro Met Val Thr Gly Pro Gly Gly Arg Pro Leu Pro Ala Thr Arg
     50                  55                  60

Arg Lys Ser Gln Asp Thr Ser Ser Val Ala Phe Thr Pro Asn Leu Glu
65                  70                  75                  80

Ile Ser Arg His Ile Arg Arg Leu Tyr Cys Tyr Ala Ser Ser Ser Val
                85                  90                  95

Gly Leu Ser Phe Leu Ala Asn Phe Ile Ser Val Ile Ala His Thr Leu
            100                 105                 110

Glu Glu Ser Arg Asn Leu Asp Thr Lys Tyr Ser Trp Trp Cys Gly Glu
        115                 120                 125

Glu Thr Ser Arg Val Val Asn Phe Leu Val Pro Asn Gln Ile Gly Asn
    130                 135                 140

Ile Thr Asp Ala Phe Glu Ser Lys Asn Gly Leu Pro Trp Leu Glu Ile
145                 150                 155                 160

Leu Thr Leu Ile Phe Tyr Lys Val Leu Gln Gly Gln Gly Leu Leu
                165                 170                 175

Gly Ser Val Arg Ser Leu Ile Trp Ile Pro Val Ser Gln Tyr Ser Tyr
            180                 185                 190

Arg Ala Leu Thr Thr Ala Ala Phe Glu His Val His Ser Leu Ser Leu
        195                 200                 205
```

```
Asp Phe His Leu Gly Lys Arg Thr Gly Glu Val Leu Ser Ala Leu Asn
210                 215                 220

Lys Gly Ala Ala Ile Asn Ser Phe Leu Glu Gln Val Thr Phe Gln Val
225                 230                 235                 240

Phe Pro Met Leu Val Asp Leu Leu Val Ala Ile Val Tyr Phe Leu Phe
                245                 250                 255

Arg Phe Gly Ala Ile Tyr Ala Thr Ile Ala Ala Val Ile Thr Val Tyr
                260                 265                 270

Tyr Leu His Met Thr Val Lys Met Ala Ser Thr Arg Ala Asp Leu Arg
            275                 280                 285

Arg Asp Met Val Asn Ala Asp Arg Glu Glu Ala Val Lys Asn Asp
290                 295                 300

Ser Ile Thr Ser Tyr Glu Thr Val Lys Tyr Phe Asn Ala Glu Ala Phe
305                 310                 315                 320

Glu Phe Asn Arg Tyr Arg Asn Ala Ile Lys Ser Phe Gln Val Ala Glu
                325                 330                 335

Ala Lys Val Thr Trp Gly Met Asn Asn Met Asn Ile Cys Gln Ala Leu
                340                 345                 350

Val Phe Met Cys Gly Ile Leu Val Met Leu Met Val Ala Ala Val Glu
            355                 360                 365

Val Asn Gln Gly Met Arg Ser Val Gly Asp Phe Val Val Met Thr Thr
370                 375                 380

Tyr Leu Gly Gln Leu Gln Gly Pro Leu Asn Phe Phe Gly Ser Phe Tyr
385                 390                 395                 400

Arg Thr Val Gln Gln Ala Met Ile Ser Gly Glu Arg Leu Leu Glu Leu
                405                 410                 415

Phe Lys Ile Arg Pro Thr Val Val Asp Arg Pro Gly Val Lys Thr Leu
                420                 425                 430

Ser Gln Cys Arg Gly His Ile Arg Trp Thr Asn Val Lys Phe Trp Tyr
            435                 440                 445

Asp Ala Lys Arg Thr Ala Leu Arg Asp Leu Ser Phe Asp Cys Trp Pro
            450                 455                 460

Gly Thr Thr Thr Ala Phe Val Gly Glu Ser Gly Gly Gly Lys Ser Thr
465                 470                 475                 480

Ile Phe Arg Leu Met Phe Arg Tyr Tyr Asn Cys Gln Gly Gly Tyr Ile
                485                 490                 495

Glu Ile Asp Gly Asn Asn Val Glu Asp Val Thr Ile Asp Ser Val Arg
            500                 505                 510

Arg His Ile Gly Val Val Pro Gln Asp Thr Ile Leu Phe Asn Glu Thr
            515                 520                 525

Ile Met Tyr Asn Leu Lys Tyr Ala Asn Pro Ser Ala Ser Asn Glu Glu
530                 535                 540

Val Phe Asp Ala Cys Arg Ala Ala Ser Ile His Asp Arg Ile Leu Ser
545                 550                 555                 560

Phe Pro Tyr Gly Tyr Asn Thr Arg Val Gly Asp Arg Gly Thr Arg Leu
                565                 570                 575

Ser Gly Gly Glu Lys Gln Arg Val Ala Ile Ala Arg Thr Ile Leu Lys
            580                 585                 590

Asn Pro Lys Ile Ile Met Leu Asp Glu Ala Thr Ser Ala Leu Asp Ser
            595                 600                 605

Glu Thr Glu Gln Gln Ile Gln Ala Lys Leu Ile Arg Gly Gly Ser Leu
610                 615                 620

Gly Gln Asp Arg Thr Leu Leu Ile Ile Ala His Arg Leu Ser Thr Ile
```

```
                625                 630                 635                 640
        Thr His Ala Asp Gln Ile Ile Val Leu His Ala Gly Gly Ile Val Glu
                        645                 650                 655

Arg Gly Thr His Asn Glu Leu Leu Glu Leu Arg Gly Arg Tyr Ala Ser
                        660                 665                 670

Met Trp Glu Lys Gln Ser Gln Ala Glu Gln Ala Ala Val Ala Ala Arg
                        675                 680                 685

Asp Ala Thr Val Arg Ala Asn Gln Leu Leu Arg Gln Ala His Ile Ser
                        690                 695                 700

Asn Ser Pro Ile Gln Arg Arg Gly Gly Asp Glu Asn Ser Asp Gly Tyr
        705                 710                 715                 720

Thr Ser Leu Ser Ser Ser Thr Val Leu Ala Thr Gly Thr Thr Thr Pro
                        725                 730                 735

Arg Gln Gly Ser Ile Ala Arg Ser Pro Asp Ser Ser Asp Asp Asp Gln
                        740                 745                 750

Arg Pro Pro Ala His
                        755

<210> SEQ ID NO 15
<211> LENGTH: 996
<212> TYPE: PRT
<213> ORGANISM: Grosmannia clavigera
<220> FEATURE:
<223> OTHER INFORMATION: GcABC-B6

<400> SEQUENCE: 15

Met Leu Phe Cys Val Leu Ser Tyr Pro Ala Gln Ile Ala Val Val
        1               5                   10                  15

Val Pro Ser Ile Ile Thr Lys Lys Trp Leu Gly Gln Gln Asp Cys Met
                        20                  25                  30

Ile Ser Phe Leu Ser Cys Ile Leu Val Phe Gly Ile Gln Leu Ala Asn
                        35                  40                  45

Leu Ser Asp Ser Glu Glu Val Val Trp Tyr Pro His Ile Gly Pro Tyr
                50                  55                  60

Leu Leu Ala Leu Ile Phe Glu Pro Ala Leu Glu Ile Ile Ser Leu Ser
        65                  70                  75                  80

Ala Arg Glu Pro Gly Ala Leu Thr Ala Ser Glu Thr Ala Gln Leu Cys
                        85                  90                  95

Val Val Ala Ser Arg Tyr Leu Val Ile Thr Leu Ile Val Ala Thr Tyr
                        100                 105                 110

Phe Phe Ser Arg Asp Pro Pro Lys Ala Asn Gly Asn Val Asp Ser Glu
                        115                 120                 125

Gln Gln Pro Leu Ile Pro Lys Asn Asn Asn Gly Thr Pro Asn Glu Asn
                        130                 135                 140

Leu Asp Asp Ser Ala Gly Ser Gln Thr Ser Gln Thr Ser Gly Tyr Gly
        145                 150                 155                 160

Ser Thr Thr Asn Asn Ser Ser Ser Ser Arg Ser Thr Ser Asp Glu Glu
                        165                 170                 175

Ala Glu Ser Gly Thr Ala Ser Asn Thr Lys Lys Gly Asn Glu Ser Ser
                        180                 185                 190

Trp Glu Arg Arg Glu Arg Asp Ala Arg Glu Gly Met Glu Lys Arg Leu
                        195                 200                 205

Lys Glu Asn Gly Asn Trp Leu Glu Tyr Ala Lys Arg Phe Leu Ile Phe
                        210                 215                 220

Ile Pro Tyr Ile Trp Pro Val Asp Asn Arg Ser Leu Gln Val Arg Ala
```

-continued

```
                225                 230                 235                 240
Val Leu Val Gly Val Cys Leu Leu Ala Asn Asn Val Leu Asn Val Leu
                    245                 250                 255
Met Pro Arg Gln Leu Gly Ile Ile Ile Asp Ser Leu Ser His Val Asn
                260                 265                 270
Gly Lys Asn Pro Trp Ile Gln Val Ile Ile Tyr Ala Gly Leu Lys Phe
                    275                 280                 285
Cys Gly Ser Glu Ala Gly Leu Ser Leu Leu Arg Gln Trp Leu Trp Val
                290                 295                 300
Pro Val Glu Phe Tyr Ser Phe Asp Ala Met Ser Thr Ala Ala Tyr Ser
305                 310                 315                 320
His Val Leu Asn Leu Ser Ser Asp Phe His Asp Ser Lys Ser Ser Ser
                    325                 330                 335
Asp Ile Met Met Ala Ile Thr Ser Gly Gln Ser Val Ser Asn Leu Leu
                340                 345                 350
Glu Ser Ile Cys Phe Ser Ala Ile Pro Met Leu Ile Asp Met Phe Ile
                355                 360                 365
Ala Phe Leu Tyr Leu Ser Val Thr Phe Gly Pro Tyr Glu Gly Phe Ile
                370                 375                 380
Thr Leu Ala Thr Ala Ile Ile Phe Leu Tyr Ile Ala Gly Arg Met Ile
385                 390                 395                 400
Ser Gly Leu Lys Gln Ala Arg Arg Asn Glu Val Ser Ala Trp Phe Glu
                    405                 410                 415
Glu His Tyr Val Arg Gln Ala Gly Ile Gln Gly Trp Ser Thr Val Ala
                420                 425                 430
Ser Phe Asn Gln Val Ser His Glu Glu Gln Arg Tyr Ser Ile Ala Val
                    435                 440                 445
Lys Asp Arg Val Ala Lys Ser Gln Ala Val Tyr Phe Gly Tyr Leu Met
                450                 455                 460
Ala Tyr Ala Phe Gln Tyr Leu Val Leu Leu Ala Gly Leu Leu Ala Gly
465                 470                 475                 480
Ala Phe Leu Ala Val Trp Gln Val Thr Ser Gly Gln Ala Thr Pro Gly
                    485                 490                 495
Gln Phe Ile Met Leu Leu Thr Tyr Trp Thr Gln Leu Val Tyr Pro Leu
                500                 505                 510
Ser Phe Phe Ala Ser Leu Gly Lys Asn Ile Ser Arg Asn Phe Ile Gln
                    515                 520                 525
Ala Glu Ser Leu Leu Glu Ile Met Lys Thr Lys Pro Thr Ile Val Ser
                530                 535                 540
Lys Glu Asn Ala Ser Glu Leu Asp Phe Ser Gly Gly Ala Val Glu Phe
545                 550                 555                 560
Asp Arg Val Cys Phe Ser Tyr Asn Asp Lys Lys Asp Ile Leu Lys Asp
                    565                 570                 575
Ile Thr Phe Tyr Ala Gln Pro Gly Thr Thr Ile Ala Phe Val Gly Ala
                580                 585                 590
Thr Gly Ala Gly Lys Ser Thr Ile Leu Lys Leu Leu Asp Arg Phe Tyr
                    595                 600                 605
Asp Val Ser Glu Gly Ser Ile Lys Ile Asp Gly Gln Asp Val Arg Asp
                610                 615                 620
Val Glu Leu Tyr Ser Leu Arg Ser Arg Ile Gly Ile Val Pro Gln Ser
625                 630                 635                 640
Pro Ile Leu Phe Asn Asp Thr Ile Met Asn Asn Val Arg Tyr Ala Asn
                    645                 650                 655
```

```
Leu Thr Ala Thr Ala Glu Glu Val His Asp Ala Cys Arg Ala Cys
            660                 665                 670

Ile His Asp Gln Ile Leu Gly Phe Thr Asp Gly Tyr Glu Thr Arg Val
        675                 680                 685

Gly Glu Arg Gly Val Lys Leu Ser Gly Gly Glu Leu Gln Arg Val Ala
    690                 695                 700

Ile Ala Arg Ala Leu Leu Lys Asn Pro Ser Ile Val Met Leu Asp Glu
705                 710                 715                 720

Ala Thr Ser Ser Val Asp Thr Glu Thr Glu Gln Lys Ile Gln Glu Ala
                725                 730                 735

Leu His Ala Leu Cys His Gly Arg Thr Thr Phe Val Val Ala His Arg
            740                 745                 750

Leu Ser Thr Val Met Asn Ala Asp Arg Ile Ile Val Ile Ser Glu Gly
        755                 760                 765

Lys Ile Val Glu Gln Gly Cys His Asp Asp Leu Ile Ser Ala Asn Gly
    770                 775                 780

Lys Tyr Ala Ser Leu Trp Ser Lys Gln Val Phe Thr Lys Pro Lys Glu
785                 790                 795                 800

Lys Ala Lys Ser Pro Val Asp Ser Val Leu Asn Val Pro Asp Ile Val
                805                 810                 815

Asn Asp Leu Asp Pro Glu Val Thr Asn Cys Glu Leu Ala Lys Ala Gln
            820                 825                 830

Lys Lys Thr Thr Ala Glu Thr Pro Ser Pro Asn Gly Val Asp Lys Glu
        835                 840                 845

Ser Glu Gln Ala Leu Asp Ser Gly Lys Gly Lys Asp Ile Ala Val Pro
    850                 855                 860

Ile Glu Asp Ala Pro Ser Ser Thr Thr His Val Ala Ala Asp Ser Glu
865                 870                 875                 880

Val Thr Val Ala Glu Ala Leu Pro Ser Met Thr Glu Lys Asp Gly Leu
                885                 890                 895

Ser Arg Arg Ser Asp Tyr Arg Arg Leu Gly Gly Ser Arg His Asn Asp
            900                 905                 910

Arg Thr Asp Ser Cys Glu Asp Leu Gly Asp Leu Ala His Ala Ile Asp
        915                 920                 925

Ala Gly Ser Ser Thr Ile Ser Gly Arg Ser Gly Ser Asn Arg Glu Leu
    930                 935                 940

Ser Glu Ser Leu Gln Arg Ser Thr Asp Ala Thr Glu Ala Asp Glu Ser
945                 950                 955                 960

Leu Glu Met Ala Ala Pro Gln Ala Leu Glu Ile Lys Ser Gln Ala Ala
                965                 970                 975

Ala Ala Asn Asn Ile Ser Thr Gly Ser Val Lys Ser Arg His Lys Ser
            980                 985                 990

Ser Arg Val Arg
        995

<210> SEQ ID NO 16
<211> LENGTH: 1153
<212> TYPE: PRT
<213> ORGANISM: Grosmannia clavigera
<220> FEATURE:
<223> OTHER INFORMATION: GcABC-B7

<400> SEQUENCE: 16

Met Ala Tyr Thr Asp Asp Ala Val Leu Ala Lys Leu Ser Ala Leu Asn
1               5                   10                  15
```

```
Glu Thr His Asp Ser Ile Ala Thr Ala Ala Gln Trp Ile Met Phe His
            20                  25                  30

Arg Arg His Ala Glu Arg Thr Val Gln Leu Trp Phe Gln Arg Leu Lys
        35                  40                  45

Asp Ser Pro Ser Pro Lys Arg Leu Asn Leu Val Tyr Leu Ala Asn Glu
    50                  55                  60

Val Thr Gln Gln Ser Lys Ala Arg His Lys Glu Asp Phe Val Val Ala
65                  70                  75                  80

Phe Ser Pro Val Ile Ala Glu Ala Ile Ala Ser Ala Tyr Lys Gly Ala
                85                  90                  95

Pro Ser Glu Val Gln Asn Lys Leu Arg Arg Val Asp Val Trp Arg
            100                 105                 110

Glu Arg Asn Ile Phe Glu Val Pro Ile Gln Thr Ala Val Glu Thr Arg
        115                 120                 125

Ile Gly Glu Leu Asp Lys Ala Lys Gly Thr Ser Arg Pro Ala Phe Gly
    130                 135                 140

Gly Gly Ser Ile Phe Gly Ser Ser Ser Gly Pro Val Pro Ala Glu
145                 150                 155                 160

Leu Gly Pro Val Val Ala Ser Gln Gln Lys Leu Ser Lys Val Leu Leu
                165                 170                 175

Ser Ala Gln Gly Ser Val Ser Val Ala Asp Ala Asp Phe His Lys Ile
            180                 185                 190

Met Asp Gly Thr Pro Pro Ala Ala Pro Val Tyr Ala Ala Arg Leu Asn
        195                 200                 205

Gly Leu Met Lys Ser Ile Ala Ser Ala Glu Gln Ala Met Gly Gln Thr
    210                 215                 220

Val Lys Ala Arg Ser Glu Leu Lys Ala Val Leu Glu Gly Leu Leu Ala
225                 230                 235                 240

Ser Cys Gln Thr Ala Leu Glu Ala Glu Val Gln Gln Leu Thr Glu Leu
                245                 250                 255

Gly Gln Arg Arg Ala His Val Asp Ala Thr Lys Arg Asp Val Glu Asp
            260                 265                 270

Arg Ile Met Arg Gly Leu Asn Ala Thr Asp Asn Glu Ala Gly Arg Ser
        275                 280                 285

Ser Thr Gly Ala Gly Gln Pro Gln Glu Pro Arg Pro Glu Met Glu
    290                 295                 300

Ala Leu Thr Pro Pro Ala Thr Glu Pro Asp Glu Thr Gly Gly Glu Pro
305                 310                 315                 320

Phe Ala Gly Val Val Ser Ile Ser Glu Val Ala Glu Gln Met Thr Asp
                325                 330                 335

Ser Ala Val Val Ala Glu Gln Ser Leu Pro Ala Ser Ile Ser Ser Ala
            340                 345                 350

Ser Gly Ile Glu Ile Leu Ser His Leu Ala Ser Gln Ala Gln Pro Val
        355                 360                 365

Ser Thr Asn Gly Ala His Lys Arg Arg Val Leu Glu Glu Lys Gly
    370                 375                 380

Asp Glu Val Pro Asp Leu Asp Asp Gly Ile Asp Ala Asp His Ala Asp
385                 390                 395                 400

Leu Arg Arg Arg Ser Asp Gly Phe Arg Gly Pro Ala Ala Pro Gly Arg
                405                 410                 415

Ala Ala Thr Pro Gly Thr Arg Ser Gly Gly Ser Trp Arg Gln Arg Ala
            420                 425                 430
```

```
Val Ala Gly Ala Thr Gly Ser Asp Val Gly Asp Glu Ala Gly Ser
            435                 440                 445

Val Asp Thr Gly Gly Ile Glu Arg Gly Arg Cys Cys Gly Gly Gly Ser
450                 455                 460

Thr Glu Asp Asp Arg Thr Ala Arg Leu Ala Gly His Ala Thr Arg Thr
465                 470                 475                 480

Val Asp Asp Asn Ala Thr Arg Thr Ser Asp Asp Arg Thr Ala Arg Ala
                485                 490                 495

Ser Asp Gly Ser Ser Thr Ala Glu Arg Ala Glu Gln Ala Thr Gln Val
            500                 505                 510

Asn Leu Gln Ala Arg Leu Ser Lys Glu Gly Lys Thr Gln Ser Arg Ala
            515                 520                 525

Thr Ala Ser Glu Val Trp Arg Leu Val Arg Ile Ala Arg Pro Glu Phe
530                 535                 540

Arg Trp Leu Ala Leu Ala Phe Gly Phe Leu Leu Phe Ser Ser Ala Val
545                 550                 555                 560

Ser Met Ser Ile Pro Phe Ser Val Gly Arg Leu Leu Asp Leu Ala Thr
                565                 570                 575

Lys Gly Ala Val Ala Asp Val Arg Val Leu Gly Leu Thr Leu Asn Gln
            580                 585                 590

Phe Phe Val Ala Phe Gly Ala Val Leu Thr Val Gly Ala Leu Ser Ser
            595                 600                 605

Phe Leu Arg Ile Ile Ile Leu Arg Ile Val Ser Glu Arg Val Val Ala
            610                 615                 620

Arg Leu Arg Thr Gln Leu Tyr Arg His Thr Tyr Thr Gln Asp Ala Glu
625                 630                 635                 640

Phe Phe Asp Ala Asn Arg Val Gly Asp Leu Ile Ser Arg Leu Ser Ser
                645                 650                 655

Asp Thr Ile Ile Val Gly Lys Ser Ile Thr Gln Asn Leu Ser Asp Gly
            660                 665                 670

Met Arg Ala Val Val Ser Gly Ser Ala Gly Leu Ala Ala Met Leu Trp
            675                 680                 685

Met Ser Pro Gln Leu Thr Ser Ile Leu Val Val Met Phe Pro Pro Ile
690                 695                 700

Ala Val Gly Ala Val Leu Tyr Gly Arg Val Ile Arg Ser Val Ala Arg
705                 710                 715                 720

Arg Ile Gln Ala Asn Leu Gly Ser Leu Thr Lys Ile Ala Glu Glu Arg
                725                 730                 735

Leu Gly Asn Val Lys Thr Ser Gln Ala Phe Ala Gly Glu Val Gln Glu
            740                 745                 750

Val Ala Arg Tyr Asn Arg Gln Val Arg Ile Phe Ala Leu Gly Arg
            755                 760                 765

Arg Glu Ala Leu Val Ser Ala Ala Tyr Phe Gly Ala Asn Gly Trp Phe
    770                 775                 780

Gly Asn Met Thr Ile Leu Ala Leu Val Val Gly Gly Asn Leu Val
785                 790                 795                 800

Arg Ser Gly Ala Met Ser Val Gly Asp Leu Thr Ser Phe Met Met Tyr
                805                 810                 815

Thr Ala Phe Ala Gly Ser Ser Leu Phe Gly Val Ser Gly Phe Tyr Ser
            820                 825                 830

Glu Leu Met Lys Gly Val Gly Ala Ala Glu Arg Leu Phe Glu Leu Leu
            835                 840                 845

Asp Arg Gln Pro Ala Val Arg Ala Thr Val Gly Arg Arg Val Val Ser
```

```
                850                 855                 860
Ala Gln Gly Pro Ile Val Phe Asp Asn Val Arg Phe Ala Tyr Pro Thr
865                 870                 875                 880

Arg Pro Ala Val Arg Ile Phe Asp Gly Leu Ser Phe Thr Ile Pro Ser
                885                 890                 895

Gly Ser Asn Val Cys Ile Val Gly Pro Ser Gly Gly Lys Ser Thr
                900                 905                 910

Val Ala Ser Leu Leu Leu Arg Phe Tyr Asp Pro Thr Ala Gly Arg Met
                915                 920                 925

Ala Ile Asn Gly Val Asp Val Thr Ser Met Asn Ala Lys Ser Leu Arg
        930                 935                 940

Arg Arg Ile Gly Met Val Ser Gln Glu Pro Val Leu Phe Ser Gly Ser
945                 950                 955                 960

Ile Ala Asp Asn Ile Ala Tyr Gly Arg Pro His Ala Ser Arg Ala Asp
                965                 970                 975

Ile Ile Ala Ala Ala Gln Arg Ala Asn Cys Gln Phe Ile Ser Asp Phe
                980                 985                 990

Pro Asp Gly Leu Glu Thr Ala Val Gly Pro Arg Gly Ala Gln Leu Ser
                995                 1000                1005

Gly Gly Gln Lys Gln Arg Ile Ala Ile Ala Arg Ala Leu Ile Lys Asp
        1010                1015                1020

Pro Asp Ile Leu Ile Leu Asp Glu Ala Thr Ser Ala Leu Asp Ala Glu
1025                1030                1035                1040

Ser Glu Thr Leu Val Asn Ala Ala Leu Ala Glu Leu Leu Lys Ser Arg
                1045                1050                1055

Ser Thr Thr Ile Ser Ile Ala His Arg Leu Ser Thr Ile Lys Arg Ser
                1060                1065                1070

Asp Gln Ile Ile Val Leu Asn Ser His Gly Thr Val Ala Glu Thr Gly
        1075                1080                1085

Arg Tyr Ala Asp Leu Ser Ala Asp Pro Ala Ser Ala Phe Ser Arg Leu
        1090                1095                1100

Met Glu Trp Gln Met Ser Gly Ser Asp Leu Pro Ala Ser Ala Val Ala
1105                1110                1115                1120

Thr Ala Arg Ile Asp Gly His Val Thr Glu Arg Glu Ile Glu Asp
                1125                1130                1135

Asp Leu Glu Lys Pro Asp Glu Thr Asp Val Asp Ser Ser Lys Ala Arg
                1140                1145                1150

Pro

<210> SEQ ID NO 17
<211> LENGTH: 1746
<212> TYPE: PRT
<213> ORGANISM: Grosmannia clavigera
<220> FEATURE:
<223> OTHER INFORMATION: GcABC-C1

<400> SEQUENCE: 17

Met Gly Gln Pro Ser Cys Ser Trp Pro Ile Trp Arg Val Asp Asp Phe
1               5                   10                  15

Thr Val Cys Phe Gln Arg Asp Tyr Leu Lys Thr Leu Phe Pro Ala Ile
                20                  25                  30

Ile Ile Ser Ile Ser Phe Leu Ile Val Leu Ser Gln Thr Leu Leu Arg
        35                  40                  45

Ala Val Lys Leu Lys Arg Thr Thr Asn Tyr Arg Ala Leu Arg Thr Asp
    50                  55                  60
```

```
Leu Asp His Thr Ala Leu Pro Gln Ala Asp Ser Ile Asp Ser Glu Asp
 65                  70                  75                  80

Asp Thr Val Ala Ala Val Ala Ser Arg Ser Ala Asp Ala Asp Ala
             85                  90                  95

Asp Asp Asp Asp Asp Asp Gly Leu Ser Ile Asn Thr Gly Arg Asn
                100                 105                 110

Thr Leu Val Arg Thr Ile Thr Lys Gly Ser Ile Val Gln Ala Asp Thr
            115                 120                 125

Pro Val Gly Gln Thr Leu Ser Ile Val Val Glu Asp Leu Ala Ile Ala
130                 135                 140

Gly Leu Val Ala Val Asn Ala Ile Ala Leu Ala Thr Gly Ala Tyr Gly
145                 150                 155                 160

Gly Ser Arg Tyr Gly Ala Pro Glu Lys Gly Lys Gly Ser Ile Ala Ala
                165                 170                 175

Val Val Gly Leu Leu Leu Trp Val Tyr Ala Phe Val Leu Val Thr Leu
            180                 185                 190

Arg Leu Val Leu Val Lys Thr Gln Trp Arg Ile Ser His Leu Trp Asn
            195                 200                 205

His Thr Ala Ile Ile Tyr Phe Leu Gln Trp Leu Met Asp Ser Val Ile
210                 215                 220

Cys Arg Ser Val Ile Ile His Pro Thr Ser Arg Thr Val Glu Val Leu
225                 230                 235                 240

Val Ile Val Glu Phe Ala Leu Thr Ser Leu Leu Phe Met Ala Ile
                245                 250                 255

Thr Thr Arg Lys Gly Asn Lys Thr Val Leu Leu Glu Trp Glu Asp Gly
            260                 265                 270

Val Pro Pro Ser Arg Glu Ser Leu Ala Ser Leu Phe Ser His Tyr Thr
    275                 280                 285

Phe Ser Trp Val Asp Ser Ile Val Trp Asp Gly Tyr Arg Glu Pro Leu
290                 295                 300

Glu Met Ser Arg Val Trp Asn Leu Asp Pro Lys Asp Lys Ala Ala Ala
305                 310                 315                 320

Val Leu Ser His Tyr Arg Arg Met Gln Lys Arg Ala Ser Leu Ala Ala
                325                 330                 335

His Leu Leu Phe Phe Phe Lys Gly Ser Leu Ala Val Gln Ala Gly Trp
                340                 345                 350

Ala Ile Ile Ser Gly Ile Phe Thr Phe Ala Pro Thr Met Leu Leu Lys
            355                 360                 365

Ala Ile Leu Glu Tyr Val Glu Asp Ser Lys Gly Ala Pro Ile Asn Val
370                 375                 380

Leu Trp Leu Tyr Val Phe Leu Leu Pro Ile Thr Asp Leu Val Arg Ala
385                 390                 395                 400

Val Gly Asp Asn Arg Ala Leu Trp Val Gly Arg Lys Ile Cys Ile Asn
                405                 410                 415

Ile Arg Ala Ile Leu Val Gly Glu Ile Tyr Ala Lys Ala Leu Arg Arg
                420                 425                 430

Lys Ala Ala Thr Gly Lys Asp Ser Val Leu Gly Gly Ser Glu Thr Lys
            435                 440                 445

Asp Ala Thr His Ala Lys Asp Lys Ser Trp Ile Ala Ser Ile Arg Gly
            450                 455                 460

Lys Leu Gly Leu Ser Ala Lys Lys Gly Ala Ala Asp Ser Ala Asn
465                 470                 475                 480
```

```
Gly Ala Ser Lys Lys Ala Gly Ser Ser Ala Asp Ala Ser Ala Gln Asp
            485                 490                 495

Glu Gln Ala Asn Ile Gly Thr Ile Ile Asn Leu Met Ser Val Asp Ser
        500                 505                 510

Phe Lys Val Ser Glu Val Thr Ala Tyr Leu His Tyr Leu Val Ala Ser
        515                 520                 525

Ala Pro Thr Gln Leu Leu Val Ser Val Tyr Leu Leu Tyr Arg Val Met
        530                 535                 540

Gly Leu Ser Ala Ile Pro Gly Phe Ile Val Met Ala Ala Leu Leu Pro
545                 550                 555                 560

Ile Asn Ile Ala Phe Ala Lys Ala Phe Thr Thr Thr Gln Lys Lys Ile
                565                 570                 575

Met Ala Ala Thr Asp Lys Arg Ile Gln Thr Thr Asn Glu Val Leu Gln
                580                 585                 590

Asn Ile Arg Ile Val Lys Tyr Phe Ala Trp Glu Leu Arg Phe Gly Lys
                595                 600                 605

Ile Val Asp Glu Lys Arg Arg Ile Glu Leu Arg Ala Leu Arg Lys Arg
        610                 615                 620

Tyr Thr Ile Trp Ala Cys Ala Val Ala Ile Trp Asn Thr Val Pro Ile
625                 630                 635                 640

Leu Ile Thr Phe Phe Cys Phe Leu Val Tyr Thr Val Ile Glu Lys Lys
                645                 650                 655

Pro Leu Tyr Pro Ser Val Ala Phe Thr Ala Ile Ser Leu Phe Met Leu
                660                 665                 670

Leu Arg Tyr Pro Leu Asp Gln Leu Gly Asp Met Ile Ala His Val Gln
            675                 680                 685

Glu Ser Arg Val Ser Ile Asp Arg Ile Glu Glu Phe Leu Ser Glu Glu
        690                 695                 700

Glu Thr Glu Lys Phe Ile Gln Leu Gly Glu Glu Asn Ile Asp Glu Ser
705                 710                 715                 720

Thr Gly Glu Arg Val Ile Gly Phe Arg Asn Asn Ala Ser Phe Ile Trp
                725                 730                 735

Gly Gly Arg Asp Val Val Ala Ser Asp Gly Thr Thr Ala Phe Arg Leu
            740                 745                 750

Met Asp Leu Asn Val Asp Phe Ala Ile Gly Lys Leu Asn Val Ile Thr
        755                 760                 765

Gly Pro Thr Gly Ser Gly Lys Thr Ser Leu Leu Met Ala Leu Leu Gly
        770                 775                 780

Glu Met Thr Leu Thr His Gly Arg Val Tyr Leu Pro Gly Gly Arg Ser
785                 790                 795                 800

Arg Glu Asp Ile Arg Pro Asp Pro Glu Thr Gly Leu Ala Glu Ser Cys
                805                 810                 815

Ala Tyr Val Ala Gln Gln Ala Trp Leu Val Asn Gly Thr Ile Arg Glu
                820                 825                 830

Asn Ile Leu Phe Ser Ser Ala Phe Asp Glu Gln Arg Tyr Arg Asp Val
            835                 840                 845

Ile Val Ala Cys Ala Leu Glu His Asp Ile Asp Glu Thr Leu Asp Asn
        850                 855                 860

Gly Asp Glu Thr Leu Val Gly Glu Lys Gly Ile Thr Leu Ser Gly Gly
865                 870                 875                 880

Gln Lys Gln Arg Ile Ser Leu Ala Arg Ala Leu Tyr Ser Asn Ser Arg
                885                 890                 895

His Leu Leu Leu Asp Asp Cys Leu Ser Ala Val Asp Ser His Thr Ala
```

```
                900             905             910
Lys Trp Ile Phe Ser Asn Cys Ile Arg Gly Pro Leu Met Arg Gly Arg
            915             920             925

Thr Cys Ile Leu Val Thr His Asn Val Ser Leu Cys Val Pro His Ser
        930             935             940

Glu Tyr Ser Val Ile Met Asn Asn Gly Arg Ile Ala Asp His Gly Pro
945             950             955             960

Thr Gln Gly Leu Ile Asp Ala Gly Lys Tyr Gly Asp Glu Val Gln Gln
            965             970             975

Lys Ser Leu Pro Gly Ser Ala Thr Ile Ser Arg Ile Pro Ser Arg Val
        980             985             990

Pro Ser Ser Val Gly Asp Glu Ala Glu Asn Glu Thr Asn Gly Thr Leu
    995             1000            1005

Val Asp Asp Gly Gly Ala Ala Asp Pro Ser Leu Pro Ser Thr Thr Thr
    1010            1015            1020

Asn Arg Thr Lys Arg Ala Lys Gln Ala Ala Thr Arg Gln Asp Ser Thr
1025            1030            1035            1040

Glu Glu Thr Lys Ser Thr Gly Ala Val Lys Trp Ser Val Met Lys Leu
            1045            1050            1055

Tyr Leu Ser Ser Met Gly Ser Trp Trp Phe Trp Leu Val Ala Val Leu
            1060            1065            1070

Val Phe Ser Thr Gln Gln Phe Ser Leu Val Ala Ser Asn Leu Trp Ile
        1075            1080            1085

Lys Gln Trp Ala Asn Gln Tyr Thr Glu Glu Ser Ala Asp Ala Ala Ala
        1090            1095            1100

Thr Ile Trp Asn Ser Thr Val Ser Val Ala Thr Gly Leu Gly Arg Gln
1105            1110            1115            1120

Pro Ser Ile Tyr Ala Arg Ser Met Val Gln His Val Met Ser Pro Asp
            1125            1130            1135

Thr Ser Ser Tyr Leu Ser Thr Val Ser Gln Thr Trp Met Pro Lys Asn
            1140            1145            1150

Ser Thr Val Phe Gln Ala Asp Ser Ala Leu Ala Ala Ala Met Asp Pro
        1155            1160            1165

Gln Val Asn Val Gln Tyr Tyr Leu Leu Ile Leu Ala Ile Gly Ile
    1170            1175            1180

Ala Gly Ser Val Leu Ala Phe Val Arg Asp Ile Trp Ile Phe Gly
1185            1190            1195            1200

Ser Leu Thr Ala Ser Trp Lys Leu His Asp Gln Leu Met His Tyr Val
            1205            1210            1215

Ala Phe Ser Lys Phe Lys Phe Asp Val Thr Pro Leu Gly Gln Met
            1220            1225            1230

Met Asn Arg Phe Ser Lys Asp Leu Glu Ala Val Asp Gln Glu Val Ala
        1235            1240            1245

Pro Val Ala Ile Thr Val Met Thr Cys Ala Leu Gly Ile Val Ile Thr
    1250            1255            1260

Ile Val Leu Ile Ala Met Ile Thr Pro Gly Phe Leu Val Ala Ala Leu
1265            1270            1275            1280

Phe Ile Thr Val Leu Tyr Val Leu Leu Gly Lys Phe Tyr Leu Ala Ser
            1285            1290            1295

Ser Arg Asp Leu Lys Arg Leu Glu Ser Val Gln Arg Ser Pro Leu Phe
            1300            1305            1310

Gln Gln Phe Gly Glu Thr Leu Ser Gly Val Thr Thr Ile Arg Ala Tyr
        1315            1320            1325
```

```
Gly Asp Glu Arg Arg Phe Val Arg Asp Asn Leu Ala Arg Ile Asn Ala
    1330                1335                1340

Gln Leu Arg Pro Phe Ile Tyr Leu Trp Ala Ala Asn Arg Trp Leu Ser
1345                1350                1355                1360

Leu Arg Thr Asp Leu Leu Gly Asn Met Val Ser Phe Phe Ala Gly Val
            1365                1370                1375

Phe Val Ile Leu Ser Leu Gly Leu Ile Asp Ala Gly Ser Ala Gly Ile
        1380                1385                1390

Ser Leu Ser Tyr Ala Ile Gly Phe Ala Glu Asn Ile Leu Trp Leu Val
        1395                1400                1405

Arg Leu Tyr Ala Met Asn Glu Gln Asn Met Asn Ser Val Glu Arg Ile
    1410                1415                1420

Lys Glu Tyr Leu Glu Val Glu Gln Glu Ala Pro Ala Val Val Glu Asp
1425                1430                1435                1440

Cys Arg Pro Pro Ala Asn Trp Pro Ser Gln Gly Ala Val Glu Phe Val
            1445                1450                1455

Asp Tyr Thr Thr Arg Tyr Arg Glu Asp Leu Asp Pro Val Leu Arg His
        1460                1465                1470

Leu Thr Phe Arg Ile Ala Pro His Glu Lys Val Gly Ile Val Gly Arg
        1475                1480                1485

Thr Gly Ala Gly Lys Ser Ser Leu Ala Leu Ala Leu Phe Arg Ala Leu
    1490                1495                1500

Glu Ala Glu Thr Gly Lys Val Leu Ile Asp Gly Leu Asp Ile Gly Gln
1505                1510                1515                1520

Met Gly Leu Arg Asp Leu Arg Glu Ala Ile Thr Ile Val Pro Gln Glu
            1525                1530                1535

Pro Thr Leu Phe Met Gly Thr Ile Arg Ser Asn Leu Asp Pro Phe Asp
        1540                1545                1550

Asn Tyr Ser Asp Glu Asp Ile Phe Ala Ala Leu Arg Arg Val His Leu
        1555                1560                1565

Ile Gly Pro Asp Glu Arg Ile Pro Gly Glu Pro Leu Gly Glu Ala Thr
    1570                1575                1580

Ala Ala Ala Glu Gly Ser Ser Ser Ser Glu Ala Asp Val Pro Thr
1585                1590                1595                1600

Pro Thr Ser Pro Thr Asn Lys Asn Val Phe Leu Asp Leu Ser Thr Ser
            1605                1610                1615

Val Ala Glu Ser Gly Ser Asn Leu Ser Gln Gly Gln Arg Gln Leu Leu
        1620                1625                1630

Cys Leu Ala Arg Ala Met Leu Lys Asn Pro Asn Val Leu Leu Met Asp
        1635                1640                1645

Glu Ala Thr Ala Ser Ile Asp Tyr Ala Thr Asp Ala Lys Ile Gln Asp
    1650                1655                1660

Thr Ile Arg Glu Leu Thr Ser Thr Ile Thr Ile Ala His Arg Leu
1665                1670                1675                1680

Gln Thr Ile Ala Asp Tyr Asp Lys Val Leu Val Leu Asp Arg Gly Ser
            1685                1690                1695

Leu Val Glu Tyr Asp His Pro Trp Lys Leu Met Ser Lys Glu Asp Gly
        1700                1705                1710

Val Phe Arg Ser Met Cys Asp Met Ser Gly Asp Tyr Glu Thr Leu Ala
        1715                1720                1725

Lys Ile Ala Lys Lys Ala Phe Glu Thr Lys Thr Leu Ile Asp Val Glu
    1730                1735                1740
```

Gln Gln
1745

<210> SEQ ID NO 18
<211> LENGTH: 1717
<212> TYPE: PRT
<213> ORGANISM: Grosmannia clavigera
<220> FEATURE:
<223> OTHER INFORMATION: GcABC-C2

<400> SEQUENCE: 18

Met Asp Asp Ser Ser Trp Ala Leu Leu His Pro Ile Thr Gly Thr Gly
 1               5                  10                  15

Thr Leu Gly Phe Val Phe Leu Ser Ser Leu Pro Ala Leu His Gln Leu
             20                  25                  30

Trp Leu Arg Ala Ser Phe Ala Arg Arg Asn Arg Gly Ala Glu Gly Asp
         35                  40                  45

Gly Gly His Glu Ala Val Pro Gln Leu Phe Glu Ser Pro Asp Gly Gln
     50                  55                  60

Ala Thr Ala Glu Ser Val Ala Ala Phe Ser Asp His Gln Pro Arg Leu
65                  70                  75                  80

Ala Val Trp Thr Ser Leu Leu Leu Gly Leu Ala Ser Leu Ile Gly
             85                  90                  95

Ala Val Leu Ser Ser Ile Gly Pro Asp Gly Gly His Phe Ser Pro Thr
            100                 105                 110

Ser Thr Ser Trp Leu Arg Val Leu Asp Asn Trp Ile Asp Val Pro Thr
        115                 120                 125

Trp Gly Leu Gly Leu Leu Gln Cys Ala Ser Ile Pro Thr Lys Ser Gln
    130                 135                 140

Tyr Asp Cys Arg Phe Leu Leu Ala Thr Ile Gly Phe Trp Ser Gly Ala
145                 150                 155                 160

Ala Leu Thr Thr Ser Val Leu Val Arg His Gly Phe Gly Ile Val Leu
                165                 170                 175

Ala Leu Ser Gly Lys Ser Glu Gly Gly Tyr Asn Gly Val Val Val Gly
            180                 185                 190

Ala Ala Val Cys Trp Leu Val Glu Val Leu Cys Ala Leu Ala Ala Ser
        195                 200                 205

Leu Ala Phe Ala Ser Phe Pro His Arg Pro Asp Val Tyr Tyr Arg Gly
    210                 215                 220

Gly Leu Val Asp Gln Gln His Ala Val Ser Arg Leu Gln Leu Phe Gly
225                 230                 235                 240

Phe Thr Trp Asn Arg Val Ile Phe Asp Ile Ala His Glu Arg Lys Leu
                245                 250                 255

Glu Leu Glu Asp Leu Pro Asn Leu Asp Gly Glu Thr Arg Ser Ser Ser
            260                 265                 270

Ile Leu Glu Thr Tyr Leu Ala Asp Gly Gly Ser Ala Gly Gly Glu Lys
        275                 280                 285

Gly Arg Leu Trp Trp Gln Leu Ala Lys Ala Tyr Arg Trp Pro Leu Phe
    290                 295                 300

Gln Gln Trp Thr Leu Thr Phe Val Arg Ser Ile Leu Ala Leu Phe Pro
305                 310                 315                 320

Gln Tyr Val Leu Tyr Gln Phe Leu Glu Gly Leu Asp Lys His Lys Asp
                325                 330                 335

Gly Asn Lys Ala Ala Asn Pro Gln Leu Trp Gly Trp Val Ile Ser Leu
            340                 345                 350

```
Gly Val Ser Leu Val Leu Gln Val Trp Val Asn Ser Ile Gln Arg Trp
            355                 360                 365

Leu Thr Ala Ser Arg Leu Glu Ala Pro Val Ser Ser Leu Ile Gln Ala
    370                 375                 380

Leu Ile Phe Gln Lys Ala Leu His Leu Asp Glu Ala Ala Glu Pro Gly
385                 390                 395                 400

Gln Ala Thr Val Gly His Thr Lys Val Ala Gly Leu Asp Lys Lys
                405                 410                 415

Asp Pro Lys Lys Asn Ser Gly Asp Ile Arg Gln Ser Val Val Asn
            420                 425                 430

His Met Lys Leu Asp Ser Gly Arg Met Thr Ile Phe Cys Thr Tyr Asn
            435                 440                 445

Tyr Trp Ile Pro Leu Ala Val Phe Lys Leu Ile Leu Ala Gly Thr Ala
    450                 455                 460

Leu Gly Arg Leu Leu Gly Trp Thr Ala Phe Leu Ser Gly Leu Gly Cys
465                 470                 475                 480

Ser Leu Leu Val Tyr Pro Ile Ser Gln Val Met Ser Lys Lys Tyr Ala
                485                 490                 495

Thr Ile Gln Phe Gly Leu Met Lys Tyr Arg Asp Ala Lys Ser His Val
                500                 505                 510

Leu Thr Glu Ala Leu Gln Gly Met Arg Gln Ile Lys Tyr Ser Ala Leu
    515                 520                 525

Glu Gln Ile Tyr Glu Lys Lys Ile Leu Asp Ser Arg Asn Glu Glu Leu
    530                 535                 540

Arg Gln Phe Trp Arg Val Ala Lys Trp Met Phe Gly Leu Ser Leu Val
545                 550                 555                 560

Ile Ala Thr Gly Pro Ile Leu Leu Ser Cys Val Ser Leu Ala Ile Tyr
                565                 570                 575

Thr Leu Thr Thr Gln Thr His Val Arg Ala Ser Val Ile Phe Ala Ser
                580                 585                 590

Leu Gly Leu Phe Asp Gln Leu Asp Glu Ala Ile Gly Tyr Leu Pro Leu
                595                 600                 605

Ile Gln Val Tyr Leu Met Glu Ala Trp Thr Ser Cys Val Arg Val Glu
    610                 615                 620

Lys Tyr Leu Asn Gln Pro Asp Arg Pro Val Ser Val Pro Gly Glu
625                 630                 635                 640

Ala Ile Val Phe Glu Asp Ala Thr Val Arg Trp Pro Arg Ala Glu Asp
                645                 650                 655

Ala Ile Leu Glu Thr Ala Ser Glu Thr Ser Leu Ser Pro Ser Ser Ser
                660                 665                 670

Ser Ala Pro Asp Val Gln Ser Ser Leu Val Thr Pro Ser Asp Asp Gln
                675                 680                 685

Gln Thr Arg Ser Ile Leu Arg Asn Val Asn Leu Ser Phe Pro Ala Gly
    690                 695                 700

Glu Leu Ser Leu Ile Thr Gly Lys Thr Gly Ser Gly Lys Ser Leu Leu
705                 710                 715                 720

Leu Ala Ala Ile Leu Gly Glu Val Arg Leu Leu Ser Gly Thr Val Arg
                725                 730                 735

Val Pro Glu Ala Pro Pro Val Ser Thr Ile Glu Ser Asp Lys Ala Thr
                740                 745                 750

Asp Ala Asp Trp Val Leu Pro Ser Leu Thr Ala Phe Val Ser Gln Thr
            755                 760                 765

Pro Trp Ile Glu Ser Gly Thr Phe Lys Asp Asn Ile Leu Phe Gly Met
```

-continued

```
                770               775               780
Pro Phe Arg Glu Ser Arg Tyr Lys Lys Val Leu Gln Ala Cys Ala Leu
785               790               795               800

Glu Lys Asp Ile Glu Leu Leu Ala Asn Gly Asp Ala Thr Glu Val Gly
                805               810               815

Pro Lys Gly Val Thr Leu Ser Gly Gly Gln Arg Trp Arg Val Ala Leu
                820               825               830

Ala Arg Ala Leu Tyr Ser Arg Ala Gly Ile Leu Ile Leu Asp Asp Val
                835               840               845

Leu Ser Ala Val Asp Ala His Val Gly His Ile Ile Val Glu Gln Ala
                850               855               860

Leu Ser Gly Asp Leu Ala Arg Gly Arg Thr Arg Ile Leu Ala Thr His
865               870               875               880

His His Glu Met Cys Leu Ala His Ala Ser Tyr Leu Val Arg Leu Glu
                885               890               895

Ser Gly Arg Val Gln Asn Val Glu Asn Ile Glu His Val Glu Glu Pro
                900               905               910

Leu Leu Ser Ala Gly Val Glu Ala Ser Ala Glu Glu Ala Gln Asp
                915               920               925

Ala Asp Ser Ser Ser Ala Ala Gln Ile Ala Ala Ser Lys Lys Lys
                930               935               940

Asp Glu Glu Gly Arg Glu Thr Gly Arg Val Lys Ser Arg Val Tyr Gln
945               950               955               960

Glu Tyr Ile Lys Ala Ser Asn Ser Ile Phe Leu Trp Val Ala Ile Met
                965               970               975

Ala Phe Val Val Gly Arg Leu Cys Gly Val Ala Thr Thr Trp Ser
                980               985               990

Leu Lys Glu Leu Ala Gly Ser Tyr Gln Ser Asn Asp Thr Tyr Asp Ser
                995               1000              1005

Leu Ser Ser His Lys Phe Ile Ser Gln Ser Ala Glu Pro Glu Leu Val
                1010              1015              1020

Trp His Ala Ala Asn Leu Pro His Thr Thr Thr Ser Thr Leu Gln Thr
1025              1030              1035              1040

Ser Gly Asp Asp Ser Ala Tyr Arg Arg Thr Ala Leu Phe Trp Ile Ser
                1045              1050              1055

Ala Tyr Ile Val Phe Glu Leu Cys Ser Leu Leu Val Gly Ala Asn Thr
                1060              1065              1070

Gln Leu Leu Ile Met Phe Thr Gly Leu Arg Ala Ser Arg Val Leu Phe
                1075              1080              1085

Glu Arg Met Thr His Ser Ile Leu His Ala Pro Leu Arg Trp Ile Asp
                1090              1095              1100

Thr Ile Pro Ser Gly Arg Ile Leu Asn Arg Phe Thr Ser Asp Thr Phe
1105              1110              1115              1120

Ile Val Asp Arg Arg Leu Ala Ser Asp Leu Gly Thr Phe Leu Ser Ser
                1125              1130              1135

Ser Phe Val Leu Val Val Ile Ile Ala Thr Ser Ile Ser Val Ser Pro
                1140              1145              1150

Tyr Ile Ile Ile Phe Gly Leu Leu Leu Val Val Tyr Gly Arg Ile
                1155              1160              1165

Ala Val Phe Tyr Ile Ala Ala Ala Arg Glu Val Lys Arg Ile Asn Ser
                1170              1175              1180

Val Ala Tyr Ser Pro Val Tyr Asp Gln Phe Ser Ser Val Leu Thr Gly
1185              1190              1195              1200
```

```
Leu Ser Thr Ile Arg Ala Phe Gln Arg Pro Glu Phe Tyr Met Asp Arg
            1205                1210                1215
Met Phe Gly Leu Ile Asp Asn Gly Thr Lys Ala Ser Trp Ala Met Gln
    1220                1225                1230
Leu Leu Ala Arg Trp Met Asn Phe Arg Met Gly Met Phe Gly Ala Thr
        1235                1240                1245
Phe Val Thr Val Val Ala Thr Cys Ile Ile Phe Gly Asn Ile Asn Ala
    1250                1255                1260
Ser Leu Ala Gly Phe Gly Leu Ile Phe Ala Leu Arg Tyr Thr Ser Ala
1265                1270                1275                1280
Leu Ser Arg Leu Leu Ala Asn Val Thr Ser Val Glu Leu Gly Phe Asn
            1285                1290                1295
Ala Ala Glu Arg Ile Leu Glu Tyr Ile Glu Ile Asp Thr Glu Pro Glu
                1300                1305                1310
Thr Gly Arg Asp Ala Pro Ala Ala Trp Pro Thr Lys Gly His Val Glu
            1315                1320                1325
Val Glu Asp Leu Thr Val Ser Tyr Ala Pro Glu Leu Pro Pro Val Leu
        1330                1335                1340
Lys Ser Leu Asn Phe Glu Ala Arg Pro Gly Glu Arg Ile Gly Val Val
1345                1350                1355                1360
Gly Arg Thr Gly Ala Gly Lys Ser Thr Leu Ala Ala Val Phe Phe Arg
            1365                1370                1375
Leu Leu Glu Pro Arg Gln Gly Cys Ile Arg Ile Asp Gly Ile Asp Ile
            1380                1385                1390
Ala Thr Leu Lys Leu Glu Gln Leu Arg Ser Arg Leu Ala Ile Ile Pro
            1395                1400                1405
Gln Asp Pro Phe Leu Phe Ala Gly Thr Leu Arg Ser Asn Leu Asp Leu
            1410                1415                1420
Asp Gly Ser Ile Asp Asp Tyr Asp Leu His Gln Val Leu Arg Arg Val
1425                1430                1435                1440
His Leu Val Glu Ala Asp Asp Glu Asp Thr Gly Pro Pro Val Thr Ile
                1445                1450                1455
Ser Ala Val Asp Arg Gly Thr Asp Leu Gln Ile Val Glu Asp Gln Thr
            1460                1465                1470
Gln Glu Glu Val Ala Leu Leu Ile Glu Ser Thr Leu Thr Asp Ser Ala
        1475                1480                1485
Thr Ala Asp Asp Val Pro Glu Asn Asn Thr Val Thr Val Val Ser Glu
        1490                1495                1500
Ser Pro Thr Glu Val Ala Ser Ser Val Pro Glu Gly Glu Glu Ser Asp
1505                1510                1515                1520
His Thr Ala Asn Asn Asp Thr Ser Ile Ala Asp Glu Ala Asp Asn Asn
                1525                1530                1535
Asn Arg Asp Val Asp Asp Ser Asn Ser Pro Arg His Thr Phe Lys Asp
            1540                1545                1550
Leu Asp Met Pro Val Ser Thr Gly Gly Gly Asn Leu Ser Gln Gly Gln
        1555                1560                1565
Arg Gln Leu Val Cys Leu Ala Arg Ala Leu Leu Thr Arg Pro Lys Ile
    1570                1575                1580
Val Val Leu Asp Glu Ala Thr Ser Ala Val Asp Arg Gly Thr Asp Ser
1585                1590                1595                1600
Ala Ile Gln Glu Ser Leu Arg Arg Glu Phe Ala Ser Gly Gly Cys Thr
                1605                1610                1615
```

-continued

```
Val Leu Val Ile Ala His Arg Leu Ser Thr Val Asp Phe Asp Arg
            1620                1625                1630

Ile Leu Val Leu Lys Glu Gly Arg Val Ala Glu Ile Gly Thr Pro Lys
        1635                1640                1645

Glu Leu Met Glu Lys Gly Met Ala Leu Asp Ala Ser Gln Lys Glu Val
    1650                1655                1660

Thr Ser Ala Ala Gly Glu Gly Leu Ser Gln Thr Ser Glu Gly Asp
1665                1670                1675                1680

Val Ala Glu Glu Glu Arg Asp Asp Ser Gly Ala Phe Trp Glu Leu Val
                1685                1690                1695

Lys Arg Ser Ala Glu Lys Asp Lys Leu Val Gly Met Val Phe Gly Glu
            1700                1705                1710

Lys Ala Lys Thr Glu
        1715

<210> SEQ ID NO 19
<211> LENGTH: 1512
<212> TYPE: PRT
<213> ORGANISM: Grosmannia clavigera
<220> FEATURE:
<223> OTHER INFORMATION: GcABC-C3

<400> SEQUENCE: 19

Met His Asp Asp Ser Met Ile Val Gly Val Gly Thr Ala Leu Ala Val
1               5                   10                  15

Ile Ala Leu Ser Thr Tyr Pro Ala Val Ser Gly Leu Val Leu Gln Val
                20                  25                  30

Phe Asn Arg Gln Pro Arg Asp Asp Ala Leu Tyr Glu Ala Asp Gly
            35                  40                  45

Lys Ala Thr Ala Ala Ser Val Lys Ala Phe Thr Ala Lys Leu Pro Lys
50                  55                  60

Ala Ala Ile Phe Leu Ser Ala Val Leu Gly Ser Ala Val Ser Leu Ser
65                  70                  75                  80

Ala Ser Ile Leu Val Thr Leu His Leu Ala His Asp Gly Phe Leu Val
                85                  90                  95

Glu Asp Trp Leu Ala Thr Ala Ala Trp Asn Leu Ile Leu Leu Gln Ala
            100                 105                 110

Ile Ala Ile Val Phe Thr Arg Asn Ser Thr Arg Ala Tyr Ser Tyr Gly
        115                 120                 125

Leu Tyr Thr Phe Thr Ser Gly Leu Leu Leu Ser Phe Val Val Leu Thr
130                 135                 140

Gln Asp Ser Gln Val Leu Asp Glu Val Leu Asn Glu Tyr Pro Val Leu
145                 150                 155                 160

Phe Gly Leu Arg Val Ala Glu Ile Val Ala Ile Val Gly Val Cys Met
                165                 170                 175

Ala Gly Ile Leu Leu Pro Arg Arg Pro Asp Val Tyr Phe Lys Asp Glu
            180                 185                 190

Met Val Asp Arg Met Tyr Ser Thr Ser Ala Tyr Gly Arg Phe Thr Phe
        195                 200                 205

Ser Trp Ser Asn Asp Leu Leu Gly Leu Ser Lys Lys Gln Thr Leu
210                 215                 220

Asp Leu Asp Asp Leu Pro Arg Pro Asp His Asn Thr Arg Ser Glu Asp
225                 230                 235                 240

Val Ala Arg Val Trp Lys Glu Asn Gly Tyr Ser Ser Glu Arg Leu Trp
                245                 250                 255
```

```
Leu Ser Ile Val Gln Ala His Ala Phe Asp Phe Ala Met Gln Trp Val
            260                 265                 270

Leu Thr Ile Ile Gly Ala Phe Leu Asn Phe Ala Pro Gln Trp Val Ile
        275                 280                 285

Leu Gln Leu Leu Arg Ile Leu Glu Thr Arg Ser Ser Asp Glu Ala Arg
    290                 295                 300

Gly Ile Asp Val Trp Ile Trp Leu Val Glu Ser Tyr Val Phe Trp Leu
305                 310                 315                 320

Ser Trp Ala Glu Leu Ala Ile Pro Ile Arg Ala Gln Leu Ser Ala Leu
                325                 330                 335

Ile Phe Glu Lys Ala Met Arg Arg Lys Asp Val Lys Ser Asn Lys Lys
            340                 345                 350

Ala Ala Lys Ala Ala Val Ala Asp Ser Ser Ile Ala Ala Asn Pro Thr
        355                 360                 365

Glu Ala Ser Ala Glu Asp Glu Gly Glu Ala Gly Asp Asp Glu Leu Glu
    370                 375                 380

Ser Ala Lys Lys Thr Lys Gln Gly Thr Val Asn Leu Ile Gly Leu Phe
385                 390                 395                 400

Val Ser Leu Ala Phe Leu Val Gln Leu Leu Gly Trp Ile Pro Leu Leu
                405                 410                 415

Ala Gly Phe Ser Ala Met Ala Ile Ile Met Pro Val Asn Ile Lys Phe
            420                 425                 430

Ser Lys Lys Tyr Ser Asp Ala Gln Asp Lys Leu Met Lys Leu Arg Asp
        435                 440                 445

Glu Lys Leu Ala Val Val Thr Glu Ala Leu Gln Gly Ile Arg Gln Ile
    450                 455                 460

Lys Phe Ser Ala Leu Glu Pro Gln Trp Glu Gly Lys Val Gly Glu Val
465                 470                 475                 480

Arg Asp Arg Glu Leu Lys Ser Val Trp Asn Val Phe Met Phe Asp Thr
                485                 490                 495

Ala Leu Met Ala Cys Trp Ile Thr Ser Pro Ile Ala Leu Ser Ala Ile
            500                 505                 510

Cys Leu Leu Val Tyr Ala Tyr Ile His Gly Glu Leu Thr Pro Ser Val
        515                 520                 525

Ala Phe Val Ser Leu Gly Ile Phe Arg Ser Leu Glu Thr Thr Leu Ser
    530                 535                 540

Val Val Pro Glu Leu Thr Thr Asp Leu Leu Asp Ala Trp Val Ser Ile
545                 550                 555                 560

Lys Arg Ile Glu Asp Tyr Leu Ser Ser Pro Asp Ile Asp Lys Val Ala
                565                 570                 575

Lys Asp Gly Asp Val Val Phe Glu Asn Ala Thr Ile Ala Trp Pro
            580                 585                 590

Ser Glu Glu Lys Leu Glu Asp Ser Glu His Phe Ile Leu Arg Asp Leu
        595                 600                 605

Asn Val Thr Phe Pro Ala Gly Glu Leu Ser Ile Ile Ser Gly Lys Thr
    610                 615                 620

Gly Ser Gly Lys Ser Leu Leu Leu Ala Ala Ile Leu Gly Glu Val Asp
625                 630                 635                 640

Leu Leu Ala Gly Ser Ile Gln Val Pro His Cys Leu Pro Ile Ala Glu
                645                 650                 655

Arg His Asp Glu Lys Ala Thr Lys Ala Asn Trp Ile Leu Pro Lys Ser
            660                 665                 670

Met Ala Phe Ile Ala Gln Ile Pro Trp Ile Glu Asn Ala Thr Ile Lys
```

-continued

```
            675                 680                 685
Glu Asn Ile Val Phe Gly Leu Pro Val Asp Glu Asp Arg Tyr Arg Lys
            690                 695                 700

Thr Lys Trp Arg Ile Thr Leu Ala Arg Ala Ile Tyr Ser Arg Ala Gly
705                 710                 715                 720

Ile Leu Ile Met Asp Asp Ile Phe Ser Ala Val Asp Ala His Val Gly
            725                 730                 735

Arg His Ile Phe Glu Lys Cys Leu Thr Gly Glu Leu Cys Ala Gly Arg
            740                 745                 750

Thr Arg Ile Leu Val Thr His His Val Ala Leu Cys Ala Pro Arg Thr
            755                 760                 765

Asn Phe Leu Val Glu Leu Gly Asp Gly Arg Ile Ala His Ala Gly Leu
            770                 775                 780

Leu Ser Glu Leu Ala Arg Asp Gly Thr Leu Asp Gln Asp Ser Lys Ser
785                 790                 795                 800

His Val Glu Thr Ala Glu Glu Ala Ala Glu Asp Glu Thr Val Asp Ala
                    805                 810                 815

Thr Ala Val Asn Ser Asp Asn Ser Thr Asp Ser Gly Glu Ala Asp Gly
            820                 825                 830

Gly Ser Ala Leu Asp Lys Val Ala Ser Arg Ala Thr Gln Pro Gln Glu
            835                 840                 845

Pro Glu Arg Gln Ala Arg Lys Phe Val Glu Glu Lys Arg Glu Glu
850                 855                 860

Gly Ala Val Arg Lys His Val Tyr Met Ala Tyr Leu Asn Ala Ser Gly
865                 870                 875                 880

Gly Trp Ala Phe Trp Thr Gly Ala Leu Val Phe Leu Leu Leu Glu
                    885                 890                 895

Leu Asn Ala Ile Ser Arg Ser Trp Trp Leu Arg Ile Trp Thr Gly His
                    900                 905                 910

Tyr Gln Gly Gly Asp Glu Glu Thr Val Leu Asn Leu Ser Ala Met Gly
            915                 920                 925

Leu Ser Ala Leu Ser Gln Arg Ser Val Val Gln Gln Ser Ala Asp Leu
            930                 935                 940

Gln Tyr Ser Tyr Gly Leu Asp Gln Pro Val Leu Ala Gly Ser Gly Ser
945                 950                 955                 960

Glu Ser Gly Ser His Ser Ser Gln Tyr Tyr Met Thr Ile Tyr Val Val
                    965                 970                 975

Leu Ala Gly Ile Ser Ala Leu Phe Gly Ser Leu Arg Cys Tyr Tyr Val
            980                 985                 990

Tyr Arg Gly Ser Ile Arg Ala Ser Arg Thr Leu Phe Ala Lys Leu Asn
            995                 1000                1005

Phe Ile Ile Leu Arg Ser Pro Leu Arg Trp Leu Asp Thr Val Pro Val
            1010                1015                1020

Gly Arg Ile Leu Asn Arg Phe Thr Ala Asp Phe Asn Thr Ile Asp Thr
1025                1030                1035                1040

Gln Met Ala Asn Ser Ile Ser Phe Gly Gly Ala Ala Val Ile Arg Val
                    1045                1050                1055

Phe Gly Val Ile Ile Ala Gly Leu Met Val Ser Tyr Phe Val Val Leu
            1060                1065                1070

Leu Ser Val Leu Leu Leu Leu Ala Cys Thr Tyr Phe Ala Phe Leu Tyr
            1075                1080                1085

Ile Ala Ala Val Arg Pro Val Lys Arg Leu Glu Ser Thr Ala Lys Ser
            1090                1095                1100
```

Pro Val Phe Glu Gln Phe Gly Thr Ala Leu Ser Gly Val Ala Thr Ile
1105                1110                1115                1120

Arg Gly Phe Asp Lys Pro Ser Val Tyr Ile Glu Arg Met Tyr Arg Arg
            1125                1130                1135

Leu Asp Asp Trp Ser Thr Thr Thr Trp His Met Met Leu Phe Asn Arg
        1140                1145                1150

Trp Val Gly Trp Arg Met Ser Leu Val Gly Ser Phe Phe Ser Val Met
            1155                1160                1165

Val Ala Ala Ile Val Leu Ser Ser Pro Gln Met Asp Ser Ala Leu Ala
    1170                1175                1180

Gly Phe Ala Leu Ala Tyr Ala Met Glu Phe Ala Ala Ser Ile Met Trp
1185                1190                1195                1200

Ala Val Arg Leu Tyr Ala Asn Val Glu Leu Gln Met Asn Ala Ala Glu
            1205                1210                1215

Arg Ile Ile Glu Tyr Thr Glu Leu Ser Thr Glu Ser Leu Glu Gly Gly
        1220                1225                1230

Ser Pro Pro Ala Ala Trp Pro Thr Glu Gly Arg Ile Glu Val Asp Asn
            1235                1240                1245

Leu Val Val Ser Tyr Ala Ala Asp Leu Pro Pro Val Leu Lys Gly Val
    1250                1255                1260

Ser Phe Asp Val Asp Arg Cys Gln Arg Val Gly Val Val Gly Arg Thr
1265                1270                1275                1280

Gly Ala Gly Lys Ser Ser Leu Thr Leu Ala Leu Phe Arg Phe Leu Glu
            1285                1290                1295

Ala Gln Ser Gly Ser Ile His Val Asp Gly Ile Asp Asn Ser Lys Ile
        1300                1305                1310

Lys Leu His Asp Leu Arg Ser Arg Leu Ala Ile Pro Gln Asp Pro
            1315                1320                1325

Val Leu Phe Ser Gly Thr Ile Arg Thr Asn Leu Asp Pro Phe Asp Ala
    1330                1335                1340

Tyr Thr Asp Ala Glu Leu Gln Asp Cys Leu Ala Arg Val His Leu Thr
1345                1350                1355                1360

Thr Pro Val Ser Asp Ser Ser Ala Ser Ala Ala Ser Ala Ser Ser Ala
            1365                1370                1375

Val His Asn Ser Asn Ile Phe Asp Asp Leu Gln Ser Ser Val Ser Glu
        1380                1385                1390

Gly Gly Leu Asn Leu Ser Gln Gly Gln Arg Gln Leu Leu Cys Leu Ala
            1395                1400                1405

Arg Ala Ile Val Arg Arg Pro Arg Val Met Val Leu Asp Glu Ala Thr
    1410                1415                1420

Ser Ala Val Asp Met His Thr Asp Gly Leu Ile Gln Arg Ser Ile Arg
1425                1430                1435                1440

Glu Glu Phe Thr Gly Ala Thr Leu Leu Val Ile Ala His Arg Leu Ser
            1445                1450                1455

Thr Ile Ala Asp Phe Asp Arg Ile Leu Val Leu Gln Asp Gly Thr Val
        1460                1465                1470

Ala Glu Tyr Gly Ser Pro Arg Asp Leu Trp Ala Lys Gly Ser Asp His
    1475                1480                1485

Gly Val Phe Arg Ala Met Cys Glu Glu Ser Gly Glu Arg Asp Arg Leu
    1490                1495                1500

Glu Lys Val Val Leu Gly Glu Ser
1505                1510

<210> SEQ ID NO 20
<211> LENGTH: 1601
<212> TYPE: PRT
<213> ORGANISM: Grosmannia clavigera
<220> FEATURE:
<223> OTHER INFORMATION: GcABC-C4

<400> SEQUENCE: 20

```
Met Leu Ser Pro Pro Asp Gly Gln Asn Ser Ile Trp Pro Cys Tyr Ser
 1               5                  10                  15

Cys Cys Arg Gln Val Trp Val Pro Glu Thr Ala Ala Phe Ser Asp Gly
            20                  25                  30

Cys Pro Gly Leu Val Ala Tyr Ile Pro Ala Leu Val Ala Ile Val Val
        35                  40                  45

Val Leu Gly Arg Tyr Ser Leu Arg Pro Leu Trp Arg Arg Arg Pro Ile
     50                  55                  60

Trp Leu Arg Asp Phe Ala Thr Glu Lys Asp Glu Leu Gly Pro Ala Thr
 65                  70                  75                  80

Gly Trp Ser Leu Pro Asp Asp Glu Ala Asp Glu Glu Glu Ala
                85                  90                  95

Glu Ala Pro Phe Cys Asn Arg Pro Ser Leu Ala Val Gly Pro Asp Ser
            100                 105                 110

Phe Thr Gly Arg Ser Ile Glu Phe Gly Thr Thr Ala Glu Val Ile Ser
        115                 120                 125

Asn Asn Asp Ser Asp Asp Ser Asn Glu Ile Thr Ile Val Ser Pro Gly
130                 135                 140

Asn Arg Phe Thr Leu Ser Lys Ile Arg Ile Trp Thr Met Glu Val Thr
145                 150                 155                 160

Leu Phe Leu Leu Ser Leu Ile Gly Val Ile Thr Ser Leu Leu Leu Thr
                165                 170                 175

Phe Ala Ala Gly Leu Gly Leu Leu Tyr Leu Thr Pro Leu Val Pro Cys
            180                 185                 190

Leu Ala Ser Cys Leu Leu Leu Ala Ile Asp Arg Pro Arg Thr Leu Pro
        195                 200                 205

Gly Ala Val Tyr Leu Leu His Ala Ala Thr Leu Ala Ile Gln Leu Ala
    210                 215                 220

Leu Leu Leu Gly Val Pro Asp Leu Tyr Arg Trp Pro Leu Cys Pro Leu
225                 230                 235                 240

Trp Leu Ser Glu Ile Ser Val Thr Gly Leu Ser Leu Ala Ile Met Thr
                245                 250                 255

Thr Met Pro Leu Arg Asp Pro Ser Leu Gly Asn Arg Ala Ser Gly Thr
            260                 265                 270

Asp Gly Glu Thr Ile Ala Leu Pro Phe Glu Thr Pro Ser Asn Lys Leu
        275                 280                 285

Arg Ser Pro Glu Asp Ala Leu Thr Leu Trp Gln Trp Met Thr Val Ser
    290                 295                 300

Trp Met Gly Pro Leu Ile Gly Leu Gly Tyr Thr Arg Gln Leu His Ser
305                 310                 315                 320

Glu Asp Val Trp Asn Leu Pro Tyr Gln Phe Gln His Gly Arg Leu Tyr
                325                 330                 335

Arg Leu Phe Gln Asp Val Arg Gly Thr Val Thr Ser Arg Val Val Lys
            340                 345                 350

Val Asn Thr Pro Asp Leu Ile Ile Thr Ser Val Leu Gly Ile Leu Asp
        355                 360                 365
```

```
Ser Leu Leu Ser Met Leu Pro Ile Val Phe Leu Lys Ala Leu Leu Ala
370                 375                 380
Ser Met Glu Gly Ser Asn Pro Asn Val Arg Val Ala Thr Ile Tyr Ala
385                 390                 395                 400
Val Leu Ile Cys Ile Thr Asn Leu Leu Arg Ser Gln Cys Gly Val Phe
                405                 410                 415
Ser Leu Trp Tyr Ala Arg Arg Cys Tyr Glu Arg Ser Arg Gly Glu Leu
            420                 425                 430
Ile Thr Met Ile Tyr Glu Lys Thr Leu Arg Arg Lys Ala Phe Thr Phe
        435                 440                 445
Pro Ser His Thr Asp Ala Ser Thr Lys Asn Gly Gly Glu Val Ala Glu
450                 455                 460
Asp Leu Val Gln Gly Pro Ala Ser Thr Gly Lys Ile Leu Asn Leu Met
465                 470                 475                 480
Arg Asn Asp Val Tyr Glu Val Ala Gln Arg Phe Trp Glu Phe Pro Thr
                485                 490                 495
Leu Phe Thr Lys Pro Leu Asn Phe Val Leu Ser Met Val Leu Leu Trp
            500                 505                 510
Arg Ile Leu Gly Ala Ala Ser Leu Val Gly Ile Leu Val Val Val Met
        515                 520                 525
Ala Gln Leu Ile Asn Val Phe Val Ile Arg Ile Leu Val Arg Trp Glu
530                 535                 540
Thr Ala Arg Arg Ala Val Thr Asp Ile Lys Leu Gln Val Thr Ser Gln
545                 550                 555                 560
Phe Ile Glu Ser Ile Arg His Leu Arg Trp Tyr Asp Trp Gln Asp Arg
                565                 570                 575
Trp Leu Ala Asp Ile Leu Lys Ala Arg Gln Lys Glu Leu Arg Tyr Arg
            580                 585                 590
Val Ile Thr Asn Ile Ile Gln Arg Ile Ile Ser Val Val Asn Gln Met
        595                 600                 605
Ser Ala Ser Phe Phe Pro Val Ala Ala Phe Tyr Ala Tyr Thr Val Trp
610                 615                 620
Glu Arg Arg Pro Leu Thr Val Asp Val Ala Phe Pro Ala Leu Asn Leu
625                 630                 635                 640
Phe Asn Leu Leu Glu Gln Ser Leu Arg Glu Leu Pro Asp Leu Ile Thr
                645                 650                 655
Val Leu Leu Asn Ala Thr Val Ala Met Arg Arg Ile Asp Ala Phe Met
            660                 665                 670
Ser Glu Pro Glu Lys Ser Asp Gly Ala Ala Asp Val Ile Leu Lys
        675                 680                 685
Gln Ala Pro Gly Gly Ala Ile Val Asp Gly Ile Leu Arg Pro Pro Gly
690                 695                 700
Pro Leu His Val Glu Ile Thr Asp Gly Ser Phe Ser Trp Pro Thr Val
705                 710                 715                 720
Lys Lys Pro Val Leu Thr Lys Val Asp Leu Ile Ala Asp Gly Gly Ser
                725                 730                 735
Leu Thr Val Ile Phe Gly Lys Val Gly Thr Gly Lys Thr Ala Leu Leu
            740                 745                 750
Met Ser Ile Leu Gly Glu Met Asp Gln His Ser Gly Thr Arg Phe Val
        755                 760                 765
Pro Arg Glu Thr Ile Gly Tyr Cys Ala Gln Thr Pro Trp Leu Gln Ser
770                 775                 780
Met Ser Val Arg Glu Asn Ile Leu Phe Cys Thr Pro Phe Asp Glu Gln
```

```
                785                 790                 795                 800
        Arg Tyr Asn Ser Val Val Glu Ala Cys Cys Leu Leu Gln Asp Phe Ser
                        805                 810                 815

Glu Phe Glu Ala Gly Asp Met Ser Asn Ile Gly Glu Asn Gly Ile Gly
                        820                 825                 830

Leu Ser Gly Gly Gln Lys Ala Arg Val Ala Leu Ala Arg Ala Val Tyr
                        835                 840                 845

Ser Arg Ala Arg Ile Leu Leu Leu Asp Asp Pro Ile Ala Ala Leu Asp
                850                 855                 860

His Asn Thr Ala Glu Ser Ile Met Lys Lys Leu Phe Thr Asp Ser Gly
        865                 870                 875                 880

Leu Met Arg Asn Arg Leu Ala Leu Phe Val Thr His Arg Leu Asp Leu
                        885                 890                 895

Val Ala Gly Tyr Ala Asp Gln Ile Tyr Glu Val Ser Glu Asn Gly
                        900                 905                 910

Ile Val Thr Lys Val Asp Ile Gly Thr Val Arg Lys Ser Ala Gly Val
                        915                 920                 925

Ser Ala Ala Ala Pro Thr Thr Thr Ala Asp Ser Glu Gly Ser Ser Ala
                930                 935                 940

Ala Asp Asp Asn Glu Gly Asp Ser Ser Pro Glu Asn Asn Val Ala Gly
        945                 950                 955                 960

Lys Pro Ala Ser Thr Thr Asn Gly Ala Asn Lys Phe Ile Glu Glu
                        965                 970                 975

Tyr Arg Ala His Gly Gly Val Met Met Ser Val Tyr Trp Arg Tyr Val
                        980                 985                 990

Lys Ala Gly Gly Leu Arg Trp Trp Val Leu Thr Leu Phe Thr Phe Ile
                        995                 1000                1005

Gly Phe Arg Ile Ala Lys Ile Ala Tyr Leu Tyr Phe Leu Lys Ile Trp
                        1010                1015                1020

Gly Glu Ala Tyr Asp Lys Asp Ala Thr Ala Asp Ala Ala Ile Glu Ala
        1025                1030                1035                1040

Thr Leu Thr Leu Val Pro Arg Val Phe Thr Tyr Leu Gln Pro Trp Lys
                        1045                1050                1055

Gln Leu Leu Thr Ser Gly Ser His Gly Asp Glu Asp Met Phe Ser Ile
                        1060                1065                1070

Ala Thr Val Val Asn Pro Asp Asn Ala Asn Thr Thr Gly Trp Tyr Glu
                        1075                1080                1085

Gly Asp Phe Gly Leu Pro Ser Pro Met Thr Asn Val Val Pro Trp Leu
                        1090                1095                1100

Leu Trp Leu Thr Leu Leu Ala Ile Phe Thr Leu Leu Phe Arg Thr Leu
        1105                1110                1115                1120

Ser Asp Ile Ile Leu Ile Ile Ile Thr Tyr Val Ala Gly Lys Arg Val
                        1125                1130                1135

Phe Gln Glu Val Met Val Arg Val Ser Thr Ala Pro Phe Arg Phe Phe
                        1140                1145                1150

Asp Ile Thr Pro Val Gly Arg Leu Met Asn Arg Val Thr Ser Asp Ile
                        1155                1160                1165

Gly Thr Ile Asp Gly Ala Val Ala Gln Gln Ile His Arg Cys Ala Trp
                        1170                1175                1180

Phe Met Leu Asn Trp Leu Thr Ser Ile Leu Val Ile Ala Thr Ala Thr
        1185                1190                1195                1200

Pro Thr Phe Leu Ala Met Ala Val Phe Met Thr Val Ala Phe Val Leu
                        1205                1210                1215
```

-continued

```
Val Phe Ile Arg Phe Leu Pro Thr Ser Gln Ser Leu Arg Arg Leu Glu
            1220                1225                1230

Met Val Ser Leu Ser Pro Leu Met Ser Asn Phe Gly Thr Leu Leu Glu
            1235                1240                1245

Gly Leu Thr Thr Val Arg Ala Phe Arg Ala Gln Pro Asp Phe Gln Glu
            1250                1255                1260

Arg Ile Ile Ser Thr Thr Asp Ala Phe Gln Arg Met Asp His Phe Tyr
1265                1270                1275                1280

Trp Ser Leu Gln Ala Trp Leu Gln Trp Arg Phe Asn Ser Met Thr Ala
                1285                1290                1295

Leu Ser Thr Phe Ala Leu Thr Ile Thr Ala Leu Ala Thr Gly Leu Ser
            1300                1305                1310

Ser Gly Leu Val Ala Phe Val Leu Thr Ala Ala Asn Phe Val Asn
            1315                1320                1325

Ser Thr Gln Val Leu Cys Arg Arg Tyr Gly Glu Leu Gln Met Gln Phe
            1330                1335                1340

Val Ser Val Glu Arg Val Ile Glu Leu Leu Asp Leu Asp Gln Glu Pro
1345                1350                1355                1360

Ile Gly Asp Ile Asp Pro Pro Ala Ala Trp Pro Thr Thr Asn Asp Asp
                1365                1370                1375

Ile Val Phe Asp Asp Val Thr Val Arg Tyr Ala Pro His Leu Glu Pro
            1380                1385                1390

Ser Leu Arg Asn Ile Thr Met Arg Ile Pro Ala Gly Ser Thr Val Ala
            1395                1400                1405

Val Thr Gly Arg Thr Gly Ser Gly Lys Ser Thr Leu Ala Leu Ala Leu
            1410                1415                1420

Leu Gly Thr Val Leu Pro Asp Asn Asn Glu Ala Thr Gln Gly Ser Ile
1425                1430                1435                1440

Tyr Ile Gly Gly Met Asp Val Ala Lys Val Asn Lys His Ala Leu Arg
                1445                1450                1455

Gln Arg Ile Ser Phe Val Ala Gln Asp Pro Val Leu Phe Pro Gly Thr
            1460                1465                1470

Leu Arg Glu Asn Leu Asp Pro Ile Gly His His Thr Asp Glu Glu Cys
            1475                1480                1485

Ile Ala Val Leu Ala Lys Val Leu Gly Asp Ala Thr Gly Glu Phe Lys
            1490                1495                1500

Leu Asp Ser Arg Ile Asp Gly Gly Lys Asn Met Ser Gln Gly Gln
1505                1510                1515                1520

Arg Gln Leu Val Gly Leu Gly Arg Ala Val Leu Arg Arg Ser Pro Ile
                1525                1530                1535

Val Ile Leu Asp Glu Ala Thr Ala Ser Ile Asp Lys Ala Thr Ala Phe
            1540                1545                1550

Arg Ile Gln Glu Val Leu Arg Glu Glu Leu Lys His Ser Thr Val Ile
            1555                1560                1565

Thr Ile Ala His Arg Leu Glu Ala Val Arg Asp Ala Asp Phe Ser Val
            1570                1575                1580

Ile Leu Glu Asn Gly Arg Val Val Leu Ala Ala Pro Val Thr Glu Leu
1585                1590                1595                1600

Ser

<210> SEQ ID NO 21
<211> LENGTH: 1549
<212> TYPE: PRT
```

<213> ORGANISM: Grosmannia clavigera
<220> FEATURE:
<223> OTHER INFORMATION: GcABC-C5

<400> SEQUENCE: 21

```
Met Ala His Leu Gln Ile Pro Leu Gln Ser Ala Asp Phe Ile Pro Asp
 1               5                  10                  15

Val Ser Gln Pro Ser Gln Trp Pro Asn His Val Ala Ala Ile Ile Arg
             20                  25                  30

Phe Ile Ala Arg Gly Asp Leu Phe Leu Ala Cys Ala Gly Val Ser Val
         35                  40                  45

Leu Leu Leu Leu Leu Tyr Leu His Leu Trp Thr Val Arg Asn Lys Lys
 50                  55                  60

Leu Trp Arg Gln Lys Thr Leu Pro Lys Ala Thr Asp Thr Ser Asp Asp
 65                  70                  75                  80

Arg Ser Glu Phe Glu Glu Leu Leu Ser Ala Asp Ser Val Ser Glu
                 85                  90                  95

Asp Asp Thr Leu His Thr Ser Ser Thr Pro Ile Glu Asn Glu Gly
             100                 105                 110

Ser Leu Leu Ser Phe Phe Ala Val Ser Leu Ser Gln Ile Val Ala Val
             115                 120                 125

Ala Val Ala Phe Ala Leu Ser Val Ile Ser Ser Ala Arg Asn Ser Ser
130                 135                 140

Pro Gly Ala Ala Trp Lys Glu Pro Val Thr Leu Gly Tyr Leu Leu Leu
145                 150                 155                 160

Leu Cys Val Ile Gln Leu Leu Leu Ala Ser Ser Arg Arg Gly Phe Ser
             165                 170                 175

Leu Arg His Val Phe Tyr His His Ile Asn Ala Val Gly Thr Ala Leu
             180                 185                 190

Thr Val Leu Lys Ala Val Cys Leu Leu Pro Leu Ala Leu Arg Gly
             195                 200                 205

Thr His Ala Arg Leu Gly Ala Val Pro Gly Ala Lys Leu Ala Ala Leu
             210                 215                 220

Ser Ala Val Pro Leu Thr Ala Phe Ala Ala Pro Arg Asp Gly Ser Arg
225                 230                 235                 240

Val Asn Ile Ser Ala Ser Phe Gly Val Ser Lys Ser Lys Ser Asp
                 245                 250                 255

Ile His Ala Asp Gln Glu Ser Gly Lys Thr Ala Gly Ser Leu Pro Leu
             260                 265                 270

Ser Pro Glu Glu Ser Cys Ser Trp Ala Ser Tyr Tyr Leu Ser Tyr Gly
             275                 280                 285

Trp Leu Thr Pro Val Ile Leu His Gly Trp Arg Arg Asp Leu Glu Leu
             290                 295                 300

Asp Asn Leu Pro Ala Leu Pro Ser Tyr Asp Ala Pro Leu Asn Leu Leu
305                 310                 315                 320

Glu Arg Met Gly Arg Gln Arg Gln Arg Gln His Arg Arg Gly Thr
                 325                 330                 335

Leu Ala Thr Leu Cys Leu Val Phe Gln Gly His Ile Arg Arg Ile Met
             340                 345                 350

Ile Trp Gly Thr Leu Thr Ala Met Ala Glu Tyr Val Ala Pro Val Ala
             355                 360                 365

Met Phe Gln Leu Leu Ala Tyr Leu Glu Ala Gly Ser Ser Ser Ala Ile
             370                 375                 380

Pro Val His Pro Ser Val Trp Val Gly Leu Leu Phe Ile Gly Pro Met
```

```
                385                 390                 395                 400
Leu Arg Ser Val Cys Tyr Gln Gln Ser Ile Phe Leu Ser Thr Arg Leu
                405                 410                 415

Leu Val Thr Trp Arg Ala Ser Val Ile Gln Glu Val Phe Gln Arg Met
                420                 425                 430

Leu Arg Leu Arg Val Asp Gly Ser Pro Ala Gln Pro Arg Leu Gln Gln
                435                 440                 445

Lys Gln Thr Gln Ser Ser Gly Gln Lys Asn Thr Val Lys Thr Glu Ser
                450                 455                 460

Leu Val Ser Tyr Asp Val Asp Met Ile Ser Asn Ser Ser Asp Met Phe
465                 470                 475                 480

Tyr Ser Phe Thr Ala Ser Leu Val Ser Thr Ala Leu Ala Met Thr Phe
                485                 490                 495

Leu Tyr Arg Leu Leu Gly Trp Pro Ser Leu Leu Gly Val Ala Val Leu
                500                 505                 510

Val Cys Leu Thr Pro Leu Pro Val Val Phe Ser Gly Arg Val Ser Arg
                515                 520                 525

Leu His Arg Arg Val Met Gln Ala Thr Asp Ala Arg Leu Ala Gln Val
                530                 535                 540

Ala Glu Phe Leu Gly Ala Val Arg Thr Leu Lys Tyr Phe Gly Trp Glu
545                 550                 555                 560

Pro Val Ala Ala Arg Ala Leu Asn Glu Ala Arg Ala Thr Glu Gln Arg
                565                 570                 575

Gln Ile Trp Arg Arg Asn Leu Thr Ser Met Leu Val Ala Met Thr Gly
                580                 585                 590

Asp Met Met Ser Leu Val Ser Leu Leu Val Met Phe Ala Ala Val Val
                595                 600                 605

Leu Leu Ala Arg Gln Pro Leu His Ala Pro Ala Ala Phe Thr Ala Leu
                610                 615                 620

Ser Ile Thr Glu Thr Leu Arg Ala Gln Tyr Val Trp Met Ala Lys Val
625                 630                 635                 640

Val Gln Trp Val Ala Gln Gly Arg Glu Ser Phe Arg Arg Val Asp Gly
                645                 650                 655

Phe Leu Ser Gly Gly Glu Pro Arg Gln Arg His Pro Val Gly Pro Pro
                660                 665                 670

Ser Phe Ala Gly Ala Asp Val Val Gly Arg Glu Glu Ser Glu Thr
                675                 680                 685

Ala Asn Ala Pro Ser Gln Pro Pro Phe Ser Leu His Leu Ser Val Ser
                690                 695                 700

Phe Arg Glu Asp Ala Leu Asn Val Val Thr Gly Ala Thr Gly Ser Gly
705                 710                 715                 720

Lys Ser Thr Leu Leu Leu Ser Leu Leu Gly Glu Thr Ala Leu Val Ala
                725                 730                 735

Gly Thr Val Thr Cys Pro Ala Asp Val Ala Phe Val Pro Gln Thr Ala
                740                 745                 750

Trp Leu Leu Ser Gly Thr Val Arg Glu Asn Ile Val Phe His Gly Thr
                755                 760                 765

His Asp Asp Val Arg Tyr Arg Ala Val Leu Ala Ala Cys Ala Leu Asp
                770                 775                 780

Arg Asp Leu Ala Ala Leu Pro Leu Gly Asp Gln Thr Phe Ile Gly Glu
785                 790                 795                 800

Arg Gly Ala Ala Leu Ser Gly Gly Gln Arg Gln Arg Ile Ala Leu Ala
                805                 810                 815
```

```
Arg Ala Leu Tyr Ala Pro Pro Thr Ala Leu Leu Leu Asp Asp Val
            820                 825                 830

Phe Ser Ala Leu Asp Ala His Thr Ala Val Gln Val Tyr Arg Gly Cys
            835                 840                 845

Phe Gly Ala Ala Ala Asp Val Val Arg Leu Glu His Gly Arg Val
850                 855                 860

Ala Ser Met Thr Glu Arg Trp Lys Lys Asp Gly Gly Arg His Val Glu
865                 870                 875                 880

Gly Phe Val Glu Glu Glu Asp Glu Asp Val Asp Glu Ile Leu Glu Glu
                885                 890                 895

Glu Val Asp Arg Gly Glu Gly Ala Ser Gly Glu Gly Thr Ala Glu Glu
            900                 905                 910

Arg Thr Thr Glu Glu Gly Val Lys Ala Phe Ala Ser Asp His Ser Asn
            915                 920                 925

Trp Ser Pro Ser Ile Thr Glu Lys Arg Ala Ser Gly Arg Val Pro Arg
    930                 935                 940

Ser Met Ile Val Gln Tyr Met Leu Leu Phe Gly Val Pro Asn Ala
945                 950                 955                 960

Leu Leu Ala Met Ala Gly Ser Leu Met Val Gln Leu Ala Tyr Phe Ser
                965                 970                 975

Ile Thr Leu Trp Leu Ser Ile Trp Thr Ser Lys Glu Ser Ser Ser
            980                 985                 990

Ser Ser Ser Ser Ser Ser Ser Ala His Leu Leu Val Tyr Ala Gly
        995                 1000                1005

Thr Val Leu Thr Phe Val Gly Leu Gln Leu Leu Asn Asn Tyr Leu Phe
    1010                1015                1020

Gln Arg Gly Gly Trp Arg Ala Ala Gln Thr Met His Ser Arg Leu Val
1025                1030                1035                1040

Thr Ala Val Leu Ala Ala Pro Leu Ser Trp Phe Asp Arg Thr Pro Ala
            1045                1050                1055

Gly Gln Ile Leu Asn Arg Phe Gly Leu Asp Thr Gln Ser Leu Asp Ala
            1060                1065                1070

Val Leu Val Asp Trp Leu Arg Met Thr Leu Asp Asn Gly Leu Arg Phe
            1075                1080                1085

Gly Leu Arg Leu Ala Gly Ile Ala Ser Ile Leu Pro Val Phe Ala Val
            1090                1095                1100

Pro Ala Ala Val Phe Cys Gly Leu Gly Phe Ala Thr Gly Glu Leu Tyr
1105                1110                1115                1120

Ser Arg Ala Glu Ile Ser Val Lys Arg Leu Val Ala Ala His Phe Ala
            1125                1130                1135

Pro Val Leu Ser Gln Phe Ala Asp Leu Asp Gly Gly Gly Ser Leu Asp
            1140                1145                1150

Ser Gly Leu Ala Val Val Arg Ala Arg Arg Gly Leu Asp Arg Val Phe
            1155                1160                1165

Arg Gln Gln Leu Ala Asp His Val Ser Asp His Met Arg Ala Ala Glu
            1170                1175                1180

Ala Gln Phe Asn Cys Asn Arg Trp Val Ser Val Arg Ser Ser Arg Ala
1185                1190                1195                1200

Gly Leu Val Gly Phe Ser Leu Thr Asn Ala Ile Gly Leu Ser Gln Thr
            1205                1210                1215

Ile Leu Thr Leu Val Arg Asn Met Asn Glu Leu Glu Val Glu Leu Asn
            1220                1225                1230
```

```
Ser Leu Gln Arg Ile Asp Gln Tyr Thr His Ile Gln Pro Glu Lys Asp
        1235                1240                1245

Val Glu Met Ala Gly Asp Asp Ile Pro Thr Asp Trp Pro Thr Ala Gly
    1250                1255                1260

Glu Ile Ser Phe Asp Asp Val Thr Ala Thr Tyr Glu Ala Glu Asp Gly
1265                1270                1275                1280

Ser Ser Asp Pro Arg Asn Lys Asn Pro Thr Ser Thr Asn Ser Asn Ile
            1285                1290                1295

Leu Asn Glu Asn Ser Ser Ser Thr Thr Thr Thr Thr Ser Ser Pro
        1300                1305                1310

Pro Pro Leu Gly His Val Ser Phe Val Ala His Pro Gly Glu Arg Leu
        1315                1320                1325

Ala Val Val Gly Arg Thr Gly Ser Gly Lys Ser Thr Leu Leu Arg Thr
    1330                1335                1340

Leu Leu Arg Ser Thr His Val Val Gln Gly Arg Val Ser Val Asp Gly
1345                1350                1355                1360

Ile Asp Ile Arg Arg Val Pro Leu Arg Arg Leu Arg His Ala Val Cys
            1365                1370                1375

Leu Ile Pro Gln Asp Thr Leu Leu Leu Ala Gly Asp Val Arg Ser Asn
        1380                1385                1390

Leu Asp Pro Glu Gly Asp Cys Thr Asp Glu Glu Leu Val Glu Val Leu
        1395                1400                1405

Arg Ser Cys Ala Gly Asp Thr Ala Lys Thr Val Leu Ser Leu Ser Thr
        1410                1415                1420

Pro Val Ala Thr Gly Gly Thr Asn Phe Ser Ser Gly Gln Arg Gln Val
1425                1430                1435                1440

Leu Gly Leu Ala Arg Ala Leu Cys Arg Arg Ala Arg Val Val Val Leu
            1445                1450                1455

Asp Glu Ala Thr Ala Ser Val Asp Leu Ala Thr Asp Arg Arg Met Gln
        1460                1465                1470

Gln Leu Ile Arg Thr Ala Phe Ala Gly Ser Thr Val Val Thr Ile Ala
        1475                1480                1485

His Arg Leu Arg Thr Ile Met Asp Tyr Asp Arg Ile Leu Val Met Ala
    1490                1495                1500

Glu Gly Arg Val Ile Gln Ile Gly Ser Pro Arg Glu Leu Ala Thr Arg
1505                1510                1515                1520

Gln Gly Val Phe Ser Asp Met Leu Lys Ser Thr Gly Glu Tyr Glu Glu
            1525                1530                1535

Leu Leu Ala Thr Val Gly Leu Asn Ala Thr Thr Leu Glu
        1540                1545

<210> SEQ ID NO 22
<211> LENGTH: 1461
<212> TYPE: PRT
<213> ORGANISM: Grosmannia clavigera
<220> FEATURE:
<223> OTHER INFORMATION: GcABC-C6

<400> SEQUENCE: 22

Met Val Phe Leu Pro Asp Val Pro Met Ile Asn Val Gln Ala Ile Gly
1               5                   10                  15

Trp Ile Gly Thr Ile Ile Thr Ser Thr Ser Ser Leu Gly Ala His Tyr
            20                  25                  30

Ile Arg Lys Ser Val Asn Arg Glu Asp Leu Asp Asp Glu Thr Ser Thr
        35                  40                  45
```

```
Glu Glu Gln Ile Arg Thr Pro Val Gly Tyr Ser Leu Leu Gln Leu Ala
 50                  55                  60
Thr Arg Ala Leu Leu Ala Ser Val Val Ser His Leu Arg Asp
 65                  70                  75              80
Gly Ser Ser Leu Ile Glu Thr Ala Ala Leu Ala Tyr Val Phe Ala
                 85                  90                  95
Leu Asp Leu Ala Arg Val Val Leu Ala Met Arg Gln Pro Ser Leu Arg
                100                 105                 110
Ser Ser Leu Leu His His Ala Asn Val Leu Val Phe Val Glu Ala Val
                115                 120                 125
Ala Ala Phe Ala Gln Leu Ser Pro Ala Ile Val Ser Leu His Asp Pro
130                 135                 140
Gln Pro Ala Ala Ser Arg Trp Leu Val Leu Lys Leu Ala Ser Ala Ile
145                 150                 155                 160
Leu Ala Leu Leu Cys Ala Phe Val Ser Pro Arg Glu Trp Lys Pro Leu
                165                 170                 175
Pro Leu Ser Phe Gly Leu Ala Gln Arg Glu Leu Ser Glu Pro Ser Pro
                180                 185                 190
Glu Gln Thr Cys Ser Tyr Phe Ser Tyr Tyr Met Ser Tyr Gly Trp Leu
                195                 200                 205
Thr Asn Leu Ile Leu Arg Gly Thr Arg Arg Leu Val Leu Gln Asp
            210                 215                 220
Thr Leu Pro Leu Pro Glu Tyr Asp Glu Pro Leu Met Trp Lys Glu Arg
225                 230                 235                 240
Ile Met Glu Ala Arg Glu Lys Tyr Lys Thr Thr Ala Lys Thr Leu Ala
                245                 250                 255
Tyr Ala Leu Arg Glu Ser Ile Ala Ala Met Val Phe Phe Ser Ala Leu
                260                 265                 270
Thr Ala Val Ala Gly Phe Ile Ser Pro Leu Ala Leu Tyr Arg Leu Leu
                275                 280                 285
His His Ile Gln Glu Pro Glu Leu Ser Thr Val Arg Pro Trp Ile Trp
                290                 295                 300
Val Ala Leu Leu Phe Ile Gly Pro Val Leu Arg Ser Ser Cys Tyr Gln
305                 310                 315                 320
Gln Tyr Ile Phe Asn Ser Thr Arg Leu Ile Val Arg Thr Lys Met Cys
                325                 330                 335
Leu Ile Gln Glu Leu Tyr Ala Lys Ala Gly Arg Cys Tyr Asp Ser Asp
                340                 345                 350
Ala Thr Ser Leu Pro Ser Gln Glu Lys Ala Ser Ser Ala Ser Gly Leu
                355                 360                 365
Gly Lys Asp Ile Lys Lys Gly Lys Ser Asn Asn Val Thr Thr Leu Met
                370                 375                 380
Ala Tyr Asp Val Asp Ala Ile Cys Asn Ser Arg Asp Phe Ile Ile Val
385                 390                 395                 400
Cys Thr Ser Thr Pro Ile Glu Ile Thr Met Gly Leu Val Phe Leu Tyr
                405                 410                 415
Ile Leu Phe Gly Leu Tyr Ser Leu Val Ala Leu Val Leu Leu Leu Ala
                420                 425                 430
Ser Phe Pro Leu Ala Ala Leu Leu Ser Arg Leu Met Ser Arg Phe Gln
                435                 440                 445
Arg Glu Leu Met Arg Arg Thr Asp Ile Arg Val Ala Ser Ile Ser Glu
                450                 455                 460
Tyr Leu Ala Ser Ile Arg Thr Ile Lys Tyr Leu Gly Trp Glu Pro Ile
```

-continued

```
            465                 470                 475                 480
        Met Thr Glu Arg Ile Asn Ala Glu Arg Arg Ala Glu Glu Lys Gln Ile
                        485                 490                 495

Trp Arg Arg Asn Leu Ser Ala Val Ala Val Thr Val Leu Gly Asp Phe
                        500                 505                 510

Val Pro Leu Leu Ala Leu Phe Val Met Phe Ala Thr Tyr Thr Leu Val
                        515                 520                 525

Glu Gly Gln Pro Leu Thr Ala Ala Lys Ala Phe Thr Ser Val Thr Ile
                        530                 535                 540

Ile Glu Ser Leu Arg Leu Gln Phe Val Trp Ile Ala Asn Ala Thr Arg
        545                 550                 555                 560

Tyr Tyr Ser Gln Ala Arg Val Ala Phe Gly Arg Ile Asp Lys Phe Met
                        565                 570                 575

Val Asn Glu Arg Glu Thr Ala Pro His Pro Ser Gly Glu Pro Ala Phe
                        580                 585                 590

His Asn Ala Val Phe Arg Arg Ala Val Ala Glu Asp Ser Phe Arg Leu
                        595                 600                 605

His Ile Asp Cys Lys Phe Val Pro Gly Gly Phe Asn Ala Ile Val Gly
                        610                 615                 620

Ala Ser Gly Ser Gly Lys Ser Thr Leu Leu Ser Leu Thr Gly Glu
        625                 630                 635                 640

Thr Ile Leu Glu Ser Gly Ser Ala Met Cys Pro Ala Pro Val Ala Tyr
                        645                 650                 655

Ala Pro Gln Ile Pro Trp Met Leu Asn Asp Thr Val Arg Ala Asn Ile
                        660                 665                 670

Leu Met His Gln Glu Phe Asp Ala Met Arg Tyr Lys Arg Val Leu His
                        675                 680                 685

Ala Cys Ala Leu Leu Tyr Asp Leu Glu Lys Leu Asp Glu Arg Asp Leu
                        690                 695                 700

Thr Glu Val Gly Val Asn Gly Ser Asn Leu Ser Gly Gly Gln Arg Gln
        705                 710                 715                 720

Arg Val Cys Leu Ala Arg Ala Leu Tyr Ala Gln Ser Lys Ile Leu Val
                        725                 730                 735

Leu Asp Asp Ile Phe Ser Ala Leu Asp Ser Ala Thr Gln Lys His Ile
                        740                 745                 750

Trp Asp Phe Cys Phe Cys Asn Asp Ala Val Ile Gln Gly Arg Thr Val
                        755                 760                 765

Ile Leu Val Thr Gln Phe Gln Ala Ala Lys Glu Ser Ala Asp Leu Leu
                        770                 775                 780

Val Glu Ile Ser Asn Gly Arg Val Ser Lys Leu Thr Arg Arg Ser Glu
        785                 790                 795                 800

Gly Thr Arg Gln Val Arg Leu Val His Asp Asp Pro Ala Ile Arg Ala
                        805                 810                 815

Pro Ser Ser Ala Asn Trp Val Leu Glu Lys Thr Glu Asn Ala Ala Phe
                        820                 825                 830

His His Thr Arg Ala Ile Glu Lys Lys Ile Asn Gln Glu Val Ala Gly
                        835                 840                 845

Glu Glu Arg Asn Pro Arg Thr Leu Phe Tyr His Tyr Met Tyr Leu Phe
                        850                 855                 860

Gly Gly His Ser Arg Ala Ile Met Ala Met Val Ile Cys Leu Cys Leu
        865                 870                 875                 880

Gln Leu Ala Tyr Phe Ser Leu Pro Ile Trp Leu Ser Ala Trp Val Gly
                        885                 890                 895
```

```
Ala Pro Asp Pro Gly Ser Glu Gly Ala His Ser Thr Gly Phe Tyr Ile
            900                 905                 910

Ser Val Tyr Gly Ala Ile Leu Gly Ser Phe Leu Gly Phe Ser Ile Leu
            915                 920                 925

Ser Arg Val Tyr Leu Gln Lys Gly Ala Trp Glu Ala Ala His Thr Met
            930                 935                 940

His Glu Lys Leu Val Ser Ala Ala Met Trp Val Ser Val His Trp Tyr
945                 950                 955                 960

Asp Lys Asn Pro Pro Gly Arg Phe Ile Asn Arg Phe Ser Ser Asp Met
                965                 970                 975

Phe Ser Met Asp Cys Val Met Val Asp Tyr Leu Arg Ile Ala Met Asp
            980                 985                 990

Asn Val Phe Arg Phe Met Leu Arg Leu Thr Ala Val Gly Ser Ile Met
            995                 1000                1005

Pro Val Phe Ala Leu Pro Ala Ala Phe Val Cys Thr Ile Gly Leu Val
            1010                1015                1020

Cys Ala Glu Met Tyr Thr Arg Thr Gln Leu Ser Ala Lys Ala Leu Ala
1025                1030                1035                1040

Ser Ala Ala Gln Ser Pro Ile Phe Ser Phe Val Glu Ser Met Ala
            1045                1050                1055

Gly Lys Ala Val Ile Arg Ser Gly Pro Gly Phe Gln Ala Ala Phe Ala
            1060                1065                1070

Asp Asp Leu Gly Arg Arg Leu Arg Val Tyr Ala Arg Ser Ser Glu Thr
            1075                1080                1085

Arg Phe Asn Leu Asn Arg Trp Ile Cys Val Arg Ala Asp Gly Cys Ala
            1090                1095                1100

Ala Val Ile Ala Met Leu Thr Gly Ile Ile Ala Leu Ser Tyr Gly Pro
1105                1110                1115                1120

Asp Val Ser Ala Gly Arg Leu Gly Phe Ser Leu Thr Ser Ala Ile Gly
            1125                1130                1135

Leu Gly Gln Thr Ile Leu Thr Met Val Arg Ser Met Asn Asp Leu Glu
            1140                1145                1150

Ala Glu Met Asn Cys Phe Phe Arg Ile Arg Glu Tyr Ala Ser Leu Pro
            1155                1160                1165

His Glu Asp Asp Gly Val Asp Asp Lys Asp Ser Leu Ala Thr Ser Val
            1170                1175                1180

Pro Asp His Trp Pro Phe Glu Gly Arg Val Gln Phe Glu Gly Val Ser
1185                1190                1195                1200

Val Lys Tyr Ala Leu Asp Gly Pro Asp Ile Leu His Asp Val Ser Leu
            1205                1210                1215

Ser Val Ser Pro Gly Glu Arg Val Ala Ile Val Gly Arg Thr Gly Ser
            1220                1225                1230

Gly Lys Ser Thr Met Ala Leu Ser Leu Leu Gly Phe Thr Asn Ile Thr
            1235                1240                1245

Lys Gly Ser Val Arg Ile Asp Gly Val Asp Leu Ala Ala Val Pro Leu
            1250                1255                1260

Arg Val Leu Arg Arg Arg Leu Thr Ile Ile Pro Gln Glu Pro Val Leu
1265                1270                1275                1280

Phe Ser Gly Asp Val Arg Phe Asn Leu Asp Pro Ala Glu Ser Ser Thr
            1285                1290                1295

Ser Asp Gln Leu Thr Glu Ala Ile Gly Ala Cys Ser Val Met Ala Ser
            1300                1305                1310
```

-continued

```
Leu Ala Gly Asn Thr Thr Ala Glu Arg His Val Asp Glu Gln Pro Ile
        1315                1320                1325

Arg Ala Leu Asp Leu Asp Thr Ala Val Ala Pro Gln Gly Ser Asn Phe
    1330                1335                1340

Ser Val Gly Gln Arg Gln Val Leu Ser Leu Ala Arg Ala Thr Val Arg
1345                1350                1355                1360

Gln Ser Gln Val Val Ile Leu Asp Glu Ala Thr Ala Ser Ile Asp Tyr
                1365                1370                1375

Arg Ser Asp Val Ala Ile Gln Lys Val Leu Arg Ser Ala Phe Arg Gly
            1380                1385                1390

Arg Thr Ile Ile Ala Ile Val His Arg Leu Ser Thr Ile Met Asp Tyr
        1395                1400                1405

Asp Arg Val Ile Val Met Asp Ala Gly Gln Val Arg Glu Thr Gly Ser
    1410                1415                1420

Pro Ala Gln Leu Tyr Arg Gln Gly Gly Met Phe Gln Arg Met Val Lys
1425                1430                1435                1440

Gln Ser Ile Glu His Gly Lys Gly Ser Glu Trp Thr Pro Glu Lys Leu
                1445                1450                1455

Gln Gln Leu Glu Lys
            1460

<210> SEQ ID NO 23
<211> LENGTH: 1143
<212> TYPE: PRT
<213> ORGANISM: Grosmannia clavigera
<220> FEATURE:
<223> OTHER INFORMATION: GcABC-C7

<400> SEQUENCE: 23

Met Ala Val Leu Val Trp Glu Ser Met Gly Leu Asp Ser Arg Lys Thr
1               5                   10                  15

Ser Ala Ala Ala Gly Ile Val Ala Leu Glu Gln Arg Ser Ser Phe Trp
            20                  25                  30

Ser Arg Thr Ala Tyr Ala Trp Leu Ala Val Thr Phe Trp Arg Gly His
        35                  40                  45

Lys Arg Val Ile Ser Val Asp Asp Leu Pro Pro Leu Asp Gly Arg Leu
    50                  55                  60

Glu Ser Ser Arg Ile Gln Ile Glu Ile Glu Ile Thr Ala Glu Ala Trp
65                  70                  75                  80

Ser Ala Pro Gly His Ser Ser Thr Leu Asp Trp Gln Ser Val Tyr Gln
                85                  90                  95

Tyr Gln Ser Phe Arg Phe Val Thr Arg Leu Arg Gly Ser Leu Ile Ala
            100                 105                 110

Leu Val Tyr Gln Gln Met Leu Gln Thr Arg Ala Ala Asn Val Gly Ser
        115                 120                 125

Ile Thr Gly Leu Thr Leu Met Gly Thr Asp Val Glu Arg Ile Val Ala
    130                 135                 140

Gly Val Pro Ser Leu His Glu Ala Trp Ala Ser Leu Leu Glu Ile Gly
145                 150                 155                 160

Leu Ala Cys Trp Leu Leu Glu Arg Gln Leu Ser Leu Ala Cys Ile Ala
                165                 170                 175

Pro Ile Leu Leu Val Ser Val Phe Ile Ala Ala Thr Ser Arg Val Ser
            180                 185                 190

Leu Arg Leu Arg Asp Thr Gln Val Ala Trp Ile Glu Lys Ile Gln Glu
        195                 200                 205
```

```
Arg Leu Arg Ile Thr Ala Ala Val Leu Gly Asp Met Lys Thr Val Lys
    210                 215                 220

Met Leu Gly Ile Ser Ser Val Val Pro Val Ile Gln Gly Leu Arg
225                 230                 235                 240

Arg Asp Glu Ile Asp Thr Ser Arg Arg Phe Arg Lys Asn Leu Val Val
                245                 250                 255

Met Ile Leu Leu Ser Pro Val Leu Thr Phe Ala Val Tyr Ser Val Val
                260                 265                 270

Ala Val Phe Trp Lys Asn Glu Thr Leu Leu Thr Thr Lys Ala Phe Thr
                275                 280                 285

Ser Leu Thr Leu Val Ser Leu Leu Thr Ala Pro Val Ile Ser Phe Ile
    290                 295                 300

Gln Gly Leu Pro Asn Val Val Gln Cys Leu Gly Asn Phe Ser Arg Ile
305                 310                 315                 320

Gln Glu Phe Cys Asn Tyr Glu Thr Gly Gly Asp Ala Pro Gly Ser Ala
                325                 330                 335

Ser Ser Ser Ser Lys Glu Thr Ser Gln Arg Arg Pro Leu Met Ala Tyr
                340                 345                 350

Cys Ala Gln Gln Pro Trp Leu Glu Asn Gly Thr Ile Arg Arg Ser Ile
    355                 360                 365

Val Gly Ala Ser Pro Trp Asp Ser Arg Trp His Gly Thr Val Cys Thr
370                 375                 380

Ala Cys Cys Leu Asp Pro Asp Met Pro Gln Leu Glu Met Gly Asp Leu
385                 390                 395                 400

Thr His Val Gly Ser Lys Gly Val Asn Leu Ser Asp Gly Gln Lys Gln
                405                 410                 415

Arg Ile Ala Leu Ala Arg Ala Val Tyr Ser Arg Arg Arg Thr Leu Leu
                420                 425                 430

Leu Asp Asp Val Phe Ser Gly Met Asp Ala Tyr Thr Ala Gly Phe Val
            435                 440                 445

Ile Ala Arg Leu Leu Gly Cys His Gly Gly Leu Leu Arg Asn Glu Gln
    450                 455                 460

Thr Thr Val Ile Leu Thr Thr His Ser Arg Leu Val Asp Glu Val Ile
465                 470                 475                 480

Val Leu Glu Asp Gly Gln Val Thr Glu Met Gly Ser Pro Thr Ala Leu
                485                 490                 495

Leu Gln Asn Lys Gly Gly Tyr Leu Arg Lys Ile Gly Phe Ser Lys Leu
            500                 505                 510

Ala Glu Glu Asn Asp Met Lys Leu Thr Ala Ala Ser His Pro Gly Pro
            515                 520                 525

Ala Ser Gly Ser Val Pro Arg Glu Glu Ile Pro Gly Met Gly Thr Val
    530                 535                 540

Gly Asp Thr Asp Ala Thr Val Asn Leu Asp Asp Gly Gln Glu Thr Ala
545                 550                 555                 560

Thr Ala Glu His Thr Asp Val Arg Lys Asn Cys Glu Leu Ser Ile
                565                 570                 575

Tyr Thr Tyr Tyr Leu Arg Ser Ser Gly Tyr Val Ala Val Ala Leu Tyr
            580                 585                 590

Ala Ala Ser Met Ile Phe Trp Ile Phe Cys Thr Glu Phe Ser Thr Val
            595                 600                 605

Trp Val Ser Trp Trp Ser Ala Ala Asn Asp Leu His Pro Asn Arg Asn
610                 615                 620

Leu Gly Leu Tyr Met Gly Ile Tyr Ala Met Val Gly Val Val Gly Thr
```

```
                625                 630                 635                 640
Ala Ala Ala Cys Cys Ala Ala Trp Phe Ala Tyr Ile Ser Ile Ile Ser
                645                 650                 655

Asn Ser Ala Ser Lys Leu His Leu Asp Leu Leu Lys Ala Thr Phe Arg
                660                 665                 670

Ala Pro Phe Arg Phe Phe Ala Asn Thr Asp Thr Gly Glu Leu Leu Asn
                675                 680                 685

Arg Cys Ile Tyr Asp Leu Arg Pro Ser Ala Leu Ser Cys Phe Thr Gln
                690                 695                 700

Val Val Leu Leu Ala Ile Tyr Ser Arg Ser Leu Ala Val Ala Met Pro
705                 710                 715                 720

Phe Val Ala Ala Phe Leu Tyr Ala Leu Gln Arg Phe Tyr Leu Gln Thr
                725                 730                 735

Ser Arg Gln Met Arg Leu Leu Met Ile Glu Ala Lys Ala Pro Leu Tyr
                740                 745                 750

Thr Gln Phe Ser Glu Met Gly Thr Pro Gly Thr Thr Ala Ser Glu Arg
                755                 760                 765

Ser Gly Ser Thr Ala Gly Thr Gly Thr Gly Thr Ile Thr Ile Arg Ala
                770                 775                 780

Phe Gly Trp Gln Arg Ala Tyr Ala Ala Arg Val Ala Ala Leu Val Asp
785                 790                 795                 800

Arg Ser Gln Arg Pro Ala Tyr Ile Gln Ser Cys Ile Gln His Trp Leu
                805                 810                 815

Asp Phe Val Leu Thr Leu Thr Met Ala Val Leu Val Val Leu Val
                820                 825                 830

Ala Thr Val Val Ser Trp Gln Asp Arg Leu Asp Ile Ser Ala Gly Gly
                835                 840                 845

Val Gly Val Ser Leu Val Val Leu Leu Gly Leu Ser Thr Thr Leu Thr
                850                 855                 860

Arg Leu Ile Arg Thr Trp Thr Arg Leu Glu Pro Ser Val Gly Ala Val
865                 870                 875                 880

Ala Arg Val Arg Arg Phe Val Thr Glu Thr Glu Thr Ala Gly Glu
                885                 890                 895

Glu Val Pro Val Ser Glu Leu Ser Gln Pro Val Gly Thr Val Cys Phe
                900                 905                 910

Asp Asp Leu Val Ala Ala Tyr Glu Pro Asp Ala Ala Ser Pro Val Leu
                915                 920                 925

Gln His Val Ser Leu Ser Val Pro Pro Gly Gln His Leu Ala Ile Cys
                930                 935                 940

Gly Arg Ser Gly Ser Gly Lys Thr Ser Leu Val Met Ala Leu Leu His
945                 950                 955                 960

Met Met Asp Val Arg Ser Gly Ile Ala Val His Gly Arg Val Ser
                965                 970                 975

Val Val Ser Gln Asp Pro Phe Leu Val Pro Gly Thr Ser Leu Arg Phe
                980                 985                 990

Asn Met Asp Pro Leu Leu Ala Ala Val Ser Asp Ala Gln Ile Val Arg
                995                 1000                1005

Val Leu Gln Arg Val Gly Leu Trp Glu Val Val Glu Gly Gln Gly Ser
                1010                1015                1020

Arg Gly Arg Gly Ser Ser Ser Gly Cys Leu Asp Gln Lys Val Asp Gly
1025                1030                1035                1040

Leu Ala Leu Ser Ala Gly Gln Arg Gln Leu Leu Cys Phe Ser Arg Ala
                1045                1050                1055
```

```
Leu Val Tyr Arg Asp Gln Thr Asp Val Leu Val Leu Asp Glu Ala Thr
            1060                1065                1070

Cys Ser Leu Asp Ser Ser Ala Glu Ala Val Val Gln Gln Ile Ile Asp
            1075                1080                1085

Thr Asp Phe Arg Gly Cys Thr Val Leu Ala Val Met His Arg Leu Ala
            1090                1095                1100

His Val Ala Ser Tyr Asp Arg Val Ala Val Met Asp Ala Gly Ala Leu
1105                1110                1115                1120

Val Glu Asp Gly Ala Pro Gly Glu Leu Ile Ala Asn Glu Ser Ser Arg
            1125                1130                1135

Phe Ala Glu Leu Tyr Leu Thr
            1140

<210> SEQ ID NO 24
<211> LENGTH: 153
<212> TYPE: PRT
<213> ORGANISM: Grosmannia clavigera
<220> FEATURE:
<223> OTHER INFORMATION: GcABC-C7

<400> SEQUENCE: 24

Met Asp Cys Pro Arg Gly Ser Asp Tyr Ala Phe Gly Pro Arg Ile Arg
1               5                   10                  15

Ser Glu Cys Arg Ser Phe Asp Phe Thr Leu Gln Phe Glu Asp Ser Leu
            20                  25                  30

Phe Gly Cys Leu Pro Ala Ala Thr Phe Leu Leu Ala Ala Ala Ala Asp
        35                  40                  45

Val Ile Trp Leu Val Arg Ser Pro Val Ala Tyr Gln Arg Gln Gly Gly
    50                  55                  60

Ile Val Ser Leu Lys Leu Cys Thr Leu Ala Ser Leu Leu Ala Ala Gln
65                  70                  75                  80

Leu Ala Leu Leu Val Val Arg Val Arg Val Pro Ala Ile Ser Ser Gly
                85                  90                  95

Ala Ser Leu Pro Ala Asp Ile Leu Ala Ser Leu Ala Val Leu Ala Ala
            100                 105                 110

Thr Thr Leu Leu Val Leu Tyr Gln Gln Arg Ala Ser Arg Pro Ser Thr
        115                 120                 125

Val Leu Ser Leu His Leu Ser Ala Thr Val Leu Leu Gly Val Ala Arg
    130                 135                 140

Val Arg Thr Leu Trp Leu Val Ala Asn
145                 150

<210> SEQ ID NO 25
<211> LENGTH: 1316
<212> TYPE: PRT
<213> ORGANISM: Grosmannia clavigera
<220> FEATURE:
<223> OTHER INFORMATION: GcABC-C8

<400> SEQUENCE: 25

Met Ala Cys Pro Ala Asp Phe Met Phe Gly Ala Ile Leu Ser Phe Asp
1               5                   10                  15

Asp His Ser Val Thr Cys Arg Asn Phe Asp Phe Arg Ile Ile Phe Glu
            20                  25                  30

Asp Ala Leu Leu Val Leu Thr Pro Ser Leu Ala Leu Leu Pro Thr Val
        35                  40                  45

Ala Met Arg Phe Phe Ser Ile Val Arg Lys Pro Lys Ile Val Val Trp
```

```
            50                  55                  60
Gln Trp Met Gln Lys Leu Lys Leu Ala Leu Tyr Ala Ile Phe Gly Ile
 65                  70                  75                  80

Leu Gln Leu Ala Glu Leu Gly Leu Phe Ala Ser Gly Asn Asp Tyr Thr
                 85                  90                  95

Lys Thr Arg Leu Thr Val Pro Ala Tyr Ala Ser Met Phe Val Ala Thr
                100                 105                 110

Val Cys Leu Ala Leu Leu Ser Ser Leu Glu His Gly Ser Ser Leu Arg
                115                 120                 125

Pro Ser Val Val Ile Gln Ser Phe Leu Ser Leu Thr Leu Leu Phe Asn
130                 135                 140

Val Ala Leu Leu Arg Thr Arg Trp Leu Leu His Gly Glu Gln Thr Leu
145                 150                 155                 160

Ala Ala Leu Leu Ser Thr Ala Phe Ala Leu Gln Cys Ala Leu Leu Gly
                165                 170                 175

Val Glu Ser Leu Pro Lys Ser Ser His Ile Leu Pro Ser Lys Ala Ala
                180                 185                 190

Arg Leu Ser Pro Glu Glu Arg Ala Gly Phe Phe Ser Arg Ser Leu Phe
                195                 200                 205

Leu Trp Leu Ile Pro Leu Phe Arg Arg Gly Tyr Cys Ser Pro Leu Gln
210                 215                 220

Glu Lys Asp Leu Phe Pro Ile Gly Asp Glu Leu Ala Ser Ser Lys Leu
225                 230                 235                 240

Thr Asp Asn Leu Asp Ala Ala Trp Gln Asn Thr Ser Ile Thr Ser Arg
                245                 250                 255

Arg Arg Leu Ala Leu Ala Leu Thr Lys Ala Phe Tyr Arg Gln Leu Leu
                260                 265                 270

Phe Leu His Leu Pro Arg Leu Ala Leu Val Gly Phe Ala Ile Ala Gln
                275                 280                 285

Pro Val Leu Val Gln Ser Ala Leu Ser Tyr Ile Thr His His Ala Thr
                290                 295                 300

Arg Pro Thr Gln Phe Gly Tyr Gly Leu Ile Gly Ala Phe Ala Leu Asp
305                 310                 315                 320

Tyr Ile Cys Val Ala Val Ser Thr Ala Trp Tyr Gln His Gln Thr Tyr
                325                 330                 335

Arg Leu Leu Ala Met Ile Arg Gly Ser Leu Val Gly Met Ile Phe Lys
                340                 345                 350

His Ser Leu Arg Leu Pro Ala Ser Glu Asp Ala Asp Gly Ser Ser Ala
                355                 360                 365

Ile Ser Leu Met Ser Thr Asp Val Glu Arg Val Val Gln Thr Leu Gln
370                 375                 380

Trp Ser Leu Asn Ile Val Pro Asp Ile Val Gln Val Ala Leu Gly Leu
385                 390                 395                 400

Trp Ile Leu Glu Thr His Leu Gly Gly Ile Cys Ile Ala Pro Leu Ile
                405                 410                 415

Val Ala Thr Gly Lys Arg Thr Pro Pro Arg Gln Arg Arg Trp Met Gln
                420                 425                 430

Ala Ile Gln Ser Arg Leu Lys Val Thr Thr Lys Ala Val Ser Glu Met
                435                 440                 445

Lys Gly Ile Lys Met Cys Gly Leu Thr Asp Ile Val Val Lys Gln Ile
                450                 455                 460

Gln Gly Leu Arg Val Ser Glu Ile Asn Asp Gln Lys Ala Phe Arg Lys
465                 470                 475                 480
```

```
Leu Gln Ile Thr Asn Ile Ala Val Gly Asn Ala Pro Ala Met Ile Thr
                485                 490                 495
Pro Ala Ile Thr Phe Ala Thr Phe Ala Ile Glu Gln Asn Leu Cys Ser
            500                 505                 510
Gly Asn Ser Leu Ala Ser Ala Leu Gly Cys Leu Asp Arg Ile Gln Glu
        515                 520                 525
Phe Leu Gln Lys Glu Ala Gln Gln Asp Gly Arg Ile Leu Leu Pro Ala
    530                 535                 540
Ala Thr Ala Asn Leu Glu Asp Ser Ser Ile Ala Ser Thr Thr Pro Gly
545                 550                 555                 560
Thr Glu Leu Gln Pro Val Gly His Gln Ser Leu Arg Phe Gln Ser Lys
                565                 570                 575
Ser Arg Gly Pro Ile Ala Ile His Asn Gly Thr Ile Gly Trp Val
            580                 585                 590
Pro Ser Gln Pro Ile Leu Arg Ala Ile Ser Leu Lys Val Leu Ala Ser
        595                 600                 605
Thr Phe Thr Ile Ile Ile Gly Pro Val Gly Ser Gly Lys Ser Thr Leu
    610                 615                 620
Leu Arg Ser Leu Leu Gly Glu Arg Cys Leu Ile Ser Gly Ser Val Glu
625                 630                 635                 640
Cys Val Ser Pro Lys Gln Thr Ala Tyr Cys Asp Gln Gln Pro Trp Ile
                645                 650                 655
Leu Asn Ile Ser Leu Lys Gln Asn Ile Leu Gly Ile Ser Asp Tyr Asp
            660                 665                 670
Asp Asp Arg Tyr Lys Met Ala Ile Glu Ala Cys Gln Leu Gln Gln Asp
        675                 680                 685
Phe Ala Gln Met Pro Ala Gly Asp Ser Thr Leu Ala Gly Ser Lys Gly
    690                 695                 700
Val Ser Leu Ser Gly Gly Gln Lys Gln Arg Ile Lys Gly Arg Tyr Asp
705                 710                 715                 720
Ile Lys Ser Asp His Glu Ile Met Pro Leu Glu Leu Thr Asp Met Pro
                725                 730                 735
Lys Ala Ala Leu Arg Thr Ser Ala Val Ala Leu Val Ala Ser Lys Ala
            740                 745                 750
Tyr Asp Asn Ser Thr Asp Glu Ser Asn Thr Gln Gln Lys Glu Arg Lys
        755                 760                 765
Lys Lys Thr Gly Ala Leu Leu Tyr Tyr Ile Ser Ser Leu Gly Phe Gly
    770                 775                 780
Ala Ile Trp Gly Phe Phe Ala Leu Val Thr Ala Leu Val Gly Cys Asn
785                 790                 795                 800
Ala Ala Gln Ser Gly Phe Leu Tyr Ser Phe Thr Gly Gly Arg Cys
                805                 810                 815
Ala Asn Leu Ser Leu Phe Leu Leu Ala Leu Trp Leu Lys Tyr Trp Val
            820                 825                 830
Ala Ala Tyr Asn His His Pro Asn Glu Ser Leu Gly Lys Trp Ala Gly
        835                 840                 845
Ile Tyr Val Leu Phe Ala Val Gly Ser Ile Leu Phe Ile Ala Leu Asp
    850                 855                 860
Thr Gly Ser Arg Leu Ser Phe Ile Thr Ala Gln Asp Thr Gly Thr Ile
865                 870                 875                 880
Ile Asn His Phe Ser Gly Asp Leu Asn Leu Thr Asp Leu Ala Leu Pro
                885                 890                 895
```

```
Leu Ser Phe Ile Leu Thr Ser Glu Arg Leu Ser Thr Val Ser Glu
                900                 905                 910

Ile Val Leu Ala Cys Leu Ala Ser Gly Tyr Leu Ala Leu Ser Ile Pro
        915                 920                 925

Ile Leu Val Pro Thr Leu Tyr Ile Leu Gln Arg Val Tyr Leu Lys Thr
        930                 935                 940

Ser Arg Arg Leu Arg Thr Leu Asp Tyr His Ser Arg Phe Leu Val Thr
945                 950                 955                 960

Ser Thr Ala Glu Arg Glu Asn Met Glu Leu Asn Ser Ala Gln Arg
                965                 970                 975

Pro Tyr Tyr Leu Leu Phe Cys Ala Gln Arg Trp Leu Thr Leu Val Leu
        980                 985                 990

Asp Leu Val Thr Ala Gly Leu Ala Thr Leu Leu Met Gly Leu Ala Val
        995                 1000                1005

Ala Leu Arg His Ser Ile Asp Pro Gly Phe Leu Gly Val Ala Leu Val
        1010                1015                1020

Ser Val Ile Ser Phe Gly Ala Ile Ala Ala Gly Leu Ile Gln Asn Trp
1025                1030                1035                1040

Thr Ser Leu Glu Met Ser Leu Gly Ala Ile Thr Arg Ile Arg Asn Phe
                1045                1050                1055

Ile Asp Asp Val Pro Ala Glu Ala Gln Ser Arg Asp Thr Glu Ala Lys
        1060                1065                1070

Ile Pro Ala Asp Trp Pro Ser Ser Gly Glu Leu Val Leu Arg Asn Val
        1075                1080                1085

Ser Ala Ser Tyr Asp Asn Gly Ser His Lys Val Leu Asn Asn Ile Ser
        1090                1095                1100

Leu Ala Ile Pro Ala Gly Ser Lys Val Ala Ile Cys Gly Arg Thr Gly
1105                1110                1115                1120

Ser Gly Lys Ser Ser Leu Leu Ser Leu Leu Gln Arg Leu Leu Asp Pro
                1125                1130                1135

Asp Ser Gly Ser Ile Arg Ile Asp Gly Val Gly Leu Phe Asp Ile Pro
        1140                1145                1150

Pro Asn Arg Thr Arg Thr Ser Leu Val Ala Leu Pro Gln Asp Pro Val
        1155                1160                1165

Phe Leu Ser Gly Ser Ile Arg Leu Asn Leu Asp Pro Phe Glu Gln His
        1170                1175                1180

Asn Gly Asp Asp Gly Pro Leu Leu Gln Ala Leu Glu Lys Ala Gly Leu
1185                1190                1195                1200

Ser Ser Leu Val Ala Asp Lys Gly Glu Leu Asp Ala Asp Leu Lys Val
                1205                1210                1215

Asp Gln Leu Ser Thr Gly Gln Arg Gln Leu Phe Cys Val Ala Arg Ala
        1220                1225                1230

Met Leu Arg Lys Ser Arg Ile Leu Leu Leu Asp Glu Ala Thr Ser His
        1235                1240                1245

Leu Asp Ala Asn Thr Glu Lys Leu Ile Thr Trp Leu Ile Arg Thr Glu
        1250                1255                1260

Phe Gln Asp Trp Thr Val Leu Val Val Thr His Leu Val Lys Ser Val
1265                1270                1275                1280

Ala Glu Ala Asp Ser Gly Phe Asp Glu Val Ile Ile Leu Glu Asn Gly
                1285                1290                1295

Arg Ile Val Glu Gln Gly Asn Pro Ala Val Leu Gln Glu Arg Met Ala
        1300                1305                1310

Ser Phe Gly Arg
```

-continued

```
                1315
```

<210> SEQ ID NO 26
<211> LENGTH: 1335
<212> TYPE: PRT
<213> ORGANISM: Grosmannia clavigera
<220> FEATURE:
<223> OTHER INFORMATION: GcABC-C9

<400> SEQUENCE: 26

Met Ser Cys Leu Ser Asp Ala Ser Ile Gly Pro Ala Leu Leu Ala Thr
 1               5                  10                  15

Ile Tyr Ala Val Leu Ser Leu Ala Leu Val Val Ile Ile Ser Ile Gln
                20                  25                  30

Thr Ser His Ala Leu Val Gln Gly Arg Leu Ser Leu Val Ala Ala Ser
            35                  40                  45

Leu Gly Phe Ile Ala Ala Leu Thr Leu Val Leu Leu Ser Tyr Gln Glu
        50                  55                  60

His Ala Arg Ser Pro Arg Pro Ser Ile Leu Ile Val Thr Tyr Leu Ala
 65                  70                  75                  80

Ile Thr Cys Leu Phe Asp Val Ala Lys Thr Arg Thr Leu Trp Leu Leu
                85                  90                  95

Phe Asp Gly Pro Ser Pro Leu Ala Ala Ile Ser Thr Val Met Val Ala
            100                 105                 110

Leu Lys Val Val Met Ile Leu Val Lys Ser Gln Asn Lys Thr Lys Trp
        115                 120                 125

Leu Thr Trp Ser Asp Ser Lys Glu His Ser Pro Glu Glu Thr Ser Gly
130                 135                 140

Ile Phe Gly Leu Val Val Phe Tyr Trp Leu Tyr Arg Leu Phe Met Asn
145                 150                 155                 160

Gly His Arg Thr Ile Leu Cys Ser Glu Thr Leu Phe Pro Leu Asp Gln
                165                 170                 175

Ala Val Ser Ala Ser Val Leu Ala Pro Lys Leu Ala Lys Lys Leu Arg
            180                 185                 190

Thr Ser Ser Trp Arg Gly Arg Lys Trp Gly Leu Ala Lys Val Leu Phe
        195                 200                 205

Ser Thr Leu Ala Pro Gln Leu Leu Pro Pro Ile Ile Pro Arg Leu Ala
    210                 215                 220

Leu Leu Ala Ala Ser Met Cys Gln Ser Phe Leu Ile Glu Ala Leu Leu
225                 230                 235                 240

Asp Phe Leu Gln Glu Asp Ser Glu Lys Ser His Gly Tyr Gly Leu Ile
                245                 250                 255

Gly Ala Thr Ile Leu Thr Tyr Gly Leu Leu Ala Leu Ser Thr Ala Leu
            260                 265                 270

Tyr Gly Tyr Phe Gln Glu Arg Phe Val Ile Met Thr Arg Gly Cys Leu
        275                 280                 285

Ile Thr Ala Ile Tyr Asp Gln Thr Val Gln Leu Glu Leu Ala Ser Ser
    290                 295                 300

Ala Glu Ser Gly Val Leu Thr Leu Met Ser Thr Asp Ile Ser Arg Ile
305                 310                 315                 320

Met Thr Gly Phe Leu Asp Ile His Glu Tyr Trp Ala Ser Ser Ile Gln
                325                 330                 335

Val Gly Leu Ser Cys Trp Leu Leu Gln Lys Lys Leu Gly Thr Ala Phe
            340                 345                 350

Val Ala Pro Leu Val Val Val Leu Ser Phe Leu Ala Met Phe Phe

```
            355                 360                 365
Leu Gly Lys Val Val Gly Arg Cys Gln Arg Ala Trp Met Glu Ala Val
370                 375                 380
Gly Ile Arg Val Gly Thr Met Ala Thr Ala Ile Ser Gln Met Lys Leu
385                 390                 395                 400
Ile Lys Met Ser Gly Met Asp Ala Pro Ile Lys Lys Arg Ile Gln Gln
                405                 410                 415
Leu Arg Ile Ala Glu Ile Arg Val Gly Glu Arg Trp Arg Met Leu Ala
            420                 425                 430
Val Thr Gly Ala Ala Ile Ser Gln Val Pro Leu Leu Ile Ser Pro Val
        435                 440                 445
Leu Ala Phe Ala Thr Ala Met Lys Thr Leu Asn Thr Thr Ser Ile Phe
    450                 455                 460
Val Ser Ile Ser Tyr Leu Thr Leu Leu Ala Ala Pro Leu Leu Val Leu
465                 470                 475                 480
Phe Gln Lys Val Pro Gln Leu Leu Ser Ala Phe Thr Ser Leu Gln Arg
                485                 490                 495
Ile Gln Glu Phe Leu Glu Arg Asp Thr Arg Lys Asp Tyr Arg Ile Ser
            500                 505                 510
His Ser His Ser Met Phe Ala Asp Met Gly Met Glu Ala His Asn Gly
        515                 520                 525
Phe Asp Met Asn Leu Leu Glu Gly Ser Gly Thr Arg Asp Ser Cys Ile
    530                 535                 540
Ser Ile Cys Asp Gly Glu Phe Gly Trp Ser Gln Asp Thr Pro Val Leu
545                 550                 555                 560
Lys Asp Val Asn Ile Ser Ile Pro Ala Ser Cys Leu Thr Ala Val Leu
                565                 570                 575
Gly Pro Val Gly Ser Gly Lys Thr Thr Phe Cys Arg Tyr Ile Leu Gly
            580                 585                 590
Glu Leu Pro Phe Ala Arg Gly Phe Val His Leu Ser Thr Arg Arg Asn
        595                 600                 605
Ile Gly Tyr Cys Asp Gln Gln Pro Phe Leu Thr Asn Ala Pro Val Arg
    610                 615                 620
Asp Asn Ile Val Ala Tyr Gly Val Phe Asp Gln Asp Arg Tyr Asp Gly
625                 630                 635                 640
Val Val Ile Ala Thr Met Leu Asp Arg Asp Ile Ala Ser Phe Pro Gln
                645                 650                 655
Gly Asp Leu Thr Val Ile Gly Ser Gly Gly Ile Ala Leu Ser Gly Gly
            660                 665                 670
Gln Arg Gln Arg Val Ser Met Ala Arg Ala Leu Tyr Met Ala Asp Thr
        675                 680                 685
Asp Leu Leu Val Phe Asp Asp Val Leu Ser Gly Leu Asp Ala Leu Thr
    690                 695                 700
Glu Ser Arg Val Leu Gln Arg Val Phe Gly Pro Asp Gly Leu Leu Arg
705                 710                 715                 720
Lys Arg Arg Ala Thr Ala Ile Leu Cys Thr His Asn Pro Arg His Ile
                725                 730                 735
Glu Phe Val Asp Arg Val Ile Arg Leu His Glu Gly Gly Arg Val Thr
            740                 745                 750
Glu Glu Gly Leu Pro Ala Ser Lys Lys Met Ala Thr Met Pro Thr Ala
        755                 760                 765
Asp Ser Gln Ser Asp Thr Thr Ile Pro Ser Gly Ala Glu Leu Leu Ala
    770                 775                 780
```

```
Thr Ile Pro Thr Gln Thr Glu Thr Glu Ser Gln Asp Val Ala Arg Lys
785                 790                 795                 800

Arg Arg Asp Leu Lys Val Tyr Gly Tyr Tyr Phe Ser Thr Ala Gly Lys
            805                 810                 815

Ile Thr Leu Val Ser Phe Val Phe Thr Ser Ala Cys Tyr Ser Phe Phe
            820                 825                 830

Leu Asn Phe Pro Arg Ile Trp Leu Thr Phe Trp Ser Asp Asp Ala Ala
            835                 840                 845

Arg Lys Asp Gly Gly Leu Arg Gln Met His Ser Arg Gly Tyr Tyr Ile
            850                 855                 860

Gly Ile Tyr Gly Leu Leu Gln Leu Met Cys Leu Met Ser Phe Ser Ala
865                 870                 875                 880

Ala Ala Ala Leu Val Leu Gly Pro Met Ile Arg Gln Ser Gly Ser Ile
            885                 890                 895

Leu His Arg Arg Ala Leu Asp Thr Val Val Asn Ala Ser Leu Gln Leu
            900                 905                 910

Phe Val Lys Thr Asp Leu Gly Val Ile Thr Asn Leu Phe Ser Gln Asp
            915                 920                 925

Ile Thr Leu Ile Asp Gly Glu Leu Pro Leu Ala Phe Leu Asn Leu Val
            930                 935                 940

Leu Asp Ile Phe Ser Val Ile Phe Met Gly Ala Val Ile Ile Ala Ser
945                 950                 955                 960

Thr Pro Trp Leu Gly Leu Thr Tyr Pro Ala Ile Val Gly Ile Leu Tyr
            965                 970                 975

Ala Ile Gln His Phe Tyr Leu Phe Thr Ser Arg Gln Leu Arg Leu Leu
            980                 985                 990

Asp Leu Glu Ala Lys Ser Pro Leu Tyr Ser His Phe Val Asp Thr Leu
            995                 1000                1005

Lys Gly Ile Ser Thr Ile Arg Ala Ser Gly Trp Thr Asp Lys Ser Ile
1010                1015                1020

Glu Lys Asn Leu Ala Leu Leu Asp Arg Ser Gln Lys Pro Ala Tyr Leu
1025                1030                1035                1040

Leu Ala Met Val Gln Arg Trp Leu Tyr Leu Met Leu Asn Thr Val Val
                1045                1050                1055

Met Leu Ile Ala Ile Val Leu Ala Ser Met Met Thr Gln Leu Arg Pro
                1060                1065                1070

Ser Ser Thr Leu Ser Gly Ala Ser Leu Val Thr Leu Met Ser Leu Ser
                1075                1080                1085

Gln Ser Leu Gly Asp Ile Val Arg Phe Tyr Ala Ser Leu Glu Thr Ser
                1090                1095                1100

Ile Gly Ala Val Thr Arg Leu Arg Asn Phe Ser Met Gln Thr Pro Leu
1105                1110                1115                1120

Glu Lys Ser Asp Gly Phe Gln Pro Asp His Asn Trp Pro Ser Asn Gly
                1125                1130                1135

Ser Ile Glu Val Ser Lys Ala Trp Ala Ser Tyr Gly Lys Ser Ser
                1140                1145                1150

Leu Ile Leu Leu Leu Leu Gly Phe Ile Asp Pro Val Glu His Glu Gly
                1155                1160                1165

Val Gln Gly Ser Asp Thr Val Phe Leu Pro Thr Gly Ser Thr Val Met
                1170                1175                1180

Glu Asn Leu Asp Pro Gly Gly Val Ala Thr Pro Glu Gln Cys Arg Glu
1185                1190                1195                1200
```

```
Ala Leu Glu Asp Leu Asp Leu Trp Gln Pro Val Gln Leu Arg Gly Gly
            1205                1210                1215

Leu Gly Ser Leu Phe Asp Glu Ser Leu Phe Ser His Gly Gln Arg Gln
        1220                1225                1230

Leu Phe Ser Leu Ala Arg Val Val Leu Lys Arg Arg Leu Met Val Ala
        1235                1240                1245

Gly Gly Gly Gly Ala Val Leu Leu Leu Asp Glu Phe Ser Ser Ser Val
        1250                1255                1260

Asp Ala Val Ser Glu Gln Arg Met Met Val Ala Val Asp Lys His Phe
1265                1270                1275                1280

Ser Gly Cys Thr Val Val Met Val Ala His Arg Leu Lys Thr Val Thr
            1285                1290                1295

Glu Phe Ser Asp Arg Val Phe Val Ile Asp Arg Gly Gln Val Val Glu
            1300                1305                1310

Ser Gly Asp Pro Arg Val Leu Gly Arg Met Glu Gly Thr Trp Phe Ala
            1315                1320                1325

Ser Leu Leu Lys Ala Ser Glu
            1330                1335

<210> SEQ ID NO 27
<211> LENGTH: 728
<212> TYPE: PRT
<213> ORGANISM: Grosmannia clavigera
<220> FEATURE:
<223> OTHER INFORMATION: GcABC-C10

<400> SEQUENCE: 27

Met Ser Leu Arg Trp Cys Gly Glu Glu Val Glu Asn Ser Phe Gly Pro
 1               5                  10                  15

Thr Val Arg Asp Cys Arg Asp Gly Phe Asp Phe Thr Val Phe Phe Glu
            20                  25                  30

Gln Leu Phe Leu Ala Ile Val Pro Ser Ala Val Leu Val Leu Leu Val
        35                  40                  45

Pro Phe Arg Ile Tyr Lys Leu Tyr Arg Ala Ser Pro Lys Ala Arg Gly
    50                  55                  60

Gly Trp Leu Leu Pro Leu Lys Ile Leu Ala Ala Thr Thr Tyr Thr Thr
65                  70                  75                  80

Leu Gln Leu Tyr Leu Leu Val Arg Trp Val Ala Ser Pro Pro Phe Pro
                85                  90                  95

Ala Arg Ala Ala Thr Ser Ala Ala Ala Leu Ser Val Leu Ala Gly Cys
            100                 105                 110

Ala Val Leu Ala Leu Ser Pro Leu Glu His Leu Arg Ala Leu Arg Pro
        115                 120                 125

Ser Thr Leu Leu Gln Ser Tyr Leu Leu Ser Val Leu Phe Asp Ala
    130                 135                 140

Ala Leu Cys Arg Thr Leu Trp Met Ile Gly Arg Asp Ser Ala Ile Glu
145                 150                 155                 160

Arg Val Ser Thr Ala Ile Thr Ala Leu Lys Leu Val Leu Leu Cys Leu
                165                 170                 175

Glu Met Val Glu Lys Arg Arg Trp Leu Lys Pro Gln Tyr Arg Asp Glu
            180                 185                 190

Lys Ala Glu Ala Leu Cys Gly Ile Ile Leu Val Leu Ala Asp Ile Asp
        195                 200                 205

Asp Met Glu Glu Ser His Arg Ala Glu Ala Leu Glu Arg Asn Leu Gln
    210                 215                 220
```

-continued

```
Glu Ser Trp Ala Lys Leu Gln Glu Thr Glu Gln Arg Pro Ser Ser Arg
225                 230                 235                 240

Asn Lys Pro His Ala Leu Leu Arg Thr Leu Ala Trp Thr Leu Arg Arg
            245                 250                 255

Pro Leu Ala Ala Thr Val Phe Pro Arg Leu Cys Ala Ile Gly Phe Lys
        260                 265                 270

Phe Ala Gln Pro Phe Leu Ile Gly Ser Leu Ile Arg Tyr Leu Asp Asp
    275                 280                 285

Ala Ala Pro Glu Asn Asn Ser Ser Gly His Gly Leu Ile Ser Ala
290                 295                 300

Phe Ala Leu Val Tyr Ser Gly Val Ala Val Ser Thr Gly Leu Tyr Trp
305                 310                 315                 320

Tyr Gln Ala Tyr Arg Thr Ile Thr Met Val Arg Gly Ser Leu Ile Ala
                325                 330                 335

Val Val Tyr Ala Arg Thr Leu Asp Leu Asp Leu Gly Ala Pro Ser His
                340                 345                 350

Ala Ser Ser Ser Thr Leu Met Ser Thr Asp Val Glu Arg Ile Cys Thr
            355                 360                 365

Cys Ile Val Asn Leu His Glu Leu Trp Ala Asn Val Leu Glu Val Gly
370                 375                 380

Leu Ala Ile Tyr Ile Leu Ala Thr Gln Leu Gly Gly Ala Cys Ile Ala
385                 390                 395                 400

Val Ala Phe Leu Ala Leu Ala Cys Gly Phe Gly Thr Leu Leu Leu Thr
                405                 410                 415

Lys Pro Ile Glu Lys Arg Gln Glu Ala Trp Leu Lys Ala Ala Gln Lys
            420                 425                 430

Arg Leu Arg Ala Thr Glu Ala Thr Leu Gly Ser Ile Lys Ser Ile Lys
        435                 440                 445

Met Met Gly Trp Thr Glu Pro Met Gln Asn Val Ile Gln Gly Leu Arg
    450                 455                 460

Ile Asp Glu Leu Arg Gln Ala Met His Tyr Arg Lys Leu Gln Val Leu
465                 470                 475                 480

Ser Ile Val Val Ser Leu Val Met Thr Val Ala Gly Pro Ala Thr Ala
                485                 490                 495

Ile Thr Thr Phe Thr Val Ile Ser Val Val Arg Gly Ala Ile Ala Leu
            500                 505                 510

Leu Pro Ser Lys Ala Phe Thr Ser Ile Ala Val Leu Ala Leu Ile Ser
        515                 520                 525

Thr Pro Leu Ile Thr Leu Phe Gln Ala Leu Pro Leu Leu Lys Ser Ala
    530                 535                 540

Val Ala Ser Met Thr Arg Ile Gln Asp Phe Leu Asn Gln Pro Cys Arg
545                 550                 555                 560

Lys Asp Ser Gln Gln Gly Lys Asn Ala Thr Leu Phe Pro Gln Ser Leu
                565                 570                 575

Gly Ser Ser Thr Asp Met Ala Ile Pro Met Val Asp Phe Glu Thr Asn
            580                 585                 590

Arg Ser Ala Ser Lys Gln Gly Pro Ser Arg Gly Asp Gly Lys Val Asp
        595                 600                 605

Asp Pro Ile Thr Met Ser Glu Ala Ser Met Gly Trp Gly Asp His Gly
    610                 615                 620

Asp Lys Val Val Leu His Asp Ile Ser Ile Thr Ile Ala His Gly Ala
625                 630                 635                 640

Leu Ala Met Val Ile Gly Pro Val Gly Cys Gly Lys Ser Asn Leu Leu
```

```
            645                 650                 655
Lys Ala Met Leu Gly Glu Thr Arg Val Cys Gln Gly Val Ile Asn Val
                660                 665                 670

Leu Tyr Glu Glu Val Ala Phe Ser Asp Gln Thr Pro Trp Met Met Phe
                675                 680                 685

Gly Thr Ile Arg Asp Asn Ile Thr Gly Met Thr Gly His Ala Phe Asp
                690                 695                 700

Glu Thr Trp Tyr Arg Thr Val Leu His Ala Cys Ala Leu Glu Lys Asp
705                 710                 715                 720

Leu Glu Gln Leu Pro Asp Gly Gly
                725
```

<210> SEQ ID NO 28
<211> LENGTH: 563
<212> TYPE: PRT
<213> ORGANISM: Grosmannia clavigera
<220> FEATURE:
<223> OTHER INFORMATION: GcABC-C10

<400> SEQUENCE: 28

```
Met Ala Arg Val Leu Tyr Ser Arg Lys Lys Leu Val Ile Leu Asp Asp
1               5                   10                  15

Val Phe Ala Gly Leu Asp Arg Asn Thr Glu Ser Gln Val Phe Ala Arg
                20                  25                  30

Val Phe Gly Pro Ser Gly Leu Leu Arg Gln Gln Lys Ile Thr Thr Val
                35                  40                  45

Leu Val Thr Asn Arg Ala Asn Gln Leu Ala Ala Ser Thr Gln Ile Ile
50                  55                  60

Ala Leu Asp Gln Ala Gly Arg Ile Ser Gln Gln Gly Ala Tyr Asp Lys
65                  70                  75                  80

Leu Cys Cys Val Arg Gly Tyr Val Gln Thr Leu Ser Ser Gln Pro Gly
                85                  90                  95

Ser Gly Ala Ala Glu Gln Asp Asp Leu Thr Ser Val Glu Lys Thr Ile
                100                 105                 110

Val Ala Arg Ala Ser Pro Ala Thr Ser Asn Thr Asp Arg Val Ala Glu
                115                 120                 125

Leu Ala Arg Gln Thr Gly Asp Ile Ser Leu Tyr Gln Tyr Tyr Leu Gln
130                 135                 140

Phe Ala Gly Thr Gly Thr Phe Ile Leu Ala Val Cys Ala Leu Phe Val
145                 150                 155                 160

Tyr Ser Phe Cys Ile Val Phe Pro Ile Val Cys Ile Thr Ala Lys
                165                 170                 175

Tyr Val Ala Thr Val Met Pro Leu Ser Leu Phe Val Ile Tyr Val Ile
                180                 185                 190

Gln Lys Gly Tyr Leu Arg Thr Ser Arg Gln Leu Arg Tyr Leu Asp Leu
                195                 200                 205

Glu Ala Lys Ala Pro Ile Tyr Thr Leu Phe Val Glu Thr Leu Asp Gly
                210                 215                 220

Leu Ala Thr Ile Arg Ala Phe Gly Trp Gln Gly Ser Phe Arg Arg His
225                 230                 235                 240

Gly His Glu Leu Leu Asp Gly Ala Gln Arg Pro Phe Tyr Leu Leu Asn
                245                 250                 255

Cys Ile Gln Arg Trp Leu Gly Phe Val Leu Asp Met Leu Leu Thr Gly
                260                 265                 270

Val Ser Val Leu Val Val Phe Phe Ala Val Arg Leu Arg Ser Gln Thr
```

```
                 275                 280                 285

Thr Gly Gly Thr Thr Gly Val Ala Leu Val Asn Ile Leu Ser Cys His
             290                 295                 300

Gln Asn Leu Ala Gly Phe Val Leu Arg Trp Thr Leu Glu Thr Ser
305                 310                 315                 320

Ile Gly Ala Val Ser Arg Ile Arg Ala Phe Ser Leu Gln Cys Pro Thr
                 325                 330                 335

Glu Leu Arg Glu Ala Val Val Gln Pro Pro Ala Asn Trp Pro Gln Ser
             340                 345                 350

Gly Ser Ile Leu Val Gln Asn Ile Ser Ala Ser Tyr Ser Gly Lys Ser
             355                 360                 365

Ser Phe Ile Leu Cys Leu Leu Gln Met Leu Asp Leu Asp Asp Gly Ser
         370                 375                 380

Ile Thr Ile Asp Asn Val Asp Leu Ser Lys Ile Thr Arg Glu Ala Val
385                 390                 395                 400

Arg Ser Val Phe Ala Ser Val Pro Gln Asp Ser Val Leu Phe Glu Gly
                 405                 410                 415

Ser Val Arg Phe Asn Leu Asp Pro Arg Gly Val Val Glu Asp Ser Arg
             420                 425                 430

Met Gln Ala Ala Leu Arg Lys Val Gln Leu Trp Asp Leu Val Asn Arg
             435                 440                 445

Pro Gly Ser Asp Gly Ser Gly Leu Asp Ser Leu Ile Gly Asp Leu His
         450                 455                 460

Leu Ser His Gly Gln Arg Gln Leu Phe Ser Leu Ala Arg Ala Leu Leu
465                 470                 475                 480

Ser Lys Ala Glu Met Leu Val Leu Asp Glu Ala Thr Ser Ser Met Asp
                 485                 490                 495

Lys Glu Thr Asn Lys Val Met Gln Ser Leu Ile Arg Ser Glu Phe Ala
             500                 505                 510

Asp His Thr Val Leu Cys Val Asp His His Leu Glu Asn Leu Leu Asp
         515                 520                 525

Tyr Asp Val Ile Ala Tyr Phe Asp Asp Gly Ser Leu Val Glu Phe Ser
         530                 535                 540

Ser Ser Ser Val Leu Leu Gln Gln Ser Asn Ser Arg Phe Gln Gln Leu
545                 550                 555                 560

Leu Glu Gly

<210> SEQ ID NO 29
<211> LENGTH: 1258
<212> TYPE: PRT
<213> ORGANISM: Grosmannia clavigera
<220> FEATURE:
<223> OTHER INFORMATION: GcABC-C11

<400> SEQUENCE: 29

Met Lys Arg Thr Trp Ser Ser Val Thr Ser Val Pro Asp Gly Gly Arg
 1               5                  10                  15

Lys Pro Arg Ala Leu Phe Trp Ala Leu Leu Arg Ala Asn Ile Gln Ala
             20                  25                  30

Leu Ala Ser Cys Cys Ile Pro Arg Leu Leu Gln Ile Gly Phe Arg Tyr
         35                  40                  45

Ala Gln Pro Leu Leu Leu Ser Arg Thr Val Ser Tyr Ala Ser Asp Leu
     50                  55                  60

Ser Gln Pro Glu Ser Val Gly Trp Gly Leu Thr Gly Ala Phe Phe Leu
65                  70                  75                  80
```

-continued

Val Met Val Gly Leu Ala Val Ser Asn Gly Trp Tyr Ser His Leu Thr
            85                  90                  95

Tyr Arg Phe Thr Thr Ser Val Arg Gly Ser Leu Ile Gly Leu Ile Tyr
            100                 105                 110

Gly Lys Thr Val Asp Leu Ser Val Thr Ala Leu Asp Glu Ser Val Ala
            115                 120                 125

Val Thr Leu Met Ser Ser Asp Thr Ala Ala Val Cys Thr Gly Leu Gln
            130                 135                 140

Gln Val His Glu Leu Trp Ala Val Pro Val Glu Ile Ala Ile Ala Leu
145                 150                 155                 160

Val Leu Leu His Arg Gln Leu Gly Val Ala Met Val Ala Pro Ala Val
                165                 170                 175

Leu Ala Thr Phe Ser Trp Val Ala Ile Met Ala Leu Ala Arg His Leu
                180                 185                 190

Gly Arg Ala Gln Glu Met Trp Met Glu Gly Ile Gln Thr Arg Val Asp
                195                 200                 205

Val Thr Ala Arg Met Leu Gly Ala Met Lys Ser Val Lys Met Leu Gly
210                 215                 220

Phe Ser Gly Arg Met Glu Arg Asp Val Gln Thr Leu Arg Val Ala Glu
225                 230                 235                 240

Met Asp Ala Ser Thr Met Phe Arg Lys Leu Ile Thr Val Arg Val Phe
                245                 250                 255

Leu Ala Asn Ile Leu Asp Met Leu Gly Pro Phe Met Thr Phe Ala Val
                260                 265                 270

Phe Val Ile Ala Ala His His Gly Asp Ala Ser Gly Asp Ser Val Leu
                275                 280                 285

Lys Ala Gly Arg Ala Tyr Thr Ala Leu Ser Leu Ile Ser Leu Leu Ser
            290                 295                 300

Thr Pro Val Asn Gly Leu Ile Ala Val Ile Pro Met Val Ile Ala Ala
305                 310                 315                 320

Leu Ala Ser Leu Gly Arg Ile Gln Thr Phe Leu Ala Ser Asp Ala Arg
                325                 330                 335

Arg Asp His Arg Leu Pro Leu Gly Ser Asn Gly Gln Ser Thr Ser Thr
                340                 345                 350

Val Thr Ser Thr Asp Ser Ile Glu Leu Ala Ser Val Pro Ser Thr Asp
            355                 360                 365

Ala Val Met Val Ala Gln Asp Val Ser Phe Ser Trp Thr Gln Ser Val
            370                 375                 380

Pro Val Val Arg Asp Val Asn Phe Thr Ile Ala Arg Gly Glu Ile Cys
385                 390                 395                 400

Ile Val Ile Gly Pro Val Gly Cys Gly Lys Ser Thr Leu Leu Lys Gly
                405                 410                 415

Ile Leu Gly Glu Thr Pro Ser Thr Gln Gly Phe Leu Tyr Thr Ala Cys
                420                 425                 430

Pro Glu Val Ala Tyr Val Asp Gln Thr Ala Trp Ile Arg Asn Thr Thr
            435                 440                 445

Phe Arg Asp Asn Val Leu Gly Met Ser Val Tyr Asp Asp Ala Trp Tyr
450                 455                 460

Arg Glu Val Val Ser Ala Cys Gly Leu Asp Glu Asp Val Ala Ala Leu
465                 470                 475                 480

Pro His Gly His His Thr Lys Val Gly Ser Ser Gly Ile Ser Leu Ser
                485                 490                 495

-continued

```
Gly Gly Gln Lys Gln Arg Leu Ala Leu Ala Arg Ala Val Tyr Ala Arg
            500                 505                 510

Lys Ser Val Val Val Leu Asp Asp Val Phe Ser Gly Leu Asp Ala Asp
        515                 520                 525

Thr Glu Glu His Ile Phe Ala Arg Leu Phe Ser Arg Gln Gly Gly Leu
    530                 535                 540

Phe Arg Asn Arg Gln Pro Gly Ala Thr Lys Thr Met Thr Thr Val Leu
545                 550                 555                 560

Leu Val Thr His Ala Val His Arg Leu Ala Tyr Ala Asp His Val Ile
            565                 570                 575

Ala Met Ala Pro Asp Gly Thr Ile Ala Glu Gln Gly Thr Leu Gly Gln
        580                 585                 590

Leu Glu Lys Ala Gly Gly Tyr Val Ala Ser Leu Lys Ala Arg Gln Arg
    595                 600                 605

Gly Gln Glu Gly Glu Glu Thr Asp Gly Lys Val Arg Ala Asp Gln Asn
            610                 615                 620

Arg Thr Asp Lys Gln Ala Ala Pro Gly Ile Val Met Ala Glu Glu Ser
625                 630                 635                 640

Glu Gly Gly His Met Leu Asp Glu Ser Asp His Arg Ser Thr Gly Asp
            645                 650                 655

Phe Ser Leu Tyr Met Tyr Phe Phe Gly Thr Val His Trp Ser Ser Thr
        660                 665                 670

Ala Leu Trp Ile Gly Cys Phe Leu Ala Phe Gly Val Ala Ser Lys Leu
    675                 680                 685

Ala Glu Phe Val Val Tyr Phe Trp Thr Asn Ala Ala Lys Arg Asp Gly
690                 695                 700

Ser Arg Val Asp Gly Phe Tyr Leu Gly Met Leu Gly Leu Thr Ala Val
705                 710                 715                 720

Phe Thr Thr Cys Gly Leu Ile Ser Gly Leu His Tyr Val Leu Tyr
            725                 730                 735

Phe Ala Pro Arg Ser Ala Ala Val Leu His Gln Arg Leu Leu Arg Thr
        740                 745                 750

Val Met Arg Ala Pro Leu Ala Phe Phe Ser Ala Val Asp Thr Gly Thr
    755                 760                 765

Thr Thr Asn Arg Phe Ser Gln Asp Met Thr Leu Leu Asp Asn Asp Leu
770                 775                 780

Ala Tyr Ser Met Ile Asn Phe Thr Val Ala Leu Phe Ser Gly Ala Met
785                 790                 795                 800

Ser Ala Leu Leu Met Cys Ile Ser Ala Arg Tyr Phe Ala Ala Val Met
            805                 810                 815

Pro Val Val Ala Leu Val Ala Trp Val Leu Gln Arg Tyr Tyr Leu Arg
        820                 825                 830

Thr Ser Arg Gln Met Arg Leu Leu Asp Leu Glu Ala Lys Ser Pro Leu
    835                 840                 845

Phe Gly His Phe Leu Glu Thr Leu Ser Gly Leu Val Ser Leu Arg Ala
850                 855                 860

Phe Gly Trp Thr Asp Ala Phe Glu Ser Arg Gly Met Ala Leu Leu Asp
865                 870                 875                 880

Ala Ser Gln Arg Pro Phe Tyr Leu Leu Phe Cys Leu Gln Arg Trp Leu
            885                 890                 895

Lys Leu Val Leu Asp Leu Leu Val Ala Gly Leu Ala Val Val Leu Met
        900                 905                 910

Val Leu Val Val Lys Leu Arg Glu Glu Val Gly Ala Gly Phe Val Gly
```

```
                915                 920                 925
Leu Ala Ile Leu Asn Val Leu Thr Phe Ser Glu Ser Leu Thr Met Ile
    930                 935                 940

Ile Arg Asp Trp Thr Val Leu Glu Thr Ser Leu Gly Ala Val Ala Arg
945                 950                 955                 960

Val Arg Ser Phe Thr Thr Thr Ala Asp Glu Asn Arg Pro Asp Glu
                965                 970                 975

Asp Gln Pro Leu Pro Glu Gly Thr Gly Asp Glu Leu Trp Pro Ser Arg
            980                 985                 990

Gly Ala Ile Glu Phe Arg Asn Val Ser Ala Ser Tyr Thr Glu Asn Gly
        995                 1000                1005

Lys Leu Val Val Arg Ser Val Ser Leu Ser Ile Arg Pro Gly Glu Lys
    1010                1015                1020

Val Gly Ile Cys Gly Arg Ser Gly Ser Gly Lys Ser Ser Leu Leu Val
1025                1030                1035                1040

Thr Leu Phe Arg Met Leu Glu Ile Val Pro Gly Gln Asp Gly Arg Ile
                1045                1050                1055

Gly Ser Ile Ile Ile Asp Gly Val Asp Ile Ser Arg Ala Arg Arg Asn
            1060                1065                1070

Asp Val Arg Ser Arg Leu Asn Val Ile Pro Gln Asp Pro Phe Phe Leu
        1075                1080                1085

Pro Arg Ala Thr Val Arg Glu Asn Ala Asp Pro Trp Thr Arg His Asp
    1090                1095                1100

Asp Ala Val Val Met Asp Ala Leu Gln Arg Val Gly Leu Trp Glu Thr
1105                1110                1115                1120

Val Met Ala Glu Ser Gly Gly Leu Asp Ala Leu Leu Asp Ala Asp Ala
                1125                1130                1135

Ala Gly Ser Leu Ser His Gly Gln Arg Gln Leu Phe Cys Leu Ala Arg
            1140                1145                1150

Ala Leu Leu Arg Ala Arg Pro Arg Thr Arg Asp Gly Ser Asp His Asn
        1155                1160                1165

Gly Ser Asp Asp Asp Gly Gly Cys Gly Arg Val Ile Val Leu Asp Glu
    1170                1175                1180

Ala Ser Ser Ser Val Asp Val Glu Ala Asp Ala Arg Met Gln Ala Val
1185                1190                1195                1200

Ile Arg Ser Glu Phe Val Gly Cys Thr Val Leu Ala Val Ala His Arg
                1205                1210                1215

Leu Asp Thr Ile Leu Asp Phe Asp Arg Val Ala Val Met Trp Asp Gly
            1220                1225                1230

Glu Leu Val Glu Leu Gly Thr Pro Ala Glu Leu Leu Gln Arg Glu Gly
        1235                1240                1245

Gly Ala Phe Lys Glu Leu Tyr Glu Ser Arg
    1250                1255

<210> SEQ ID NO 30
<211> LENGTH: 252
<212> TYPE: PRT
<213> ORGANISM: Grosmannia clavigera
<220> FEATURE:
<223> OTHER INFORMATION: GcABC-C11

<400> SEQUENCE: 30

Met Asp Val Leu Thr Leu Ser Arg Gly Ile Pro Ser Ser Asn Thr Ser
1               5                   10                  15

Gln Gly Ser Gly Asp Val Arg Leu Asn Met Tyr His Tyr Phe Gly Pro
```

```
              20                  25                  30
Ala Ala Ala Gly Gly Gln Phe Asp Phe Ala Pro Leu Phe Glu Asp Thr
         35                  40                  45
Ile Leu Gly Ile Leu Pro Ser Ala Leu Leu Val Val Leu Pro Tyr
 50                  55                  60
Arg Ile Leu Ala Leu Gln Arg Gln Pro Lys Val Ala Pro Gly Gly
 65                  70                  75                  80
Leu Leu His Asp Asn Lys Leu Ala Phe Leu Thr Val Phe Ala Ala Met
                 85                  90                  95
Gln Leu Ala Ile Leu Val Leu Ser Ser Thr Ile Leu Gly Pro Gly Met
            100                 105                 110
Arg Thr Ser Ala Ser Val Ala Ala Pro Ala Leu Ser Phe Ala Ala Ser
            115                 120                 125
Val Gly Leu Val Val Leu Ser His Leu Glu His Val Arg Ser Leu Arg
            130                 135                 140
Pro Ser Leu Val Ile Asn Ser Tyr Leu Leu Leu Thr Leu Pro Phe Asp
145                 150                 155                 160
Ala Ala Arg Thr Arg Thr Leu Phe Leu Gln Arg Gly Asn Arg Asn Gly
                165                 170                 175
Val Leu Ala Ser Cys Val Ala Ser Met Met Gly Val Lys Leu Leu Ala
                180                 185                 190
Leu Leu Ala Glu Ala Val Glu Lys Arg Gly Arg Leu Leu Glu Pro Tyr
            195                 200                 205
Arg Gly Leu Ser Pro Glu Glu Thr Ser Gly Ile Tyr Ser Arg Ser Met
            210                 215                 220
Phe Trp Trp Leu Asn Arg Leu Leu Arg Gly Gly Ala Phe Glu Ala Arg
225                 230                 235                 240
Cys Lys Arg Pro Ile Cys Ile Arg Ser Thr Glu Lys
                245                 250

<210> SEQ ID NO 31
<211> LENGTH: 1551
<212> TYPE: PRT
<213> ORGANISM: Grosmannia clavigera
<220> FEATURE:
<223> OTHER INFORMATION: GcABC-C12

<400> SEQUENCE: 31

Met Asp Asp Gly Phe Glu Gly Leu Phe Pro Ala Phe Ser Ala Ser Ser
 1               5                  10                  15
Gln Lys Val Met Ala Gln Thr Gly Ser Phe Ser Gly Tyr Arg Pro Leu
             20                  25                  30
His Pro Leu Gly Ser Gly Tyr Leu Ser Ser Ala Arg Ser Glu Gln Pro
         35                  40                  45
Phe Cys Lys Asn Asp Glu Gly Trp Gly Pro Leu Ser Pro Phe Arg Tyr
 50                  55                  60
Asp Phe Thr Pro Cys Phe Ile Asp Ile Trp Val Ala Ser Val Ser Ala
 65                  70                  75                  80
Phe Gly Val Leu Phe Gly Ala Val Thr Leu Trp Trp Leu Phe Ala Lys
                 85                  90                  95
Lys Thr Ser Asn Ser Leu Pro Lys Asn Trp Ala Phe Trp Leu Lys Gln
            100                 105                 110
Thr Leu Leu Leu Thr Val Ile Ser Asp Phe Val Ala Gln Leu Val Phe
            115                 120                 125
Gln Ile Thr Ser Tyr Ser Ser Leu Trp Phe Ala Asp Phe Arg Val Tyr
```

```
              130                 135                 140
Thr Thr Ile Leu Thr Ile Val Ser Phe Ala Val Ile Phe Ala Ile Gln
145                 150                 155                 160

Trp Ala Glu His Thr Arg Leu Arg Asn Ala Asn Ala Val Val Leu Phe
                165                 170                 175

Tyr Trp Leu Phe Leu Ile Ile Ala Leu Ser Val Lys Leu Arg Ser Leu
            180                 185                 190

Val Ser Gln Gln Ile Tyr Val Asp His Leu Ala Tyr Phe Val Thr Tyr
        195                 200                 205

Ala Val Gly Phe Gly Leu Ala Ala Ala Thr Phe Phe Ile Glu Trp Leu
    210                 215                 220

Ala Pro Arg Gln Ile Ser Ser Asp Tyr Glu Val Leu Val Asp Glu Arg
225                 230                 235                 240

Glu Glu Cys Pro Ala Glu His Ala Thr Ile Phe Ser Leu Leu Thr Phe
                245                 250                 255

Ser Trp Met Thr Pro Leu Met Arg Tyr Gly Tyr Ser Thr Tyr Leu Thr
                260                 265                 270

Glu Gly Asp Leu Trp Gly Leu Val Ser Ser Asp Arg Thr Ala Val Thr
            275                 280                 285

Gly Ala Thr Phe Glu Ala Ala Trp Glu Arg Glu Leu Lys Thr Arg Pro
        290                 295                 300

Asp Arg Pro Ser Leu Trp Thr Thr Leu Phe Arg Ala Phe Gly Ala Pro
305                 310                 315                 320

Tyr Ala Met Ala Ala Val Phe Lys Val Gly Asn Asp Leu Ala Ala Phe
                325                 330                 335

Ser Gln Pro Gln Leu Leu Arg Tyr Leu Ile Ala Phe Val Asp Ser Tyr
                340                 345                 350

Asn Leu Ser Thr Glu Pro Gln Pro Ala Ile Gln Gly Ala Ala Ile Ala
            355                 360                 365

Leu Gly Met Phe Gly Val Ala Val Phe Gln Thr Ile Met Ile His Gln
        370                 375                 380

Tyr Phe Gln Leu Thr Phe Val Ser Gly Met Arg Ile Lys Gly Gly Leu
385                 390                 395                 400

Thr Ser Ser Ile Tyr Arg Lys Ala Leu Lys Leu Ser Asn Glu Gly Arg
                405                 410                 415

Ala Ser Lys Thr Thr Gly Asp Ile Val Asn Tyr Met Ala Val Asp Val
                420                 425                 430

Gln Arg Leu Gln Asp Leu Thr Gln Phe Ala His Gln Leu Trp Ser Ala
            435                 440                 445

Pro Phe Gln Met Val Ile Cys Met Phe Ser Leu Tyr Gln Leu Val Gly
        450                 455                 460

Trp Thr Met Phe Ala Gly Val Ser Ala Met Ile Val Met Val Pro Val
465                 470                 475                 480

Asn Gly Phe Ile Ala Arg Arg Met Lys Thr Leu Gln Lys Gln Gln Met
                485                 490                 495

Lys Asn Lys Asp Ala Arg Ser Arg Leu Ile Ser Glu Ile Ile Asn Asn
                500                 505                 510

Met Lys Ser Ile Lys Leu Tyr Ala Trp Gly Ala Ala Phe Met Asn Lys
            515                 520                 525

Leu Asn Tyr Ile Arg Asn Asp Met Glu Leu Lys Asn Leu Arg Arg Ile
        530                 535                 540

Gly Ala Asn Gln Ala Phe Ala Asn Phe Thr Trp Thr Thr Thr Pro Phe
545                 550                 555                 560
```

```
Leu Val Ser Cys Met Thr Phe Ala Val Phe Leu Thr His Asp Glu
                565             570             575

Pro Leu Thr Thr Glu Ile Ile Phe Pro Ala Leu Ala Leu Phe Asn Leu
                580             585             590

Leu Ser Phe Pro Leu Ser Val Leu Pro Met Val Ile Thr Ser Ile Ile
                595             600             605

Glu Ala Ser Val Ala Val Ser Arg Leu Thr Asn Phe Leu Ile Ala Glu
                610             615             620

Glu Ile Gln Ser Asp Ala Val Thr Ser Lys Pro Ser Val Glu Ala Gly
625             630             635             640

Glu Glu Ala Val Ser Ile Arg Asp Gly Ser Phe Ser Trp Asp Arg His
                645             650             655

Glu Asn Lys Pro Ala Leu Ser His Ile Asp Phe Phe Ala His Lys Gly
                660             665             670

Glu Leu Thr Cys Leu Val Gly Arg Val Gly Thr Gly Lys Ser Ser Leu
                675             680             685

Leu Gln Ala Ile Leu Gly Asp Leu Trp Lys Ile Lys Gly Thr Val Glu
                690             695             700

Val Ala Gly Cys Val Ala Tyr Val Ala Gln Gln Ser Trp Ile Met Asn
705             710             715             720

Ala Thr Val Lys Glu Asn Ile Leu Phe Gly His Arg Phe Asp Ser His
                725             730             735

Phe Tyr Glu Gln Thr Val Gln Ala Cys Ala Leu Leu Asp Asp Phe Leu
                740             745             750

Gln Leu Pro Asp Gly Asp Glu Thr Val Val Gly Glu Arg Gly Ile Ser
                755             760             765

Leu Ser Gly Gly Gln Lys Ala Arg Val Thr Leu Ala Arg Ala Val Tyr
                770             775             780

Ala Arg Ala Asp Val Tyr Leu Leu Asp Asp Val Leu Ser Ala Val Asp
785             790             795             800

Ser His Val Gly Arg His Leu Ile Asp Asn Val Leu Gly Pro Glu Gly
                805             810             815

Leu Leu Ser Ser Lys Thr Arg Ile Leu Ala Thr Asn Ser Ile Pro Val
                820             825             830

Leu Thr Glu Cys Asn Ser Ile Tyr Met Leu Arg Asp Gly Lys Ile Ala
                835             840             845

Glu Lys Gly Thr Tyr Asp Gln Leu Met Ala Met Lys Gly Leu Val Ser
850             855             860

Asp Leu Ile Arg Thr Ser Gly His Glu Ser Gly Ser Ala Ser Ala Ala
865             870             875             880

Glu Ser Gly Ser Glu Thr Ser Thr Val Ile Asp Thr Glu Thr Thr Pro
                885             890             895

Leu Met Asp Asp Glu Ile Glu Glu Ala Gln Glu Gly Leu Ala Pro Leu
                900             905             910

Glu Ser Phe Arg Pro Gly Ala Ser Ser Arg Pro Lys Lys Gln Arg
                915             920             925

Ala Asn Ser Thr Val Thr Leu Arg Arg Ala Ser Ala Ala Ser Phe Arg
                930             935             940

Gly Pro Arg Gly Lys Leu Gly Asp Glu Glu Ala Thr Gly Asn Arg Thr
945             950             955             960

Lys Gln Asn Lys Glu His Ser Glu Gln Gly Lys Val Lys Trp Gln Val
                965             970             975
```

```
Tyr Ile Glu Tyr Ala Lys Ala Asn Asn Leu Val Ala Val Ala Val Tyr
            980                 985                 990

Leu Val Ala Leu Val Ala Ser Gln Thr Ala Ser Met Gly Gly Ser Val
            995                1000                1005

Trp Leu Lys Lys Trp Ala Glu Tyr Asn Ala Gly Asn Gly Gly Asn Phe
           1010                1015                1020

His Val Gly Lys Tyr Ile Gly Val Tyr Phe Ala Phe Gly Ile Gly Gly
1025                1030                1035                1040

Ala Leu Leu Thr Ala Ala Gln Met Leu Ile Leu Trp Ile Leu Cys Ser
                1045                1050                1055

Ile Glu Ala Ser Arg Lys Leu His Glu Arg Met Ala Thr Ala Ile Phe
                1060                1065                1070

Arg Ser Pro Met Ser Phe Phe Asp Val Thr Pro Ala Gly Arg Ile Leu
                1075                1080                1085

Asn Arg Phe Ser Ser Asp Ile Tyr Arg Val Asp Glu Val Leu Ala Arg
                1090                1095                1100

Thr Phe Asn Met Leu Phe Val Asn Ile Ser Lys Ser Gly Phe Thr Leu
1105                1110                1115                1120

Ala Ile Ile Ser Val Ser Thr Pro Ala Phe Thr Ala Leu Val Ile Pro
                1125                1130                1135

Leu Ser Ile Met Tyr Ile Trp Ile Gln Arg Tyr Tyr Leu His Thr Ser
                1140                1145                1150

Arg Glu Leu Lys Arg Leu Asp Ser Val Thr Lys Ser Pro Ile Tyr Ala
                1155                1160                1165

His Phe Gln Glu Ser Leu Gly Gly Thr Ser Thr Ile Arg Ala Tyr Gly
                1170                1175                1180

Gln Gln Lys Arg Phe Glu Met Glu Asn Glu Trp Arg Met Asp Ala Asn
1185                1190                1195                1200

Leu Arg Ala Phe Phe Pro Ser Ile Ser Ser Asn Arg Trp Leu Ala Val
                1205                1210                1215

Arg Leu Glu Phe Ile Gly Ala Ala Val Ile Leu Gly Ala Ala Gly Leu
                1220                1225                1230

Ser Val Ile Ser Val Ala Asn His Ser Gly Leu Ser Ala Gly Met Val
                1235                1240                1245

Gly Leu Ala Met Ser Tyr Ala Leu Gln Ile Val Thr Ala Leu Asn Trp
                1250                1255                1260

Ile Val Arg Leu Ser Val Glu Val Glu Thr Asn Ile Val Ser Val Glu
1265                1270                1275                1280

Arg Val Leu Glu Tyr Ala Gln Leu Pro Ser Glu Ala Pro Glu Ile Ile
                1285                1290                1295

Lys Arg His Arg Pro Pro Val Ser Trp Pro Ser Asn Gly Glu Val Glu
                1300                1305                1310

Phe Arg Asp Tyr Ser Ala Arg Tyr Arg Glu Gly Leu Asp Leu Val Leu
                1315                1320                1325

Lys Asn Ile Thr Leu Asp Ile Lys Pro Arg Glu Lys Ile Gly Val Val
                1330                1335                1340

Gly Arg Thr Gly Ala Gly Lys Ser Ser Leu Thr Leu Ala Leu Phe Arg
1345                1350                1355                1360

Ile Ile Glu Pro Asp Thr Gly His Ile Arg Ile Asp Asp Leu Asn Thr
                1365                1370                1375

Ser Thr Ile Gly Leu Leu Asp Leu Arg Arg Arg Leu Ala Ile Ile Pro
                1380                1385                1390

Gln Asp Ala Ala Leu Phe Glu Gly Thr Val Arg Asp Asn Leu Asp Pro
```

```
                1395                1400                1405
Ala His Val His Asp Asp Thr Asp Leu Trp Ser Val Leu Glu His Ala
        1410                1415                1420

Arg Leu Lys Asp His Val Ser Ser Met Gly Gly Gly Leu Glu Ser Arg
1425                1430                1435                1440

Ile Asn Glu Gly Gly Ser Asn Leu Ser Gln Gly Gln Arg Gln Leu Val
                1445                1450                1455

Ser Leu Ala Arg Ala Met Leu Thr Pro Ser Asn Ile Leu Val Leu Asp
        1460                1465                1470

Glu Ala Thr Ala Ala Val Asp Val Gly Thr Asp Arg Met Leu Gln Thr
        1475                1480                1485

Thr Leu Arg Ser Pro Met Phe Ala Asn Arg Thr Ile Ile Thr Val Ala
        1490                1495                1500

His Arg Ile Asn Thr Ile Leu Asp Ser Asp Arg Val Val Leu Asp
1505                1510                1515                1520

Lys Gly Glu Val Ala Glu Phe Gly Thr Pro Gln Glu Leu Ile Ala Lys
                1525                1530                1535

Arg Gly Arg Phe Tyr Gly Leu Val Lys Gln Ala Gly Leu Thr Asp
        1540                1545                1550

<210> SEQ ID NO 32
<211> LENGTH: 1487
<212> TYPE: PRT
<213> ORGANISM: Grosmannia clavigera
<220> FEATURE:
<223> OTHER INFORMATION: GcABC-C13

<400> SEQUENCE: 32

Met Ala Asp Asp Arg Asp Tyr Glu Asp Glu Arg Glu His Glu Val Glu
1               5                   10                  15

Met Asn Glu Ser Pro Asp Pro Ile Ala Lys Ala Val Leu Pro Ser Thr
                20                  25                  30

Gly Glu Asp Val Met Gly Glu Lys Glu Val Val Gly Ala Met Glu
            35                  40                  45

Gln Asn Ser Asp Leu Asp Asp Glu Val Ser Arg Glu Gln Thr Met
50                  55                  60

Gln Arg Gln Glu Leu Asp Arg Thr Arg Ser Ala Ala Thr Asp Ala Ser
65                  70                  75                  80

Ala Ala Ser Ala Ala Thr Ser Ala Pro Glu Thr Met Pro Pro Ser Trp
                85                  90                  95

Ile Arg Lys Ile Asn Pro Leu Arg Trp Gly Ser Val Pro Pro Val Pro
                100                 105                 110

Ala Glu Arg Val Glu Cys Pro Glu Ala Thr Ala Thr Phe Phe Ser Arg
            115                 120                 125

Leu Ser Phe His Trp Gln Ala Ser Met Met Arg Val Gly Tyr Lys Arg
130                 135                 140

Pro Leu Glu Lys Asn Asp Ile Trp Leu Val Asn His Asn Arg Ala Val
145                 150                 155                 160

Lys Pro Met Ser Glu Arg Val Arg Glu Ser Phe Lys Arg Arg Val Ala
                165                 170                 175

Asn Gly Asp Lys His Pro Leu Leu Trp Ala Leu Asn Glu Ala Phe Phe
            180                 185                 190

Val Glu Phe Trp Leu Gly Gly Leu Phe Gln Leu Ser Ser Thr Ile Phe
        195                 200                 205

Gln Val Leu Ser Pro Phe Ile Leu Arg Tyr Leu Ile Lys Phe Ala Thr
```

```
              210                 215                 220
Lys Ala Tyr Arg Ala Asn His Asp Gly Gly Pro Ala Pro His Ile Gly
225                 230                 235                 240

His Gly Ile Gly Leu Val Phe Gly Ile Thr Ile Met Gln Ile Cys Gln
                245                 250                 255

Ser Leu Gly Thr Asn His Phe Ile Phe Arg Gly Met Met Ile Gly Gly
                260                 265                 270

Gln Val Arg Ala Thr Leu Ile Asn Leu Ile Tyr Glu Lys Ser Met Val
            275                 280                 285

Ile Ser Ala Arg Ala Lys Ala Gly Gly Val Ala Pro Gly Glu Lys Thr
290                 295                 300

Glu Pro Val Lys Ala Glu Asp Arg Thr Asn Gly Glu Lys Gly Asp Lys
305                 310                 315                 320

Pro Arg Thr Lys Asp Lys Glu Ser Ala Leu Ala Val Ser Val Asp Gly
                325                 330                 335

Val Gly Trp Gly Asn Gly Arg Val Val Asn Leu Met Gly Val Asp Thr
                340                 345                 350

Tyr Arg Val Asp Gln Ala Cys Gly Leu Phe His Ile Ile Trp Ala Ala
            355                 360                 365

Pro Leu Ser Cys Leu Ile Thr Leu Ala Leu Leu Leu Val Asn Leu Thr
370                 375                 380

Tyr Ser Ala Leu Ala Gly Phe Gly Leu Leu Ile Val Gly Ile Pro Leu
385                 390                 395                 400

Leu Thr Arg Ala Met Arg Ser Leu Phe Val Arg Arg Lys Gln Ile Asn
                405                 410                 415

Arg Val Thr Asp Gln Arg Val Ser Leu Thr Gln Glu Ile Leu Ser Ser
                420                 425                 430

Val Arg Phe Val Lys Asn Phe Gly Trp Glu Ser Ser Phe Leu Ala Arg
            435                 440                 445

Leu Glu Glu Tyr Arg Ala Thr Glu Ile Arg Met Ile Gln Val Leu Leu
450                 455                 460

Ser Ile Arg Asn Ala Ile Met Ala Ile Ser Leu Ala Leu Pro Ile Phe
465                 470                 475                 480

Ala Ser Met Leu Ala Phe Ile Thr Tyr Ser Leu Thr Gln His Gly Leu
                485                 490                 495

Asp Pro Ala Ser Val Phe Ser Ser Leu Ala Leu Phe Asn Gly Leu Arg
                500                 505                 510

Met Pro Leu Asn Leu Leu Pro Leu Val Leu Gly Gln Val Thr Asp Ala
            515                 520                 525

Trp Asn Ser Leu Lys Arg Ile Gln Glu Tyr Leu Leu Ala Glu Glu Arg
530                 535                 540

Glu Asp Glu Ala Glu Trp Asn Thr Asp Gly Pro Asn Thr Val Glu Val
545                 550                 555                 560

His Asp Ala Ser Phe Thr Trp Glu Arg Thr Pro Thr Gln Glu Thr Asp
                565                 570                 575

Asp Ala Gly Gly Lys Lys Ser Pro Lys Lys Glu Ala Thr Lys Gln Pro
                580                 585                 590

Ala Thr Glu Thr Val Leu Pro Leu Ser Asp Gly Asn Ala Gly Asp Thr
            595                 600                 605

Ala Ser Thr Leu Val Glu Glu Arg Glu Pro Phe Lys Leu His Asp Leu
610                 615                 620

Asp Phe Thr Ile Gly Arg Ser Glu Leu Val Ala Val Ile Gly Ser Val
625                 630                 635                 640
```

-continued

```
Gly Ser Gly Lys Thr Ser Leu Leu Ala Ala Leu Ala Gly Asp Met Arg
            645                 650                 655

Lys Thr Lys Gly Ser Val Val Leu Gly Gly Thr Arg Ala Phe Cys Pro
            660                 665                 670

Gln Tyr Ala Trp Ile Gln Asn Thr Thr Leu Arg Asn Asn Ile Ile Phe
            675                 680                 685

Gly Lys Asp Met Asp Glu Asn Arg Tyr Arg Glu Val Ile Lys Ala Cys
            690                 695                 700

Ala Leu Gln Pro Asp Leu Asp Met Leu Pro Ser Gly Asp Ala Thr Glu
705                 710                 715                 720

Ile Gly Glu Arg Gly Ile Thr Ile Ser Gly Gln Lys Gln Arg Leu
            725                 730                 735

Asn Ile Ala Arg Ala Ile Tyr Phe Asn Ala Asp Ile Val Leu Met Asp
            740                 745                 750

Asp Pro Leu Ser Ala Val Asp Ala His Val Gly Arg His Ile Phe Asp
            755                 760                 765

Asn Ala Ile Leu Gly Met Val Lys Asp Lys Cys Arg Ile Leu Ala Thr
            770                 775                 780

His Gln Leu Trp Val Leu Asn Arg Cys Asp Arg Ile Ile Trp Met Glu
785                 790                 795                 800

Gly Gly Lys Ile Gln Ala Val Asp Thr Phe Pro Asn Leu Met Arg Asp
            805                 810                 815

His Ala Gly Phe Gln Gln Met Met Glu Ser Thr Ala Val Glu Asp Glu
            820                 825                 830

Asp Glu Ser Ala Pro Ala Pro Ala Thr Lys Glu Ala His Ala Asp Thr
            835                 840                 845

Lys Lys Lys Ser Lys Ser Lys Gly Leu Met Gln Gln Glu Glu Arg Ala
            850                 855                 860

Val Ala Ser Val Pro Trp Ser Ala Tyr Thr Asp Tyr Leu Arg Glu Ser
865                 870                 875                 880

Gly Ser Ile Phe Asn Gly Leu Leu Val Phe Ile Leu Leu Ile Leu Ala
            885                 890                 895

Gln Gly Ser Asn Ile Thr Thr Ser Leu Trp Leu Ser Tyr Trp Thr Ser
            900                 905                 910

Arg Lys Phe Asp Leu Ser Thr Gly Ala Tyr Ile Gly Ile Tyr Ala Ala
            915                 920                 925

Leu Gly Ala Ala Gln Gly Ser Leu Ala Met Leu Arg Arg Ala Ile Thr
930                 935                 940

Arg Val Leu Arg Ala Pro Met Ser Phe Phe Asp Thr Thr Pro Leu Gly
945                 950                 955                 960

Arg Ile Thr Asn Arg Phe Ser Arg Asp Val Asp Val Met Asp Asn Ser
            965                 970                 975

Leu Thr Asp Ala Ile Arg Ile Tyr Phe Phe Ser Val Gly Asn Ile Ile
            980                 985                 990

Ala Val Phe Ala Leu Ile Ile Ala Tyr Phe His Tyr Phe Ala Ile Ala
            995                 1000                1005

Leu Gly Pro Leu Phe Ile Ile Phe Leu Leu Ala Thr Ser Tyr Tyr Arg
            1010                1015                1020

Gln Ser Ala Arg Asp Ile Lys Arg Tyr Glu Ser Val Leu Arg Ser His
1025                1030                1035                1040

Val Phe Ala Lys Phe Gly Glu Gly Leu Ser Gly Val Ser Ile Arg
            1045                1050                1055
```

```
Ala Tyr Gly Leu Arg Asp Arg Phe Val Ala Gly Leu His Glu Ala Ile
            1060                1065                1070

Asp Asp Met Asn Arg Ala Tyr Tyr Leu Thr Phe Ser Asn Gln Arg Trp
        1075                1080                1085

Leu Ser Leu Arg Leu Asp Ala Ile Gly Asn Ile Leu Val Phe Ile Val
    1090                1095                1100

Gly Ile Leu Val Val Thr Ser Arg Phe Asn Val Ser Pro Ser Ile Ala
1105                1110                1115                1120

Gly Leu Val Leu Ser Tyr Ile Leu Ala Ile Val Gln Met Ile Gln Phe
                1125                1130                1135

Thr Val Arg Gln Leu Ala Glu Val Glu Asn Gly Met Asn Ala Val Glu
            1140                1145                1150

Arg Leu Gln Tyr Tyr Gly Arg Glu Leu Glu Glu Glu Ala Pro Ala His
        1155                1160                1165

Thr Val Glu Val Arg Lys Ser Trp Pro Glu Lys Gly Glu Ile Val Phe
    1170                1175                1180

Asp Asp Val Lys Met Arg Tyr Arg Ala Gly Leu Pro Leu Val Leu Gln
1185                1190                1195                1200

Gly Leu Ser Met His Val Gln Gly Gly Glu Arg Ile Gly Ile Val Gly
                1205                1210                1215

Arg Gly Gly Gly Gly Lys Ser Ser Ile Met Ser Thr Leu Phe Arg Leu
            1220                1225                1230

Val Glu Ile Ser Gly Gly His Ile Thr Ile Asp Gly Ile Asp Ile Ser
        1235                1240                1245

Thr Ile Gly Leu Ser Asp Leu Arg Ser Arg Leu Ala Ile Ile Pro Gln
    1250                1255                1260

Asp Pro Thr Leu Phe Arg Gly Thr Val Arg Ser Asn Leu Asp Pro Phe
1265                1270                1275                1280

Asn Glu His Thr Asp Leu Glu Leu Trp Glu Ala Leu Arg Gln Ala Asp
                1285                1290                1295

Leu Val Ser Asp Glu Ala Ala Glu Gln Ala Thr Ala Asp Ile Asn Glu
            1300                1305                1310

Pro Gly Ser Gly Gly Glu Thr Arg Asp Ala Gly Arg Ile Gln Leu Asp
        1315                1320                1325

Ser Val Val Glu Glu Asp Gly Leu Asn Phe Ser Leu Gly Gln Arg Gln
    1330                1335                1340

Leu Met Ala Leu Gly Arg Ala Leu Val Arg Gly Ser Gln Ile Ile Val
1345                1350                1355                1360

Cys Asp Glu Ala Thr Ser Ser Val Asp Met Glu Thr Asp Asp Lys Ile
                1365                1370                1375

Gln Gln Thr Ile Ala Ser Gly Phe Arg Gly Asn Arg Leu Arg Tyr Ile
            1380                1385                1390

Ala His Arg Leu Arg Thr Ile Val Gly Tyr Asp Arg Ile Cys Val Met
        1395                1400                1405

Asp Gln Gly Arg Ile Ala Glu Leu Asp Ser Pro Leu Val Leu Trp Gln
    1410                1415                1420

Lys Glu Gly Gly Ile Phe Arg Ser Met Cys Glu Arg Ser Gly Phe Glu
1425                1430                1435                1440

Lys Lys Thr Ser Asp Arg Pro Arg Ala Ser Trp Thr Ala Met Trp Leu
                1445                1450                1455

Ala Lys Arg Ala Ser Arg Arg Ile Cys Arg Ser Glu Ala His Asp Leu
            1460                1465                1470

Val Pro Arg Arg Tyr Pro Gly His Met Leu Ala Tyr Ser Ile Val
```

<210> SEQ ID NO 33
<211> LENGTH: 734
<212> TYPE: PRT
<213> ORGANISM: Grosmannia clavigera
<220> FEATURE:
<223> OTHER INFORMATION: GcABC-D1

<400> SEQUENCE: 33

```
Met Ala Ala Gln Ser Lys Leu Thr Ala Thr Gly Pro Arg Leu Leu Ala
  1               5                  10                  15

Asp Gln His Arg Arg Thr Val Ala Trp Ala Ile Arg Ala Leu Val Lys
             20                  25                  30

Ala Tyr Val Ala Asn Arg Thr Arg Ile Ser Arg Val Val Tyr Val Thr
         35                  40                  45

Leu Leu Val Ala Val Val Asn Arg Val Arg Gln Ala Ile Ala Glu Gln
 50                  55                  60

Arg Gln Ala Ser Glu Pro Gly Glu Ser Glu Arg Asp Ser Arg His Cys
 65                  70                  75                  80

Asn Ala Lys Glu Asp Glu Ala Gly Ser Gly Ser Ser Gly Gly Gly Arg
             85                  90                  95

Gln Arg Lys Met Glu Leu Asp Arg Ala Phe Phe His Ser Leu Gly Arg
            100                 105                 110

Leu Leu Arg Ile Val Val Pro Gly Trp Arg Ser Lys Glu Ala Arg Leu
        115                 120                 125

Leu Ala Ser His Ser Ala Phe Leu Val Ala Arg Thr Leu Leu Ser Leu
130                 135                 140

Gln Ile Ala Ala Met Asp Gly Ala Leu Val Lys Ser Leu Val Arg Gly
145                 150                 155                 160

Gln Gly Gln Gln Phe Leu Arg Arg Ile Ala Trp Trp Met Val Val Ala
                165                 170                 175

Val Pro Ala Thr Phe Thr Asn Ser Met Leu Ala Tyr His Gln Ala Gln
            180                 185                 190

Leu Ala Leu Arg Tyr Arg Thr Arg Leu Thr Gln His Ile His Glu Gln
        195                 200                 205

Tyr Leu Thr Arg Met Thr Phe Tyr Gly Leu Ser Ala Leu Asp Asp Arg
    210                 215                 220

Val Lys Asn Pro Asp Gln Leu Ile Ala Val Asp Ala Arg Phe Ala
225                 230                 235                 240

Ser Ser Leu Ala Glu Leu Tyr Gly Asn Leu Ala Lys Pro Leu Leu Asp
                245                 250                 255

Met Thr Ile Tyr Thr Tyr Ser Leu Ser Arg Ser Val Gly Gly Glu Gly
            260                 265                 270

Val Val Ser Met Ala Leu Leu Val Gln Leu Ser Ala Leu Ala Met Arg
        275                 280                 285

Ala Leu Thr Pro Pro Phe Gly Arg Tyr Val Ala Asp Glu Ala Arg Leu
    290                 295                 300

Glu Gly Glu Phe Arg Phe Gln His Ala Arg Leu Ile Asp His Gly Glu
305                 310                 315                 320

Glu Val Ala Leu Tyr Ala Gly His Gly Ala Glu Lys Asp Thr Leu Asp
                325                 330                 335

Lys Gly Tyr Phe Thr Leu Ile Lys His Val Asn Tyr Ile Leu Arg Gln
            340                 345                 350

Arg Phe Tyr His Gly Phe Met Glu Asp Tyr Val Ile Lys Tyr Leu Trp
```

```
                355                 360                 365
Gly Ala Leu Gly Leu Val Leu Cys Ser Val Pro Val Phe Val Pro Leu
370                 375                 380

Pro Ala Ala Arg Gln Ala Leu Ala Ser Thr Ala Ser Gly Ser Ser
385                 390                 395                 400

Met Ala Asp Arg Thr Glu Ser Phe Val Thr Asn Arg Arg Leu Leu Leu
            405                 410                 415

Ser Ala Ser Asp Ala Phe Gly Arg Ile Met Phe Ser Tyr Arg Glu Ile
                420                 425                 430

Met Glu Leu Ala Gly Tyr Thr Ala Arg Val Ala Ser Leu Leu Asp Val
            435                 440                 445

Met Thr Asp Val Arg Ala Gly His Phe Glu Lys Asn Leu Val Ser Ser
            450                 455                 460

Ser Ala Gly Asn Thr Ala Asp His Ala Ala Val Leu Arg Arg Arg Gly
465                 470                 475                 480

Ser Val Val Glu Ser Asp Thr Ile Gln Phe Thr Asp Val Pro Ile Ile
                485                 490                 495

Ser Pro Asn Gly Asp Val Leu Val Pro Lys Leu Ser Phe Ser Leu Arg
            500                 505                 510

Pro Gly Glu His Leu Leu Val Val Gly Pro Asn Gly Cys Gly Lys Ser
            515                 520                 525

Ser Leu Phe Arg Ile Leu Gly Gly Leu Trp Pro Val Tyr Gly Gly Thr
530                 535                 540

Val His Arg Pro Pro Ala Asp Ile Phe Tyr Ile Pro Gln Arg Pro
545                 550                 555                 560

Tyr Leu Pro His Gly Ser Leu Arg Gln Gln Ile Thr Tyr Pro Asp Ser
                565                 570                 575

Leu Arg Ala Met Arg Ala Lys Gly Val Thr Asp Ala Asp Leu Leu Gln
            580                 585                 590

Leu Leu Arg Leu Leu Ser Leu Glu Glu Leu Val Ala Gly Gln Ser Ala
            595                 600                 605

Gly Trp Asp Thr Val Ala Glu Trp Arg Glu Val Leu Ser Val Gly Trp
610                 615                 620

Gln Gln Arg Val Ala Met Ala Arg Leu Leu Tyr His Arg Pro Arg Tyr
625                 630                 635                 640

Ala Ile Leu Asp Glu Cys Thr Ser Ser Val Thr Leu Glu Met Glu Lys
                645                 650                 655

Thr Met Tyr Glu Gln Ala Lys Ala Met Gly Val Thr Leu Met Thr Val
            660                 665                 670

Ser His Arg Arg Ser Leu Trp Lys Tyr His Asn Arg Ile Leu Gln Phe
        675                 680                 685

Asp Gly Gln Gly His Tyr Val Phe Thr Arg Leu Asp Ala Glu Arg Arg
    690                 695                 700

Leu Gln Leu Glu Asp Glu Lys Asp Asp Leu Asp Leu Leu Arg Gln
705                 710                 715                 720

Val Pro Asp Ala Glu Arg Arg Ile Ala Glu Leu Glu Ala Ala
            725                 730

<210> SEQ ID NO 34
<211> LENGTH: 816
<212> TYPE: PRT
<213> ORGANISM: Grosmannia clavigera
<220> FEATURE:
<223> OTHER INFORMATION: GcABC-D2
```

-continued

```
<400> SEQUENCE: 34

Met Ala Ala Gln Ser Thr Leu Arg Gln Ser Ala Ala Glu Ala Ala Ile
1               5                   10                  15

Ala Gly Phe Ile Ser Lys Tyr Gly Ala Met Val Ser Arg Arg Leu Arg
            20                  25                  30

Arg Thr Thr Arg Thr Thr Arg Leu Leu Ala Thr Val Ser Leu Leu Val
        35                  40                  45

Ser Ile Leu Leu Gly Ala Glu Gly Gly Arg Arg Trp Trp His Arg Ser
    50                  55                  60

Arg Leu Glu Gln Glu Gln Gly Leu Lys Leu Val Arg Thr Asn Ser Trp
65                  70                  75                  80

Leu His Asn Lys Asp Gly Ser Arg Thr Ile Tyr Val Pro Tyr Arg Gly
                85                  90                  95

Gly Thr Ser Lys Val Val Ile Pro Thr Thr Lys Pro Leu Thr Phe Glu
            100                 105                 110

Ala His Arg Arg Leu Phe Leu Asn Pro Pro Arg Val Ser Gly Leu His
        115                 120                 125

Ser Gly Asn Ser Asp Gly Tyr Val Pro Gly Thr Gln Thr Lys Pro Gly
    130                 135                 140

Leu Asn Leu Ala Phe Leu His Gln Phe Leu Ser Leu Met Ser Ile Met
145                 150                 155                 160

Val Pro Arg Trp Thr Ser Lys Glu Ser Gly Leu Leu Val Ser His Ala
                165                 170                 175

Gly Phe Leu Val Leu Arg Thr Tyr Leu Ser Leu Val Val Ala Arg Leu
            180                 185                 190

Asp Gly Glu Ile Val Arg Asp Leu Val Val Gly Asn Gly Lys Leu Phe
        195                 200                 205

Ile Trp Gly Leu Leu Lys Trp Cys Gly Phe Gly Gly Val Ala Ser Tyr
    210                 215                 220

Thr Asn Ala Met Ile Lys Phe Leu Glu Ser Lys Val Ser Ile Ala Phe
225                 230                 235                 240

Arg Thr Arg Leu Thr Arg Tyr Ile His Asp Leu Tyr Leu Asn Asp Asn
                245                 250                 255

Leu Asn Tyr Tyr Lys Leu Ser Asn Leu Asp Gly Gly Leu Gly Gln Ser
            260                 265                 270

Ala Asp Gln Tyr Ile Thr Gln Asp Leu Thr Leu Phe Cys Ala Ala Ala
        275                 280                 285

Ala Gly Ile Tyr Ser Ser Leu Gly Lys Pro Leu Ile Asp Leu Cys Val
    290                 295                 300

Phe Asn Tyr Gln Leu Tyr Arg Ala Leu Gly Pro Leu Ala Leu Ser Gly
305                 310                 315                 320

Ile Met Ser Asn Tyr Phe Val Thr Ala Ser Ile Leu Arg Arg Leu Ser
                325                 330                 335

Pro Pro Phe Gly Lys Leu Lys Ala Val Glu Gly Arg Lys Glu Gly Glu
            340                 345                 350

Phe Arg Ser Leu His Ala Arg Leu Ile Ala Asn Ala Glu Glu Val Ala
        355                 360                 365

Phe Tyr Gly Gly Ala Asp Met Glu Lys Gln Ala Leu Asn Arg Glu Phe
    370                 375                 380

Lys Glu Leu Lys Thr Trp Met Glu Gly Ile Tyr Phe Leu Lys Ile Arg
385                 390                 395                 400

Tyr Asn Met Leu Glu Asp Phe Ile Val Lys Tyr Ser Trp Ser Ala Tyr
                405                 410                 415
```

Gly Tyr Leu Leu Ser Ala Leu Pro Val Phe Leu Pro Ala Trp Gly Gly
            420                 425                 430

Leu Gly Gly Leu Thr Glu Leu Ala Gly Asn Gly Leu Thr Ala Thr Ser
        435                 440                 445

Thr Gly Asp Arg Glu Arg Ser Arg Thr Lys Asp Phe Ile Thr Asn Arg
    450                 455                 460

Arg Leu Met Leu Ser Leu Ala Asp Ala Gly Gly Arg Met Met Tyr Ser
465                 470                 475                 480

Ile Lys Asp Leu Ala Glu Leu Ala Gly His Thr Ser Arg Val Tyr Thr
                485                 490                 495

Leu Ile Ser Thr Leu His Arg Val His Ala Asn Ala Tyr Tyr Pro Gln
            500                 505                 510

Ala Gly Arg Gln Ser Glu Leu Tyr Ser Leu Ser Asp Val Gln Gly Thr
        515                 520                 525

Met Gln Lys Gly Phe Asp Gly Val Arg Leu Glu Asn Val Pro Val Val
    530                 535                 540

Ala Pro Gly Leu Trp Pro His Glu Gly Glu Leu Leu Glu Ser Leu
545                 550                 555                 560

Ser Leu Ile Val Arg Arg Gly Glu His Leu Leu Ile Ser Gly Pro Asn
                565                 570                 575

Gly Ala Gly Lys Ser Ser Ile Gly Arg Ile Val Ala Gly Leu Trp Pro
            580                 585                 590

Val Tyr Arg Gly Leu Val Ser Arg Pro Lys Ala Val Gly Glu Asp Gly
        595                 600                 605

Ile Met Phe Leu Pro Gln Arg Ser Tyr Leu Ser Ile Gly Thr Leu Arg
    610                 615                 620

Asp Gln Val Ile Tyr Pro Asp Gly Glu Ala Asp Met Arg Asn Lys His
625                 630                 635                 640

Lys Asn Glu His Asp Leu Lys Arg Val Leu Glu Asp Ala His Leu Gly
                645                 650                 655

Tyr Leu Pro Ala Arg Glu Gly Gly Trp Asp Thr Lys Lys Glu Trp Lys
            660                 665                 670

Asp Val Leu Ser Gly Gly Glu Lys Gln Arg Met Ala Ile Ala Arg Leu
        675                 680                 685

Leu Tyr His Glu Pro Gln Tyr Ala Phe Ile Asp Glu Gly Thr Ser Ala
    690                 695                 700

Val Ser Ser Asp Val Glu Gly Leu Leu Tyr Glu Lys Cys Lys Glu Arg
705                 710                 715                 720

Gly Ile Thr Leu Ile Thr Ile Ser Thr Arg Ala Ser Leu Lys Lys Tyr
                725                 730                 735

His Thr Phe Asn Leu Ile Met Gly Met Gly Glu Asn Gly Asp Glu Trp
            740                 745                 750

Leu Phe Glu Arg Ile Gly Thr Glu Arg Glu Lys Gln Asn Val Glu Arg
        755                 760                 765

Glu Leu Gln Glu Leu Arg Glu Arg Leu Ser Gln Val Glu Ala Trp Arg
    770                 775                 780

Ala Arg Arg Ala Glu Ile Glu Lys Glu Leu Ala Gln Val Trp Val Glu
785                 790                 795                 800

Gly Ser Asp Glu Pro Leu Pro Pro Ala Lys Glu Val Glu Gly Gln
                805                 810                 815

<210> SEQ ID NO 35
<211> LENGTH: 608

```
<212> TYPE: PRT
<213> ORGANISM: Grosmannia clavigera
<220> FEATURE:
<223> OTHER INFORMATION: GcABC-E1

<400> SEQUENCE: 35
```

| | | | | | | | | | | | | | | |
|---|---|---|---|---|---|---|---|---|---|---|---|---|---|---|
| Met | Ala | Asp | Lys | Leu | Thr | Arg | Ile | Ala | Ile | Val | Ser | Ser | Asp | Lys | Cys |
| 1 | | | | 5 | | | | | 10 | | | | | 15 | |

Lys Pro Lys Lys Cys Arg Gln Glu Cys Lys Lys Ser Cys Pro Val Val
            20                  25                  30

Arg Ser Gly Lys Leu Cys Ile Glu Val Ala Ser Asp Ser Arg Ile Ala
            35                  40                  45

Phe Leu Ser Glu Ser Leu Cys Ile Gly Cys Gly Ile Cys Pro Lys Lys
 50                  55                  60

Cys Pro Phe Gly Ala Ile Thr Ile Ile Asn Leu Pro Thr Asn Leu Asp
 65                  70                  75                  80

Thr Gln Leu Thr His Arg Tyr Ser Ala Asn Ser Phe Lys Leu His Arg
                85                  90                  95

Leu Pro Met Pro Arg Pro Gly Gln Val Leu Gly Leu Val Gly Thr Asn
            100                 105                 110

Gly Ile Gly Lys Ser Thr Ala Leu Lys Ile Leu Ser Gly Lys Leu Lys
            115                 120                 125

Pro Asn Leu Gly Arg Phe Asp Asn Pro Pro Asp Trp Glu Asp Val Ile
130                 135                 140

Lys His Phe Arg Gly Ser Glu Leu Gln Asn Tyr Phe Thr Lys Leu Leu
145                 150                 155                 160

Glu Asp Asp Leu Lys Ala Val Val Lys Pro Gln Tyr Val Asp Gln Ile
                165                 170                 175

Pro Lys Ala Ile Arg Gly Pro Ile Lys Ser Val Gln Lys Leu Ile Glu
            180                 185                 190

Ser Arg Ala Thr Met Asp Asn Leu Asp Asp Val Leu Asp Val Leu Glu
            195                 200                 205

Leu Arg His Ile Tyr Asp Arg Asp Val Thr Leu Leu Ser Gly Gly Glu
            210                 215                 220

Leu Gln Arg Phe Ala Ile Gly Thr Val Cys Val Gln Lys Ala Asp Val
225                 230                 235                 240

Tyr Met Phe Asp Glu Pro Ser Ser Tyr Leu Asp Val Lys Gln Arg Leu
                245                 250                 255

Ala Ala Ala Arg Met Ile Arg Ser Leu Val Arg Ser Asp Asp Tyr Val
            260                 265                 270

Ile Val Val Glu His Asp Leu Ser Val Leu Asp Tyr Leu Ser Asp Tyr
            275                 280                 285

Ile Cys Val Leu Tyr Gly Gln Pro Ala Val Tyr Gly Val Val Thr Leu
 290                 295                 300

Pro Tyr Ser Val Arg Glu Gly Ile Asn Ile Phe Leu Asp Gly His Ile
305                 310                 315                 320

Pro Thr Glu Asn Leu Arg Phe Arg Gln Glu Ser Leu Thr Phe Lys Leu
                325                 330                 335

Ser Glu Gly Ala Asp Asp Phe Ile Ala Asp Arg Ser Arg Ala Phe His
            340                 345                 350

Tyr Pro Lys Met Glu Lys Thr Met Gly Asn Phe Lys Leu Asp Ile Asp
            355                 360                 365

Ser Gly Asp Phe Thr Asp Ser Glu Ile Leu Val Leu Met Gly Glu Asn
            370                 375                 380

```
Gly Thr Gly Lys Thr Thr Phe Cys Arg Leu Leu Ala Gly Ala Leu Lys
385                 390                 395                 400

Pro Asp Gly Thr Arg Arg Val Pro Glu Met Lys Ile Ser Met Lys Pro
            405                 410                 415

Gln Thr Ile Thr Pro Lys Phe Asp Gly Thr Val Arg Gln Leu Phe Phe
            420                 425                 430

Lys Lys Ile Arg Pro Ala Phe Leu Ser Pro Gln Phe Gln Thr Asp Val
            435                 440                 445

Val Lys Pro Leu Lys Leu Asp Asp Phe Ile Asp Gln Glu Val Lys Asn
        450                 455                 460

Leu Ser Gly Gly Glu Leu Gln Arg Val Ala Ile Val Leu Ala Leu Gly
465                 470                 475                 480

Leu Pro Ala Asp Ile Tyr Leu Ile Asp Glu Pro Ser Ala Tyr Leu Asp
                485                 490                 495

Ser Glu Gln Arg Ile Ile Cys Ala Arg Val Ile Lys Arg Phe Ile Met
                500                 505                 510

His Ala Lys Lys Thr Ala Phe Ile Val Glu His Asp Phe Ile Met Ala
                515                 520                 525

Thr Tyr Leu Ala Asp Arg Val Ile Val Phe Asp Gly Gln Pro Gly Ile
530                 535                 540

His Ser His Ala Asn Glu Pro Glu Ser Leu Leu Thr Gly Cys Asn Thr
545                 550                 555                 560

Phe Leu Lys Asn Leu Asp Val Ser Phe Arg Arg Asp Pro Val Asn Tyr
                565                 570                 575

Arg Pro Arg Ile Asn Lys Ala Asn Ser Gln Leu Asp Gln Glu Gln Lys
                580                 585                 590

Ala Ala Gly Asn Tyr Phe Phe Leu Glu Glu Asp Asn Ser Lys Ala Ser
            595                 600                 605

<210> SEQ ID NO 36
<211> LENGTH: 618
<212> TYPE: PRT
<213> ORGANISM: Grosmannia clavigera
<220> FEATURE:
<223> OTHER INFORMATION: GcABC-F1

<400> SEQUENCE: 36

Met Val Ser Ala Ser Lys Glu Lys Arg Leu Ala Lys Lys Ala Ala Asp
1               5                   10                  15

Gly Lys Asp Lys Lys Ser Lys Val Gly Ser Lys Lys Ala Ala Ala Ala
            20                  25                  30

Glu Val Glu Leu Asp Gly Asn Gly Asn Pro Ile Val Asn Glu Glu Asp
        35                  40                  45

Thr Ser Asn Arg Asp Glu Glu Val Lys Arg Leu Ala Ala Gln Met Asp
    50                  55                  60

Lys His Gly Leu Ser Asp Arg Val Thr Thr Gly Val Leu Ser Ser Thr
65                  70                  75                  80

Pro Thr Ser Arg Asp Val Lys Ile Thr Ser Val Ser Leu Val Phe His
                85                  90                  95

Gly Arg Val Leu Ile Gln Asp Ser Thr Leu Glu Leu Thr Tyr Gly Arg
            100                 105                 110

Arg Tyr Gly Leu Leu Gly Glu Asn Gly Cys Gly Lys Ser Thr Leu Met
        115                 120                 125

Lys Ala Ile Asp Lys Arg Glu Phe Pro Ile Pro Glu His Val Asp Ile
    130                 135                 140
```

```
Tyr Leu Leu Asn Glu Gly Ala Pro Pro Thr Glu Leu Gly Ala Leu Glu
145                 150                 155                 160

Trp Val Val Arg Glu Ala Gln Asn Glu Leu Glu Arg Leu Asp Lys Leu
            165                 170                 175

Ala Glu Lys Tyr Leu Glu Asp Glu Gly Pro Asp Ser Pro Val Leu Met
        180                 185                 190

Asp Leu Tyr Asp His Met Glu Arg Met Asp Pro Ser Thr Phe Ser Thr
    195                 200                 205

Arg Ala Ser Leu Ile Leu Thr Gly Leu Gly Phe Asn Lys Val Thr Ile
210                 215                 220

Asn Lys Lys Thr Lys Asp Met Ser Gly Gly Trp Arg Met Arg Val Gly
225                 230                 235                 240

Leu Ala Lys Ala Leu Phe Val Gln Pro Ser Leu Leu Leu Asp Asp
                245                 250                 255

Pro Thr Ala His Leu Asp Leu Glu Ala Cys Val Trp Leu Glu Glu Tyr
            260                 265                 270

Leu Lys Arg Trp Glu Arg Thr Leu Val Leu Val Ser His Ser Gln Asp
        275                 280                 285

Phe Leu Asn Gly Val Cys Ser Asn Met Ile Asp Met Arg Ser Lys Gln
    290                 295                 300

Leu Leu Tyr Tyr Gly Gly Asn Tyr Asp Ser Tyr Ile Lys Thr Arg Ser
305                 310                 315                 320

Glu Gln Glu Thr Asn Gln Met Lys Ala Tyr Thr Lys Gln Gln Glu Glu
                325                 330                 335

Ile Ala His Ile Lys Lys Phe Ile Ala Ser Ala Gly Thr Tyr Ala Asn
            340                 345                 350

Leu Val Arg Gln Ala Lys Ser Arg Gln Lys Ile Leu Asp Lys Met Glu
        355                 360                 365

Ala Asp Gly Phe Ile Gln Pro Val Thr Glu Asp Arg Val Phe Ser Phe
    370                 375                 380

Arg Phe Ala Asp Val Asp Lys Leu Pro Pro Val Leu Ser Phe Asp
385                 390                 395                 400

Asn Val Thr Phe Ser Tyr Ser Gly Asp Pro Lys Asp Asp Leu Tyr Arg
                405                 410                 415

Asn Ile Asp Leu Gly Phe Asp Met Asp Ser Arg Thr Ala Leu Val Gly
            420                 425                 430

Pro Asn Gly Val Gly Lys Ser Thr Leu Leu Arg Leu Met Thr Gly Lys
        435                 440                 445

Leu Ser Pro Thr Glu Gly Val Val Ala Arg His Thr His Leu Lys Leu
450                 455                 460

Gly Val Tyr Ser Gln His Ser Ala Glu Gln Leu Asp Leu Thr Lys Ser
465                 470                 475                 480

Ala Leu Asp Phe Val Arg Glu Lys Tyr Arg Glu Lys Ser Gln Asp Tyr
                485                 490                 495

Gln Tyr Trp Arg Gln Leu Gly Lys Tyr Gly Leu Ser Gly Glu Ser
            500                 505                 510

Gln Thr Ala Leu Ile Gly Thr Leu Ser Glu Gly Gln Lys Ser Arg Ile
        515                 520                 525

Val Phe Ala Leu Leu Ala Ile Asp Ser Pro Asn Met Leu Leu Leu Asp
    530                 535                 540

Glu Pro Thr Asn Gly Leu Asp Ile Pro Thr Ile Asp Ser Leu Ala Asp
545                 550                 555                 560

Ala Ile Lys Ala Phe Ser Gly Gly Val Val Val Val Ser His Asp Phe
```

-continued

```
                   565                 570                 575
Arg Leu Asp Lys Ile Ala Asn Gln Ile Met Val Cys Glu Asn Arg
            580                 585                 590

Thr Ile Arg Gln Trp Asp Gly Thr Ile Ser Asp Tyr Lys Asn Tyr Leu
            595                 600                 605

Arg Lys Lys Met Ile Thr Ala Gly Ala Val
        610                 615

<210> SEQ ID NO 37
<211> LENGTH: 769
<212> TYPE: PRT
<213> ORGANISM: Grosmannia clavigera
<220> FEATURE:
<223> OTHER INFORMATION: GcABC-F2

<400> SEQUENCE: 37

Met Glu Thr Glu Ile Arg Ala Ile Ile Pro Asn Ile Asp Pro Val Val
 1               5                  10                  15

Ser Glu Tyr Ser Val Gly Tyr Leu Thr His Ala Ser Thr Ala Trp Ser
            20                  25                  30

Gly Gly Ser Gly Asp Asp Gly Glu Glu Ala Gly Gly Gly Asp Ala
        35                  40                  45

Ala Gln Pro Leu Ala Asp Ala Ala Thr Ala Val Thr Asp Leu Leu Leu
    50                  55                  60

Ser Ala Ala Gly Asp Thr Ala Ser Thr Ala Gln Gln Asp Ser Ile Ser
65                  70                  75                  80

Lys Leu Val Ala Lys Trp Val Glu Arg Tyr Ala Glu Glu Ala Thr Gly
                85                  90                  95

Ala Asn Gly Arg Arg Gly Ala Pro Ser Ala Val Arg Arg Leu Asp Gln
            100                 105                 110

Thr Ile Gln Val Ser Ala Gln Arg Asn Met Ser Ser Thr Leu Ala Val
            115                 120                 125

Ala Thr Gly Gly Ser Val Asp Leu Glu Ser Val Asn Ala Arg Lys Val
        130                 135                 140

Glu Ser Lys Val Asp Arg Arg Lys Leu Glu Lys Ala Glu Arg Lys Ile
145                 150                 155                 160

Ala Ala Lys Gln Asn Lys Lys Thr Tyr Lys Thr Val Glu Tyr Glu Ala
                165                 170                 175

Ser Arg Leu Leu Asn Gln Gln Asp Glu Ala Gln Ser Tyr Glu Asp Phe
            180                 185                 190

Tyr Met Ala Val Asn Pro Leu Gln Leu Gly Ala Ala Gly Asp Ala Ser
        195                 200                 205

Ala Gly Lys Pro Lys Asp Ile Lys Leu Asp Asn Ile Asp Val Thr Ile
    210                 215                 220

Gly Gly Ile Arg Ile Leu Thr Asp Thr Asn Leu Ala Leu Ser Tyr Gly
225                 230                 235                 240

His Arg Tyr Gly Leu Val Gly His Asn Gly Val Gly Lys Ser Thr Leu
                245                 250                 255

Leu Arg Ala Leu Ser Arg Arg Glu Leu Ala Val Pro Leu His Ile Ser
            260                 265                 270

Ile Leu His Val Glu Gln Glu Ile Thr Gly Asp Thr Ser Ala Leu
        275                 280                 285

Gln Ala Val Leu Asp Ala Asp Val Trp Arg Lys Tyr Leu Leu Lys Glu
    290                 295                 300

Gln Thr Val Ile Thr Ala Lys Leu Ala Glu Ile Glu Thr Gln Arg Ala
```

```
            305                 310                 315                 320
     Ser Leu Ala Asp Thr Ser Ala Asp Ala Ala Arg Leu Asp Arg Asp Arg
                         325                 330                 335

Glu Ala Gln Asp Gln Arg Leu Gly Asp Ile Gln Gly Lys Leu Ser Glu
                         340                 345                 350

Met Glu Ser Asp Lys Ala Glu Ser Arg Ala Ala Ser Ile Leu Ala Gly
                         355                 360                 365

Leu Gly Phe Ser Ala Glu Arg Gln Gln Phe Ala Thr Lys Thr Phe Ser
                 370                 375                 380

Gly Gly Trp Arg Met Arg Leu Ala Leu Ala Arg Ala Leu Phe Cys Glu
     385                 390                 395                 400

Pro Asp Leu Leu Leu Asp Glu Pro Ser Asn Met Leu Asp Val Pro
                         405                 410                 415

Ser Ile Thr Phe Leu Ser Gly Tyr Leu Gln Asn Tyr Pro Ser Thr Val
                 420                 425                 430

Leu Val Val Ser His Asp Arg Ala Phe Leu Asn Glu Val Ala Thr Asp
                 435                 440                 445

Ile Ile His Gln His Ser Gln Arg Leu Asp Tyr Tyr Arg Gly Ala Asn
             450                 455                 460

Phe Asp Ser Phe Tyr Ala Thr Arg Glu Glu Arg Lys Lys Thr Ala Arg
     465                 470                 475                 480

Arg Glu Tyr Glu Asn Gln Met Ala Gln Arg Ala His Leu Gln Ala Phe
                         485                 490                 495

Ile Asp Lys Phe Arg Tyr Asn Ala Ala Lys Ser Ser Glu Ala Gln Ser
                 500                 505                 510

Arg Ile Lys Lys Leu Glu Arg Met Pro Val Leu Glu Ala Pro Glu Thr
                 515                 520                 525

Glu Tyr Ser Val His Phe Ser Phe Pro Glu Val Glu Lys Leu Ser Pro
                 530                 535                 540

Pro Ile Val Gln Met Ser Asp Val Ser Phe Gly Tyr Gly Pro Gly
     545                 550                 555                 560

Gly Val Pro Leu Leu Arg Asn Val Asp Leu Asp Val Gln Leu Asp Ser
                         565                 570                 575

Arg Ile Gly Ile Val Gly Pro Asn Gly Ala Gly Lys Thr Thr Val Leu
                 580                 585                 590

His Leu Leu Thr Gly Arg Leu Gln Pro Val Ser Gly Leu Val Ser Thr
                 595                 600                 605

Asn Pro Arg Leu Arg Ile Gly Phe Phe Ala Gln His His Val Asp Ala
             610                 615                 620

Leu Asp Leu Thr Ile Ser Ala Val Ser Phe Met Ala Arg Glu Tyr Pro
     625                 630                 635                 640

Gly Arg Thr Asp Glu Glu Tyr Arg Arg Gln Leu Gly Ala Phe Gly Ile
                         645                 650                 655

Thr Gly Thr Thr Gly Leu Gln Lys Met Val Val Leu Ser Gly Gly Gln
                         660                 665                 670

Lys Ser Arg Val Ala Phe Ala Cys Leu Ala Leu Thr Ser Pro His Ile
                 675                 680                 685

Leu Val Leu Asp Glu Pro Ser Asn His Leu Asp Ile Glu Ala Met Asp
                 690                 695                 700

Ala Leu Ala Asp Ala Leu Arg Ser Phe Glu Gly Gly Val Leu Met Val
     705                 710                 715                 720

Ser His Asp Val Thr Met Leu Gln Asn Val Cys Thr Ser Leu Trp Val
                         725                 730                 735
```

```
Cys Asp Gly Gly Thr Val Glu Lys Phe Pro Gly Asp Val Gln Gln Tyr
            740                 745                 750

Lys Lys Arg Ile Ala Ala Gln Ala Asn Ala Ala Gly Val Val Lys Ala
            755                 760                 765

His

<210> SEQ ID NO 38
<211> LENGTH: 1121
<212> TYPE: PRT
<213> ORGANISM: Grosmannia clavigera
<220> FEATURE:
<223> OTHER INFORMATION: GcABC-F3

<400> SEQUENCE: 38

Met Pro His Pro Val Leu Pro Ser Met Asn Lys Ser Leu Pro Ile Leu
 1               5                  10                  15

Thr Lys Ala Asp Gly Asp Gly Pro Ser Gln Ala Asp Ile Thr Ala Thr
             20                  25                  30

Leu Asn Glu Ile Phe Thr Ala Thr Ser Asn Ala Ser Val Glu Ala
         35                  40                  45

Ala Tyr Arg Leu Cys Asp Ala Leu Leu Ser Ser Pro Ala Ala Gly Phe
     50                  55                  60

Arg Gly Leu Thr Lys Tyr Gly Val Val Ala Glu Leu Lys Lys Ala Ala
 65                  70                  75                  80

Gly Asp Lys Lys Ser Gly Leu Arg Arg Glu Ser Ala Gln Asn Leu Leu
                 85                  90                  95

Gly Ala Leu Phe Glu Arg Phe Pro Ser Arg Gln Pro Ile Ser Glu Val
            100                 105                 110

Ile Phe Leu Ile Gln Asp Gly Gly Leu Val Ala Cys Ala Leu Asp Ala
            115                 120                 125

Leu Ala Asp Lys Gly Ser Val Val Arg Asp Ala Ala Gln Tyr Gly Leu
    130                 135                 140

Asp Ala Leu Phe Thr Gln Leu His Ala Glu Ala Leu Val Ser Gly Leu
145                 150                 155                 160

Leu Pro Ala Leu Ile Thr Tyr Leu His Lys Lys Thr Gly Lys Trp Gln
                165                 170                 175

Gly Thr Val Gly Ala Leu Lys Leu Ile Gln Arg Met Ala Asp Lys Ala
            180                 185                 190

Gln Ile Asp Ile Ser Thr Thr Lys Ala Glu Ala Ile Glu Lys Glu Ala
        195                 200                 205

Leu Arg Asp Ile Met Gly Ser Arg Leu Ala Ser Leu Ile Pro Ile Val
    210                 215                 220

Glu Ala Gly Met His Asp Leu Lys Thr Glu Val Glu Lys Gln Ser Val
225                 230                 235                 240

Gln Thr Met Thr Ser Val Thr Ala Leu Leu Ser Asn Asp Asp Val Ala
                245                 250                 255

Pro Arg Leu Pro Leu Leu Ile Asp Thr Met Gln His Pro Ser Ala Gln
            260                 265                 270

Thr Leu Gln Lys Ala Ile His Ala Leu Ala His Thr Thr Phe Val Ala
        275                 280                 285

Ile Val Thr Ser Pro Val Leu Ala Leu Leu Thr Pro Phe Leu Glu Arg
    290                 295                 300

Ser Leu Asn Thr Pro Thr Thr Ala Gln Glu Val Leu Arg Gln Thr Val
305                 310                 315                 320
```

-continued

Val Ile Val Glu Asn Leu Thr Arg Leu Val His Asp Pro Ile Glu Ala
            325                 330                 335

Arg Thr Phe Leu Pro Lys Leu Gln Pro Gly Val Lys Ser Val Met Gln
            340                 345                 350

Arg Ala Ser Leu Pro Glu Val Arg Asp Leu Ala Thr Arg Ala Leu Asn
            355                 360                 365

Val Met Asp Val Ala Met Thr Ala Asp Glu Ala Ala Val Val Glu Arg
            370                 375                 380

Thr Thr Ala Asp Asp Val Ala Lys Val Leu Asp Ala Glu Ile Ala Lys
385                 390                 395                 400

Lys Gly Gly Leu Ala Ala Asp Arg Ala Ala Tyr Asp Val Leu Arg Pro
            405                 410                 415

Tyr Ile Gly Ser Met Val Ala Glu Asp Val Asn Phe Arg Tyr Val Thr
            420                 425                 430

Arg Val Ser Thr Gln Ile Ala Pro Tyr Ile Ala Pro Val Leu Lys Asp
            435                 440                 445

Ser Ser Ala His Gln Ala Ile Ala Asp Ala Val Gln Glu Phe Tyr Val
            450                 455                 460

Ser Glu Asp His Arg Lys Tyr Gly Glu Pro Glu Lys Asp Asp Asp Gly
465                 470                 475                 480

Glu Thr Glu Ile Val Asn Ala Asp Phe Ser Leu Gly Tyr Gly Gly Met
            485                 490                 495

Leu Leu Leu Ser His Thr Asn Met Arg Leu Leu Lys Gly His Arg Tyr
            500                 505                 510

Gly Leu Val Gly Arg Asn Gly Ala Gly Lys Ser Thr Leu Met Lys Ser
            515                 520                 525

Ile Ala Gly Gly Lys Leu Glu Gly Phe Pro Pro Gln Asp Val Leu Arg
530                 535                 540

Thr Cys Tyr Val Glu His Asn Gln Gly Glu Asp Ala Glu Ile Ser Ile
545                 550                 555                 560

Leu Asp Phe Val Ser Lys Asp Pro Glu Ile Ala Lys Ala Gly Arg Ala
            565                 570                 575

Arg Ile Ile Glu Val Leu Asp Glu Phe Gly Phe Thr Ser Gly Pro Asp
            580                 585                 590

Gly Arg Gln Ala Gln Lys Val Gly Ser Leu Ser Gly Gly Trp Lys Met
            595                 600                 605

Lys Leu Ala Leu Ala Arg Ala Met Leu Gln Lys Ala Asp Val Leu Leu
            610                 615                 620

Leu Asp Glu Pro Thr Asn His Leu Asp Val Ala Asn Ile Arg Trp Leu
625                 630                 635                 640

Glu Asn Tyr Leu Lys Thr His Leu Asp Val Thr Ser Leu Ile Val Ser
            645                 650                 655

His Asp Ser Gly Phe Leu Asp Glu Val Thr Thr Asp Ile Tyr His Tyr
            660                 665                 670

Glu Pro Gly Lys Lys Leu Ala His Tyr Lys Gly Asn Leu Ala Thr Phe
            675                 680                 685

Val Ser His His Pro Glu Ala Lys Ser Tyr Tyr Thr Leu Thr Ala Ser
            690                 695                 700

Gln Val Gln Phe Lys Phe Pro Pro Gly Leu Leu Ser Gly Ile Lys
705                 710                 715                 720

Ser Gln Thr Arg Ala Ile Ile Arg Met Thr Asn Val Ser Tyr Ala Tyr
            725                 730                 735

Pro Gly Ala Thr Lys Pro Gln Leu Ser Asp Val Ser Cys Gln Leu Ser

```
            740                 745                 750
Leu Ser Ser Arg Val Ala Ile Ile Gly Pro Asn Gly Ala Gly Lys Ser
        755                 760                 765

Thr Leu Ile Lys Leu Leu Thr Gly Glu Thr Ile Pro Ser Thr Gly Lys
    770                 775                 780

Val Glu Lys His Pro Asn Leu Arg Ile Gly Tyr Ile Lys Gln His Ala
785                 790                 795                 800

Leu Glu His Val Glu Met His Leu Glu Lys Thr Pro Asn Gln Tyr Leu
                805                 810                 815

Gln Trp Arg Tyr Ala His Gly Asp Asp Arg Glu Val His Met Lys Gln
            820                 825                 830

Thr Arg Ile Val Ser Glu Met Asp Arg Leu Gln Met Glu Lys Phe Ile
        835                 840                 845

Glu Pro Ala Ala Gly Met Gly Gln Arg Gln Ile Glu Thr Leu Val Gly
    850                 855                 860

Arg Gln Lys Tyr Lys Lys Thr Phe Gln Tyr Glu Val Lys Trp Lys Asn
865                 870                 875                 880

Met Leu Pro Lys His Asn Thr Gln Val Thr Arg Glu Lys Leu Leu Glu
                885                 890                 895

Trp Gly Tyr Asp Lys Leu Ile Gln Glu Phe Asp His Glu Ser Ser
            900                 905                 910

Arg Glu Gly Leu Ser Phe Arg Glu Leu Gln Pro Ala Thr Ile Ser Lys
        915                 920                 925

His Phe Glu Asp Leu Gly Leu Asp Pro Glu Ile Ala Asn His Asn Glu
    930                 935                 940

Ile Gly Ser Leu Ser Gly Gly Gln Lys Val Lys Val Ile Ala Gly
945                 950                 955                 960

Ala Met Trp Asn Asn Pro His Leu Leu Val Leu Asp Glu Pro Thr Asn
                965                 970                 975

Phe Leu Asp Arg Asp Ser Leu Gly Gly Leu Ala Val Ala Ile Arg Asp
            980                 985                 990

Phe Lys Gly Gly Val Val Met Ile Ser His Asn Glu Glu Phe Val Gly
        995                 1000                1005

Ala Leu Ser Ser Glu Gln Trp His Val Ala Asp Gly Arg Val Thr His
    1010                1015                1020

Lys Gly Arg Glu Ala Val Ser Thr Asp Arg Phe Glu Asp Ser Arg Pro
1025                1030                1035                1040

Gly Ser Gly Leu Thr Thr Pro Gly Val Ala Thr Pro Ala Met Ser Ser
                1045                1050                1055

Ala Ile Ser Ser Ala Val Asn Ser Gly Leu Glu Asp Asn Ala Val Gly
            1060                1065                1070

Asp Leu Lys Phe Lys Ala Lys Lys Arg Lys Lys Thr Lys Lys Asp
        1075                1080                1085

Met Lys Glu Gln Glu Asn Arg Arg Arg Gln Arg Glu Ile Val Trp Leu
    1090                1095                1100

Asn Ser Pro Lys Gly Thr Pro Lys Pro Leu Asp Thr Asp Asp Glu Glu
1105                1110                1115                1120

Asp

<210> SEQ ID NO 39
<211> LENGTH: 1054
<212> TYPE: PRT
<213> ORGANISM: Grosmannia clavigera
<220> FEATURE:
```

<223> OTHER INFORMATION: GcABC-F4

<400> SEQUENCE: 39

```
Met Ala Ser Glu Asn Ala Lys Ser Asp Lys Val Leu Ser Asp Leu Val
 1               5                  10                  15

Gln Lys Leu Thr Leu Ser Thr Asp Ala Ala Asp Ile Lys Ala Ser Ser
             20                  25                  30

Gly Ala Ile Ala Thr Phe Ile Asn Gly Asp Ile Lys Asp Leu Asp Val
         35                  40                  45

Pro Ser Lys Thr Ile Glu Ala Leu Lys Lys Gln Leu Ala Asn Lys Lys
     50                  55                  60

Asp Ala Gly Ala Arg Glu Lys Ala Leu Asn Ala Ile Gln Ala Ile Ala
 65                  70                  75                  80

Gln His Ser Glu Val Ser Ala Ser Val Glu Pro Phe Leu Val Val Leu
                 85                  90                  95

Leu Pro Ala Val Leu Ala Ala Gly Asp Lys Ile Thr Ala Val Lys
             100                 105                 110

Thr Ala Ser Ile Ala Ala Gly Leu Ala Ile Ala Glu Ala Ile Asn Pro
             115                 120                 125

Asn Ala Ser Lys Ala Ala Leu Pro Ser Val Ile Asp Ser Leu Arg Asn
130                 135                 140

Ala Gln Lys Phe Pro Glu Arg Leu Leu Ala Leu Asp Phe Ile Asp Thr
145                 150                 155                 160

Leu Ile Arg Thr Ser Pro Val Gln Ile Ser Val Arg Val Pro Glu Leu
                165                 170                 175

Ile Pro Ala Val Ser Glu Ala Met Trp Val Thr Lys Lys Glu Val Ser
            180                 185                 190

Ala Arg Ala Tyr Gln Thr Met Glu Lys Val Cys Gly Leu Ile Val Asn
        195                 200                 205

Lys Asp Ile Glu Lys Phe Ile Pro Glu Leu Ile Lys Cys Ile Ala Lys
    210                 215                 220

Pro Glu Asn Val Pro Glu Thr Val His Leu Leu Gly Ala Thr Thr Phe
225                 230                 235                 240

Val Thr Glu Val Gln Glu Pro Thr Leu Ala Leu Met Val Pro Leu Leu
                245                 250                 255

Asp Arg Gly Leu Ala Glu Arg Glu Thr Ala Ile Lys Arg Lys Thr Ala
            260                 265                 270

Val Ile Val Asp Asn Met Cys Lys Leu Val Asp Asp Pro Asn Ile Val
        275                 280                 285

Ala Pro Phe Leu Pro Lys Met Met Pro Gly Leu Gln Lys Asn Phe Asp
    290                 295                 300

Thr Leu Ala Asp Pro Glu Ala Arg Asp Lys Thr Arg Gln Ala Leu Asp
305                 310                 315                 320

Thr Leu Thr Arg Val Gly Asn Val Lys Asp Gly Lys Ile Pro Glu Ala
                325                 330                 335

Ser Asn Phe Gly Asp Leu Gln Val Val Leu Ala His Leu Lys Thr Val
            340                 345                 350

Leu Ser Gly Lys Pro Ala Ala Thr Ala Glu Lys Phe Ser Pro Val Leu
        355                 360                 365

Ala Tyr Val Ala Ala Ile Ala Gly Gln Leu Ile Asp Glu His Glu Ser
    370                 375                 380

Glu Gln Thr Thr Trp Ile Thr Asn Leu Lys Ser Phe Val Ser Val Leu
385                 390                 395                 400
```

```
Val Gly Asp Ala Ala Glu Gly Val Ile Asp Ser Leu Arg Lys Lys
            405                 410                 415

Ala Leu Pro Gly Ala Ala Glu Glu Ala Glu Val Glu Ala Asp Glu Glu
        420                 425                 430

Glu Gly Glu Asp Leu Cys Asn Cys Thr Phe Ser Leu Ala Tyr Gly Ala
        435                 440                 445

Lys Ile Leu Leu Asn Gln Thr Ser Leu Arg Leu Lys Arg Gly Gln Arg
    450                 455                 460

Tyr Gly Leu Cys Gly Pro Asn Gly Ser Gly Lys Ser Thr Leu Met Arg
465                 470                 475                 480

Ala Ile Asn Asn Glu Gln Val Glu Gly Phe Pro Lys Gln Ser Glu Val
                485                 490                 495

Lys Thr Val Phe Val Glu His Asp Leu Asp Ser Ala Asp Thr Glu Met
            500                 505                 510

Thr Thr Ile Glu Trp Thr Met Lys Lys Leu Ala Glu Ala Lys Val Asp
        515                 520                 525

Val Ser Lys Glu Gln Val Glu Lys Gln Leu Glu Phe Gly Phe Ser
    530                 535                 540

Pro Met Met Ile Ser Gly Glu Ile Thr Ala Leu Ser Gly Gly Trp Lys
545                 550                 555                 560

Met Lys Leu Ala Leu Cys Arg Ala Val Phe Glu Thr Pro Asp Ile Leu
                565                 570                 575

Leu Leu Asp Glu Pro Thr Asn His Leu Asp Val Lys Asn Val Lys Trp
            580                 585                 590

Leu Glu Asp Tyr Leu Ile Asn Ser Pro Cys Thr Ser Ile Ile Val Ser
        595                 600                 605

His Asp Ser Gly Phe Leu Asp Asn Val Cys Gln His Ile Val His Tyr
    610                 615                 620

Glu Arg Phe Lys Leu Lys Arg Tyr Lys Gly Asn Leu Lys Asp Phe Val
625                 630                 635                 640

Asn Arg Leu Pro Ser Ala Lys Ala Tyr Tyr Glu Leu Gly Ala Ser Glu
                645                 650                 655

Phe Glu Phe Ser Phe Pro Glu Pro Gly Phe Leu Glu Gly Val Lys Thr
            660                 665                 670

Lys Ala Lys Ala Ile Leu Arg Ala Thr Asn Met Ser Phe Gln Tyr Pro
        675                 680                 685

Asn Thr Pro Lys Pro Gln Leu Ser Asp Ile Thr Phe Gln Cys Ser Leu
    690                 695                 700

Asn Ser Arg Ile Ala Val Ile Gly Pro Asn Gly Ala Gly Lys Ser Thr
705                 710                 715                 720

Leu Val Asn Val Leu Thr Gly Glu Leu Ile Pro Thr Gly Gly Glu Ile
                725                 730                 735

Tyr Gln His Glu Asn Met Arg Ile Ala Tyr Ile Lys Gln His Ala Phe
            740                 745                 750

Ala His Ile Asp Asn His Leu Asp Lys Thr Pro Ser Glu Tyr Ile Gln
        755                 760                 765

Trp Arg Phe Gln Thr Gly Glu Asp Arg Glu Thr Met Asp Arg Ala Asn
    770                 775                 780

Lys Ile Ile Thr Glu Glu Asp Glu Ala Ala Met Asn Lys Val Phe His
785                 790                 795                 800

Leu His Asp Ser Tyr Arg Arg Ile Ile Gly Ile His Ser Arg Arg Lys
                805                 810                 815

Phe Lys Asn Ser Tyr Glu Tyr Glu Cys Ser Phe Ala Leu Gly Glu Asn
```

```
                820                 825                 830

Ile Gly Met Lys Ser Glu Arg Trp Val Pro Met Met Thr Ala Asp Asn
            835                 840                 845

Asp Trp Leu Pro Arg Ser Glu Leu Leu Ala Ser His Gln Lys Leu Val
        850                 855                 860

Ala Asp Val Asp Met Lys Glu Ala Leu Ala Ser Gly Gln Phe Arg Pro
865                 870                 875                 880

Leu Val Arg Lys Glu Ile Glu Thr His Cys Ala Asn Phe Gly Leu Asp
                885                 890                 895

Ala Glu Leu Ile Ser His Ser Arg Met Arg Gly Leu Ser Gly Gly Gln
            900                 905                 910

Arg Val Lys Val Val Leu Ala Ala Cys Ser Trp Gln Arg Pro His Leu
        915                 920                 925

Ile Val Leu Asp Glu Pro Thr Asn Tyr Leu Asp Arg Asp Ser Leu Gly
    930                 935                 940

Ala Leu Ser Lys Ala Leu Lys Lys Phe Glu Gly Gly Val Ile Ile Ile
945                 950                 955                 960

Ser His Ser Ser Glu Phe Thr Lys Asp Leu Thr Glu Glu Val Trp Ala
                965                 970                 975

Val Leu Asp Gly Lys Met Thr Pro Ser Gly His Asn Trp Val Gln Gly
            980                 985                 990

Gln Gly Ser Gly Pro Arg Leu Lys Ala Asp Glu Gly Glu Glu Glu Asp
        995                 1000                1005

Lys Phe Asp Ala Met Gly Asn Lys Ile Ala Ala Thr Lys Lys Lys Ala
    1010                1015                1020

Lys Leu Thr Ser Ser Glu Ala Arg Lys Lys Lys Lys Asp Arg Met Ala
1025                1030                1035                1040

Arg Arg Lys Arg Gly Glu Glu Val Phe Ser Asp Glu Asp Glu
                1045                1050

<210> SEQ ID NO 40
<211> LENGTH: 1443
<212> TYPE: PRT
<213> ORGANISM: Grosmannia clavigera
<220> FEATURE:
<223> OTHER INFORMATION: Gc ABC multidrug transporter
<220> FEATURE:
<221> NAME/KEY: DOMAIN
<222> LOCATION: (154)...(389)
<223> OTHER INFORMATION: NBF; PDR Domain 1
<220> FEATURE:
<221> NAME/KEY: DOMAIN
<222> LOCATION: (501)...(711)
<223> OTHER INFORMATION: TMD 1
<220> FEATURE:
<221> NAME/KEY: DOMAIN
<222> LOCATION: (845)...(1047)
<223> OTHER INFORMATION: NBF; PDR Domain 2
<220> FEATURE:
<221> NAME/KEY: DOMAIN
<222> LOCATION: (1141)...(1325)
<223> OTHER INFORMATION: TMD 2

<400> SEQUENCE: 40

Met Ala Arg Ser Ala Val Ser Gln Glu Ser Leu Arg Leu Ala Asp Ser
1               5                   10                  15

Ser Arg Ser Ser Glu Glu Ala Gly Pro Glu Glu Phe Met Ala Ile Arg
            20                  25                  30

Thr Asn Gly Pro Glu Ala Ser Asp Ala Gly Thr Tyr Arg Pro Gln Arg
        35                  40                  45
```

Arg Asp Ser Thr Ala Met Ile Glu Glu Ser Asp Val Gln Glu Leu Arg
 50                  55                  60

Met Leu Ala Thr Ala Ile Ser Gln Arg Arg Gln Ser His Ala Thr
 65                  70                  75                  80

Gly Ser Glu Ala Gly Asn Glu Asp Phe Asp Ala Ala Asp Ser Ala Met
                 85                  90                  95

Asp Pro Ser Ser Lys Ser Phe Asp Leu Gly Val Phe Leu Arg Arg Ile
            100                 105                 110

Ile Lys Asp Phe Arg Lys Glu Gly Phe Lys Glu Arg Arg Leu Gly Ile
        115                 120                 125

Ser Tyr Lys Asp Leu Thr Val Ser Gly Thr Gly Glu Ala Leu Gln Leu
    130                 135                 140

Gln Ser Thr Val Gly Thr Val Leu Gln Met Pro Leu Arg Leu Gly Glu
145                 150                 155                 160

Ser Phe Ser Phe Gly Lys Lys Ser His Lys Thr Ile Leu His Asn Phe
                165                 170                 175

Asp Gly His Val Glu Ser Gly Glu Leu Leu Ile Val Leu Gly Arg Pro
            180                 185                 190

Gly Ser Gly Cys Ser Thr Leu Leu Lys Thr Ile Thr Gly Gln Leu His
        195                 200                 205

Gly Leu Lys Ile Gly Glu Gln Ser Thr Ile Asp Tyr Asn Gly Ile Pro
    210                 215                 220

Met Lys His Met Ile Lys Val Phe Lys Gly Glu Val Leu Lys Asn Gln
225                 230                 235                 240

Glu Val Asp Lys His Phe Pro His Leu Thr Val Gly Gln Thr Leu Glu
                245                 250                 255

Phe Ala Ala Ala Thr Arg Thr Pro Ser Lys Arg Ile His Ala Ile Thr
            260                 265                 270

Arg Glu Glu His Ile Lys His Ala Ala Arg Ile Val Met Ala Ile Cys
        275                 280                 285

Gly Leu Ser His Thr Tyr Asn Thr Lys Val Gly Asn Asp Phe Ile Arg
    290                 295                 300

Gly Val Ser Gly Gly Glu Arg Lys Arg Val Ser Ile Ala Glu Met Met
305                 310                 315                 320

Leu Ala Gly Ser Pro Ile Ala Ala Trp Asp Asn Ser Thr Arg Gly Leu
                325                 330                 335

Asp Ser Ala Thr Ala Leu Lys Phe Val Gln Ser Leu Arg Leu Ala Ala
            340                 345                 350

Asp Phe Thr His Ser Val His Cys Val Ala Ile Tyr Gln Ala Ser Gln
        355                 360                 365

Ala Ile Tyr Asp Leu Phe Asp Lys Ala Val Val Leu Tyr Glu Gly Arg
    370                 375                 380

Gln Ile Tyr Phe Gly Pro Ala Pro Ala Lys Ala Tyr Phe Glu Thr
385                 390                 395                 400

Met Gly Trp Phe Cys Pro Gln Arg Gln Thr Thr Gly Asp Phe Leu Thr
                405                 410                 415

Ser Val Thr Asn Pro Gln Glu Arg Val Ala Arg Glu Gly Met Glu Asn
            420                 425                 430

Lys Val Pro Arg Thr Pro Glu Phe Glu Ala Tyr Trp Tyr Gln Ser
        435                 440                 445

Pro Asp Cys Lys Ala Leu Arg Asn Ala Met Glu Lys His Glu Ala Ile
    450                 455                 460

His Pro Ile Asp Pro His Gly Gln Thr Ala Val Asn Met Arg Glu Asn

```
              465                 470                 475                 480
Lys Gln Gln Arg Gln Ala Lys His Val Arg Pro Lys Ser Pro Tyr Ile
                    485                 490                 495
Ile Ser Val Ala Met Gln Val Arg Leu Thr Thr Lys Arg Ala Tyr Gln
                500                 505                 510
Arg Ile Leu Asn Asp Ile Ser Ala Thr Ala Thr Gln Ala Val Met Gln
                515                 520                 525
Val Val Leu Ala Leu Ile Ile Gly Ser Val Phe Tyr Gly Thr Pro Asn
    530                 535                 540
Ala Thr Ala Gly Phe Tyr Ala Lys Gly Ser Val Ile Phe Gln Ala Ile
545                 550                 555                 560
Leu Met Asn Ala Leu Thr Ala Ile Ser Glu Ile Asn Lys Leu Tyr Ala
                    565                 570                 575
Gln Arg Pro Ile Val Glu Lys His Ala Ala Tyr Ala Phe Tyr His Pro
                580                 585                 590
Tyr Thr Glu Ala Leu Ala Gly Ile Met Thr Asp Ile Pro Ile Lys Phe
    595                 600                 605
Ile Thr Gly Thr Ile Phe Asn Leu Ile Val Tyr Phe Met Ser Gly Leu
    610                 615                 620
Arg Arg Glu Pro Ala Gln Phe Phe Leu Phe Leu Ile Thr Tyr Thr
625                 630                 635                 640
Thr Thr Phe Val Met Ser Ala Ile Phe Arg Thr Leu Ala Ala Ile Thr
                    645                 650                 655
Lys Thr Val Ser Gln Ala Met Met Leu Ala Gly Val Met Val Leu Ala
                660                 665                 670
Leu Val Ile Tyr Thr Gly Phe Val Thr Val Pro Lys Met His Pro
    675                 680                 685
Trp Phe Ser Trp Ile Arg Trp Ile Asn Pro Val Tyr Tyr Ala Phe Glu
    690                 695                 700
Val Leu Ile Ala Asn Glu Phe His Gly Arg Ser Phe Thr Cys Ser Ser
705                 710                 715                 720
Ile Ile Pro Ala Tyr Thr Pro Leu Val Gly Asp Ser Trp Ile Cys Ser
                725                 730                 735
Val Ala Ser Ser Val Ala Gly Gln His Thr Val Ser Gly Asp Ala Phe
                740                 745                 750
Ile Gly Val His Tyr Lys Tyr Tyr Ala His Ala Trp Arg Asn Phe
    755                 760                 765
Gly Ile Leu Leu Ala Phe Leu Phe Ala Phe Met Phe Val Tyr Phe Val
    770                 775                 780
Ser Thr Glu Leu Asn Ser Gln Thr Thr Ser Ala Ala Glu Val Leu Val
785                 790                 795                 800
Phe Gln Arg Gly His Val Pro Ala Tyr Leu Leu Asn Gly Gly Asn Lys
                805                 810                 815
Gly Ala Ile Thr Glu Asp Met Thr Lys Ala Ser Pro Gln Gln Asp Gly
                820                 825                 830
Asn Glu Lys Thr Asp Ala Ile Glu Pro Gln Thr Asp Val Phe Thr Trp
                835                 840                 845
Arg Asp Val Val Tyr Asp Val Thr Ile Lys Gly Gln Asp Arg Arg Leu
    850                 855                 860
Leu Asn His Val Ser Gly Trp Val Lys Pro Gly Thr Leu Thr Ala Leu
865                 870                 875                 880
Met Gly Val Ser Gly Ala Gly Lys Thr Thr Leu Leu Asp Ala Leu Ala
                885                 890                 895
```

```
Gln Arg Thr Thr Met Gly Val Ile Thr Asp Leu His Leu Ser Thr Ala
                900                 905                 910

Thr Val Arg Glu Ser Leu Arg Phe Ser Ala Met Leu Arg Gln Pro Gln
        915                 920                 925

Ser Val Ser Lys Glu Gly Lys Phe Thr Phe Val Glu Glu Val Ile Asp
    930                 935                 940

Met Leu Asp Met Arg Asp Phe Ala Asn Ala Val Val Gly Val Pro Gly
945                 950                 955                 960

Gln Gly Leu Asn Val Glu Gln Arg Lys Leu Leu Thr Ile Gly Val Glu
                965                 970                 975

Leu Ala Ala Lys Pro Lys Leu Leu Leu Phe Leu Asp Glu Pro Thr Ser
        980                 985                 990

Gly Leu Asp Ser Gln Ser Ser Trp Ala Ile Cys Ala Phe Leu Arg Lys
    995                 1000                1005

Leu Ala Asp His Gly Gln Ala Val Leu Cys Thr Ile His Gln Pro Ser
    1010                1015                1020

Ala Val Leu Phe Gln Gln Phe Asp Arg Leu Leu Phe Leu Ala Ala Gly
1025                1030                1035                1040

Gly Lys Thr Val Tyr Phe Gly Asp Ile Gly Glu Asn Ser Arg Thr Leu
                1045                1050                1055

Leu Glu Tyr Phe Glu Thr His Gly Ala Glu Lys Cys Gly Asp Glu Glu
        1060                1065                1070

Asn Pro Ala Glu Tyr Met Leu Asn Ile Val Asn Arg Gly Ser Asn Ser
    1075                1080                1085

Gln Gly Glu Asp Trp His Asp Val Trp Asn Asn Ser Arg Glu Arg Gln
    1090                1095                1100

Asp Val Met Ala Glu Ile Asn Arg Ile His Val Asp Arg Ala Ala Gln
1105                1110                1115                1120

Pro Leu Ala Thr His Glu Asp Pro His Ser Arg Asp Glu Phe Ala Met
                1125                1130                1135

Pro Phe Gly Ala Gln Leu Ala Arg Val Ala Thr Arg Val Cys Gln Gln
        1140                1145                1150

Tyr Trp Arg Ser Pro Thr Tyr Val Phe Ser Lys Phe Ile Leu Gly Thr
    1155                1160                1165

Val Ala Gly Leu Phe Ile Gly Phe Ser Phe Gly Ala Asp Gly Thr
    1170                1175                1180

Leu Ala Gly Met Gln Asn Arg Asp Leu Tyr Glu Val Arg Glu Arg Pro
1185                1190                1195                1200

Ser Lys Ala Tyr Ser Trp Lys Ala Phe Met Ile Ala Asn Val Ile Val
                1205                1210                1215

Glu Ile Pro Tyr Gln Ile Leu Thr Gly Ile Leu Ile Tyr Ala Ser Phe
        1220                1225                1230

Tyr Tyr Ala Val Ile Gly Ile Gln Ser Ser Ala Arg Gln Gly Leu Ile
    1235                1240                1245

Leu Leu Phe Cys Ile Gln Phe Met Leu Tyr Ala Ser Ser Phe Ala Gln
    1250                1255                1260

Met Thr Ile Ala Ser Met Pro Val Ala Glu Thr Ala Ala Ser Ile Val
1265                1270                1275                1280

Thr Leu Leu Leu Leu Phe Ser Leu Thr Phe Cys Gly Val Leu Gln Thr
                1285                1290                1295

Pro Ser Ala Leu Pro Gly Phe Trp Ile Phe Met His Arg Val Ser Pro
        1300                1305                1310
```

```
Phe Thr Tyr Trp Val Ala Gly Ile Val Ser Thr Gln Leu His Gly Arg
        1315                1320                1325

Ala Val Asp Cys Ser Lys Ser Glu Thr Ser Ile Phe Ser Pro Pro Ala
    1330                1335                1340

Gly Met Thr Cys Gly Glu Tyr Met Ala Pro Tyr Leu Thr Gln Ala Pro
1345                1350                1355                1360

Gly Asn Leu Gln Asn Pro Asn Asp Thr Glu Asn Cys Arg Tyr Cys Ser
                1365                1370                1375

Leu Lys Val Ala Val Gln Tyr Leu Ala Gln Ser Ser Ile Phe Tyr Ser
            1380                1385                1390

Gln Arg Trp Arg Asn Phe Gly Ile Met Trp Ala Tyr Ile Ala Phe Asn
        1395                1400                1405

Ile Phe Ile Ala Val Ile Ser Tyr Trp Ala Phe Arg Val Lys Lys Trp
    1410                1415                1420

Asn Arg Gly Gly Lys Ser Ala Lys Lys Thr Ser Glu Lys Asn Lys Thr
1425                1430                1435                1440

Glu Lys Ala
```

<210> SEQ ID NO 41
<211> LENGTH: 1506
<212> TYPE: PRT
<213> ORGANISM: Grosmannia clavigera
<220> FEATURE:
<223> OTHER INFORMATION: GcABC-G4

<400> SEQUENCE: 41

```
Met Thr Ala Asp Ala Ala Ser Pro Ser Gly Ala Leu Gln Asp Val
 1               5                  10                  15

Asp Asp Glu Ser Glu Gln Gln Ala Ala Pro Val Pro His Ser Leu Asn
            20                  25                  30

Pro Pro Ser Glu Ser Ser Gln Pro Thr Glu Tyr Ser Thr Ala Ala Ala
        35                  40                  45

Glu Lys Pro His His Val Val Ala Leu Glu Ala Glu Asp Leu Gln Ile
    50                  55                  60

Arg Ala Thr Leu Glu Ala Leu Arg Ala Arg Asp Glu Gln Ser Gly Leu
65                  70                  75                  80

Pro Ala Gly Glu Leu Gly Met Thr Trp Arg Asp Val Thr Val Lys Ala
                85                  90                  95

Val Ser Ser Glu Ala Ala Leu His Glu Asn Val Val Ser Gln Leu Asn
            100                 105                 110

Leu Ile Arg Thr Leu Arg Asp Ala His Arg Lys Pro Pro Leu Lys Thr
        115                 120                 125

Leu Val Asp His Ser His Gly Cys Val Arg Pro Gly Glu Met Leu Leu
    130                 135                 140

Val Leu Gly Arg Pro Gly Ala Gly Cys Thr Thr Leu Leu Asn Ile Leu
145                 150                 155                 160

Ala Asn Arg Arg Arg Gly Phe Asp Ser Val Glu Gly Asp Val Arg Tyr
                165                 170                 175

Gly Ser Met Thr Ala Ile Glu Ala Lys Arg Tyr Arg Gly Gln Ile Val
            180                 185                 190

Met Ser Thr Glu Glu Leu His Tyr Pro Thr Leu Thr Val Lys Gln
        195                 200                 205

Thr Leu Asp Phe Ala Thr Arg Leu Lys Val Pro Phe His Ala Pro Val
    210                 215                 220

Gly Ala Asp Ser Ile Glu Glu Val Arg Thr Gln Leu Arg Asn Phe Leu
```

```
            225                 230                 235                 240
        Leu Ala Ser Leu His Ile Glu His Thr Val Gly Thr Lys Val Gly Asp
                        245                 250                 255
        Ala Phe Val Arg Gly Val Ser Gly Glu Lys Arg Val Ser Ile
                        260                 265                 270
        Ala Glu Ala Met Ala Thr Gln Gly Ser Val Tyr Leu Trp Asp Asn Cys
                        275                 280                 285
        Thr Arg Gly Leu Asp Ala Asn Thr Ala Leu Glu Phe Ile Lys Ala Val
                        290                 295                 300
        Arg Ala Met Thr Asp Val Leu Gly Leu Thr Ser Val Met Thr Leu Tyr
        305                 310                 315                 320
        Gln Ala Gly Asn Gly Ile Tyr Asn Leu Phe Asp Lys Val Leu Val Leu
                        325                 330                 335
        Asp Arg Gly Gln Gln Val Tyr Tyr Gly Pro Thr Val Glu Ala Arg Pro
                        340                 345                 350
        Phe Leu Glu Asp Gln Gly Phe Val Cys Arg Pro Gly Ala Asn Val Ala
                        355                 360                 365
        Asp Phe Leu Thr Gly Val Thr Val Ser Thr Glu Arg Ile Ile Arg His
                        370                 375                 380
        Gly Cys Glu Ala Thr Phe Pro Arg Thr Thr Ala Gln Leu Arg Thr Ala
        385                 390                 395                 400
        Tyr Glu Lys Ser Glu Leu Cys His Arg Met Glu Leu Glu Tyr Val Tyr
                        405                 410                 415
        Pro Asp Ser Asp Ala Ala Arg Val Ala Thr Glu Arg Phe Gln Ala Arg
                        420                 425                 430
        Val Val Ala Leu Arg Asp Asn Arg Phe Ile Gly Leu Leu Gly Arg His
                        435                 440                 445
        Ser Pro Leu Thr Val Gly Phe Ala Ser Gln Val Arg Ala Cys Val Ile
                        450                 455                 460
        Arg Gln Tyr Gln Val Leu Trp Gly Asp Lys Pro Thr Leu Ile Ala Arg
        465                 470                 475                 480
        Gln Cys Val Cys Leu Val Met Val Leu Ile Val Gly Ser Leu Phe Tyr
                        485                 490                 495
        Asn Ala Ala Asp Asp Ser Leu Gly Leu Phe Leu Lys Gly Gly Ala Leu
                        500                 505                 510
        Phe Phe Ser Leu Val Phe Phe Thr Met Leu Ala Met Pro Glu Val Met
                        515                 520                 525
        Asn Ser Phe Glu Gly Arg Pro Ile Met Met Glu Gln Arg His Ala Ala
                        530                 535                 540
        Leu Phe Asn Pro Ala Ala Phe Cys Ile Ala Gln Ile Ser Ala Asp Val
        545                 550                 555                 560
        Pro Met Thr Leu Phe Ile Val Ser Tyr Phe Ser Leu Val Leu Tyr Phe
                        565                 570                 575
        Met Val Gly Leu Lys Glu Thr Pro Ala Ala Phe Phe Thr Phe Trp Ile
                        580                 585                 590
        Leu Leu Phe Thr Ile Ser Met Thr Ile Thr Ala Leu Cys Arg Ala Val
                        595                 600                 605
        Gly Ala Leu Cys Arg Thr Phe Asp Ala Ala Ser Lys Ile Met Gly Ile
                        610                 615                 620
        Leu Met Ile Ala Phe Leu Thr Tyr Ser Gly Tyr Met Ile Phe Lys Pro
        625                 630                 635                 640
        Lys Met His Pro Trp Phe Val Trp Ile Tyr Trp Ile Ser Pro Met Ser
                        645                 650                 655
```

```
Tyr Ala Phe Asp Ala Leu Leu Ser Asn Glu Leu Ser Gly Ala Val Ile
            660                 665                 670

Ala Cys Ser Gly Ile Asn Leu Ile Pro Arg Gly Pro Gly Tyr Glu Asn
        675                 680                 685

Ala Ser Ala Pro Tyr Gln Ser Cys Ala Gly Val Pro Gly Ala Thr Leu
690                 695                 700

Phe Ser Thr Ile Val Glu Gly Asn Ser Tyr Leu Ser Ala Leu Ser Tyr
705                 710                 715                 720

Ser His Gly His Val Trp Arg Asn Phe Gly Val Leu Trp Gly Trp Trp
                725                 730                 735

Ser Leu Phe Val Phe Val Thr Ile Val Ala Thr Ala Asn Trp Arg Ala
            740                 745                 750

Ala Ser Glu Ser Gly Pro Ala Leu Leu Ile Pro Arg Glu Lys Ala Asn
        755                 760                 765

Lys Val Lys Leu Pro Asn Val Glu Asp Gly Leu Gly Thr Asp Asp Val
770                 775                 780

Ala Gly Met Gly Ser Glu Lys Lys Glu Leu Ser Asn Ala Asp Asn Asn
785                 790                 795                 800

Ala Ser Asp Ser Ser Thr Pro Ala Leu Met Lys Asn Thr Ala Val Phe
                805                 810                 815

Thr Trp Lys His Leu His Tyr Thr Val Gln Ala Gly Arg Asp Leu
            820                 825                 830

Lys Leu Leu Asp Asn Val Gln Gly Trp Val Arg Pro Gly Met Leu Gly
        835                 840                 845

Ala Leu Met Gly Ser Ser Gly Ala Gly Lys Thr Thr Leu Leu Asp Val
850                 855                 860

Leu Ala Gln Arg Lys Thr Glu Gly Val Ile Lys Gly Ser Val Leu Val
865                 870                 875                 880

Asp Gly Arg Glu Leu Pro Val Ser Phe Gln Arg Ser Thr Gly Tyr Cys
                885                 890                 895

Glu Gln Leu Asp Val His Glu Ala Leu Ala Thr Val Arg Glu Ala Leu
            900                 905                 910

Glu Phe Ser Ala Leu Leu Arg Gln Asp Arg His Thr Pro Arg Ala Glu
        915                 920                 925

Lys Leu Ala Tyr Val Asp Thr Ile Ile Asn Leu Leu Glu Leu Asn Asp
930                 935                 940

Leu Ala Asp Thr Leu Ile Gly Arg Ile Gly Asn Gly Leu Ser Val Glu
945                 950                 955                 960

Gln Arg Lys Arg Val Thr Ile Gly Val Glu Leu Val Ala Lys Pro Ser
                965                 970                 975

Leu Leu Ile Phe Leu Asp Glu Pro Thr Thr Gly Leu Asp Gly Gln Ser
            980                 985                 990

Ala Phe Asn Thr Val Arg Phe Leu Arg Lys Leu Ala Asp Ala Gly Gln
        995                 1000                1005

Ala Val Leu Val Thr Ile His Gln Pro Ser Ala Gln Leu Phe Ala Gln
1010                1015                1020

Phe Asp Thr Leu Leu Leu Leu Thr Met Gly Gly Lys Met Val Tyr Phe
1025                1030                1035                1040

Gly Asp Ile Gly Val Arg Ser Asp Ile Asn Gly Leu Ala His Ala Ala
                1045                1050                1055

Pro Ala Asp Ser Ser Gly His Val Glu Asp Ser Ser Thr Gln Thr Val
            1060                1065                1070
```

```
Arg Glu Tyr Phe Ala Arg Tyr Gly Ala Pro Cys Pro Ser Gly Val Asn
        1075                1080                1085

Pro Ala Glu His Met Ile Asp Val Val Ser Gly Arg Leu Ser Gln Asn
    1090                1095                1100

Lys Asp Trp His Gln Ile Trp Leu Asp Ser Pro Glu Lys Ala Ala Met
1105                1110                1115                1120

Asp Ala Glu Leu Asp Arg Met Val Val Glu Ala Arg Ala Lys Pro Arg
                1125                1130                1135

Leu Ala Leu Thr Gln Thr Arg Ser Gln Glu Gly Thr Asn Gly Asn Leu
            1140                1145                1150

Gln Leu His Arg Thr Leu Thr Asn Ala Thr Asp Ala Thr Tyr Asp Ser
        1155                1160                1165

Thr Ala Pro Ala Pro Pro Ser Leu Asn Thr Asp Ser Glu Phe Ala
    1170                1175                1180

Ala Pro Leu Trp Glu Gln Ile Cys Val Ala Ser Thr Arg Met Asn Arg
1185                1190                1195                1200

Ala Leu Tyr Arg Asn Thr Asp Tyr Ile Asn Asn Lys Ile Tyr Leu His
                1205                1210                1215

Ile Leu Thr Ser Leu Phe Thr Gly Phe Ser Phe Trp Lys Ile Gly Ser
            1220                1225                1230

Ser Val Leu Asp Leu Gln Leu Arg Leu Phe Ala Val Phe Ser Phe Val
        1235                1240                1245

Phe Val Ala Pro Gly Val Ile Asn Gln Leu Gln Pro Leu Phe Ile Glu
    1250                1255                1260

Arg Arg Asp Ile Phe Glu Thr Arg Glu Lys Lys Ala Lys Met Tyr Ser
1265                1270                1275                1280

Trp Ile Ala Phe Val Thr Ala Leu Ile Val Ser Glu Leu Pro Tyr Leu
                1285                1290                1295

Val Val Cys Ser Ile Ile Tyr Phe Phe Cys Trp Tyr Tyr Thr Val Gly
            1300                1305                1310

Phe Pro His Ala Thr Ser Arg Ala Gly Ser Thr Tyr Phe Met Val Leu
        1315                1320                1325

Leu Tyr Glu Phe Leu Tyr Thr Gly Ile Gly Gln Phe Val Ala Ala Tyr
    1330                1335                1340

Ala Pro Asn Ala Val Phe Ala His Leu Met Asn Pro Phe Val Ile Gly
1345                1350                1355                1360

Ile Leu Leu Ala Phe Cys Gly Val Leu Val Pro Tyr Ser Glu Ile Gln
                1365                1370                1375

Pro Phe Trp Arg Tyr Trp Met Tyr Tyr Leu Asn Pro Asn Tyr Leu
            1380                1385                1390

Met Ser Gly Leu Leu Val Phe Asp Ser Trp Asp Ser Lys Val Arg Cys
        1395                1400                1405

Arg Lys Asp Glu Phe Ala Tyr Phe Asn Pro Pro Asp Gly Gln Thr Cys
    1410                1415                1420

Gly Glu Tyr Leu Gly Ile Tyr Leu Gln Thr Tyr Gly Arg Ile Asn Asn
1425                1430                1435                1440

Leu Glu Asn Pro Glu Asp Thr Ser Leu Cys Arg Val Cys Gln Tyr Arg
                1445                1450                1455

Ser Gly Thr Asp Tyr Leu Tyr Thr Val Asn Ile Asp Lys Tyr Gly Asn
            1460                1465                1470

Gly Trp Arg Asp Ala Gly Ile Leu Val Ile Phe Val Leu Ser Ser Tyr
        1475                1480                1485

Ser Leu Val Tyr Gly Leu Met Lys Leu Arg Thr Lys Met Ser Lys Lys
```

-continued

```
        1490            1495            1500

Ala Glu
1505

<210> SEQ ID NO 42
<211> LENGTH: 1123
<212> TYPE: PRT
<213> ORGANISM: Grosmannia clavigera
<220> FEATURE:
<223> OTHER INFORMATION: GcABC-G5

<400> SEQUENCE: 42

Met Asp Ala Ser Asp Asn Glu Lys Thr Val Tyr Gly Ala Asp His Asp
  1               5                  10                  15

Gly Asp Arg Met Pro Gln Lys His Leu Thr Val Ser Phe Gln Asp Val
                 20                  25                  30

Asn Ile Leu Val His Gly Gln Gly Glu Asp Phe Ala Pro Thr Phe Thr
             35                  40                  45

Ser Val Val Ala Asn Leu Ile Pro Thr Arg Gln Lys Asp Ile His Phe
 50                  55                  60

Pro Thr Leu Thr Val Gly Gln Thr Ile Asn Phe Ala Thr Ala Thr Lys
 65                  70                  75                  80

Leu Pro Gly Ser Arg Pro Gly Arg Thr Lys Thr Lys Asn Asp Tyr Leu
                 85                  90                  95

Ala His Thr Gln Asp Lys Ile Leu Ser Asp Leu Gly Ile Ala His Thr
            100                 105                 110

Arg Asn Thr Ile Val Gly Asn Glu Phe Met Arg Gly Val Ser Gly Gly
            115                 120                 125

Glu Arg Lys Arg Val Ser Leu Ala Glu Val Leu Ala Thr Gln Ala Pro
130                 135                 140

Leu Gln Cys Trp Asp Asn Ser Thr Arg Gly Leu Asp Ala Ser Asn Ala
145                 150                 155                 160

Leu Asp Phe Ala Lys Val Leu Arg Arg Met Ala Asp Glu Glu Gln Lys
                165                 170                 175

Thr Ile Ile Ala Thr Leu Tyr Gln Ala Gly Asn Gly Ile Tyr Asp Leu
            180                 185                 190

Phe Asp Lys Val Leu Val Leu Ala Glu Gly Arg Glu Ile Tyr Tyr Gly
            195                 200                 205

Leu Ala Ser Glu Ala Arg His Tyr Phe Glu Ser Met Gly Phe Thr Phe
210                 215                 220

Pro Pro Gly Ala Asn Val Ala Asp Phe Leu Thr Gly Val Ala Val Pro
225                 230                 235                 240

Thr Glu Arg Met Val Thr Pro Gly Phe Glu Gly Lys Val Pro Asn Thr
                245                 250                 255

Ala Glu Glu Phe Glu Thr Arg Tyr Lys Ser Ser Ala Thr Phe Glu Met
            260                 265                 270

Ala Met Gln Glu Ile Gln Ser Val Ser Glu Asp Val Leu Ala Arg Glu
            275                 280                 285

Ile Ala Asn Leu Lys Ala Thr Arg Asp Leu Glu Lys Asn Arg Thr Val
            290                 295                 300

Ser Leu Leu Ser Arg Asn Glu Ser Pro Tyr His Val Ser Phe Phe Arg
305                 310                 315                 320

Gln Val Asn Ala Leu Thr Val Arg Met His Pro Trp Phe Arg Trp Ile
                325                 330                 335

Ala Tyr Ile Asn Pro Ala Ser Tyr Ala Phe Glu Ala Val Ile Ala Ser
```

```
                340                 345                 350
Glu Met Gly His Arg Thr Met Glu Cys Val Ser Pro Gln Leu Val Pro
            355                 360                 365
Phe Gly Pro Ser Tyr Ser Asn Ala His Gly Tyr Gln Ser Cys Thr Val
            370                 375                 380
Gln Gly Ser Asp Pro Gly Gln Ser Val Ile His Gly Asp Asp Tyr Val
385                 390                 395                 400
Ala Tyr Arg Tyr Gln Ala Tyr Ser Ser His Ile Trp Arg Asn Val Gly
                405                 410                 415
Ile Leu Ile Gly Phe Trp Leu Phe Phe Ala Phe Ser Thr Ala Val Ala
                420                 425                 430
Phe Glu Val Asn Leu His Ser Gly Ser Gly Ser Arg Val Leu Tyr Asn
            435                 440                 445
Arg Gly Gln Tyr Lys Lys Gln Lys Ser Lys Glu Lys Asp Pro Glu Leu
            450                 455                 460
Ala Ile Asn Thr Val Lys Ile Asp Gly Gln Pro Glu Arg Ile Thr Ser
465                 470                 475                 480
Gly Gly Thr Val Phe Thr Phe Lys Asn Ile Lys Tyr Thr Val Arg His
                485                 490                 495
Glu Gly Gln Asp Lys Leu Leu Leu Asp Ser Val Ser Gly Phe Val Lys
            500                 505                 510
Pro Gly Gln Leu Val Ala Leu Met Gly Ser Ser Gly Ala Gly Lys Thr
            515                 520                 525
Thr Leu Met Asp Val Leu Ala Gln Arg Lys Asp Ala Gly Arg Val Glu
            530                 535                 540
Gly Ser Ile Met Val Asn Gly Lys Pro Gln Gly Ile Ser Phe Gln Arg
545                 550                 555                 560
Ala Thr Gly Tyr Cys Glu Gln Asn Asp Val His Glu Pro Thr Ala Thr
                565                 570                 575
Val Leu Glu Ala Leu Leu Phe Ser Ala Arg Leu Arg Gln Pro Met Ser
            580                 585                 590
Val Pro Asp Leu Glu Lys Arg Gln His Val Ile Gln Ile Met Asp Leu
            595                 600                 605
Leu Glu Leu Thr Ser Met Gln His Ala Ile Ile Gly Ser Pro Gly Glu
            610                 615                 620
Gly Leu Ser Ile Glu Gln Arg Lys Arg Leu Thr Leu Ala Val Glu Leu
625                 630                 635                 640
Val Ala Lys Pro Ala Leu Leu Phe Leu Asp Glu Pro Thr Ser Gly Leu
                645                 650                 655
Asp Gly Gln Ser Ala Tyr Glu Ile Cys Arg Phe Met Arg Lys Leu Ser
            660                 665                 670
Ala Ser Gly Gln Thr Val Ile Cys Thr Ile His Gln Pro Ser Ala Thr
            675                 680                 685
Leu Phe Glu Asn Phe Asp Val Leu Leu Leu Ala Arg Gly Gly Lys
            690                 695                 700
Thr Thr Tyr Phe Gly Pro Thr Gly Val Asn Ser Ser Ile Val Leu Asp
705                 710                 715                 720
Tyr Phe Ser His Arg Gly Ala Pro Cys Gly Ile Asn Val Asn Pro Ala
                725                 730                 735
Glu His Ile Val Asp Val Val Gln Gly Arg Phe Gly Thr Glu Ser Asp
            740                 745                 750
Trp Pro Gln Glu Trp Leu His Ser Asp Glu Tyr Lys Gln Thr Ile Glu
            755                 760                 765
```

Glu Leu Asp Ala Leu Asn Asp Ser Ser Ala Glu Thr Asp Glu Ser Lys
        770                 775                 780

Thr Gly Val Ala Val Arg Ala Glu Leu Val Glu Glu Asn Asn Ser Asp
785                 790                 795                 800

Phe Ala Thr Thr Leu Pro Tyr Gln Ile Val Leu Val Thr Gln Arg Gln
                805                 810                 815

Leu Val Ser Leu Trp Arg Asn Pro Asp Tyr Ala Trp Asn Lys Ile Ser
            820                 825                 830

Leu His Ile Thr Asn Ala Leu Phe Gly Gly Phe Thr Phe Trp Lys Ile
        835                 840                 845

Gly Asn Ser Ser Phe Asp Leu Gln Leu Arg Leu Met Ala Val Phe Asn
    850                 855                 860

Phe Val Phe Val Ala Pro Gly Cys Ile Asn Gln Met Gln Pro Phe Phe
865                 870                 875                 880

Ile Arg Asn Arg Asp Leu Phe Glu Thr Arg Glu Lys Lys Ser Lys Ala
                885                 890                 895

Tyr His Trp Leu Ala Phe Ile Ser Ala Gln Leu Leu Ser Glu Ile Pro
            900                 905                 910

Leu Leu Val Val Cys Ala Thr Val Tyr Phe Ala Gly Trp Tyr Phe Thr
        915                 920                 925

Ala Gly Leu Pro Val Asp Ala Ser Arg Ser Gly Gln Val Tyr Leu Gln
    930                 935                 940

Met Ile Phe Tyr Glu Phe Leu Tyr Thr Ser Ile Gly Gln Ala Ile Ala
945                 950                 955                 960

Ala Tyr Ser Pro Asn Glu Tyr Phe Ala Ser Leu Ala Asn Pro Leu Ile
                965                 970                 975

Val Gly Ala Ala Leu Ile Asn Phe Cys Gly Val Val Pro Tyr Ser
            980                 985                 990

Leu Ile Pro Thr Phe Trp Arg Tyr Trp Leu Tyr Trp Met Asp Pro Phe
        995                 1000                1005

Thr Tyr Leu Ile Asp Gly Leu Leu Glu Pro Val Thr Trp Gly Val Glu
    1010                1015                1020

Val Glu Cys Thr Ala Ser Glu Leu Thr Thr Val Pro Leu Pro Pro Asn
1025                1030                1035                1040

Thr Thr Cys Ala Asp Tyr Ile Ser Glu Phe Leu Ser Glu Asn Ala Gly
                1045                1050                1055

Tyr Val Thr Asn Pro Glu Asn Thr Thr Tyr Cys Asp Tyr Cys Pro Tyr
            1060                1065                1070

Lys Ser Gly Ser Asp Tyr Met Arg Ser Met Asn Ile Asn Glu Ser Tyr
        1075                1080                1085

Tyr Gly Trp Arg Asp Val Gly Ile Thr Ala Leu Phe Cys Val Ser Ser
    1090                1095                1100

Tyr Ala Leu Val Phe Leu Met Met Lys Leu Arg Thr Lys Ala Thr Lys
1105                1110                1115                1120

Thr Ala Ser

<210> SEQ ID NO 43
<211> LENGTH: 1373
<212> TYPE: PRT
<213> ORGANISM: Grosmannia clavigera
<220> FEATURE:
<223> OTHER INFORMATION: GcABC-G6

<400> SEQUENCE: 43

-continued

```
Met Ala Tyr Thr Asn Ser Val Leu Asp Ala Pro Ser Asp Thr Asp Ile
 1               5                  10                  15

Glu Phe Thr Ile Gln Gln Asp Gly Ser Leu Gln Glu Thr Ala Arg
             20                  25                  30

Lys Ser Leu Thr Leu Thr Phe Gln Asn Leu Thr Val Asn Val Lys Ala
             35                  40                  45

Ala Glu Glu Ala Leu Gly Ala Thr Leu Leu Ser Tyr Val Asp Pro Arg
 50                  55                  60

Gln Leu Leu Val Pro Phe Met Lys Asp Lys Thr Pro Ser Arg Ser Ile
 65                  70                  75                  80

Leu Arg Asn Val Asn Gly Gln Ile Ser Pro Gly Glu Met Leu Leu Val
             85                  90                  95

Leu Gly Arg Pro Gly Ser Gly Cys Thr Ser Leu Leu Arg Val Leu Ser
             100                 105                 110

Asn His Arg Glu Ser Phe Asp Ser Val Glu Gly His Thr Trp Tyr Gly
             115                 120                 125

Ser Met Asp His Asn Glu Ala Arg Lys Tyr Arg Gln Gln Ile Met Met
             130                 135                 140

Asn Thr Glu Asp Asp Val His Phe Pro Thr Leu Thr Val Asp Glu Thr
145                 150                 155                 160

Ile Ser Phe Ala Val Lys Asn Arg Thr Pro Arg Glu Arg Glu Asp His
                 165                 170                 175

Val Lys Asp Lys Arg Gln Phe Leu Ser His Thr Lys Glu Gly Val Leu
             180                 185                 190

Gly Ala Leu Gly Ile Ser His Thr Ala Asn Thr Lys Val Gly Asn Glu
             195                 200                 205

Phe Ile Arg Gly Val Ser Gly Gly Glu Arg Lys Arg Val Ser Leu Ala
 210                 215                 220

Glu Val Leu Ala Gly Gln Ser Pro Val Gln Phe Trp Asp Gln Pro Thr
225                 230                 235                 240

Arg Gly Leu Asp Ser Lys Thr Ala Leu Glu Phe Ile Glu Phe Leu Arg
                 245                 250                 255

Ala Glu Ala Asp Gln Arg Arg Lys Thr Ile Val Val Thr Thr Tyr Gln
             260                 265                 270

Ala Ser Asn Gly Ile Phe Asp Lys Phe Asp Lys Val Leu Val Leu Ala
             275                 280                 285

Ser Gly Cys Val Ile Tyr Tyr Gly Pro Leu Asn Gln Ser Arg Arg Tyr
             290                 295                 300

Phe Glu Ala Leu Gly Phe Val Cys Ala Lys Gly Ala Asn Thr Ala Asp
305                 310                 315                 320

Phe Leu Thr Ser Val Thr Val Leu Thr Glu Arg Ile Ile Ala Ala Gly
                 325                 330                 335

Phe Glu Gly Lys Val Pro Ser Thr Ala Tyr Glu Phe Glu Glu Ala Tyr
             340                 345                 350

Gln Asn Ser Gln Ile His Arg Val Met Gln Asp Ile Gln Lys Pro Ile
             355                 360                 365

His Ser Leu Glu Lys Glu Val Asp His Leu Lys Glu Ala Val Arg Arg
 370                 375                 380

Glu Lys Lys Ala Arg Tyr Tyr Asp Lys Asn Arg Ser Val Tyr Thr Ser
385                 390                 395                 400

Gly Leu Val Ser Gln Val Leu Asn Cys Thr Val Arg Gln Phe Gln Ile
                 405                 410                 415

Met Met Gly Asp Arg Leu Ser Leu Asn Val Lys Val Leu Ser Ala Met
```

```
                420             425             430
Val Gln Ala Leu Val Cys Gly Ser Leu Phe Tyr Asn Leu Ser Asp Thr
                435             440             445
Ser Lys Ser Thr Phe Leu Arg Pro Gly Val Leu Phe Ala Val Leu
450             455             460
Tyr Phe Leu Met Glu Ala Met Ser Glu Thr Thr Ala Ser Phe Thr Gly
465             470             475             480
Arg Pro Ile Leu Ala Arg His Lys Arg Phe Gly Phe Tyr Arg Pro Thr
                485             490             495
Ala Phe Cys Ile Ala Asp Ala Leu Thr Asp Ile Pro Val Val Met Leu
                500             505             510
Gln Ile Thr Leu Phe Ala Met Ile Ile Tyr Phe Met Ser Gly Leu Gln
                515             520             525
Met Asp Ala Gly Lys Phe Phe Thr Tyr Trp Val Ile Val Asn Ala Ser
                530             535             540
Thr Leu Thr Phe Thr Gln Leu Phe Arg Met Val Gly Ala Leu Cys Thr
545             550             555             560
Asn Phe Gly Thr Ala Ser Gln Leu Thr Gly Val Leu Ser Thr Ile Cys
                565             570             575
Phe Val Tyr Gly Gly Tyr Leu Ile Pro Phe Glu Lys Met His Pro Trp
                580             585             590
Phe Arg Trp Ile Phe Tyr Leu Asn Pro Gly Ala Tyr Ala Phe Glu Ser
                595             600             605
Leu Met Gly Asn Glu Tyr Gly Gly Leu Lys Leu Lys Cys Val Ala Pro
                610             615             620
Gln Met Val Pro Phe Gly Ile Met Tyr Asp Asn Leu Gly Ser Ser Phe
625             630             635             640
His Gly Cys Thr Val Ala Gly Ser Asp Ala Asp Gly Ile Ile Asp Gly
                645             650             655
Leu Val Tyr Ile Arg Glu Gln Tyr Ser Tyr Ser Glu Gly His Ile Trp
                660             665             670
Arg Gly Phe Gly Val Leu Ile Gly Leu Trp Ile Thr Phe Ile Ala Val
                675             680             685
Thr Ala Leu Gly Phe Glu Phe Arg Asn Gly His Asn Gly Ser Ser Val
                690             695             700
Leu Leu Tyr Lys Arg Thr Ile Leu Asp Lys Ser Arg Pro Lys Asp Val
705             710             715             720
Glu Glu Ala Val Thr Thr Val Glu Lys Thr Tyr Ser Ala Pro Pro Ser
                725             730             735
Gln Ala Val Lys Gln Ser Val Phe Cys Trp His Asp Leu Asp Tyr Phe
                740             745             750
Val Gln Tyr Glu Gly Ala Gln Lys Gln Leu Leu Asn Lys Ile Phe Gly
                755             760             765
Tyr Val Gln Pro Gly Asn Leu Val Ala Leu Met Gly Cys Ser Gly Ala
                770             775             780
Gly Lys Thr Thr Leu Leu Asp Val Leu Ala Gln Arg Lys Asp Phe Gly
785             790             795             800
Thr Ile Asn Gly Ser Ile Leu Ile Asp Gly Lys Pro Gln Gly Leu Ser
                805             810             815
Phe Gln Arg Met Thr Gly Tyr Cys Glu Gln Met Asp Val His Glu Asp
                820             825             830
Thr Ser Thr Val Lys Glu Ala Leu Val Phe Ser Ala Leu Leu Arg Gln
                835             840             845
```

```
Pro Arg Glu Val Pro Ile Ser Glu Lys Leu Ala Tyr Val Glu Tyr Ile
    850                 855                 860

Ile Asp Leu Leu Glu Leu Arg Asn Phe Cys Asp Ala Leu Ile Gly Val
865                 870                 875                 880

Pro Gly Ala Gly Leu Ser Ile Glu Gln Arg Lys Arg Val Thr Leu Gly
                885                 890                 895

Val Glu Leu Val Ala Lys Pro Thr Leu Leu Phe Leu Asp Glu Pro Thr
            900                 905                 910

Ser Gly Leu Asp Gly Gln Ser Ala Tyr Asn Ile Ile Arg Phe Leu Arg
        915                 920                 925

Arg Leu Val Glu Gly Gly Gln Ala Val Leu Cys Thr Ile His Gln Pro
    930                 935                 940

Ser Ala Val Leu Phe Glu Ala Phe Asp Ala Leu Leu Leu Leu Ala Lys
945                 950                 955                 960

Gly Gly Arg Met Ala Tyr Phe Gly Glu Thr Gly Lys Asp Ser Ser Val
                965                 970                 975

Val Leu Asp Tyr Phe Ala Arg Asn Gly Ala Pro Ala Gly Ala Asp Val
            980                 985                 990

Asn Pro Ala Asp His Ile Val Glu Val Ile Gln Gly Lys Gly Lys Asp
        995                 1000                1005

Asp Val Asp Trp Val Ala Thr Trp Ser Glu Ser Ala Glu Arg Lys Glu
    1010                1015                1020

Ala Leu Asn Thr Leu Asn Ser Leu Val Ala Arg Phe Asp Ala Thr Ala
1025                1030                1035                1040

Thr Ser Glu Asn Asp Thr Arg Glu Phe Ala Ser Thr Lys Trp Tyr Gln
                1045                1050                1055

Phe Thr Leu Val Leu Glu Arg Leu Met Asn Gln Leu Trp Arg Ser Pro
            1060                1065                1070

Asp Tyr Ile Trp Asn Lys Ile Val Leu His Val Phe Ala Ala Leu Phe
        1075                1080                1085

Gly Gly Phe Thr Phe Trp Asn Ile Gly Asn Gly Thr Phe Asp Leu Gln
    1090                1095                1100

Leu Arg Leu Phe Ala Ile Phe Asn Leu Ile Phe Val Ala Pro Gly Cys
1105                1110                1115                1120

Ile Asn Gln Met Gln Pro Phe Phe Leu His Asn Arg Asp Leu Phe Glu
                1125                1130                1135

Thr Arg Glu Lys Lys Ser Lys Thr Tyr His Trp Leu Ala Phe Ile Gly
            1140                1145                1150

Ala Gln Ile Val Ser Glu Ile Pro Tyr Leu Val Ile Cys Ala Thr Ala
        1155                1160                1165

Tyr Phe Gly Cys Trp Tyr Phe Thr Val Gly Phe Pro Val Thr Ala Lys
    1170                1175                1180

Thr Ser Gly His Ile Tyr Leu Gln Met Ile Leu Tyr Glu Phe Leu Tyr
1185                1190                1195                1200

Thr Ser Ile Gly Gln Ala Ile Ala Ala Tyr Ala Pro Asn Val Tyr Phe
                1205                1210                1215

Ala Ala Ile Thr Asn Pro Leu Leu Ile Gly Cys Gly Leu Ile Ser Phe
            1220                1225                1230

Cys Gly Ile Val Val Pro Tyr Ala Ser Met Gln Thr Phe Trp Lys Tyr
        1235                1240                1245

Trp Ile Tyr Tyr Leu Asp Pro Phe Asn Tyr Leu Met Gly Gly Leu Leu
    1250                1255                1260
```

Ala Pro Val Leu Trp Asp Val Asn Val Lys Cys Gly Lys Lys Glu Leu
1265                1270                1275                1280

Thr Thr Phe Asn Pro Pro Ser Gly Gln Thr Cys Gly Gln Tyr Met Ala
            1285                1290                1295

Asp Phe Leu Gln Ser Asn Ala Gly Tyr Val Asn Asn Ala Ser Ala Thr
        1300                1305                1310

Ser Asn Cys Glu Tyr Cys Pro Tyr Gln Thr Gly Ala Asp Tyr Ala Lys
    1315                1320                1325

Thr Phe Asn Leu Arg Lys Glu Tyr Tyr Gly Trp Arg Asp Thr Gly Ile
1330                1335                1340

Thr Ala Leu Phe Cys Leu Ser Ser Tyr Ala Leu Val Ile Ile Met Met
1345                1350                1355                1360

Lys Leu Arg Ser Lys Lys Thr Lys Ser Ala Arg Ser Glu
            1365                1370

<210> SEQ ID NO 44
<211> LENGTH: 1389
<212> TYPE: PRT
<213> ORGANISM: Grosmannia clavigera
<220> FEATURE:
<223> OTHER INFORMATION: GcABC-G7

<400> SEQUENCE: 44

Met Ala Ser Asp Asn Gly Ser Ser Thr Val Ala Glu Glu Arg Pro Thr
1               5                   10                  15

Ser Ala Asp Gly Ser Asp Asn Gly Ala Gly Gln Asp Ser Asp Gly Trp
            20                  25                  30

Ala Leu Glu Tyr Lys Val Lys Glu Lys Arg Glu Arg Glu Gln Arg Ser
        35                  40                  45

Gly Ile Pro Pro Arg Gln Leu Gly Leu Thr Trp Lys Asn Leu Thr Val
    50                  55                  60

Lys Ala Val Ala Asn Asp Ala Ala Ile His Asp Asn Phe Met Ser Gln
65                  70                  75                  80

Phe Asn Ile Pro Gln Val Ile Arg Asp Ala Arg Arg Lys Pro Pro Met
                85                  90                  95

Lys Ser Ile Leu Asn Asn Thr His Gly Cys Val Lys Pro Gly Glu Met
            100                 105                 110

Leu Leu Val Leu Gly Arg Pro Gly Ala Gly Cys Thr Thr Leu Leu Ser
        115                 120                 125

Val Leu Ala Asn Arg Arg Arg Gly Tyr Ser Ser Val Asp Gly Asp Val
    130                 135                 140

Phe Tyr Gly Ser Met Thr Pro Ser Glu Ala Lys Asn Tyr Arg Gly Gln
145                 150                 155                 160

Ile Val Met Asn Thr Glu Glu Glu Leu Phe Phe Pro Thr Leu Thr Val
                165                 170                 175

Gly Gln Thr Met Asp Phe Ala Thr Gln Leu Lys Val Pro Phe Lys Met
            180                 185                 190

Pro Glu Gly Tyr Ile Asp Lys Asp Ile Arg Gln Glu Asn Lys Asp
        195                 200                 205

Phe Leu Leu Glu Ser Met Ser Ile Ser His Thr Asp Gly Thr Lys Val
    210                 215                 220

Gly Asp Ala Phe Val Arg Gly Val Ser Gly Gly Glu Arg Lys Arg Val
225                 230                 235                 240

Ser Ile Ile Glu Cys Met Ala Thr His Gly Ser Ile Phe Phe Trp Asp
                245                 250                 255

```
Asn Ser Thr Arg Gly Leu Asp Ala Ser Thr Ala Leu Glu Trp Thr Lys
            260                 265                 270

Ala Ile Arg Ala Met Thr Asp Val Leu Gly Leu Ala Thr Val Val Thr
275                 280                 285

Leu Tyr Gln Ala Gly Asn Gly Ile Tyr Asn Leu Phe Asp Lys Val Leu
    290                 295                 300

Val Leu Asp Asn Gly Asn Glu Val Phe Tyr Gly Thr Arg Glu Glu Ala
305                 310                 315                 320

Arg Pro Phe Met Glu Asp Gln Gly Phe Val Cys Arg Asp Gly Ala Asn
                325                 330                 335

Val Ala Asp Tyr Leu Thr Gly Ile Thr Val Pro Thr Glu Arg Gln Ile
            340                 345                 350

Lys Pro Gly Phe Glu Arg Thr Phe Pro Arg Ser Gly Lys Ala Val Arg
        355                 360                 365

Glu Ala Tyr Glu Lys Thr Pro Ile Phe Thr Lys Met Gln Arg Glu Tyr
370                 375                 380

Asp Tyr Pro Ser Thr Glu Glu Ala Gln Ala Asn Thr Gln Ala Phe Thr
385                 390                 395                 400

Asn Ala Ile Ala Thr Glu Lys Asn Pro His Leu Gly Ser Ser Pro Phe
                405                 410                 415

Thr Val Gly Phe Ser Thr Gln Val Lys Ala Cys Ile Ile Arg Gln Tyr
            420                 425                 430

Gln Ile Ile Trp Gly Asp Arg Ala Ser Phe Phe Ile Lys Gln Phe Ser
        435                 440                 445

Thr Ile Val Gln Ala Leu Ile Ala Gly Ser Leu Phe Tyr Asn Ala Pro
450                 455                 460

Ser Asn Ser Ala Gly Ile Phe Thr Lys Ser Gly Ala Leu Phe Phe Ser
465                 470                 475                 480

Leu Met Tyr Asn Ser Leu Leu Ser Met Ser Glu Val Thr Asp Ser Phe
                485                 490                 495

Gln Gly Arg Pro Val Leu Leu Lys His Lys Ala Leu Ala Tyr Phe His
            500                 505                 510

Pro Ala Ala Tyr Cys Val Ala Gln Ile Ala Ala Asp Ile Pro Val Ile
        515                 520                 525

Leu Phe Gln Ile Thr Cys Phe Ser Leu Ile Leu Tyr Phe Met Cys Val
530                 535                 540

Thr Ala Met Phe Arg Ala Ile Gly Ala Leu Phe Gly Thr Phe Asp Ala
545                 550                 555                 560

Ala Ser Lys Val Ser Gly Leu Val Ile Ser Ala Ile Val Met Tyr Ser
                565                 570                 575

Gly Tyr Met Ile His Tyr Thr Gln Met His Pro Trp Phe Ile Trp Leu
            580                 585                 590

Phe Trp Ile Asn Pro Leu Ala Phe Gly Phe Asp Ala Leu Leu Ser Asn
        595                 600                 605

Glu Phe His Gly Lys Val Ile Asp Cys Val Gly Gly Asn Leu Ile Pro
610                 615                 620

Asn Gly Ile Gly Tyr Glu Asn Ala Ser Gly His Gln Ser Cys Ala Gly
625                 630                 635                 640

Val Leu Gly Ala Val Gln Gly Gln Thr Ser Leu Thr Gly Asp His Tyr
                645                 650                 655

Leu Asn Ala Leu His Tyr Ser His Ser His Val Trp Arg Asn Phe Gly
            660                 665                 670

Ile Ile Trp Ala Trp Trp Leu Ile Phe Val Ile Ile Thr Ile Val Ala
```

-continued

```
            675                 680                 685
Thr Thr Asn Trp Arg Ala Ser Ser Glu Ser Gly Pro Ser Leu Leu Ile
690                 695                 700

Pro Arg Glu Lys Ala Lys Ser Leu Gly His Met Leu Ala Ala Asp Glu
705                 710                 715                 720

Glu Ala Gln Asp Glu Asp His Val Ala Asn Val Ala Glu Thr Lys
                725                 730                 735

Glu Val Ala Gly Asn Ser Ser Asp Asn Glu Ser Ser Gly Asn Leu Val
                740                 745                 750

Arg Asn Thr Ser Thr Phe Thr Trp Lys Asn Leu Cys Tyr Val Val Lys
                755                 760                 765

Thr Pro Ser Gly Asp Arg Gln Leu Leu Asn Asn Val Gln Gly Trp Val
770                 775                 780

Lys Pro Gly Met Leu Gly Ala Leu Met Gly Ser Ser Gly Ala Gly Lys
785                 790                 795                 800

Thr Thr Leu Leu Asp Val Leu Ala Gln Arg Lys Thr Asp Gly Thr Ile
                805                 810                 815

His Gly Ser Ile Met Val Asp Gly Arg Pro Leu Pro Val Ala Phe Gln
                820                 825                 830

Arg Ser Ala Gly Tyr Cys Glu Gln Leu Asp Val His Glu Pro Phe Ala
                835                 840                 845

Thr Val Arg Glu Ala Leu Glu Phe Ser Ala Leu Leu Arg Gln Ser Arg
850                 855                 860

Thr Thr Pro Arg Glu Glu Lys Leu Arg Tyr Val Asp Thr Ile Ile Asp
865                 870                 875                 880

Leu Leu Glu Leu His Asp Leu Ala Asp Thr Leu Ile Gly Gln Val Gly
                885                 890                 895

Ala Gly Leu Ser Val Glu Gln Arg Lys Arg Val Thr Ile Gly Val Glu
                900                 905                 910

Leu Val Ala Lys Pro Ser Ile Leu Ile Phe Leu Asp Glu Pro Thr Ser
                915                 920                 925

Gly Leu Asp Gly Gln Ser Ala Tyr Asn Thr Val Arg Phe Leu Arg Lys
930                 935                 940

Leu Ala Asp Ala Gly Gln Ala Val Leu Val Thr Ile His Gln Pro Ser
945                 950                 955                 960

Ala Gln Leu Phe Ala Glu Phe Asp Thr Leu Leu Leu Ala Arg Gly
                965                 970                 975

Gly Asn Thr Val Tyr Phe Gly Asp Ile Gly Asp Asn Ala Ala Thr Ile
                980                 985                 990

Lys Ala Tyr Phe Ala Arg Tyr Gly Ala Ala Cys Pro Pro Glu Thr Asn
                995                 1000                1005

Pro Ala Glu Tyr Met Ile Asp Val Ser Gly Leu Met Ser Gln Gly
                1010                1015                1020

Lys Asp Trp Ala Lys Val Trp Leu Glu Ser Pro Glu Tyr Thr Ala Val
1025                1030                1035                1040

Thr Thr Glu Leu Asp Arg Leu Ile Lys Glu Gly Ala Ser Arg Pro Ser
                1045                1050                1055

Ala Ser Asp Asn Asp Asp Gly Phe Glu Phe Ala Met Pro Leu Trp Asp
                1060                1065                1070

Gln Ile Tyr Ile Val Thr Ala Arg Met Asn Val Ala Leu Tyr Arg Asn
                1075                1080                1085

Val Asn Tyr Val Asn Asn Lys Leu Val Leu His Ile Thr Ser Ala Leu
                1090                1095                1100
```

```
Phe Asn Gly Phe Ser Phe Trp Met Ile Lys His Ser Val Ser Ala Leu
1105                1110                1115                1120

Gln Leu Arg Val Phe Thr Ile Phe Asn Phe Ile Phe Val Ala Pro Gly
            1125                1130                1135

Val Ile Ala Gln Leu Gln Pro Leu Phe Ile Ala Arg Arg Asp Ile Phe
        1140                1145                1150

Glu Thr Arg Glu Lys Lys Ser Lys Met Tyr Ser Trp Val Ala Phe Val
    1155                1160                1165

Thr Gly Leu Ile Val Ser Glu Ile Pro Tyr Leu Cys Met Cys Ala Val
1170                1175                1180

Leu Tyr Phe Val Cys Trp Tyr Tyr Thr Val Gly Phe Pro Lys Asp Ser
1185                1190                1195                1200

Ala Arg Ala Gly Gly Thr Phe Phe Val Ile Trp Leu Tyr Glu Phe Val
            1205                1210                1215

Tyr Thr Gly Ile Gly Gln Ala Ile Ala Ala Tyr Ala Pro Asn Asp Val
        1220                1225                1230

Phe Ala Thr Leu Val Asn Pro Leu Phe Ile Gly Ile Leu Val Ser Phe
    1235                1240                1245

Cys Gly Val Leu Val Pro Tyr Ser Glu Ile Gln Ser Phe Trp Arg Tyr
1250                1255                1260

Trp Leu Tyr Tyr Leu Asn Pro Tyr Asn Tyr Leu Thr Gly Ser Leu Leu
1265                1270                1275                1280

Val Phe Asp Met Trp Gly Thr Lys Val Glu Cys Gly Ser His Glu Leu
            1285                1290                1295

Ala Leu Phe Asp Pro Pro Ser Gly Ser Thr Cys Ser Ser Tyr Leu Ser
        1300                1305                1310

Thr Tyr Met Asn Gly Ala Gly Ser Gly Thr Arg Leu Leu Asn Pro Asp
    1315                1320                1325

Asp Leu Ser Gly Cys Lys Val Cys Pro Tyr Arg Asp Ala Ser Asp Tyr
1330                1335                1340

Leu His Thr Val Asn Leu Thr Lys Tyr Leu Asp Gly Trp Arg Asp Thr
1345                1350                1355                1360

Gly Ile Val Ala Ile Phe Val Phe Ser Ser Tyr Gly Met Val Tyr Leu
            1365                1370                1375

Leu Met Lys Leu Arg Thr Lys Thr Ser Lys Lys Ala Glu
        1380                1385

<210> SEQ ID NO 45
<211> LENGTH: 605
<212> TYPE: PRT
<213> ORGANISM: Grosmannia clavigera
<220> FEATURE:
<223> OTHER INFORMATION: GcABC-G8

<400> SEQUENCE: 45

Met Asp Thr Phe Ser Trp Asn Lys Ile Asn Val Ser Val Lys Asp Arg
 1               5                  10                  15

Thr Thr Lys Thr Pro Leu Ser Leu Leu Ser Asn Val Ala Gly Leu Val
            20                  25                  30

Arg Ala Gly Glu Met Leu Ala Ile Met Gly Pro Ser Gly Ser Gly Lys
        35                  40                  45

Thr Thr Leu Leu Asn Ala Leu Ala His Arg Val Ala Ala Gly Ala
    50                  55                  60

Thr Thr Thr Gly Glu Ile Cys Ala Asn Gly Gln Gln Val Thr Arg Ser
65                  70                  75                  80
```

-continued

```
Ser Ile Arg Ala Leu Ser Ser Tyr Val Glu Gln Asp Ala Leu Ile
                 85                  90                  95

Gly Ser Leu Thr Val Arg Glu Thr Met Met Phe Ala Ala Gln Leu Ser
                100                 105                 110

Leu Pro Arg Asn Val Ser Arg Lys Glu Ala Phe His Arg Val Asp Asp
                115                 120                 125

Leu Ile Ala Ser Phe Gly Leu Gln Leu Gln Ala Asn Thr Ile Val Gly
            130                 135                 140

Thr Pro Trp Ser Lys Gly Leu Ser Gly Gly Gln Lys Lys Arg Leu Ser
145                 150                 155                 160

Val Ala Ser Arg Leu Val Thr Asn Pro Lys Ile Met Phe Leu Asp Glu
                165                 170                 175

Pro Thr Ser Gly Leu Asp Ser Ala Leu Ser Arg Glu Val Cys Ser Tyr
                180                 185                 190

Ile Lys Ala Ile Gly Lys Ala Asn Asn Leu Ile Ile Ile Ala Ser Ile
            195                 200                 205

His Gln Pro Ser Ser Thr Thr Tyr His Gln Phe Asp Lys Leu Cys Leu
        210                 215                 220

Leu Ser Gly Gly Arg Thr Cys Tyr Phe Gly Gly Thr Ala Glu Ala Pro
225                 230                 235                 240

Ala Tyr Phe Ser Arg Ile Gly Tyr Pro Val Pro Leu Asp Ser Ser Ser
                245                 250                 255

Pro Glu His Phe Leu Asp Leu Val Asn Thr Asp Ile Asp Thr Thr Gly
                260                 265                 270

Glu Ile Arg Arg Arg Thr Asp Gly Ile Ser Arg Ala Trp Asn Thr Ser
            275                 280                 285

Asp Leu Ala Ala Gly Leu Gln Met Asp Val Asp His Arg Asp Asn Asp
        290                 295                 300

Gly Gln Ser Ser Pro Val Leu Asp Asn Tyr Lys Ala Asp Gly Pro Arg
305                 310                 315                 320

Pro Trp Val Val Pro Val Leu Leu His Arg Ser Trp Ile Lys Ser
                325                 330                 335

Tyr Arg Asp Val Met Ala Tyr Gly Ile Arg Leu Ala Met Tyr Leu Gly
                340                 345                 350

Leu Ala Ile Leu Met Gly Thr Val Phe Leu Arg Leu Gln Pro Glu Gln
            355                 360                 365

Lys Tyr Ile Gln Pro Tyr Thr Asn Ala Ile Phe Phe Gly Gly Ala Phe
        370                 375                 380

Met Ser Phe Met Ala Val Ala Tyr Val Pro Ala Phe Leu Glu Asp Leu
385                 390                 395                 400

Gly Thr Phe Lys Gln Glu Arg Ala Asn Gly Leu Val Thr Pro Leu Ser
                405                 410                 415

Phe Leu Val Pro Asn Phe Leu Ile Gly Leu Pro Phe Leu Phe Phe Phe
                420                 425                 430

Ala Leu Val Phe Ser Ile Ile Val Tyr Trp Leu Ser Asn Phe Thr Pro
            435                 440                 445

Ser Gly Ser Ala Phe Phe Arg Trp Val Leu Trp Leu Phe Leu Asp Leu
        450                 455                 460

Ile Ala Ala Glu Ser Leu Val Val Leu Val Ser Ser Ile Phe Asn Val
465                 470                 475                 480

Phe Val Leu Ala Leu Ala Val Thr Ala Phe Ala Asn Gly Leu Trp Met
                485                 490                 495
```

```
Cys Val Asp Gly Phe Leu Val Pro Met Ser Ile Leu Asn Val Phe Trp
            500                 505                 510

Lys Tyr Val Phe His Tyr Ile Asp Tyr Gln Ala Tyr Val Phe Gln Gly
        515                 520                 525

Met Met Val Asn Glu Phe Glu His Arg Glu Tyr Trp Cys Ala Lys Thr
    530                 535                 540

Asp Gly Gly Leu Tyr Gln Cys Ser Tyr Ser Ser Asp Leu Asn Asn Val
545                 550                 555                 560

Gly Lys Ile Arg Gly Thr Asp Val Leu Lys Glu Leu Ser Ile His Thr
                565                 570                 575

Gly Gln Glu Gly Thr Trp Ile Gly Ile Met Ile Gly Ile Ile Ala Gly
            580                 585                 590

Tyr Arg Leu Leu Ala Tyr Leu Val Leu Val Met Arg Lys
        595                 600                 605

<210> SEQ ID NO 46
<211> LENGTH: 1117
<212> TYPE: PRT
<213> ORGANISM: Grosmannia clavigera
<220> FEATURE:
<223> OTHER INFORMATION: GcABC-G9

<400> SEQUENCE: 46

Met Ala Ser Gly Arg Phe Ser Ala Leu Ala Val Gly Val Phe Ala Ala
1               5                   10                  15

Ser Met Ala Gly Val Val Ala Ala Ser Ser Asn Phe Thr Ser Leu Asp
            20                  25                  30

Ala Met Gln Ala Gln Ile Thr Leu Met Ser Gly Phe Pro Lys Asp Cys
        35                  40                  45

Pro Pro Cys Phe Asn Cys Leu Thr Pro Ser Ser Thr Cys Gly Gln Tyr
    50                  55                  60

Ala Glu Cys Asn Ser Tyr Asp Gly Thr Cys Val Cys Pro Pro Gly Trp
65                  70                  75                  80

Ala Gly Thr Asp Cys Leu Lys Pro Leu Cys Gly Ser Leu Ala Gly Gly
                85                  90                  95

Tyr Asp Arg Pro Met Arg Asp Glu Gly Ser Thr Cys Glu Cys Asp Glu
            100                 105                 110

Gly Trp Thr Gly Ile Asn Cys Asn Val Cys Thr Glu Asp Leu Ala Cys
        115                 120                 125

Asn Ala Leu Met Glu Thr Lys Glu Gly Gly Val Cys Tyr Gln Lys Gly
    130                 135                 140

Asp Val Ile Lys Asn Asn Tyr Gln Met Cys Asp Val Thr Asn Arg His
145                 150                 155                 160

Ile Leu Gly Met Leu Asp Gly Lys Ile Pro Gln Val Thr Phe Thr Cys
                165                 170                 175

Asp Arg Asn Ser Ser Glu Cys Asp Phe Gln Phe Trp Val Asp Gln Ala
            180                 185                 190

Glu Ser Phe Phe Cys His Leu Thr Asp Cys Asp Ser Asp Ala Gln Phe
        195                 200                 205

Asp Asp Ser Ser Asn Asn Thr Gln Tyr Arg Cys Lys Thr Ile Asp Cys
    210                 215                 220

Ser Cys Val Gln Asp Arg Met Leu Cys Gly Lys Asp Gly Ser Val Asp
225                 230                 235                 240

Leu Thr Asp Tyr Leu Lys Glu Glu Ile Lys Gly Pro Ala Ser Phe Glu
                245                 250                 255
```

```
Cys Ala Gln Lys Ala Arg Gly Ser Asn Asp Cys Ser Phe Glu Pro
            260                 265                 270

His Met Asn Glu Leu Ile Ser Ser Ile Phe Gly Asp Pro Asn Ile Tyr
        275                 280                 285

Leu Thr Cys Arg Ser Gly Glu Cys Leu Tyr Asn Thr Glu Val Pro Gly
    290                 295                 300

Tyr Lys Lys Pro Val Pro Lys Ile Asn Thr Pro Leu Ile Ala Ala Val
305                 310                 315                 320

Ile Ala Ala Ser Ser Leu Phe Leu Val Ala Ala Ile Leu Leu Thr Trp
                325                 330                 335

Tyr Met Ser His Arg Gln Phe Lys Tyr Gly Pro Ile Asn Leu Asp Asp
        340                 345                 350

Ser Asp Asp Glu Ser Ile Lys Leu Met Thr Asp His Arg Pro Ala Ser
    355                 360                 365

Leu Tyr Phe Glu His Val Ser Tyr Val Leu Asn Gly Lys Leu Ile Leu
    370                 375                 380

Asp Asp Ile Ser Gly Leu Ala Arg Pro Gly Glu Val Met Ala Ile Met
385                 390                 395                 400

Gly Ala Ser Gly Ala Gly Lys Thr Thr Phe Leu Asp Ile Leu Ala Arg
                405                 410                 415

Lys Asn Lys Arg Gly Asp Val Ser Gly Asp Phe Tyr Val Asn Gly Glu
        420                 425                 430

Lys Val Asp Asp Ser Asp Phe Lys Gln Val Val Gly Phe Val Asp Gln
    435                 440                 445

Glu Asp Thr Met Leu Pro Thr Leu Thr Val His Glu Thr Ile Leu Asn
450                 455                 460

Ser Ala Leu Leu Arg Leu Pro Arg Asp Met Gly Arg Ser Ala Lys Glu
465                 470                 475                 480

Gln Arg Val Phe Glu Val Glu Lys Gln Leu Gly Ile Tyr His Ile Arg
                485                 490                 495

Asp Ser Leu Ile Gly Ser Glu Glu Gly Arg Gly Arg Gly Ile Ser Gly
        500                 505                 510

Gly Glu Lys Arg Arg Val Gly Ile Ala Cys Glu Leu Val Thr Ser Pro
    515                 520                 525

Ser Ile Leu Phe Leu Asp Glu Pro Thr Ser Gly Leu Asp Ala Tyr Asn
530                 535                 540

Ala Tyr Asn Val Ile Glu Cys Leu Val Thr Leu Ala Lys Asn Tyr Lys
545                 550                 555                 560

Arg Thr Val Ile Phe Thr Ile His Gln Pro Arg Ser Asn Ile Thr Ala
                565                 570                 575

Leu Phe Asp Arg Leu Met Leu Leu Ala Gln Gly Arg Thr Val Tyr Ser
        580                 585                 590

Gly Pro Phe Thr Gln Cys Gln Asp Tyr Phe Asp Ile Gly Tyr Ser
    595                 600                 605

Cys Pro Pro Gly Phe Asn Ile Ser Asp Tyr Leu Val Asp Leu Thr Met
610                 615                 620

His Ala Ile Asn Pro Glu Pro Phe Ser Asp Asp Val Val Gly Gly
625                 630                 635                 640

Pro Ile Val Thr Val Thr Val Ser Asp Thr Ala Thr Glu Arg Pro Ser
                645                 650                 655

Ser Thr Arg Ala Val Lys Ser Ile Ala Ser Gly Ser Ala Ile Ser Leu
        660                 665                 670

Gly Ala Asp Glu Ser Val Asn Ala Ser Leu Ala Asn Val Glu Ala Thr
```

```
            675                 680                 685
Ser Ser Ala Arg His Lys Gly Lys His Arg Asp Ser Val Arg Leu
690                 695                 700
Arg Gln Glu Arg Glu Leu Phe Thr Arg Arg Lys Asn Thr Val Asp Thr
705                 710                 715                 720
Val Ala Ser Ser Glu Ala Gly Asp Asp Ala Val Asp Gly Phe Lys Leu
            725                 730                 735
Arg Leu Gln Pro Pro His Ile Val Pro Pro Gln Ile Val Asp Asp Pro
            740                 745                 750
Asp Asp Pro Leu Pro Gly Ser Phe Gly Gly Ser Asp Leu Asp Gly Leu
            755                 760                 765
Val Lys Ser Phe Ala Gln Ser Asp Ile Ala Ser Ser Thr His Asp Glu
            770                 775                 780
Met His Leu Ala Ile Ala Asp Ala Leu Ala Ala Asn Gly Leu Asn Ala
785                 790                 795                 800
Asp Val Ala Glu Asn Gly Asn Gly Asn Gly Thr Gly Ser Ser Ser Pro
                805                 810                 815
Gln Ala Asn Gly Asn Ser Ser Gly Arg Thr Lys Thr His Leu Ser Val
            820                 825                 830
Val Gly Arg Gly Tyr Ala Arg Val Gly Leu Leu Arg Gln Phe Val Ile
            835                 840                 845
Leu Ser Gln Arg Thr Trp Lys Asn Leu Tyr Arg Asn Pro Met Leu Met
850                 855                 860
Leu Thr His Tyr Ala Ile Ser Ile Leu Leu Gly Val Leu Ser Gly Phe
865                 870                 875                 880
Leu Phe Tyr Gly Leu Thr Val Asp Ile Pro Gly Phe Gln Asn Arg Leu
            885                 890                 895
Gly Leu Phe Phe Phe Val Leu Ala Leu Phe Gly Phe Ser Thr Leu Thr
            900                 905                 910
Ser Leu Ser Thr Phe Ser Gly Glu Arg Leu Leu Phe Val Arg Glu Arg
            915                 920                 925
Ala Asn Gly Tyr Tyr Ser Pro Ile Thr Tyr Phe Ala Ser Lys Val Leu
            930                 935                 940
Phe Asp Ile Ile Pro Leu Arg Ile Leu Pro Pro Ile Leu Met Gly Ser
945                 950                 955                 960
Ile Ile Tyr Pro Met Thr Gly Leu Val Pro Asp Val Gln His Phe Phe
                965                 970                 975
Val Phe Ile Leu Val Leu Val Leu Phe Asn Leu Ala Ala Ser Gly Ile
            980                 985                 990
Cys Leu Phe Ile Gly Ile Val Cys Lys Asp Ser Gly Val Ala Asn Leu
            995                 1000                1005
Ile Gly Ser Leu Val Met Leu Phe Ser Leu Leu Phe Ala Gly Leu Leu
            1010                1015                1020
Leu Asn His Asp Lys Ile Pro Ala Ser Ala Val Trp Leu Gln Tyr Leu
1025                1030                1035                1040
Ser Ile Phe His Tyr Ala Phe Glu Ser Leu Ile Val Asn Glu Val Arg
            1045                1050                1055
Phe Leu Val Leu Val Asp Arg Lys Tyr Gly Leu Asp Ile Thr Val Pro
            1060                1065                1070
Gly Ala Ala Ile Leu Ser Ser Phe Gly Phe Asn Asn Ser Ser Leu Trp
            1075                1080                1085
Lys Asp Ile Thr Ser Leu Gly Val Phe Ala Val Val Phe Val Ile Leu
            1090                1095                1100
```

```
                        Ala Tyr Gly Ala Met His Ile Leu Val Glu Lys Arg
                        1105                1110                1115

<210> SEQ ID NO 47
<211> LENGTH: 332
<212> TYPE: PRT
<213> ORGANISM: Grosmannia clavigera
<220> FEATURE:
<223> OTHER INFORMATION: GcABC-NC1

<400> SEQUENCE: 47

Met Ala Ala Thr Asp Thr Ala Leu Ile Glu Ala Ile Asp Leu Thr Tyr
  1               5                  10                  15

Thr Phe Gln Asp Tyr Ser Thr Gly Ile Ser His Ile Asn Leu Ala Leu
             20                  25                  30

Pro Ala Gly Ser Arg Thr Leu Leu Val Gly Ala Asn Gly Ala Gly Lys
         35                  40                  45

Thr Thr Leu Leu Arg Leu Leu Ala Gly Lys Arg Leu Ala Pro Ala Gly
 50                  55                  60

Ser Ile Arg Val Gly Gly Leu Asp Pro Phe Ser His Ser Ile Ala Gly
 65                  70                  75                  80

Val Thr Tyr Leu Gly Leu Glu Trp Val Leu Asn Pro Val Val Arg Arg
                 85                  90                  95

Asp Ile Gly Val Asn Glu Leu Leu Ala Ser Val Gly Gly Asp Ala Tyr
            100                 105                 110

Pro Glu Arg Arg Asp Ala Leu Val Ala Val Leu Asp Ile Asp Thr Ser
        115                 120                 125

Trp Arg Met His Ala Val Ser Asp Gly Glu Arg Arg Val Gln Leu
130                 135                 140

Ala Met Gly Leu Ile Arg Pro Trp Asn Ile Leu Leu Leu Asp Glu Ile
145                 150                 155                 160

Thr Val Asp Leu Asp Val Trp Thr Arg Ala Gln Phe Leu Gly Trp Leu
                165                 170                 175

Arg Ser Glu Cys Glu Arg His Pro Asp Arg Ala Ser Gly Leu Pro Pro
            180                 185                 190

Pro Thr Ile Val Tyr Ala Thr His Ile Leu Asp Asn Leu Ala Gly Trp
        195                 200                 205

Pro Thr His Leu Val His Met His Leu Gly Thr Val Arg Glu Trp Gly
    210                 215                 220

Pro Ala Glu Arg Phe Leu Asn Asp Thr Ala Tyr Tyr Arg Asp Arg Met
225                 230                 235                 240

Gln Asp Asp Gly Ala Ala Gly Ala Ala Gly Asp Ala Asp Gly Glu Thr
                245                 250                 255

Lys Asp Gly Ala Ala Lys Lys His Phe Asn Pro Ser Ser Leu Leu
            260                 265                 270

Gly Ala Ser Gly Asn Ser Arg Leu Gly Asp Leu Val Leu Ser Trp Leu
        275                 280                 285

Arg Asp Asp Leu Arg Glu Arg Gly Pro Arg Ser Gln Asn Arg Arg Gly
    290                 295                 300

Pro Glu Gly Leu Thr Tyr Ala Val Gly Gly Ile Gly Gly Tyr Gly Ala
305                 310                 315                 320

Glu Lys His Val Asp Glu Glu Lys Glu Thr Glu Asn
                325                 330

<210> SEQ ID NO 48
```

```
<211> LENGTH: 645
<212> TYPE: PRT
<213> ORGANISM: Grosmannia clavigera
<220> FEATURE:
<223> OTHER INFORMATION: GcABC-NC2

<400> SEQUENCE: 48

Met Pro Ser Leu Ser Ala Leu Ser Val Arg Pro Ile Val Arg Ile
1               5                   10                  15

Ala Asn Gly Thr Phe Tyr Arg Gln His Pro Ser Ser Val Pro Ala Arg
            20                  25                  30

Thr Gly Pro Gln Ala Ala Gln Gly His Arg Pro Leu Phe Ser Asn Leu
        35                  40                  45

Arg Phe Glu Leu Pro Ala Gly Asp Gly Ala Ser Ser Trp Cys Val Val
    50                  55                  60

Gly Pro Ser Leu Ser Gly Lys Thr Thr Phe Leu Gln Leu Leu Gln Gly
65                  70                  75                  80

Gln His Ile Cys Leu Pro Pro Ala Ala Arg Ser Phe Pro Tyr Leu Ala
                85                  90                  95

Thr Glu Ala Val Pro Ala Arg Leu Lys Ser Ala Ser Gln Ala Leu Arg
            100                 105                 110

Tyr Val Gly Phe Asp Thr Glu Gly Ser Gly Leu Gly Pro Ala Thr Ser
        115                 120                 125

Ala Tyr Leu Ser Ala Arg Tyr Glu Ser Leu Arg Glu Thr Thr Asp Phe
    130                 135                 140

Ser Leu Arg Asp Tyr Leu Gly Gly Asn Thr Glu Leu Asn Pro Tyr Glu
145                 150                 155                 160

Gly Thr Asp Gln Arg Pro Ser Ser Ser Gly Leu Phe Glu Arg Val
                165                 170                 175

Val Cys Asp Leu Arg Leu Asp Ser Leu Leu Asp Leu Pro Val Ala Phe
            180                 185                 190

Leu Ser Asn Gly Gln Gly Arg Arg Ala Arg Ile Gly Arg Ala Leu Leu
        195                 200                 205

Met Arg Pro Ala Val Leu Leu Leu Asp Glu Pro Phe Met Gly Leu Asp
    210                 215                 220

Pro Pro Thr Val Ala Gly Leu Ser Pro Leu Leu Arg Asp Met Ala Ala
225                 230                 235                 240

Ala Ala Glu Pro Gln Leu Val Leu Ser Ser Arg Pro Gln Asp Pro Leu
                245                 250                 255

Pro Thr Trp Ile Thr His Leu Ala Tyr Leu Arg Thr Asp Cys Gln Val
            260                 265                 270

Ala Ala Met Gly Pro Arg Asp Met Val Leu Asp Arg Leu Arg Ser Tyr
        275                 280                 285

Val Arg Gly Val Arg Ala Gly Thr Leu Ala Glu Asp Asp Lys Met Pro
    290                 295                 300

Val Arg Thr Leu Gly Glu Met Gly Arg Leu Leu Thr Asp Arg Gly Ile
305                 310                 315                 320

Gln Gly Arg Gly Leu Asp Glu Glu Thr His Pro Ile Gln Pro Thr Gln
                325                 330                 335

Thr Val Lys Thr Thr Pro Thr Pro Leu Gly Pro Leu Val Glu Met
            340                 345                 350

Asp Gly Cys Arg Val Gln Tyr Gly Asp His Val Val Leu Gly Asn Trp
        355                 360                 365

Thr Asp Ser Ser Gln Ala Ser Ser Gly Leu Val Trp Thr Val Arg Arg
    370                 375                 380
```

Gly Glu Arg Trp Gly Leu Phe Gly Pro Asn Gly Ser Gly Lys Thr Thr
385                 390                 395                 400

Leu Val Ser Leu Leu Cys Ser Asp His Pro Gln Thr Tyr Ser Leu Pro
            405                 410                 415

Ile Arg Leu Phe Gly Arg Ser Arg Leu Pro Glu Arg Pro Ser Asp Ser
        420                 425                 430

Ser Ser Ser Ser Ser Val Pro Tyr Arg Pro Pro Leu Thr Phe Trp Asp
    435                 440                 445

Ile Gln Ala Arg Ile Gly His Ser Ser Pro Glu Val His Gln His Met
    450                 455                 460

Pro Arg Ser Leu Thr Ala Arg Gln Val Val Glu Ser Ala Trp Ala Asp
465                 470                 475                 480

Thr Phe Arg Ser Arg Pro Gln Leu Ser Ala Glu Ala Pro Asp Leu Val
                485                 490                 495

Asp Ala Cys Leu Gln Trp Phe Ala Pro Glu Leu Gly Thr Ser Arg Gly
            500                 505                 510

Gly Ser Ser Thr Asp Val Pro Leu Phe Gly Glu Leu Ser Phe Ser Ala
        515                 520                 525

Gln Arg Val Leu Leu Val Arg Ala Ala Ile Lys His Pro Asp Ile
    530                 535                 540

Val Val Leu Asp Glu Ala Phe Ser Gly Met Asp Glu Arg Val Arg Asp
545                 550                 555                 560

Lys Cys Ala His Phe Leu Ser His Gly Ile Pro His His Asp Arg Leu
                565                 570                 575

Thr Gly Leu Thr Asp Arg Gln Ala Leu Ile Cys Ile Ala His Val Arg
            580                 585                 590

Glu Glu Val Pro Asp Ile Val Arg Glu Trp Leu Cys Leu Pro Glu Ala
        595                 600                 605

Asn Thr Gly Arg Pro Pro Arg Phe Gly Arg Leu Asp Gly Pro Leu Arg
    610                 615                 620

Thr Ser Arg Arg Arg Trp Asp Asp Ile Trp Gly Gln Met Ser Thr Val
625                 630                 635                 640

Glu Ser Ser Val Asp
                645

<210> SEQ ID NO 49
<211> LENGTH: 1538
<212> TYPE: PRT
<213> ORGANISM: Ophiostoma piceae
<220> FEATURE:
<223> OTHER INFORMATION: OPP_06275

<400> SEQUENCE: 49

Met Ala Ser Ser Asn Asn Arg Ala Pro Leu Gln Gly Glu Gln Val Ser
 1               5                  10                  15

Val Pro Ala Ala Ser Thr Glu Pro Val Pro Gly Ile Glu Pro Ala Ile
            20                  25                  30

Asn Ala Asn Ala Ser Asn Ala Asn Asn Ala Asn Ser Ser Gly Ser Asp
        35                  40                  45

Asp Asp Glu Ser Leu Gln Arg Thr Asp Leu Thr Arg Thr His Thr Asn
    50                  55                  60

Asn Ile Ile Gln Glu Asp Asp Arg Thr Ala Ile His Arg Ile Ala Thr
65                  70                  75                  80

Ala Leu Ser Ala Ala Gly Asp Arg Ser Gly Ala Gly Asp Met His Ala
                85                  90                  95

```
Glu Asp Pro Ser Leu Asp Pro Gln Ser Pro Gln Phe Asp Ile Ser Lys
            100                 105                 110

Trp Leu Gly Arg Phe Ile Arg Val Arg Gly Glu Gly His Ala Ser
        115                 120                 125

Pro His Ala Glu Pro Gly Ile Met Phe Lys Asn Leu Ser Val Ser Gly
    130                 135                 140

Ser Ala Pro Asp Leu Gln Leu Gln Glu Thr Val Ala Ser Phe Val Thr
145                 150                 155                 160

Asn Ile Val Glu Leu Pro Leu Arg Val Gly Glu Leu Val Gly Leu Arg
                165                 170                 175

Glu Lys Ala Pro Asn Arg Arg Ile Leu Asn Glu Phe Asn Gly Val Ile
                180                 185                 190

Arg Gly Gly Glu Leu Leu Val Val Leu Gly Arg Pro Gly Ser Gly Cys
            195                 200                 205

Ser Thr Leu Leu Lys Thr Met Cys Gly Glu Leu His Gly Leu His Val
            210                 215                 220

Glu Pro Thr Ser Lys Ile His Tyr Ser Gly Val Pro Gln Ser Lys Met
225                 230                 235                 240

Met Lys Glu Phe Arg Gly Glu Thr Ile Tyr Asn Gln Glu Val Asp Lys
                245                 250                 255

His Phe Pro Glu Leu Thr Val Gly Gln Thr Leu Glu Phe Ala Ala Gln
                260                 265                 270

Val Arg Met Pro Ser His Lys Trp Ala His Leu Ser Lys Lys Leu Ser
            275                 280                 285

Arg Arg Asp Val Ala Asn Tyr Ile Ala Lys Val Val Met Ala Val Cys
            290                 295                 300

Gly Leu Ser His Thr Tyr Asn Thr Lys Val Gly Asn Glu Phe Val Arg
305                 310                 315                 320

Gly Val Ser Gly Gly Glu Arg Lys Arg Val Ser Ile Ala Glu Met Met
                325                 330                 335

Val Ala Gly Ser Pro Phe Met Gly Trp Asp Asn Ser Thr Arg Gly Leu
            340                 345                 350

Asp Ser Ala Thr Ala Leu Lys Phe Val Gln Thr Leu Arg Met Ala Ser
            355                 360                 365

Asp Leu Ala Gln Thr Ser Asn Ala Val Ala Ile Tyr Gln Ala Ser Glu
    370                 375                 380

Ser Ile Tyr Glu Leu Phe Asp Lys Ala Thr Val Leu Tyr Glu Gly Arg
385                 390                 395                 400

Gln Ile Tyr Phe Gly Pro Ala Asn Ala Ala Lys Ala Tyr Phe Glu Gly
                405                 410                 415

Leu Gly Trp Asp Cys Pro Thr Arg Gln Thr Thr Gly Asp Phe Leu Thr
            420                 425                 430

Ser Val Thr Asn Pro Ile Glu Arg Lys Pro Lys Glu Gly Met Asp Asp
            435                 440                 445

Arg Val Pro Arg Thr Ala Glu Glu Phe Glu Ala Cys Trp Leu Lys Ser
    450                 455                 460

Gln Ala Tyr Gln Glu Met Leu Ala Asp Val Ala Lys Tyr Asp Glu Ala
465                 470                 475                 480

His Pro Leu Asp Ala His Gly Glu Thr Val Ala Arg Leu Arg Glu Thr
                485                 490                 495

Lys Asn Ala Lys Gln Ala Lys Asn Val Arg Pro Lys Ser Pro Phe Ile
            500                 505                 510
```

```
Ile Ser Thr Gly Met Gln Val Ala Leu Asn Thr Arg Arg Ala Tyr Gln
            515                 520                 525

Arg Met Trp Asn Asp Lys Thr Pro Thr Leu Thr Thr Ala Val Thr Cys
        530                 535                 540

Ile Val Leu Ala Leu Ile Ile Gly Ser Thr Val Tyr Gly Thr Pro Asp
545                 550                 555                 560

Ala Thr Val Gly Phe Tyr Ala Lys Ala Ser Ala Leu Phe Met Ser Val
                565                 570                 575

Leu Leu Asn Ala Leu Ile Thr Leu Thr Glu Ile Asn Thr Leu Tyr Ala
            580                 585                 590

Gln Arg Pro Ile Val Glu Lys His Ala Ser Tyr Ala Phe Tyr His Pro
        595                 600                 605

Ala Thr Asp Ala Val Ala Gly Val Val Ala Asp Ile Pro Val Lys Phe
610                 615                 620

Leu Val Ala Val Cys Phe Asn Leu Val Leu Tyr Phe Met Ala Gly Leu
625                 630                 635                 640

Arg Arg Glu Pro Ala Gln Phe Phe Ile Tyr Phe Leu Ile Thr Tyr Thr
                645                 650                 655

Ser Thr Phe Thr Met Ser Ala Ile Phe Arg Thr Met Ala Ala Val Thr
            660                 665                 670

Thr Thr Val Ser Gln Ala Met Ser Leu Ala Gly Ile Phe Val Leu Gly
        675                 680                 685

Leu Val Met Tyr Thr Gly Phe Val Ile Thr Val Pro Thr Met His Pro
690                 695                 700

Trp Phe Ser Trp Ile Arg Trp Ile Asn Pro Ile Tyr Tyr Ala Phe Glu
705                 710                 715                 720

Ala Leu Val Ala Asn Glu Phe His Gly Arg Glu Phe Thr Cys Ser Val
                725                 730                 735

Ile Ile Pro Gly Tyr Ser Pro Ile Gly Asp Ser Trp Ile Cys Asn
            740                 745                 750

Val Val Gly Ala Val Ala Gly Arg Ala Thr Val Asn Gly Asp Ala Tyr
            755                 760                 765

Ile Ala Glu Ser Tyr Gly Tyr His Tyr Ser His Val Trp Arg Asn Phe
770                 775                 780

Gly Ile Met Ile Gly Phe Leu Ile Phe Phe Met Leu Leu Tyr Phe Ile
785                 790                 795                 800

Ala Thr Glu Ile Asn Ser Thr Pro Ser Ser Gly Glu Met Leu Val
                805                 810                 815

Tyr Gln Lys Gly His Val Pro Pro His Leu Arg Lys Gly Ala Ala Ala
            820                 825                 830

Ala Ala Gly Ala Ser Ala Ser Asn Glu Lys Gly Thr Gly Ser Ser Ala
        835                 840                 845

Ser Thr Ala Asn Gly Asp Ile Glu Ser Gly Gly Val Arg Pro Gly Ala
850                 855                 860

Ala Gly Glu Lys Pro Asp Thr Pro Glu Pro Ala Lys Ala Glu Val Arg
865                 870                 875                 880

Gly Ile Gln Pro Gln Lys Asp Ile Phe Thr Trp Lys Asn Val Val Tyr
                885                 890                 895

Asp Val Lys Ile Lys Gly Lys Asp Arg Arg Leu Leu Asp His Val Ser
            900                 905                 910

Gly Trp Val Lys Pro Gly Thr Leu Thr Ala Leu Met Gly Val Ser Gly
        915                 920                 925

Ala Gly Lys Thr Thr Leu Leu Asp Val Leu Ala Glu Arg Thr Thr Met
```

```
                930               935               940
Gly Val Ile Thr Gly Asp Met Phe Val Asn Gly Lys Ala Arg Gly Ala
945                 950               955                 960

Asn Phe Gln Arg Asn Thr Gly Tyr Val Gln Gln Gln Asp Leu His Leu
                965               970                 975

Glu Thr Ala Thr Val Arg Glu Ser Leu Arg Phe Ser Ala Ile Leu Arg
                980               985                 990

Gln Pro Pro Thr Val Pro Lys Ala Glu Lys Tyr Ala Phe Val Glu Glu
                995               1000                1005

Val Ile Gln Met Leu Asn Met Glu Glu Phe Ala Asp Ala Val Val Gly
                1010              1015                1020

Val Leu Gly Glu Gly Leu Asn Val Glu Gln Arg Lys Leu Leu Thr Ile
1025                1030              1035                1040

Gly Val Glu Leu Ala Ala Lys Pro Lys Leu Leu Phe Leu Asp Glu
                1045              1050                1055

Pro Thr Ser Gly Leu Asp Ser Gln Ser Ser Trp Ala Ile Cys Asn Phe
                1060              1065                1070

Leu Arg Lys Leu Ala Asp Ala Gly Gln Ala Val Leu Cys Thr Ile His
                1075              1080                1085

Gln Pro Ser Ala Val Leu Phe Glu Gln Phe Asp Arg Leu Leu Phe Leu
                1090              1095                1100

Ala Ala Gly Gly Lys Thr Val Tyr Phe Gly Glu Val Gly Arg Asp Ser
1105                1110              1115                1120

Arg Ser Leu Leu Asp Tyr Phe Glu Ala Lys Gly Ala Arg Ala Cys Gly
                1125              1130                1135

Ala Ala Glu Asn Pro Ala Glu Tyr Met Leu Glu Ile Val Asn Lys Thr
                1140              1145                1150

Lys Ala Gly Asp Gly Lys Asp Trp His Ala Thr Trp Leu Glu Ser Lys
                1155              1160                1165

Glu Arg Val Asp Val Glu Glu Val Glu Arg Ile Tyr Ala Ala Lys
                1170              1175                1180

Ala Asn Glu Ile Ser Ala Ala Asp Gln Glu Asp Ala Ala Arg Gly Asp
1185                1190              1195                1200

Lys Ser Asn Gln Asn Thr Glu Phe Ala Met Pro Phe Ser Thr Gln Leu
                1205              1210                1215

Arg Glu Val Thr Tyr Arg Val Phe Gln Gln Tyr Trp Arg Met Pro Glu
                1220              1225                1230

Tyr Val Phe Ala Lys Leu Ser Leu Gly Ile Val Ala Gly Leu Phe Val
                1235              1240                1245

Gly Phe Ser Phe Phe Gln Ala Lys Ser Ser Leu Ala Gly Met Gln Gly
                1250              1255                1260

Val Ile Phe Ser Val Phe Gln Ile Leu Thr Ile Phe Ser Ser Ile Val
1265                1270              1275                1280

Gln Gln Ile Gln Pro Leu Phe Val Thr Gln Arg Ala Leu Tyr Glu Val
                1285              1290                1295

Arg Glu Arg Pro Gly Lys Met Tyr Ser Trp Lys Ala Phe Met Ile Ala
                1300              1305                1310

Asn Ile Val Val Glu Phe Pro Trp Gln Ile Leu Thr Gly Ile Val Thr
                1315              1320                1325

Tyr Ala Cys Phe Tyr Tyr Pro Ile Val Gly Val Gln Asp Ser Gln Arg
                1330              1335                1340

Gln Gly Leu Val Leu Leu Phe Met Ile Glu Leu Met Ile Tyr Ala Ser
1345                1350              1355                1360
```

-continued

```
Ser Phe Ala His Met Cys Ile Ala Ala Leu Pro Asp Ala Gln Thr Ala
            1365                1370                1375

Gly Gly Ile Val Thr Leu Leu Val Met Thr Ser Leu Ile Phe Ser Gly
            1380                1385                1390

Val Leu Gln Thr Pro Ala Ala Leu Pro Gly Phe Trp Ile Phe Met Tyr
            1395                1400                1405

Arg Val Ser Pro Phe Thr Tyr Trp Ile Ser Gly Val Ile Ser Thr Ala
            1410                1415                1420

Val His Asp Arg Pro Ile Val Cys Ser Lys Ala Glu Thr Ser Val Phe
1425                1430                1435                1440

Asp Pro Pro Met Gly Tyr Thr Cys Gly Gln Tyr Leu Ala Pro Tyr Leu
            1445                1450                1455

Thr Leu Ala Pro Gly Gln Leu Gln Asn Pro Asp Ala Ser Ala Ala Cys
            1460                1465                1470

Gln Tyr Cys Gln Val Ser Val Ala Asp Gln Tyr Ile Ser Gln Asn Asn
            1475                1480                1485

Ile Tyr Trp Asn Thr Arg Trp Arg Asn Phe Gly Leu Met Trp Ala Tyr
            1490                1495                1500

Ile Leu Phe Asn Ile Ala Met Ala Ile Gly Thr Tyr Tyr Val Phe Arg
1505                1510                1515                1520

Val Arg Lys Phe Asp Phe Ser Arg Leu Lys Phe Trp Gly Lys Asn Lys
            1525                1530                1535

Thr Glu

<210> SEQ ID NO 50
<211> LENGTH: 1535
<212> TYPE: PRT
<213> ORGANISM: Ophiostoma piceae
<220> FEATURE:
<223> OTHER INFORMATION: OPP_07323

<400> SEQUENCE: 50

Met Ala Phe Val Gly Gly Ser Phe Gly Asn Tyr Asp His Thr Ala Gln
1               5                   10                  15

Ser Gln Gly Ala Pro Ile Thr His Arg Gln Asn Val Tyr Asp Asp Glu
            20                  25                  30

Val Asn Asn Val Pro Ser Ser Ala Asp Ala Gly Thr Arg Ala Thr
            35                  40                  45

Ser Leu Thr Glu Thr Gly Ser Ala Val Gly Pro Gly Thr Pro Ile
50                  55                  60

Ala Ser Lys Thr Lys Asn Ala Glu Gly Ser Thr Gly Gly Asp Asp Asp
65                  70                  75                  80

Asp Asp Asp Glu Pro Asp Ile Thr Ala Glu Met Arg Arg Arg His Ser
            85                  90                  95

Ala Val Gln Ala Leu Ala Arg Thr Tyr Thr His Gln Ser Leu Ala Ser
            100                 105                 110

Gly Val Ile Pro Pro Gly His His Asn Val Phe Ala Ala Ala Gln
            115                 120                 125

Pro Asp Ser Pro Leu Asn Pro Ala Ser Glu Asn Phe Asn Gly Arg Ala
            130                 135                 140

Trp Ala Lys Ala Val Val Asp Met Val Ser Ser Glu Gly His Gly Phe
145                 150                 155                 160

Arg Thr Ser Gly Val Ser Phe Gln Asp Leu Asn Val Tyr Gly Tyr Gly
            165                 170                 175
```

```
Lys Pro Thr Asp Tyr Gln Lys Asp Val Ala Asn Ile Trp Leu Glu Thr
                180                 185                 190

Val Ser Leu Ala Arg Ser Val Met Gly Gly Glu Gln Arg Arg Ile Asp
            195                 200                 205

Ile Leu Arg Asp Phe Asp Gly Val Glu Lys Gly Glu Met Leu Val
        210                 215                 220

Val Leu Gly Pro Pro Gly Ala Gly Cys Thr Thr Leu Leu Lys Thr Ile
225                 230                 235                 240

Ala Gly Glu Thr Asn Gly Ile Tyr Val Asp Glu Lys Ser Phe Phe Asn
                245                 250                 255

Tyr Gln Gly Met Thr Ala Glu Glu Met His Ser Lys His Arg Gly Glu
            260                 265                 270

Ala Ile Tyr Thr Ala Glu Val Asp Val His Phe Pro Gln Leu Ser Val
        275                 280                 285

Gly Asp Thr Leu Thr Phe Ala Ala Arg Ala Arg Ala Pro Arg Glu Ile
        290                 295                 300

Pro Ala Gly Ile Asn Arg Asn Met Phe Ala Glu His Leu Arg Asp Val
305                 310                 315                 320

Val Met Ala Met Phe Gly Ile Ser His Thr Ile Asn Thr Arg Val Gly
                325                 330                 335

Asn Glu Tyr Val Arg Gly Val Ser Gly Gly Glu Arg Lys Arg Val Thr
            340                 345                 350

Ile Ala Glu Ala Ala Leu Ser Gly Ala Pro Leu Gln Cys Trp Asp Asn
        355                 360                 365

Ser Thr Arg Gly Leu Asp Ser Ala Asn Ala Ile Glu Phe Val Arg Thr
        370                 375                 380

Leu Arg Thr Gln Thr Glu Leu Phe Gly Asn Thr Ala Val Val Ser Ile
385                 390                 395                 400

Tyr Gln Ala Pro Gln Ser Ala Tyr Asp Met Phe Asp Lys Val Thr Val
                405                 410                 415

Ile Tyr Glu Gly Arg Gln Ile Tyr Phe Gly Arg Thr Thr Asp Ala Arg
            420                 425                 430

Gln Tyr Phe Ile Asn Leu Gly Phe Asp Cys Pro Ala Arg Ala Thr Thr
        435                 440                 445

Pro Asp Phe Leu Thr Ser Met Thr Ala Pro Ala Glu Arg Val Val Arg
450                 455                 460

Ala Gly Trp Glu Gly Arg Ala Pro Arg Thr Pro Asp Glu Phe Ser Ala
465                 470                 475                 480

Cys Trp Arg Lys Ser Glu Glu Tyr Lys Ala Leu His Val Asp Ile Glu
                485                 490                 495

Ala Tyr Lys Val Ser His Pro Ile Asn Gly Pro Asp Ala Asp Ala Phe
            500                 505                 510

Arg Ala Ser Lys Arg Ala Gln Gln Ala Arg Ser Gln Arg Ala Ser Ser
        515                 520                 525

Pro Phe Thr Leu Ser Tyr Asn Gln Gln Val Lys Leu Cys Leu Trp Arg
        530                 535                 540

Gly Phe Arg Arg Leu Val Gly Asp Pro Ser Leu Ser Leu Thr Ala Leu
545                 550                 555                 560

Phe Ala Asn Ser Ile Met Ser Leu Ile Ile Gly Ser Val Phe Tyr Asn
                565                 570                 575

Leu Lys Asp Asp Thr Ser Ser Phe Tyr Gln Arg Gly Ala Leu Leu Phe
            580                 585                 590

Phe Ala Cys Leu Met Asn Ala Phe Ser Ser Ala Leu Glu Ile Leu Thr
```

```
                595                 600                 605
Leu Tyr Ser Gln Arg Pro Ile Val Glu Lys His Ala Arg Tyr Ala Leu
610                 615                 620

Tyr His Pro Ser Ala Glu Ala Val Ala Ser Met Leu Cys Asp Met Pro
625                 630                 635                 640

Tyr Lys Ile Ser Asn Ala Ile Thr Phe Asn Leu Val Leu Tyr Phe Met
                645                 650                 655

Thr Asn Leu Arg Arg Glu Pro Gly His Phe Phe Tyr Leu Leu Val
                660                 665                 670

Ser Phe Leu Thr Val Met Thr Met Ser Met Ile Phe Arg Thr Ile Ala
        675                 680                 685

Ser Ser Ser Arg Thr Leu Ser Gln Ala Met Val Pro Ala Val Ile
        690                 695                 700

Ile Leu Ala Leu Val Ile Phe Ser Gly Phe Val Ile Pro Ile Asp Tyr
705                 710                 715                 720

Met Leu Gly Trp Cys Arg Trp Ile Asn Tyr Ile Asp Pro Leu Ala Tyr
                725                 730                 735

Ala Phe Glu Ser Leu Met Val Asn Glu Phe Ser Gly Arg Gln Phe Thr
                740                 745                 750

Cys Thr Asp Phe Val Pro Ser Ala Ala Val Asp Gly Tyr Ala Asn Val
        755                 760                 765

Ala Asp Val Asn Arg Val Cys Ser Ala Val Gly Ser Val Ser Gly Gln
770                 775                 780

Ala Tyr Val Asp Gly Asn Ala Tyr Val Asn Leu Ser Phe Gln Tyr Phe
785                 790                 795                 800

His Ala His Lys Trp Arg Asn Ile Gly Ile Ile Gly Phe Leu Ile
                805                 810                 815

Phe Phe Phe Phe Thr Tyr Met Val Ser Ala Glu Phe Val Ser Glu Lys
                820                 825                 830

Lys Ser Lys Gly Glu Val Leu Val Phe Arg Arg Gly His Lys Ala Val
        835                 840                 845

Ala Phe Asp Asp Lys Tyr Lys Val Asp Ala Glu Ser Gly Thr Arg Val
850                 855                 860

Ser Gly Pro Val Ala Ala Asn Glu Lys Ser Gly Ser Gly Ser Asp Lys
865                 870                 875                 880

Glu Gly Gly Ala Gly Phe Leu Gln Ala Gln Thr Ala Val Phe His Trp
                885                 890                 895

Gln Asp Val Cys Tyr Asp Val Lys Ile Lys Lys Glu Asn Arg Arg Ile
                900                 905                 910

Leu Asp His Val Asn Gly Trp Val Lys Pro Gly Thr Met Thr Ala Leu
        915                 920                 925

Met Gly Val Ser Gly Ala Gly Lys Thr Thr Leu Leu Asp Cys Leu Ala
        930                 935                 940

Asp Arg Thr Ser Met Gly Val Ile Thr Gly Asp Met Phe Val Asp Gly
945                 950                 955                 960

Arg Glu Arg Asp Gln Ser Phe Gln Arg Lys Thr Gly Tyr Val Gln Gln
                965                 970                 975

Gln Asp Leu His Leu Gln Thr Ser Thr Val Arg Glu Ala Leu Asn Phe
        980                 985                 990

Ser Ala Leu Leu Arg Gln Pro Ala His Val Pro Arg Ala Glu Lys Leu
        995                 1000                1005

Ala Tyr Val Asp Glu Val Ile Arg Leu Leu Asp Met Gln Glu Tyr Ala
        1010                1015                1020
```

```
Asp Ala Val Val Gly Val Pro Gly Glu Gly Leu Asn Val Glu Gln Arg
1025                1030                1035                1040

Lys Arg Leu Thr Ile Gly Val Glu Leu Ala Ala Lys Pro Pro Leu Leu
                1045                1050                1055

Leu Phe Val Asp Glu Pro Thr Ser Gly Leu Asp Ser Gln Thr Ser Trp
        1060                1065                1070

Ala Ile Leu Asp Leu Leu Glu Lys Leu Thr Lys Ser Gly Gln Ala Ile
        1075                1080                1085

Leu Cys Thr Ile His Gln Pro Ser Ala Met Leu Phe Gln Arg Phe Asp
        1090                1095                1100

Arg Leu Met Phe Leu Ala Arg Gly Gly Lys Thr Val Tyr Phe Gly Glu
1105                1110                1115                1120

Ile Gly Glu Asn Ser Lys Thr Met Thr Ser Tyr Phe Glu Arg Asn Gly
                1125                1130                1135

Gly Phe Pro Cys Pro His Asp Ala Asn Pro Ala Glu Trp Met Leu Glu
                1140                1145                1150

Val Ile Gly Ala Ala Pro Gly Ser His Ser Asp Val Asn Trp Pro Glu
                1155                1160                1165

Ala Trp Arg Ala Ser Pro Glu Phe Val Ala Val Gln Thr Glu Leu Glu
        1170                1175                1180

Arg Leu Lys Asn Asn Pro Gly Pro Ala Ala Glu Lys Ser Ser Ala Asp
1185                1190                1195                1200

Tyr Arg Glu Phe Ala Ala Ser Phe Pro Ala Gln Phe Lys Glu Val Val
                1205                1210                1215

Met Arg Val Phe Glu Gln Tyr Trp Arg Thr Pro Ser Tyr Ile Tyr Ser
        1220                1225                1230

Lys Met Ala Leu Cys Ile Leu Val Ala Met Phe Ile Gly Phe Val Phe
        1235                1240                1245

Tyr Lys Ala Pro Leu Thr Ile Gln Gly Phe Gln Asn Gln Met Phe Ser
        1250                1255                1260

Ile Phe Asn Leu Leu Thr Val Phe Gly Gln Leu Val Gln Gln Thr Met
1265                1270                1275                1280

Pro His Phe Val Val Gln Arg Ser Leu Tyr Glu Val Arg Glu Arg Pro
                1285                1290                1295

Ser Lys Val Tyr Ser Trp Lys Val Phe Met Leu Ser Gln Ile Val Val
                1300                1305                1310

Glu Leu Pro Trp Asn Thr Leu Met Ala Val Ile Met Phe Val Leu Trp
        1315                1320                1325

Tyr Tyr Pro Ile Gly Leu Asn Glu Asn Ala Ile Ala Ala Gly Gln Thr
        1330                1335                1340

Ala Glu Arg Gly Phe Leu Met Phe Leu Leu Leu Trp Ala Phe Leu Leu
1345                1350                1355                1360

Phe Thr Ser Thr Phe Thr Asp Leu Ile Ile Ala Gly Cys Glu Thr Ala
                1365                1370                1375

Glu Val Gly Gly Asn Ile Ala Asn Leu Leu Phe Met Leu Cys Leu Ile
                1380                1385                1390

Phe Cys Gly Val Leu Ala Gln Pro Ser Thr Phe Pro Arg Phe Trp Ile
        1395                1400                1405

Phe Met Tyr Arg Val Ser Pro Phe Thr Tyr Leu Val Ser Ala Met Met
        1410                1415                1420

Ser Val Gly Val Ala Asn Thr Lys Val Thr Cys Ala Ala Asn Glu Tyr
1425                1430                1435                1440
```

| | | | | | | | | | | | |
|---|---|---|---|---|---|---|---|---|---|---|---|
| Leu | Thr | Phe | Asp | Pro | Pro | Ser | Gly | Asp | Thr | Cys | Tyr | Gln | Tyr | Leu | Glu |
| | | | | 1445 | | | | 1450 | | | | 1455 | | | |
| Lys | Tyr | Met | Ser | Ala | Ala | Gly | Gly | Tyr | Val | Thr | Asn | Pro | Asn | Ala | Thr |
| | | | 1460 | | | | | 1465 | | | | 1470 | | | |
| Ala | Ala | Cys | Asp | Phe | Cys | Ser | Val | Ser | Asp | Thr | Asn | Met | Ala | Leu | Ala |
| | | | 1475 | | | | | 1480 | | | | | 1485 | | |
| Asn | Val | Leu | Ser | Asn | Tyr | Ser | Glu | Arg | Trp | Arg | Asn | Phe | Gly | Ile | Leu |
| | | | 1490 | | | | | 1495 | | | | 1500 | | | |
| Trp | Ala | Tyr | Ile | Ile | Phe | Asn | Ile | Val | Gly | Ala | Leu | Ala | Ile | Tyr | Trp |
| 1505 | | | | | 1510 | | | | | 1515 | | | | | 1520 |
| Leu | Val | Arg | Val | Pro | Lys | Lys | Thr | Ser | Thr | Lys | Ala | Lys | Lys | Glu | |
| | | | | 1525 | | | | | 1530 | | | | | 1535 | |

<210> SEQ ID NO 51
<211> LENGTH: 4617
<212> TYPE: DNA
<213> ORGANISM: Ophiostoma piceae
<220> FEATURE:
<223> OTHER INFORMATION: OPP_06275

<400> SEQUENCE: 51

```
atggcttcct ccaacaacag agctcccctg cagggcgagc aggtgtctgt cccggccgcc      60
agcacagagc cagtccccgg catagagcca gccatcaacg ccaacgccag caacgccaac     120
aacgccaaca gcagcggcag cgacgacgac gaatctctgc aacgcaccga cctgaccccgt    180
acccacacca caacattat ccaggaggat gaccgcactg ctatccaccg cattgctacg      240
gccctgtcgg ctgccggcga ccgttccggg gcgggcgaca tgcacgccga ggacccatcc     300
ctcgatcccc aaagccccca gtttgacatt tccaagtggc tcggccgttt cattcgccgc     360
gtgcgcggtg agggccacgc atctccgcac gccgagccgg gcatcatgtt caagaacctg     420
tctgtgtcgg gcagcgcacc cgacctgcag ctgcaggaga cagttgcgtc gtttgttaca     480
aacattgtag agctgccgct gcgtgttggc gagctcgttg gcctgcgtga aaaggcgccc     540
aaccggcgca tcctcaacga gttcaacggt gtcatccgcg gcggcgagct gctggttgtg     600
ctgggccgac ctggctccgg ctgcagcacg ctgctcaaga ccatgtgcgg cgagctgcac     660
ggcctgcacg tcgagcccac gtcgaagatc cactacagcg gcgtacccca agcaagatg      720
atgaaggagt cccgcggcga gacgatctac aaccaggagg tcgacaagca ctttcccgag     780
ctcacagtcg gccagacgct cgagtttgcg gcccaggtgc gtatgccttc gcacaagtgg     840
gcgcacctca gcaagaagct gtcgcgccgc gacgtcgcca actacatcgc caaggtcgtg     900
atggccgtgt gcggcctgag ccacacctac aacaccaagg tcggcaacga gttcgtgcgc     960
ggtgtgtcgg gtggcgagcg caagcgtgtc agcattgccg agatgatggt ggcaggcagt    1020
cccttatgg gctgggacaa cagcacgcgc ggtctcgact cggcgacggc gcttaagttt     1080
gtgcagacgc tgcgcatggc gagcgacctc gcgcagacga gcaacgctgt cgccatctac    1140
caggccagcg agagcatcta cgagctcttc gacaaggcca ccgtgctcta cgagggccgc    1200
cagatctact ttggcccggc caacgcggcc aaggcctact tgagggcct gggctgggac     1260
tgcccgacgc gccagacgac gggtgacttt ttgacgtcgg tcacgaaccc cattgagcgc    1320
aagcccaagg agggcatgga cgaccgtgtg ccgcgcacgg ccgaggagtt tgaggcgtgc    1380
tggctcaagt cgcaggcata ccaggaaatg ctggccgacg tcgccaagta cgacgaggcg    1440
cacccgctgg acgcgcacgg cgagaccgtg gcgcggctgc gcgagaccaa gaacgcaaag    1500
caggccaaga acgtgcggcc caagtcgccg ttcatcatca gcacaggcat gcaggtggcc    1560
```

```
ctcaacacgc gccgtgccta ccagcgcatg tggaacgaca agacgccgac gctcacgacc   1620
gctgtgacgt gtatcgtcct cgcgctcatc atcggctcca cggtctacgg cacgcccgat   1680
gcgacggtcg gcttctacgc caaggcgtcg gcgctcttca tgtcggtgct gctcaacgcc   1740
ctgatcacgc tcacggaaat caacaccctg tatgcccagc gccccattgt tgagaagcac   1800
gcgtcgtatg cctttacca cccggccaca gacgctgtcg ccggtgtcgt cgccgacatc   1860
cccgtcaagt tcctcgtcgc tgtctgtttc aacctcgtgc tctacttcat ggccggcctg   1920
cgccgtgagc cagcacagtt cttcatctac ttcttgatca cctacacctc cacgttcacc   1980
atgtcggcca tcttccggac catggcggcc gtgaccacga cggtgtccca ggccatgtcg   2040
ctcgcgggca tctttgtgct cggcctcgtc atgtacacgg ctttgtgat tacagtcccg    2100
acgatgcacc cgtggttcag ctggatccgc tggatcaacc ccatctacta tgcctttgaa   2160
gcgcttgtgg ccaacgaatt ccacggccgc gagtttacct gctccgtcat catccccggc   2220
tactcgccgc ccatcggtga ctcgtggatc tgcaacgttg tcggtgctgt cgcgggccgg   2280
gccacggtca acggcgacgc gtacattgct gagagctatg ataccacta ctcgcacgtt    2340
tggcgcaact ttggcattat gatcggcttc ctcatcttct ttatgctcct atactttatc   2400
gcgaccgaga tcaacagcac gccctcgagc tccggcgaga tgctcgtgta ccagaagggt   2460
cacgtgcctc ctcacctgcg caagggtgct gctgccgcgg ccggtgcgtc ggcgtccaac   2520
gaaaagggta ctggctcctc ggcatccacg gccaacggcg acattgagtc tggcggcgtg   2580
cgccctggtg cagctggcga gaagcccgac acgcccgaac cggccaaagc ggaagtgcgc   2640
ggcatccaac cgcaaaagga tattttcaca tggaagaacg tcgtgtacga cgtcaagatc   2700
aagggcaagg accggcggct gctagaccat gtgtcgggct gggtgaagcc gggcacactg   2760
acggcgctga tgggtgtcag tggtgccggt aagacgacgc tgctggacgt gctagccgag   2820
cgcacgacca tgggcgtgat cacgggcgac atgtttgtca acggcaaggc tcgcggtgcc   2880
aacttccagc gcaacaccgg ctacgtgcag cagcaggact tgcacctgga gacggcgacg   2940
gtgcgtgagt cttttgcggtt cagtgcgatt ctgcgccagc ccccgacggt gcccaaggca   3000
gaaaagtatg cgtttgtcga ggaggtgatc cagatgctca acatggagga gtttgccgac   3060
gccgttgtgg gtgtgctggg cgagggcctg aatgtcgagc agcgcaagct gcttacgatc   3120
ggtgtcgagc tggcggccaa gccgaagctg ctgctattcc tggacgagcc gacctctggc   3180
ctggactcgc agagttcgtg ggcgatctgc aacttcttgc gcaagctggc cgacgccggc   3240
caggccgtgc tgtgcacgat ccaccagccg agcgccgtgc tctttgagca gtttgaccgc   3300
ctgctgttcc tcgcggccgg tggcaagaca gtctatttcg gcgaggttgg ccgcgactcg   3360
cggtcgctgc tggactactt tgaggccaag ggggcgcgcg cgtgcggtgc cgccgagaac   3420
ccggccgagt acatgctgga gattgtgaac aagacgaagg caggcgacgg caaggactgg   3480
cacgcgacgt ggctcgagag caaggagcgg gtcgacgtcg aggaggaggt cgagcgcatc   3540
tacgcagcca aggccaacga gatctcggcg gccgaccagg aggacgcggc gcgcggcgac   3600
aagagcaacc agaacacgga gtttgcgatg ccgttctcga cgcagctgcg cgaggtcacg   3660
taccgggtgt tccagcagta ctggcgcatg cccgagtacg tgtttgcgaa gctgtcgctg   3720
ggcattgtgg cgggcctgtt tgtgggcttc tcgttcttcc aggccaagag ctcgctcgcg   3780
ggcatgcagg gcgtgatctt ctccgtgttc cagatcctga ccatcttctc gtcgattgtg   3840
cagcagatcc agccgctgtt tgtgacgcag cgcgcactat acgaggtgcg cgagcgcccc   3900
```

| | |
|---|---|
| ggcaagatgt actcgtggaa ggcgtttatg attgccaaca tcgtggtcga gttcccctgg | 3960 |
| cagatcctga cgggcattgt gacgtacgcg tgcttctact acccgattgt gggcgtgcag | 4020 |
| gactcgcagc gccagggcct ggtgctgctg tttatgattg agcttatgat ctacgcgagc | 4080 |
| tcgtttgcgc acatgtgcat cgcggcgctg ccggacgcgc agacggcggg cggcattgtg | 4140 |
| acgctgctgg tgatgacgag tctgattttc agcggtgtgc tgcagacgcc ggcggcgctg | 4200 |
| cctggcttct ggatcttcat gtaccgcgtg tcaccgttta catactggat ctcgggcgtg | 4260 |
| atctcgacgg cggtgcacga tcggccgatt gtgtgctcga aggcggagac gtcggtgttt | 4320 |
| gacccgccca tgggctacac gtgcggccag tacctggcac cgtacctgac gctcgcgcct | 4380 |
| ggccagctgc agaacccgga tgcgtcggcg gcgtgccagt actgccaggt gtcggtggcg | 4440 |
| gaccagtaca tctcgcagaa caacatctac tggaacaccc gctggcgcaa ctttggactg | 4500 |
| atgtgggcgt acattctgtt caacattgca atggcgattg gcacgtatta tgtgttccgg | 4560 |
| gtgcgcaagt ttgactttc gcgcctaaag ttctggggca agaacaagac agagtag | 4617 |

<210> SEQ ID NO 52
<211> LENGTH: 4608
<212> TYPE: DNA
<213> ORGANISM: Ophiostoma piceae
<220> FEATURE:
<223> OTHER INFORMATION: OPP_07323

<400> SEQUENCE: 52

| | |
|---|---|
| atggcttttg tcggtggttc cttcgggaac tacgaccaca ctgcccaatc tcagggcgca | 60 |
| ccaattaccc accgtcagaa tgtctatgat gatgaggtga caacgttcc gtccagtgct | 120 |
| gacgatgccg gcacccgcgc cacgtctctg accgagactg ctctgctgt tgggcccggc | 180 |
| ggcacgccca ttgccagcaa gacgaagaat gctgagggca gcaccggtgg cgacgacgac | 240 |
| gatgacgacg agcccgatat cacggccgag atgcggcgcc gccacagcgc cgtgcaggcc | 300 |
| ctggcccgca cttacactca ccagtcgctt gcctcgggtg tcatcccacc tggccatcac | 360 |
| aacgtcttcg ccgccgccgc gcagcccgac tcccctctga acccggccag cgagaacttc | 420 |
| aacgccgcg cctgggccaa ggctgttgtc gacatggtca gcagtgaggg tcacggtttc | 480 |
| cgcacctctg gtgtcagctt ccaggacctc aacgtgtacg gctacggcaa gcctactgat | 540 |
| tatcagaagg atgtggccaa catctggctc gagactgtca gcttggcgcg ctctgtcatg | 600 |
| ggtggcgagc agcgccgtat cgatattctg cgcgattttg acggtgtcgt cgaaaagggc | 660 |
| gagatgctcg tcgtgctggg tcctcccggt gccggttgca caacattgct caagaccatt | 720 |
| gccggtgaga ccaacggtat ctacgtcgac gaaaagtcct tcttcaacta ccagggtatg | 780 |
| accgccgagg agatgcattc caagcaccgc ggtgaagcta tctacactgc tgaagttgat | 840 |
| gttcacttcc cccagctctc ggtcggcgac accctgacct tgctgctcg cgcccgcgcc | 900 |
| cctcgcgaaa tccggccgg catcaacagg aacatgttcg ccgagcactt gcgcgacgtc | 960 |
| gtcatggcca tgtttggtat ttcccacacc atcaacaccc gtgttggcaa cgagtacgtc | 1020 |
| cgtggtgttt ccggtggtga gcgcaagcgt gttaccattg ctgaggcggc cctttccggc | 1080 |
| gctcccctgc agtgctggga caactcgacc cgtggtctgg atagtgccaa cgctattgag | 1140 |
| ttcgtccgca ccctgcgcac ccagactgag ctgtttggca cactgctgt cgtctccatc | 1200 |
| taccaggcgc cccagagtgc ctacgacatg tttgacaaag ttactgtcat ctacgagggt | 1260 |
| cgccagatct actttggccg cactacggac gcacgccagt acttcatcaa cctgggtttc | 1320 |
| gattgcccgg cccgtgctac tacacctgat ttcctgacgt ccatgactgc ccctgccgag | 1380 |

```
cgtgtcgttc gcgctggctg ggaaggccgt gccccgcgca ccctgacga gttttctgct   1440
tgctggcgca agtcggagga gtacaaggct ctccatgttg acatcgaggc atacaaggtc   1500
tcccacccca tcaacggtcc tgacgctgat gcgttccgtg cctcgaagcg tgcccagcag   1560
gcccgctcgc agcgtgccag cagtcccttc actctgtcct acaaccagca ggttaagctg   1620
tgtctatggc gcggtttcag acgccttgtc ggcgaccca gcttgtctct tactgccctg    1680
tttgccaact cgattatgtc cctaatcatt ggctccgtct tctacaacct caaggatgac   1740
acttctagct tttaccagcg tggtgccctg ctcttcttcg cctgtctcat gaatgccttc   1800
tcgtctgccc tcgaaattct cacattgtac agccagcgtc cgattgtcga aaagcatgct   1860
cgatacgctc tctaccaccc gtcggccgag gcagtggcgt ctatgctttg cgatatgccc   1920
tacaagatca gtaacgctat cacgttcaac ctcgtgcttt actttatgac gaatctgcgt   1980
cgtgaacctg ccacttctt cttctatctg cttgtcagct tcctcaccgt catgaccatg    2040
tctatgattt ccgcacaat tgcctcgtcc tcgcgcactc tgtcgcaagc catggtgccc    2100
gctgcggtta tcatcctggc ccttgttatt tcagtggct ttgttatccc aattgattat    2160
atgttgggat ggtgccgctg atcaactac attgacccgc tcgcttatgc tttcgagtcc    2220
ctcatggtca acgagttttc tggtcgccag tttacttgca cagattttgt tcccagcgcc    2280
gcggttgatg gttacgcgaa cgttgccgac gtaaaccgcg tctgctctgc tgttggctcc    2340
gtcagtggtc aggcatatgt cgatggcaac gcttatgtga acctgagctt ccagtacttc    2400
cacgcacaca agtggcggaa catcggtatc atcattggtt tcctcatttt cttcttcttt    2460
acctacatgg tctccgctga gtttgtttct gagaagaagt ctaagggtga agtccttgtc    2520
ttccgccgtg gccacaaggc tgttgccttt gatgataagt acaaggttga cgccgaatct    2580
ggtacccgtg tctctggccc tgttgctgcc aacgagaaga gcggctcagg cagtgacaaa    2640
gagggtggtg ccggcttcct gcaggcccag actgctgttt tccactggca ggatgtgtgc    2700
tacgatgtca agattaagaa ggaaaaccgt cgcattctgg atcacgtcaa tggttgggtc    2760
aagcctggca ctatgaccgc tctgatgggc gtttctggtg ctggtaagac gacactgctt    2820
gactgcttgg ctgaccgtac ctcgatgggc gtgatcaccg tgacatgtt tgttgatggt    2880
cgcgagcgtg atcagtcctt ccagcgcaag actggctacg tccagcagca agatttgcat    2940
ctgcagacca gcactgtccg cgaagccctt aacttctctg ctcttctccg tcaacccgcc    3000
cacgttcccc gcgctgagaa gctcgcctat gtcgacgagg tcatccgtct gctggatatg    3060
caagaatacg ctgacgctgt cgtcggtgtc cctggtgaag gtctcaacgt cgagcagcgc    3120
aagcgcttga ccatcggtgt cgagcttgct gctaagcctc tctgttgct gttcgtcgac    3180
gagcctacct ctggtcttga ctcgcaaacc tcctgggcta ttctggatct gcttgagaag    3240
cttaccaaga gcggccaggc tattctgtgc accattcacc agccttcggc catgcttttc    3300
cagcgcttcg atcgtctcat gttccttgcc cgtggtggta agactgttta ctttggtgaa    3360
attggcgaga actctaagac catgactagc tacttcgagc gcaatggtgg cttcccctgc    3420
ccccatgatg ccaaccctgc cgagtggatg ctcgaggtta ttggtgctgc tcccggttct    3480
cactctgacg tcaactggcc cgaggcctgg cgcgcatccc ccgagttcgt tgctgttcag    3540
accgagcttg agcgtcttaa gaacaaccca ggcccggccg ctgagaagtc atctgctgat    3600
taccgcgagt ttgccgcctc gttccccgcc cagttcaagg aagttgtcat gcgtgtgttt    3660
gagcagtact ggcgtacgcc gtcgtacatc tactccaaga tggctctctg tatcctggtt    3720
```

-continued

```
gccatgttta ttggattcgt cttctacaag gccccgctca ccattcaggg cttccagaac    3780
cagatgttct ccatcttcaa cttgctcact gtctttggcc agcttgtcca gcagaccatg    3840
ccccatttcg tcgtccagcg ctctctttac gaagtccgcg agcgccctc  aaaggtctac    3900 agctggaagg tgttcatgct gtcgcagatc gtcgtcgagt tgccctggaa cacgctcatg    3960
gctgtcatta tgtttgtcct ctggtactac cccattggtc tcaacgagaa cgccatcgct    4020
gctggccaga ctgctgagcg tggcttcctc atgttcctgc tactctgggc tttcctgctt    4080
ttcacctcaa ccttcacgga tctcatcatc gccggttgcg aaactgcaga ggttggtggc    4140
aacattgcca acttgttgtt catgctctgc ctcatcttct gtggtgttct cgcccagccg    4200
tccacattcc ctcgcttctg gatcttcatg taccgagtat cgcccttcac atatttggtt    4260
tcagcaatga tgtcggtcgg tgtcgccaac accaaggtga cgtgtgctgc gaacgagtac    4320
cttacctttg accctccatc gggcgacact tgctaccagt acctcgagaa gtacatgagc    4380
gctgccggtg gttacgttac caacccaac  gccaccgcgg cctgcgattt ctgctcggtt    4440
agcgacacca acatggcctt ggccaatgtc ctgtccaact acagtgaacg ctggcggaac    4500
tttggtatcc tctgggcgta catcatcttc aacatcgtcg gtgctctggc catctactgg    4560
cttgtccgcg tgcccaagaa gacgtccacg aaggcgaaga aggagtaa               4608
```

ABC TERPENOID TRANSPORTERS AND METHODS OF USING THE SAME

RELATED APPLICATIONS

Benefit of priority is claimed to U.S. Provisional Application Ser. No. 61/589,679, filed Jan. 23, 2012, entitled "ABC TERPENOID TRANSPORTER AND METHOD OF USING THE SAME," and U.S. Provisional Application Ser. No. 61/797,936, filed Dec. 17, 2012, entitled "ABC TERPENOID TRANSPORTER AND METHOD OF USING THE SAME." The subject matter of the above-noted applications is incorporated by reference in its entirety.

This application is related to International PCT Application No. PCT/CA2013/050044, filed Jan. 23, 2013, entitled "ABC TERPENOID TRANSPORTERS AND METHODS OF USING THE SAME," which claims priority to U.S. Provisional Application Ser. Nos. 61/589,679 and 61/797, 936.

The subject matter of the above-noted applications is incorporated by reference in its entirety.

INCORPORATION BY REFERENCE OF SEQUENCE LISTING PROVIDED ON COMPACT DISCS

An electronic version on compact disc (CD-R) of the Sequence Listing is filed herewith in duplicate (labeled Copy #1 and Copy #2), the contents of which are incorporated by reference in their entirety. The computer-readable file on each of the aforementioned compact discs, created on Jan. 23, 2013, is identical, 464 kilobytes in size, and titled 235seq.001.txt

FIELD OF INVENTION

Provided herein are ATP-binding cassette transporters (ABC transporters). More specifically, the present disclosure relates to ABC terpenoid transporters, nucleic acid sequences, amino acids, proteins, vectors, cells, transgenic organisms, uses, compositions, methods, processes, and kits thereof.

BACKGROUND

Pine trees and processed wood (lumber and logs) are colonized by ascomycete ophiostomatoid fungi that include pathogens and saprobes. To colonize conifers (e.g. lodgepole pine), including to survive and become established in a pine tree, fungi and their bark beetle vectors have to cope with the host's preformed and induced defense chemicals, which include terpenoid and phenolic compounds. It is an object herein to provide molecules that induce tolerance to such chemical defenses, and methods based thereon.

SUMMARY

Provided herein are ABC terpenoid transporters, including nucleic acid sequences, amino acid sequences, proteins, vectors, cells, transgenic organisms, uses, compositions, methods, processes, and kits thereof. For example, one, or more than one ABC terpenoid transporter provided herein contains a polypeptide having the amino acid sequence set forth in SEQ ID NO:1, SEQ ID NO:3, SEQ ID NO:5 an active fragment thereof, or sequence identical thereto. Furthermore, provided herein are a nucleic acid encoding the polypeptide sequence set forth in SEQ ID NO:1, SEQ ID NO:3 or SEQ ID NO:5. The nucleic acid can contain the sequence set forth in SEQ ID NO: 2 SEQ ID NO:4, SEQ ID NO:6 or a sequence identical thereto.

Also provided herein is a method for producing a terpenoid resistant cell, by transforming the cell with a vector containing an ABC terpenoid transporter. Also provided herein is a method for producing a cell for improved secretion of terpenoids, by transforming the cell with a vector containing an ABC terpenoid transporter.

The subject matter provided herein also relates to pathogenicity marker containing an ABC terpenoid transporter. Provided herein is a method for identifying a pathogen including (a) obtaining a sample from an organism, or part thereof, infected with a pathogen, or from a culture isolated from a symptomatic or asymptomatic diseased organism; (b) contacting the sample with a probe that specifically binds to the pathogenicity marker containing an ABC terpenoid transporter; and (c) detecting the probe; thereby identifying a pathogen in an organism.

Provided herein is an isolated nucleic acid molecule encoding an ABC terpenoid transporter, wherein the ABC terpenoid transporter transports a terpenoid across a membrane of a microbial cell. The transporter is not a diterpene transporter from *Arabidopsis* or *Nicotiana* species. In some examples, the ABC terpenoid transporter transports a monoterpenoid across a membrane of a microbial cell. In some example, the ABC transporter is an ascomycete ophiostomatoid fungi ABC monoterpenoid transporter that is an *Ophiostoma piceae* or *Grosmannia clavigera* ABC transporter. The microbial cell is a fungal cell, such as a yeast cell.

Provided herein is an isolated nucleic acid molecule encoding an ABC terpenoid transporter having a sequence of nucleotides selected from among a) the polypeptide having a sequence of amino acids set forth in SEQ ID NOS:1, 3, 5 or 7; b) an active fragment of the polypeptide of a); and c) a polypeptide having a sequence of amino acids that has at least 85% sequence identity with a polypeptide of a) or b), wherein the encoded polypeptide or active fragment transports a terpenoid across a membrane of a microbial cell. In one example, the sequence of nucleotides encodes an ABC terpenoid transporter that has the sequence of amino acids set forth in SEQ ID NO:1; SEQ ID NO:3, SEQ ID NO: 5 or SEQ ID NO:7 or an active fragment thereof. In another example, the sequence of nucleotides encodes an ABC terpenoid transporter that includes the sequence of amino acids set forth in SEQ ID NO:1; SEQ ID NO:3, SEQ ID NO: 5 or SEQ ID NO:7 or an active fragment thereof. In some examples, the isolated nucleic acid molecule has a sequence of nucleotides selected from among a) the nucleic acid molecule whose sequence is set forth in any of SEQ ID NOS:2, 4, 6 or 8 or a portion thereof that encodes an active fragment; and b) a nucleic acid molecule whose sequence of nucleotides has at least 85% sequence identity to the sequence of nucleotides set forth in one of SEQ ID NOS:2, 4, 6 or 8 or the complement thereof, wherein the sequence of nucleotides encodes a polypeptide or an active fragment of the polypeptide that transports a terpenoid across a membrane of a microbial cell. In one example, the isolated nucleic acid molecule has the sequence of nucleotides set forth in any of SEQ ID NOS:2, 4, 6 or 8 or a portion thereof that encodes an active fragment. In another example, the isolated nucleic acid molecule contains the sequence of nucleotides set forth in any of SEQ ID NOS:2, 4, 6 or 8 or a portion thereof that encodes an active fragment.

Also provided herein is a nucleic acid molecule encoding an ABC terpenoid transporter having a polypeptide comprising the sequence set forth in SEQ ID NO:1; SEQ ID NO:3; SEQ ID NO:5; SEQ ID NO:7, a fragment thereof, or sequence identical thereto. In one example, the nucleic acid has the sequence set forth in SEQ ID NO:2, SEQ ID NO:4, SEQ ID NO:6, SEQ ID NO:8 or a sequence identical thereto. In another example, the nucleotide sequence is at least 70% identical to SEQ ID NO: 2; SEQ ID NO: 4, SEQ ID NO:6 or SEQ ID NO:8. In yet another example, the nucleotide sequence is at least 80% identical to SEQ ID NO: 2; SEQ ID NO: 4, SEQ ID NO:6 or SEQ ID NO:8. In a further example, the nucleotide sequence is at least 90% identical to SEQ ID NO: 2; SEQ ID NO: 4, SEQ ID NO:6 or SEQ ID NO:8. In another example, the nucleotide sequence is at least 95% identical to SEQ ID NO: 2; SEQ ID NO: 4, SEQ ID NO:6 or SEQ ID NO:8. In one example, the nucleic acid encodes a polypeptide that is at least 70% identical to SEQ ID NO:1; SEQ ID NO:3, SEQ ID NO: 5 or SEQ ID NO:7. In another example, the nucleic acid encodes a polypeptide that is at least 80% identical to SEQ ID NO:1; SEQ ID NO:3, SEQ ID NO: 5 or SEQ ID NO:7. In yet another example, the nucleic acid encodes a polypeptide that is at least 90% identical to SEQ ID NO:1; SEQ ID NO:3, SEQ ID NO: 5 or SEQ ID NO:7. In a further example, the nucleic acid encodes a polypeptide that is at least 95% identical to SEQ ID NO:1; SEQ ID NO:3, SEQ ID NO: 5 or SEQ ID NO:7.

Also provided herein are ABC terpenoid transporter polypeptides encoded by any of the isolated nucleic acid molecules provided herein. Also provided herein are vectors containing isolated nucleic acid molecules encoding ABC terpenoid transporters provided herein. Also provided herein are cells containing the vectors provided herein. The cells can be a prokaryotic or eukaryotic host cell. In some examples, the cell is selected from among a bacterial, fungal, plant, insect, amphibian and animal cell. In one example, the cell is an *E. coli* cell or a yeast cell. In another example, the cell is a fungal cell, such as a yeast cell. In some examples, the cell produces geranyl pyrophosphate or diphosphate (GPP). For example, the cell is transformed with one or more sequences that result in production of GPP.

Also provided herein is a method for increasing the production of a terpenoid in a cell, e.g., a host cell, that contains a heterologous nucleic acid molecule encoding an ABC terpenoid transporter provided herein. In some examples the method includes introducing the nucleic acid molecule encoding the ABC terpenoid transporter into a cell, e.g., a host cell. The cell can be a fungal cell, such as a yeast cell. In some examples of the method, the cell produces geranyl pyrophosphate or diphosphate (GPP). For example, the cell is transformed with one or more sequences that result in production of GPP. In some examples of the method, the terpenoid is a monoterpene. For example, the terpenoid is a monoterpene that is selected from among geraniol, linalool, R-(+)-limonene, 3-carene, α-pinene and β-pinene.

Also provided herein is a method for producing a terpenoid resistant cell, e.g., a terpenoid resistance host cell, wherein a cell is transformed with a nucleic acid molecule encoding an ABC terpenoid transporter or a vector provided herein. Also provided herein is a method for producing a cell for improved secretion of terpenoids, wherein a cell, e.g., a host cell, is transformed with a nucleic acid molecule encoding an ABC terpenoid transporter or a vector provided herein. Also provided herein is a pathogenicity marker containing any ABC terpenoid transporter polypeptide provided herein. Also provided herein is a pathogenicity marker containing any nucleic acid molecule encoding an ABC terpenoid transporter, or a fragment thereof, provided herein.

Also provided herein is a method for identifying a pathogen wherein the method involves (a) obtaining a sample from an organism, or part thereof, infected with a pathogen, or from a culture isolated from a symptomatic or asymptomatic diseased organism; (b) contacting the sample with a probe that specifically binds to the pathogenicity marker and (c) detecting the probe; thereby identifying a pathogen in an organism.

Provided are cells that encode a heterologous ABC terpenoid transporter. The cells generally are eukaryotic cells, the terpenoid transporter is a fungal species transporter and is heterologous to the host cell. An ABC terpenoid transporter transports a terpenoid across a membrane of a cell. The transporter is not native to the cell so that the cell normally does not encode the terpenoid transporter. The transporter is not encoded by nucleic acid native to the cell that encodes another transporter that has been mutated so that the native transporter transports terpenoids. Generally, because the cell expresses the terpenoid transporter it is more resistant to a terpene (generally of the type that is transported out of the cell by the transporter) than a cell of the same species or the same cell that does not express the transporter. The cells can express nucleic acids that encode enzymes and products that participate in the production of terpenes. Typically, such enzymes and products are engineered in the cell. Such enzymes and other products include terpene synthases and other enzymes, such as one or more a cytochrome P450 enzymes, that modify or result in production of terpenes and optionally a cytochrome P450 enzyme. The eukaryotic cells that express the transporter can be non-human cells, such as a fungal, plant, insect, amphibian and non-human animal cells. For example, the cell can be a fungal cell, generally of a different species from which the transporter was originally obtained. Yeast cells are exemplary of such cells, and exemplary yeast cell lines, include those that have been engineered or modified to produce terpenes. Exemplary cell lines include, but are not limited to, cells designated YPH499, WAT11, BY4741, CALI5-1, ALX7-95 and ALX11-30.

In exemplary embodiments, the terpenoids include or are monoterpenoids. The ABC transporter is an ascomycete ophiostomatoid fungi ABC monoterpenoid transporter, such as, but not limited to, an *Ophiostoma piceae* and/or *Grosmannia clavigera* ABC transporter. The cells can express a plurality of transporters, such as transporters specific for different types of terpenes. Exemplary transporters include, but are not limited to, *Neurospora crassa, Giberella zea, Nectria haemotococca* and *Magnaporthe grisea* ABC terpenoid transporters and the transporters provided herein.

ABC transporters provided include an ABC transporter selected from among: a) a polypeptide comprising a sequence of amino acids set forth in SEQ ID NOS:1, 3, 5 or 7; b) an active fragment, which fragment effects transport of a terpene or terpenoid, of the polypeptide of a); and c) a polypeptide having a sequence of amino acids that has at least 60%, 65%, 70%, 75%, 80%, 85%, 90%, 95% or more sequence identity with a polypeptide of a) or b), where the encoded polypeptide or active fragment transports a terpenoid across a membrane of the cell. Particular embodiments include, but are not limited to, the ABC terpenoid transporter that includes or contains only the sequence of amino acids set forth in SEQ ID NO:1; SEQ ID NO:3, SEQ ID NO: 5 or SEQ ID NO:7 or an active fragment thereof. These transporters are encoded by a sequence of nucleotides selected from among: a) the nucleic acid molecule whose sequence is set forth in any of SEQ ID NOS:2, 4, 6 or 8 or a portion thereof that encodes an active fragment; and b) a nucleic acid molecule includes degenerate codons of the molecule of a) and sequences of nucleotides and degenerates thereof that encode the polypeptides.

As noted, the cells provided herein can also encode a one or more terpene synthases and optionally other enzymes and products involved in terpene synthesis. The encoded synthases and/or other enzymes or other products can be native to the cell or heterologous. In particular embodiments, the cells encode a synthase that catalyzes production of a monoterpene. Exemplary of such synthases are limonene synthase, 3-carene synthase, α-pinene synthase, β-pinene synthase, geraniol synthase and linalool synthase. Cells that encoded such synthases are well known. The cells can additional encode other enzymes and products, such as, for example, a cytochrome P450 that catalyzes a reaction whereby the terpene product produced in the presence of the synthase is modified. Exemplary P450 enzymes include any that catalyze hydroxylation, oxidation, demethylation, methylation or monooxygenation of a terpene.

Also provided are methods for producing terpenes and terpenoids by culturing or growing any of the cells provided that encode a transporter and also produce terpenes. The terpene/terpenoid products or a product optionally are isolated. Employing the cells that encode the transporter increases production of any terpenoid or terpene product that such cells produce compared to such cells that do not encode the transporter. Hence provided are methods for increasing production of terpene/terpenoid products by including nucleic acid that encodes an ABC transporter in a cell that produces terpenes. Terpene synthases that are encoded in the cells generally catalyzes the formation of a terpenoid from an acyclic pyrophosphate terpene precursor, such as but not limited to, geranyl pyrophosphate (GPP), farnesyl pyrophosphate (FPP) and geranyl-geranyl pyrophosphate (GGPP), particularly precursors, such as GPP, of monoterpenes. The cells also can produce other terpenes, including a sesquiterpene and or a diterpene, and can encode a transporter that transports such terpenes. Exemplary monoterpenes include, but are not limited to, R-(+)-limonene, 3-carene, α-pinene, β-pinene, geraniol and linalool.

Also provided herein is a method for identifying ascomycete ophiostomatoid fungal infection in an organism, including the steps of (a) obtaining a sample from an organism, or part thereof, infected with a pathogen, or from a culture isolated from a symptomatic or asymptomatic diseased organism; (b) contacting the sample with a probe that specifically binds to a nucleic acid encoding an ascomycete ophiostomatoid fungi ABC monoterpenoid transporter or to the encoded transporter; and (c) detecting the probe, whereby detection of the probe identifies infection with an ascomycete ophiostomatoid fungi. In further embodiments, detection is effected by hybridization with the probe or amplification with the probe; the probe is a nucleic acid molecule that contains at least 15 contiguous nucleotides and that hybridizes or amplifies under conditions of at least low stringency to the nucleic acid encoding the ABC monoterpenoid transporter. In some examples, the probe hybridizes or amplifies under conditions of at least moderate or high stringency. In such methods, the nucleic acid encoding the ABC terpenoid transporter contains a sequence of nucleotides selected from among a) a polypeptide having the sequence of amino acids set forth in any of SEQ ID NOS:1, 3, 5 and 7; b) an active fragment of the polypeptide of a); and c) a polypeptide having a sequence of amino acids that has at least 85% sequence identity with a polypeptide of a) or b), wherein the encoded polypeptide or active fragment transports a terpenoid across a membrane of a microbial cell. In some example, the organism can be a plant, such as a tree, such as a tree of the species *Pinus contorta*, *Pinus banksiana* or *Pinus jeffriei*. In some examples, the pathogen can be *Grosmannia clavigera* or *Ophiostoma piceae*.

It is understood that this summary of subject matter provided herein does not necessarily describe all features provided herein.

BRIEF DESCRIPTION OF THE DRAWINGS

These and other features provided herein will become more apparent from the following description in which reference is made to the appended drawings wherein:

FIG. 2A. *S. cerevisiae* strain transformed with GcABC-G1 has the same growth phenotype as the control on SG medium without monoterpenoids (MT). FIG. 2B. *S. cerevisiae* transformed with GcABC-G1 showed colonies on SG with monoterpenoid (MT) treatment after 1-week incubation, while the control did not grow.

FIG. 3A RNA-seq result for the GcABCs that were up-regulated for at least one type of terpenoid treatment. 12 h CM+T and 36 h CM+T: Gc mycelia grown on complete media (CM) and treated with mono/diterpene blend for 12 and 36 h. YNB+MT: Gc mycelia grown for 10 days on YNB minimal media with a mixture of monoterpenes (MT) as sole carbon source. MT: (+)-limonene, 3-carene, α-pinene and (−)-β-pinene at a ratio of 5:3:1:1. FIG. 3B and FIG. 3C. RT-qPCR validation of the mRNA abundance of GcABC-G1 on CM-T (B) and YNB+MT (C). Growth and treatment conditions were the same as for (A). mRNA abundance was normalized using β-tubulin, a housekeeping gene. Graphs show averages of three biological replicates; error bars show standard deviations. Except for 0 hr CM+T, all time points in (B) and (C) were significantly different from the controls (p<0.01, Student's t test).

FIG. 4A. Growth after 4 days without treatment (top) or after 7 days with 200 μL mixture of monoterpenes (MT) treatment (bottom). FIG. 4B. Mycelium growth rates with 200 μL of individual or a mixture of monoterpenes. Error bars are 95% confidence intervals on means. FIG. 4C. Asexual spore germination on MEA treated with 200 μL of individual monoterpenes. Germinated spores were counted after 3 days (control) and 6 days (monoterpene treatment); percentages are relative to the non-treated control. Results are average of 5 replicates; error bars are standard deviations. Ctrl: Control, αPin: α-pinene, (−)-β-pinene, 3Car: 3-carene, Lim: (+)-limonene, MT: (+)-limonene, 3-carene, α-pinene and (−)-β-pinene at a ratio of 5:3:1:1.

FIG. 6A. Spot test. Top plate:

Sc-V and Sc-ABC on SG medium after 3 days incubation. Bottom plate: Sc-V and Sc-ABC on SG medium with 60 μL (+)-limonene after a one-week incubation. FIG. 6B. Cell survival after 4 days. Results are average of 10 replicates; error bars represent standard deviations. Lim: (+)-limonene, 3Car: 3-carene, αPin: α-pinene, βPin: (−)-β-pinene.

FIG. 10a. Representative symptoms at different times after fungal inoculation. (1) Healthy tree. The tree in this image was inoculated with a MEA agar plug with no fungus. (2) Tree with wilting shoots and browning needles. (3) Tree with brown needles on branches and leader shoots. (4) Tree with all needles and shoots dead. FIG. 10b. Percentage of healthy trees at four weeks after inoculation with *G. clavigera* and the Δgcabc-g1 mutant. Ctrl: agar inoculation without fungus. Mt: Mutant Δgcabc-g1. Because the three independent experiments were carried out at different times within two years (April 2011, May 2012 and June, 2012), the development of the leader shoots of the healthy trees differed somewhat between the experiments, therefore the result of each experiment are shown separately.

FIG. 11a. Lesion next to the point of inoculation without fungus (control), *G. clavigera* at 4 d, 7 d and 14 d, or its mutant at 7 d (M: 7 d). FIG. 11b. (b) GcABC-G1 transcript abundance at different times after inoculation. Error bars represent standard deviations from three technical replicates.

DETAILED DESCRIPTION

Figure 1:
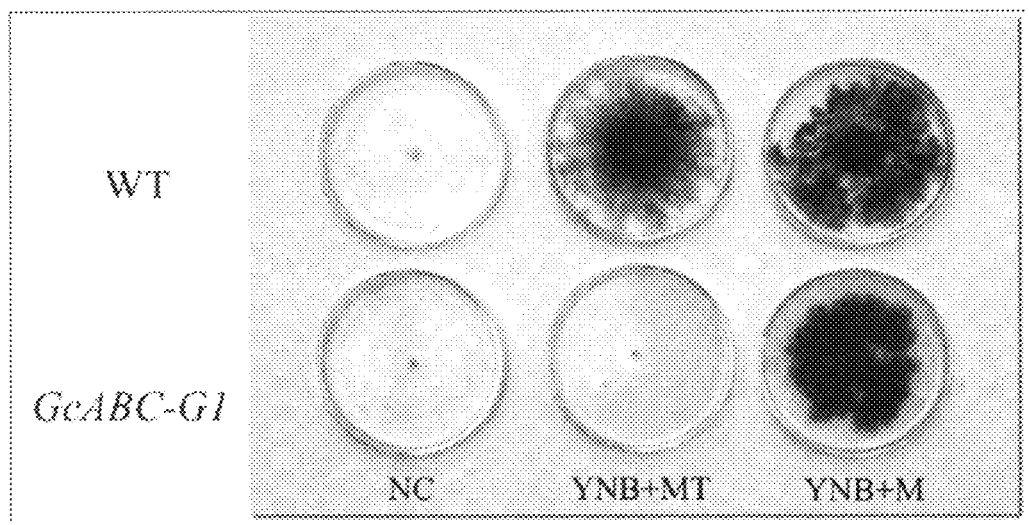
FIG. 1 shows the phenotype of wildtype *G. clavigera* and the *G. clavigera* GcABC-G1 mutant (Δgcabc-g1) when grown on YNB with different carbons. NC: YNB alone (no carbon). YNB+MT: YNB with monoterpenoids. YNB+M: YNB with mannose.

Outline
A. Definitions
B. Fungal Tolerance to Monoterpenes and Methods Based Thereon
C. ABC Terpenoid Transporter
  1. ABC Transporter from *Grosmannia Clavigera* (Gc) and Related Molecules
  2. ABC Transporter from *Ophiostoma piceae* (Op) and Related Molecules
D. Methods of Producing or Generating ABC Transporters, Vectors & Host Cells
E. Exemplary Uses of ABC Transporters
  1. Methods of Microbial Production of Terpenoids
  2. Methods for detecting, identifying, detecting and/or identifying a pathogen
F. Examples

A. DEFINITIONS

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, in general *G. clavigera* includes two cryptic species, Gc and Gs (Alamouti et al. (2011) *Mol Ecol* 20:2581-2602). The name Gc should be reserved for the holotype described in 1968. The species exemplified herein belongs to the Gs group. But for continuity with the description in DiGuistini et al. (*Proc Natl Acad Sci USA* 108:2504-2509 (2011)), the species exemplified herein is referenced herein by the name Gc. Thus, for purposes herein *Grosmannia clavigera* or Gc refers to wild type *Grosmannia clavigera* (Gc) strain kw1407 (NCBI Taxonomy ID: 655863). The strain kw1407 is available from the University of Alberta Microfungus Collection and Herbarium (UAMH Catalogue #11150). This strain also was deposited at the International Depositary Authority of Canada, National Microbiology Laboratory, Public Health Agency of Canada (1015 Arlington Street, Winnipeg, Manitoba, Canada, R3E 3R2) under Accession number 030212-01 on Feb. 3, 2012.

As used herein, *Ophiostoma piceae* or Op refers to the *O. piceae* strain that was isolated from *Pinus contorta* lumber (Uzunovic et al. (1999) *Can J Microbiol* 45(11):914-922), and is available from the University of Alberta Microfungus Collection and Herbarium, Edmonton, Alberta, Canada (UAMH Catalogue #11346).

As used herein, an ascomycete ophiostomatoid fungi refers to a fungus in the phylum Ascomycota, class Sordariomycetes, order Ophiostomatales, family Ophiostomataceae and type genus *Ophiosotoma*, including genera *Grosmannia* and *Ophiosotoma*, that are typically pathogens of coniferous and deciduous trees. Ascomycete ophiostomatoid fungi include *Grosmannia* and *Ophiostoma* species, such as *Grosmannia clavigera* or *Ophiostoma piceae*.

As used herein, "ABC terpenoid transporter" refers to a protein that contains an ABC terpenoid transporter and transport terpenoids across a membrane. Hence, an ABC terpenoid transporter includes a polypeptide capable of transporting terpenoids and related compounds across a membrane in which it is located. More specifically, the terpenoid ABC transporter includes a terpenoid efflux transporter that removes terpenes and related compounds from a cell. For example, the ABC terpenoid transporter include, ABC monoterpenoid transporter. The ABC terpenoid transporter can be derived from *Ophiostoma* or *Grosmannia* species, such as *Grosmannia clavigera* (Gc) or *Ophiostoma piceae* (*O. piceae*). Non-limiting examples of ABC monoterpenoid transporters are GcABC-G1 (SEQ ID NO:1), GcABC-G2 (SEQ ID NO:3) or GcABC-G3 (SEQ ID NO:5) or OPP_06758-RA (SEQ ID NO:7). Reference to an "ABC terpenoid transporter" herein also includes an ABC terpenoid transporter that has greater than 63%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity with the ABC terpenoid transporter set forth in SEQ ID NO:1, SEQ ID NO:3, SEQ ID NO:5 or SEQ ID NO:7 or an active fragment thereof.

As used herein, a "monoterpenoid transporter" refers to an ABC transporter that translocates a monoterpene substrate across membranes. For purposes herein, one determines whether a polypeptide encoded by a nucleic acid is an ABC monoterpenoid transporter by the enzyme characterization assay described in the examples herein.

As used herein, an active fragment of an ABC transporter, such as an active fragment of any of SEQ ID NOS: 1, 3, 5 or 7, refers to a contiguous sequence of amino acids of an ABC transporter polypeptide that exhibits activity to transport a terpenoid (e.g. monoterpenoid) across a membrane, but that does not include the full-length of the polypeptide, such as a polypeptide whose sequence is set forth in SEQ ID NO:1, 3, 5 or 7. The active fragment generally contains at least or about at least 300, 400, 500, 600, 700, 800, 900, 1000, 1100, 1200, 1300, 1400 or more amino acid residues.

As used herein, the terms "terpene" and "terpenoid" are meant to include all compounds that contain hydrocarbons containing one or more of an isoprene unit [$CH_2=C(CH_3)-CH=CH_2$ or $(C_5H_8)_n$]. The terpenoid can be one of the acyclic terpenoids, cyclic terpenoids, cycloaliphatic compounds that are structurally related to terpenoids, and mixtures thereof. Furthermore, a terpenoid can be a monoterpenoid. Monoterpenoids are terpenoids that contain two isoprene units. Examples of monoterpenoids include but are not limited to pine tree monoterpenes for example R-(+)-limonene, 3-carene, α-pinene and β-pinene.

As used herein, a terpenoid resistant cell refers to a cell that exhibits increased resistance to terpenes because it expresses an ABC transporter, including any provided herein. Such a cell is more resistant to terpenes, particularly a terpene that is transported by the transporter, than the same cell that does not express such transporter. Such cells are more resistant because the transporter facilitates transport of a terpenoid across the cell membrane thereby reducing accumulation of terpenes, which, when they accumulate, can cause cellular toxicity.

As used herein, an acyclic an acyclic pyrophosphate precursor is any acyclic pyrophosphate compound that is a precursor to the production of at least one terpene, including, but not limited, farnesyl-pyrophosphate (FPP), to geranyl-pyrophosphate (GPP), and geranylgeranyl-pyrophosphate (GGPP). Acyclic pyrophosphate terpene precursor are thus substrates for terpene synthases.

As used herein, a terpene synthase is a polypeptide capable of catalyzing the formation of one or more terpenes from an acyclic pyrophosphate terpene precursor, for example, FPP, GPP or GGPP.

As used herein, a "P450 polypeptide," "cytochrome P450," or "P450" is meant a polypeptide that contains a heme-binding domain and shows a CO absorption spectra peak at 450 nm according to standard methods. Such P450s may also include, without limitation, hydroxylase activity, dual hydroxylase activity, demethylase activity, or oxidase activity. Such enzymatic activities are determined using methods well known in the art.

As used herein, a cell containing a heterologous ABC terpenoid transporter refers to a cell that contains or encodes or expresses an ABC terpenoid transporter not normally expressed by the cell nor produced by mutation of a native transporter. Hence the transporter is non-native to the cell, and, typically is a transporter encoded by a different species.

As used herein, nucleic acids or nucleic acid molecules include DNA, RNA and analogs thereof, including peptide nucleic acids (PNA) and mixtures thereof. Nucleic acids can be single or double-stranded.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule cannot be paired. Such unpaired ends will, in general, not exceed 20 nucleotides in length.

As used herein, a peptide refers to a polypeptide that is greater than or equal to 2 amino acids in length, and less than or equal to 40 amino acids in length.

As used herein, the amino acids which occur in the various sequences of amino acids provided herein are identified according to their known, three-letter or one-letter abbreviations (Table 1). The nucleotides which occur in the various nucleic acid fragments are designated with the standard single-letter designations used routinely in the art.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

As used herein, "amino acid residue" refers to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide. NH₂ refers to the free amino group present at the amino terminus of a polypeptide. COOH refers to the free carboxy group present at the carboxyl terminus of a polypeptide. In keeping with standard polypeptide nomenclature described in J. Biol. Chem. 243:3557-3559 (1968), and adopted 37 C.F.R. §§1.821-1.822, abbreviations for amino acid residues are shown in Table 1:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

All amino acid residue sequences represented herein by formulae have a left to right orientation in the conventional direction of amino-terminus to carboxyl-terminus. In addition, the phrase "amino acid residue" is defined to include the amino acids listed in the Table of Correspondence (Table 1) and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues, to an amino-terminal group such as NH₂ or to a carboxyl-terminal group such as COOH.

As used herein, "naturally occurring amino acids" refer to the 20 L-amino acids that occur in polypeptides.

As used herein, "non-natural amino acid" refers to an organic compound containing an amino group and a carboxylic acid group that is not one of the naturally-occurring amino acids listed in Table 1. Non-naturally occurring amino acids thus include, for example, amino acids or analogs of amino acids other than the 20 naturally-occurring amino acids and include, but are not limited to, the D-isostereomers of amino acids. Exemplary non-natural amino acids are known to those of skill in the art.

As used herein, modification is in reference to modification of the primary sequence of amino acids of a polypeptide or a sequence of nucleotides in a nucleic acid molecule and includes deletions, insertions, and replacements and rearrangements of amino acids and nucleotides. Modifications can be made by making conservative amino acid replacements and also non-conservative amino acid substitutions as well as by insertions and other such changes in primary sequence. Modifications also can include post-translational modifications or other changes to the molecule that can occur due to conjugation or linkage, directly or indirectly, to another moiety, but when such modifications are contemplated they are referred to as post-translational modifications or conjugates or other such term as appropriate. Methods of modifying a polypeptide are routine to those of skill in the art, and can be performed by standard methods, such as site directed mutations, amplification methods, and gene shuffling methods.

As used herein, amino acid replacements or substitutions contemplated include, but are not limited to, conservative substitutions, including, but not limited to, those set forth in Table 2. Suitable conservative substitutions of amino acids are known to those of skill in the art and can be made generally without altering the conformation or activity of the polypeptide. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. co., p. 224). Conservative amino acid substitutions are made, for example, in accordance with those set forth in Table 2 as follows:

TABLE 2

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu; Met |

Other conservative substitutions also are permissible and can be determined empirically or in accord with known conservative substitutions.

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, "primary sequence" refers to the sequence of amino acid residues in a polypeptide.

As used herein, the phrase "identical," "substantially identical," or "substantially as set out," means that a relevant sequence is at least 60%, 65%, 70%, 75%, 80%, 85%, 90%, 92%, 95%, 96%, 97%, 98%, or 99% identical to a given sequence. By way of example, such sequences can be allelic variants, sequences derived from various species, or they can be derived from the given sequence by truncation, deletion, amino acid substitution or addition. For polypeptides, the length of comparison sequences will generally be at least 20, 30, 50, 100 or more amino acids. For nucleic acids, the length of comparison sequences will generally be at least 50, 100, 150, 300, or more nucleotides. Percent identity between two sequences is determined by standard alignment algorithms such as, for example, Basic Local Alignment Tool (BLAST) described in Altschul et al. (1990) *J. Mol. Biol.*, 215:403-410, the algorithm of Needleman et al. (1970) *J. Mol. Biol.*, 48:444-453, or the algorithm of Meyers et al. (1988) *Comput. Appl. Biosci.*, 4:11-17.

As use herein, "sequence identity" refers to the number of identical amino acids (or nucleotide bases) in a comparison between a test and a reference polypeptide or polynucleotide. Homologous polypeptides refer to two or more peptides that have a pre-determined number of identical or conservative amino acid residues. Homology also includes substitutions that do not change the encoded amino acid (i.e. "silent substitutions"). Sequence identity can be determined by standard alignment algorithm programs used with default gap penalties established by each supplier. Homologous nucleic acid molecules refer to two or more nucleotides that have a pre-determined number of identical or homologous nucleotides. Substantially homologous nucleic acid molecules hybridize typically at moderate stringency or at high stringency all along the length of the nucleic acid or along at least about 70%, 80% or 90% of the full-length nucleic acid molecule of interest. Also contemplated are nucleic acid molecules that contain degenerate codons in place of codons in the hybridizing nucleic acid molecule. (For determination of homology of proteins, conservative amino acids can be aligned as well as identical amino acids; in this case, percentage of identity and percentage homology varies). Techniques for computing amino acid sequence similarity or identity are well known to those skilled in the art. Whether any two nucleic acid molecules have nucleotide sequences (or any two polypeptides have amino acid sequences) that are at least 80%, 85%, 90%, 95%, 96%, 97%, 98% or 99% "identical" can be determined using known computer algorithms such as the "FAST A" program, using for example, the default parameters as in Pearson et al. *Proc. Natl. Acad. Sci. USA* 85: 2444 (1988) (other programs include the GCG program package (Devereux, J., et al., *Nucleic Acids Research* 12(I): 387 (1984)), BLAST (basic local alignment search tool), BLASTP, BLASTN, FASTA (Atschul, S. F., et al., *J. Molec. Biol.* 215:403-410 (1990); ALTSCHUL et al. (1997), *Nucleic Acids Res.* 25: 3389-3402; *Guide to Huge Computers*, Martin J. Bishop, ed., Academic Press, San Diego (1994), and Carillo et al. *SIAM J Applied Math* 48: 1073 (1988)). For example, the BLAST function of the National Center for Biotechnology Information database can be used to determine identity. Other commercially or publicly available programs include DNAStar "MegAlign" program (Madison, Wis.) and the University of Wisconsin Genetics Computer Group (UWG) "Gap" program (Madison Wis.)). Percent homology or identity of proteins and/or nucleic acid molecules can be determined, for example, by comparing sequence information using a GAP computer program (e.g., Needleman et al. *J. Mol. Biol.* 48: 443 (1970), as revised by Smith and Waterman (*Adv. Appl. Math.* 2: 482 (1981)). Briefly, a GAP program defines similarity as the number of aligned symbols (i.e., nucleotides or amino acids) which are similar, divided by the total number of symbols in the shorter of the two sequences. Default parameters for the GAP program can include: (1) a unary comparison matrix (containing a value of 1 for identities and 0 for non identities) and the weighted comparison matrix of Gribskov et al. *Nucl. Acids Res.* 14: 6745 (1986), as described by Schwartz and Dayhoff, eds., *Atlas of Protein Sequence and Structure*, National Biomedical Research Foundation, pp. 353-358 (1979); (2) a penalty of 3.0 for each gap and an additional 0.10 penalty for each symbol in each gap; and (3) no penalty for end gaps. Clustal analysis also can be used to align either nucleotide or protein sequences and to score their level of identity and similarity (available at ebi.ac.uk/Tools/msa/clusalw2/ or ebi.ac.uk/ebisearch/search.ebi?db=medline&t=clustal*).

Therefore, as used herein, the term "identity" represents a comparison between a test and a reference polypeptide or polynucleotide. In one non-limiting example, "at least 90% identical to" refers to percent identities from 90 to 100% relative to the reference polypeptides. Identity at a level of 90% or more is indicative of the fact that, assuming for exemplification purposes a test and reference polypeptide length of 100 amino acids are compared, no more than 10% (i.e., 10 out of 100) of amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences are defined as nucleic acid or amino acid substitutions, insertions or deletions. At the level of homologies or identities above about 85-90%, the result should be independent of the program and gap parameters set; such high levels of identity can be assessed readily, often without relying on software.

A substantially similar sequence is an amino acid sequence that differs from a reference sequence only by one or more conservative substitutions. Such a sequence can, for example, be functionally homologous to another substantially similar sequence. It will be appreciated by a person of skill in the art the aspects of the individual amino acids in a peptide provided herein can be substituted. It also is understood that the terms "substantially identical" or "similar" varies with the context as understood by those skilled in the relevant art, but that those of skill can assess such.

As used herein, an aligned sequence refers to the use of homology (similarity and/or identity) to align corresponding positions in a sequence of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound can, however, be a mixture of stereoisomers or isomers. In such instances, further purification might increase the specific activity of the compound.

As used herein, isolated or purified polypeptide or protein or biologically-active portion thereof is substantially free of cellular material or other contaminating proteins from the cell of tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as proteolytic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound.

As used herein, substantially free of cellular material includes preparations of proteins or terpene products in which the protein or product is separated from cellular components of the cells from which it is isolated or produced. In one embodiment, the term substantially free of cellular material includes preparations of having less that about or less than 30%, 20%, 10%, 5% or less (by dry weight) of non-protein or terpene product, including cell culture medium. When the synthase is recombinantly produced, it also is substantially free of culture medium, i.e., culture medium represents less than about or at 20%, 10% or 5% of the volume of the protein preparation.

As used herein, the term substantially free of chemical precursors or other chemicals includes preparations of proteins or terpene products that is separated from chemical precursors or other chemicals that are involved in the synthesis thereof. The term includes preparations of proteins or terpene products having less than about or less than 30% (by dry weight), 20%, 10%, 5% or less of chemical precursors or non-protein chemicals or components.

As used herein stringency of hybridization include the following conditions:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

or equivalent conditions. Those of skill in the art can select conditions such that hybrids of a particular percentage of mismatch/match are identified. Those of skill in this art know that the washing step selects for stable hybrids and also know the ingredients of SSPE (see, e.g., Sambrook, E. F. Fritsch, T. Maniatis, in: *Molecular Cloning, A Laboratory Manual*, Cold Spring Harbor Laboratory Press (1989), vol. 3, p. B.13, see, also, numerous catalogs that describe commonly used laboratory solutions). SSPE is pH 7.4 phophate-buffered 0.18 NaCl. Further, those of skill in the art recognize that the stability of hybrids is determined by Tm, which is a function of the sodium ion concentration and temperature (Tm=81.5° C.−16.6($\log_{10}$[Na$^+$])+0.41(% G+C)−600/l)), so that the only parameters in the wash conditions critical to hybrid stability are sodium ion concentration in the SSPE (or SSC) and temperature.

It is understood that equivalent stringencies may be achieved using alternative buffers, salts and temperatures. By way of example and not limitation, procedures using conditions of low stringency are as follows (see also Shilo and Weinberg, *Proc. Natl. Acad. Sci. USA*, 78:6789-6792 (1981)): Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA (10×SSC is 1.5 M sodium chloride, and 0.15 M sodium citrate, adjusted to a pH of 7).

By way of example and not way of limitation, procedures using conditions of moderate stringency, include For example, but not limited to, procedures using such conditions of moderate stringency are as follows: Filters containing DNA are pretreated for 6 hours at 55° C. in a solution containing 6×SSC, 5× Denhart's solution, 0.5% SDS and 100 µg/ml denatured salmon sperm DNA. Hybridizations are carried out in the same solution and 5-20×10$^6$ cpm $^{32}$P-labeled probe is used. Filters are incubated in hybridization mixture for 18-20 hours at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art. Washing of filters is done at 37° C. for 1 hour in a solution containing 2×SSC, 0.1% SDS.

By way of example and not way of limitation, procedures using conditions of high stringency include, for example: prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and 5-20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which may be used are well known in the art.

As used herein, synthetic, with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, production by recombinant methods by using recombinant DNA methods refers to the use of the well known methods of molecular biology for expressing proteins encoded by cloned DNA.

As used herein, vector (or plasmid) refers to discrete DNA elements that are used to introduce heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as bacterial artificial chromosomes, yeast artificial chromosomes and mammalian artificial chromosomes. Selection and use of such vehicles are well known to those of skill in the art.

As used herein, expression refers to the process by which nucleic acid is transcribed into mRNA and translated into peptides, polypeptides, or proteins. If the nucleic acid is derived from genomic DNA, expression can, if an appropriate eukaryotic host cell or organism is selected, include processing, such as splicing of the mRNA.

As used herein, an expression vector includes vectors capable of expressing DNA that is operatively linked with regulatory sequences, such as promoter regions, that are capable of effecting expression of such DNA fragments.

Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, vector also includes "virus vectors" or "viral vectors." Viral vectors are engineered viruses that are operatively linked to exogenous genes to transfer (as vehicles or shuttles) the exogenous genes into cells. Viral vectors include, but are not limited to, adenoviral vectors, retroviral vectors and vaccinia virus vectors.

As used herein, operably or operatively linked when referring to DNA segments means that the segments are arranged so that they function in concert for their intended purposes, e.g., transcription initiates downstream of the promoter and upstream of any transcribed sequences. The promoter is usually the domain to which the transcriptional machinery binds to initiate transcription and proceeds through the coding segment to the terminator.

As used herein, the term assessing or determining includes quantitative and qualitative determination in the sense of obtaining an absolute value for the activity of a product, and also of obtaining an index, ratio, percentage, visual or other value indicative of the level of the activity. Assessment can be direct or indirect.

As used herein, recitation that a polypeptide "consists essentially" of a recited sequence of amino acids means that only the recited portion, or a fragment thereof, of the full-length polypeptide is present. The polypeptide can optionally, and generally will, include additional amino acids from another source or can be inserted into another polypeptide or can include regulatory elements.

As used herein, the singular forms "a", "an" and "the" include plural referents unless the context clearly dictates otherwise. Thus, for example, reference to polypeptide, comprising "an amino acid replacement" includes polypeptides with one or a plurality of amino acid replacements.

As used herein, ranges and amounts can be expressed as "about" a particular value or range. About also includes the exact amount. Hence "about 5%" means "about 5%" and also "5%."

As used herein, "optional" or "optionally" means that the subsequently described event or circumstance does or does not occur, and that the description includes instances where said event or circumstance occurs and instances where it does not. For example, an optional step of isolating a terpenoid means that the terpenoid is isolated or is not isolated.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

For clarity of disclosure, and not by way of limitation, the detailed description is divided into the subsections that follow.

B. FUNGAL TOLERANCE TO TERPENOIDS AND METHODS BASED THEREON

Provided herein are ABC Transporter polypeptides, and encoding nucleic acid molecules, that induce tolerance to terpenoids that otherwise can have toxic effects on fungi and other microbial organisms. In particular, provided herein are ABC Transporter polypeptides, and encoding nucleic acid molecules, from ophiostomatoid fungi that include pathogens and saprobes. The ABC Transporter polypeptides, and encoding nucleic acid molecules, can be used in methods for improved secretion of terpenoids in microbial cells, and in particularly fungal cells such as yeast.

Pine trees and processed wood (lumber and logs) are colonized by ascomycete ophiostomatoid fungi that include pathogens and saprobes (Seifert, K. Sapstain of commercial lumber by species of *Ophiostoma* and *Ceratocystis*. In *Ceratocystis and Ophiostoma: taxonomy, ecology, and pathogenicity*. Edited by Wingfield M, Seifert K, Webber J. St. Paul, Minn.: APS Press; 1993:141-151; Harrington, T. Diseases of conifers caused by species of *Ophiostoma* and *Leptographium*. In *Ceratocystis and Ophiostoma: taxonomy, ecology, and pathogenicity*. Edited by Wingfield M, Seifert K, Webber J. St. Paul, Minn.: APS Press; 1993:161-172). As they grow in the phloem and sapwood of the trees or in the sapwood of logs or lumber, most of these fungi produce a dark melanin pigment that causes a wood discoloration known as blue stain or sap stain. Ophiostomatoid sap stain fungi were first described more than 100 years ago (Upadhyay H: Classification of the Ophiostomatoid fungi. In *Ceratocystis and Ophiostoma: taxonomy, ecology, and pathogenicity*. Edited by Wingfield M, Seifert K, Webber J. St. Paul, Minn.: APS Press; 1993:7-13) and have been recognized as an economic problem for the forest industries worldwide.

The taxonomy of this group has been under debate for almost a century and is still evolving given recent DNA sequencing and phylogenetic analysis (Zipfel et al. (2006) *Studies in Mycology* 55(1):75-97, De Beer et al. The ophiostomatoid fungi: their dual position in the Sordariomyces. In *The ophiostomatoid fungi*. Edited by Seifert K, Wingfield M. 2012). Currently, the group contains at least five genera and includes *Ophiostoma* and *Grosmannia* and 19 species complexes. Ophiostomatoid fungi produce sticky sexual and asexual spores that are readily vectored by specific or generalist bark beetles that colonize trees or processed wood (Krokene and Solheim (1998) *Phytopathology* 88(1):39-44). In Canada before 1995, *Ophiostoma* species have been reported as the major cause of pine discoloration (Seifert, K. Sapstain of commercial lumber by species of *Ophiostoma* and *Ceratocystis*. In *Ceratocystis and Ophiostoma: taxonomy, ecology, and pathogenicity*. Edited by Wingfield M, Seifertt K, Webber J. St. Paul, Minn.: APS Press; 1993:141-151; Uzunovic et al. (1999) *Can J Microbiol* 45(10:914-922). Since 1995, the fungal associates of the mountain pine beetle (MPB; *Dendroctonus ponderosae*) belonging to the genera *Grosmannia* (mainly *G. clavigera* and *Leptographium longiclavatum*) and *Ophiostoma* (*O. montium*) have become the main cause of pine wood discoloration. The wood of trees, logs and lumber has a wide range of moisture contents and a high carbon-to-nitrogen ratio (Zabel and Morrell, Wood Stains and discolorations. In *Wood Microbiology: decay and its prevention*. Edited by Zabel R, Morrell J. San Diego, Calif.: Academic Press, Inc; 1992: 326-343). *O. piceae* prefers drier pine lumber to fresh cut logs or to intact trees; *G. clavigera*, which is vectored by mountain pine beetle (MPB), colonizes healthy or stressed living pine trees, which have high moisture and low oxygen contents. Neither organism degrades lignocellulosic wood fibers (Seifert, K. Sapstain of commercial lumber by species of *Ophiostoma* and *Ceratocystis*. In *Ceratocystis and Ophiostoma: taxonomy, ecology, and pathogenicity*. Edited by Wingfield M, Seifert K, Webber J. St. Paul, Minn.: APS Press; 1993:141-151; Schirp et al. (2003) *Wood Fiber Sci.*, 35(3):434-444).

The MPB and its fungal associates have killed large areas of pine trees in western North American conifer forests (Kurtz et al. (2008) *Nature*, 452:987-990; DiGuistini et al. (2011) *Proc. Natl. Acad. Sci.*, 108:2504-2509). For example, in British Columbia, the mountain pine beetle and its fungal associates have killed over 16 million hectares of lodgepole pine, and have spread into Alberta and Saskatchewan, where they threaten the Canadian boreal forest (URL: for.gov.b-c.ca/hfp/mountain_pine_beetle/). The pathogen *G. clavigera* and the saprophyte *O. piceae* acquire nutrients from pine species by secreting extracellular enzymes to break down large molecules like polysaccharides (e.g. hemicellulose and starch), proteins and lipids. They do not degrade wood and do not affect wood structural properties (Seifert, K. Sapstain of commercial lumber by species of *Ophiostoma* and *Ceratocystis*. In *Ceratocystis and Ophiostoma: taxonomy, ecology, and pathogenicity*. Edited by Wingfield M, Seifert K, Webber J. St. Paul, Minn.: APS Press; 1993:141-151; Uzunovic et al. Microbial Discolorations. In *Wood Discolorations and their Preventions; with Emphasis on Bluestain*. Edited by Uzunovic A, Byrne T, Gignac M, Yang D. FpInnovations; 2008:16-41; Scheffer: Microbiological degradation. In *Wood Deterioration and its Prevention by Preservative Treatments*. Edited by Nicholas D. N.Y: Syracuse University Press; 1973:31-106), so they likely have limited or incomplete cellulolytic and/or lignolytic activities.

Like all conifers, the pine hosts of the MPB epidemic have developed oleoresin-based chemical defenses that protect these trees against most potential pests and pathogens (Keeling & Bohlmann (2006) *Phytochemistry* 67: 2415-2423, Keeling & Bohlmann (2006) *New Phytol* 170: 657-675, Boone et al. (2011) *Canadian Journal of Forest Research-Revue Canadienne De Recherche Forestiere* 41: 1174-1188). The oleoresin of most conifers is made up predominantly of monoterpenes and diterpene resin acids, with smaller amounts of sesquiterpenes. These terpenes can be fungistatic or fungicidal. The lipophilic terpenes interact with membranes and membrane-bound enzymes, and can change membrane fluidity and ultrastructure (Parveen et al. (2004) *J Antimicrob Chemother* 54:46-55, Bakkali et al. (2008) *Food and Chemical Toxicology* 46:446-475). They can also cause fungal cells to swell, shrink and vacuolize (Soylu et al. (2006) *Mycopathologia* 161: 119-128).

While antimicrobial properties of monoterpenes are documented, little is known about mechanisms used by some microorganisms, particularly fungi that colonize conifers, to survive and grow in the presence of monoterpenes. Despite coniferous trees having developed efficient preformed and induced chemical defenses (e.g. oleoresin terpenoids and phenolic compounds) against the beetle-fungal complex, *G. clavigera* can kill pine trees in the absence of beetles (Yamaoka et al. (1995) *European Journal of Forest Pathology*, 25: 401-404, Lee et al. (2006) *Can J Res* 36:2864-2872). Pine chemicals, which include monoterpenoids and diterpenoids, are toxic to the beetle and the fungi. The beetle-fungus complex has developed efficient systems to overcome the toxicity of host defense chemicals (Hofstetter et al. (2005) *J. Chem. Ecol.* 31: 551-572, Kopper et al. (2005) *Environ. Entomol.* 34: 486-493).

To colonize conifers (e.g. lodgepole pine), including to survive and become established in a pine tree, fungi and their bark beetle vectors have to cope with the host's preformed and induced defense chemicals, which the include terpenoid and phenolic compounds (Franceschi et al. (2005) *New Phytol.*, 167:353-375; Keeling et al. (2006) *New Phytol.*, 170:657-675; Bohlmann et al. (2012) *Tree Physiol.*, 32:943-945). Terpenoids, and specifically monoterpenes, are among the most abundant antimicrobial pine defense chemicals. Terpenoids induce a stress response and activate a cluster of fungal genes that are involved in detoxification or tolerance of host terpenoids. For example, monoterpenes can serve as sole carbon source for Gc (DiGuistini et al. (2011) *Proc Natl Acad Sci USA* 108: 2504-2509). It is important to note that the composition of defense chemicals, especially terpenoids, varies with different pine genotypes across the landscape and can be affected by the environment (Clark et al. (2010) *Can Entomol.*, 142:557-573). Further, wood processing and drying affect the concentration of chemicals in wood products and so logs and lumber contain lower concentrations of the subset of terpenoids that are volatile (Turtola et al. (2002) *J. Environ. Qual.*, 31:1694-1701); Eberhardt et al. (2009) *Canadian Journal of Forest Research*, 39:1357-1365).

It is found herein that the pine pathogens *G. clavigera* and *O. piceae* are able to tolerate and use pine defense compounds, specifically terpenoids found in pine oleoresin. It is found that both fungi overcome terpenoid defense chemicals in their pine niches by using a similar, specialized, induced ABC efflux transporter (ABC-G transporter) for exporting monoterpenes to reduce the intracellular concentration of these toxic compounds. Similar specialized transporters likely have evolved in other ophiostomatoid fungi that are vectored by insects and inhabit the phloem and sapwood of living or processed conifers.

Specifically, it is found herein that ABC Transporters from Gc, and in particular GcABC-G1, are involved in tolerance to certain monoterpenes. As described in the Examples herein, a combination of growth experiments with a genetic deletion of GcABC-G1 in Gc, as well as heterologous expression of GcABC-G1 in fungi (e.g. *S. cerevisiae*; Sc) were performed demonstrating its tolerance to monoterpenes. The results indicate that Gc employs a combination of mechanisms to cope with monoterpene host defenses. The pathogen is protected to some degree against terpenoids by the terpenoids-induced expression of GcABC-G1, which can act as an efflux PDR ABC transporter. In addition, Gc can detoxify terpenoids or metabolize monoterpenes as a carbon source. Two other ABC-G group I transporter genes (GcABC-G2 and G3) were also up-regulated in Gc in response to terpenoids, although at a lower level than GcABC-G1. GcABC-G2 has orthologues that are described as pathogenicity factors in *M. grisea* (MGG13624), *G. pulicaris* (GpABC1), and *N. haematococca* (NECHAD-RAFT 63178) (Coleman et al. (2011) *Mol Plant-Microbe Interact* 24: 368-376, Urban et al. (1999) *EMBO J* 18:512-521, Fleissner et al. (2002) *Mol Plant-Microbe Interact* 15:102-108).

As shown herein, the Gc genome contains all ABC transporter subfamilies found in closely related species, including the ABC-B, C and G subfamilies, whose members confer drug resistance. Transcript levels of members of GcABC-G and GcABC-F subfamilies were up-regulated when Gc was exposed to terpenoids or grown in the presence of monoterpenes as the sole carbon source, but not under other stress conditions tested (e.g. Lodgepole pine phenolic extractive). In the presence of terpenoids, the most highly differentially expressed gene was GcABC-G1. This gene encodes a putative PDR efflux transporter which has the full (NBF-TMD)$_2$ organization that is common to PDR transporters localized in the plasma membrane in other fungal species, such as the camalexin exporter BcatrB in *Botrytis cinierea*, or the pisatin exporter NhABC1 in *N. haematococca* (Stefanato et al. (2009). *Plant Journal* 58: 499-510, Coleman et al. (2011) *Mol Plant-Microbe Interact* 24: 368-376). No orthologue of GcABC-G1 was found in the large set of ascomycetes assessed, which demonstrates that this ABC transporter is a specialized monoterpenoid transporter that has evolved in Gc, and potentially in other ophiostomatoid fungi, which are commonly vectored by insects and inhabit the phloem and sapwood of conifer trees. Consistent with this, GcABC-G1 did not confer resistance to typical PDR substrates. Evolution of the ABC-G1 gene in Gc, and its strong induction in response to monoterpenes, is explained by the association with Gc's ecological adaptation to a unique niche: the monoterpene-rich tissues of living pine hosts. As Gc is vectored by MPB into pine trees, its exposure to monoterpenes is rather sudden, and strong inducible expression of GcABC-G1 should provide an adaptive advantage.

The unique ecological pine tree niche colonized by Gc has high levels of monoterpenes, and so would be unsuitable to most microorganisms. For example, in the broad range of niches in which fungal strains are found in nature, including grape vine berries, concentrations of terpenoids are typically low, and, to this point, no mechanisms for coping with high concentrations of monoterpenes have been reported for fungus. The heterologous expression of GcABC-G1 in fungus conferred increased resistance to monoterpenes, consistent with this transporter being an efflux pump that removes toxic monoterpenes from cells. The four monoterpenes assessed were far more toxic to *S. cereviseae* than to Gc mycelia or germinating Gc spores. When exposed for shorter periods of time to certain monoterpenes, more cells survived for *S. cereviseae* transformed with GcABC-G1 than for *S. cereviseae* transformed with only the vector.

Data show that on artificial media *O. piceae* tolerates monoterpenes but does not use them as a carbon source. *O. piceae* generally colonizes lumber that is drier than freshly cut logs; it is not found in living trees, which have the highest terpene concentrations, it is able to remain viable for extended periods in the presence of monoterpenes, and likely in the presence of diterpenes, which can account for ~0.4% of pine sapwood dry weight. Here, it is shown that monoterpenes affected the macroscopic morphology of *O. piceae*'s mycelia, and inhibited its production of synemata and asexual spores. Further, in the saprophyte, monoterpene/ diterpene treatments rapidly up-regulated expression of genes involved in transmembrane transport, showing that the fungus' primary response involves protecting itself from these chemicals. During these initial processes an ABC transporter (OPP_06758 (SEQ ID NO:7)), which is homologous to the *G. clavigera* efflux transporters provided herein, was highly expressed. This shows that the homologous ABC transporters of *O. piceae* and *G. clavigera* excrete monoterpenes, removing them from the cell and allowing both fungi to survive in toxic mixtures of terpenes. After this initial response, *O. piceae* resumes its growth; in this phase, while most of the primary protective biological functions were still active, genes involved in degrading hydrophobic compounds were up-regulated. This shows that, like *G. clavigera*, *O. piceae* is able to modify terpenes into less toxic compounds. While *G. clavigera* has a gene cluster that specifically responds to terpenes and is potentially involved in metabolizing terpenes, in *O. piceae* no such gene cluster was found.

C. ABC TERPENOID TRANSPORTERS

In many organisms, ATP-binding cassette transporters (ABC transporters) function in the active transport of a diverse set of metabolites for various biological processes. In phytopathogenic fungi, pleiotropic drug resistance (PDR) ABC transporters are involved in the excretion of exogenous or endogenous toxic compounds. Typical ABC transporters contain two transmembrane domains (TMDs) and two nucleotide-binding folds (NBFs); 'half-transporters' contain only one TMD and one NBF. The two membrane-spanning domains of ABC transporters harbor a translocation pathway for a specific substrate. Attached are two cytoplasmic adenosine triphosphate-binding cassettes (hence the name ABC). As the ABC cassettes bind and hydrolyze ATP, conformational changes occur that are transmitted to the membrane-spanning domains, where they induce rearrangements that translocate the substrate from one side of the membrane to the other. The initial motion of the ABC cassettes has been dubbed the power stroke, and it is generally assumed that this rearrangement is similar in all ABC transporters, irrespective of the size of the substrate to be transported or the directionality of the translocation (import or export).

ABC transporters are classified into subfamilies according to sequence homology and domain topology of the conserved motifs (Sipos & Kuchler (2006) *Curr Drug Targets* 7: 471-481, Lamping E, et al (2010) *Fungal Genetics and Biology* 47: 127-142). In eukaryotes, eight major subfamilies have been defined: ABC-A to ABC-H (Dean M & Allikmets R (2001) *J Bioenerg Biomembr* 33: 475-479, Verrier P J, et al. (2008) *Trends Plant Sci* 13: 151-159). Among these, full size ABC-B, ABC-C, and ABC-G are respectively referred to as multi-drug resistance (MDR), multi-drug resistance-associated protein (MRP), and pleiotropic drug resistance (PDR) (Paumi et al. (2009) *Microbiology and Molecular Biology Reviews* 73: 577-593, Kovalchuk & Driessen (2010) *BMC Genomics* 11: 177); such proteins are located in the cytoplasmic membrane and actively export compounds, contributing to drug resistance, chemical sensitivity and cellular detoxification. Full-size ABC-G (PDR) is diverse, and seems present only in fungi and plants (Lamping et al. (2010) *Fungal Genetics and Biology* 47: 127-142, Crouzet et al. (2006) *FEBS Lett* 580: 1123-1130).

Provided herein are ABC Transporter polypeptides, and encoding nucleic acid molecules, that induce tolerance to terpenoids that otherwise can have toxic effects on fungi and other microbial organisms. In particular, provided herein are ABC Transporter polypeptides, and encoding nucleic acid molecules, from ophiostomatoid fungi that include pathogens (e.g. *Grosmannia clavigera* (Gc)) and saprobes (e.g. *Ophiostoma piceae* (Op)). In particular, provided herein are one, or more than one ABC terpenoid transporter nucleic acid molecule and one, or more than one, ABC terpenoid transporter polypeptide.

In particular, provided herein is a nucleic acid molecule, such as a synthetic gene, containing one or more than one nucleic acid encoding an ABC terpenoid transporter. The nucleic acid can be operably linked to a transcriptional or translational regulatory sequence or both. The nucleic acid molecule or synthetic gene can be capable of expressing the ABC terpenoid transporter polypeptide. The nucleic acid molecule or synthetic gene can also contain terminators at the 3'-end of the transcriptional unit of the sequence. The nucleic acid molecule or synthetic gene can also contain a selectable marker.

Also provided herein are variants of the polypeptides or nucleic acid sequences provided herein exhibiting substantially the same properties as the sequences provided herein. By this it is meant that nucleic acid sequences need not be identical to the sequence disclosed herein. Variations can be attributable to single or multiple base substitutions, deletions, or insertions or local mutations involving one or more nucleotides not substantially detracting from the properties of the nucleic acid sequence as encoding a protein having the properties of the ABC terpenoid transporter provided herein.

The ABC terpenoid transporter nucleic acid molecules and polypeptides can be used as pathogenicity marker, or in the production of terpenoid resistant cells. Also provide herein are vectors containing such sequences, transformed cells, cell lines, and transgenic organisms. A method is provided herein identifying pathogens containing such sequences. Also provided are compositions, uses, and kits containing ABC terpenoid transporters.

Exemplary provided ABC Transporter polypeptide and encoding nucleic acid molecules, and methods of use thereof, are described in the following subsections and Sections.

1. ABC Transporter from *Grosmannia Clavigera* (Gc) and Related Molecules

Provided herein is an ABC Transporter from *Grosmannia clavigera* (Gc). Gc is a pathogen that colonizes living pine trees. In particular, the Gc pine pathogen is vectored by MPB, and is an active participant in the large-scale death of lodgepole pine (*Pinus contorta*) forests in western North America (Lee et al. (2005) *Mycol Res* 109: 1162-1170). While the MPB/Gc complex can successfully colonize more than 20 different pine species, its preferred host is *P. contorta* (Safranyik et al. (2010) *Can Entomol* 142: 415-442).

Provided herein is one, or more than one, nucleic acid encoding a ABC terpenoid transporter. The one or more nucleic acid encodes an ABC monoterpenoid transporter for example GcABC-G1 (set forth in SEQ ID NO:1), GcABC-G2 (set forth in SEQ ID NO:3) or GcABC-G3 (set forth in SEQ ID NO:5), or an active fragment thereof, or sequence identical thereto. For example, the nucleic acid has the sequence set forth in SEQ ID NO: 2, SEQ ID NO: 4, SEQ ID NO: 6, or a portion thereof encoding an active fragment, or sequences substantially similar thereto. In particular examples herein, the nucleic acids provided herein have a sequence substantially as set out in SEQ ID NO:2, SEQ ID NO:4, or SEQ ID NO:6. In one embodiment, the nucleic acid provided herein is at least 70%, 75%, 80%, 85%, at least 90%, or at least 95% identical to nucleotides set forth as SEQ ID NO:2, SEQ ID NO:4, or SEQ ID NO:6. As one of skill in the art would appreciate, the sequence of the nucleic acid can be changed, for example, to account for codon preference in a particular host cell. The nucleic acid can be obtained from a fungi such as *Grosmannia clavigera* (Gc), provided that the protein encoded by the nucleic acid sequence exhibits the function of the ABC monoterpenoid transporter and is capable of transporting terpenoids across a membrane in which it is located.

Thus, provided herein are nucleic acid sequences encoding for a polypeptide having a sequence that is SEQ ID NO: 1, SEQ ID NO: 3, SEQ ID NO: 5 or sequences substantially identical thereto that has at least 63%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with the ABC terpenoid transporter set forth in SEQ ID NO:1, SEQ ID NO:3, SEQ ID NO:5 or an active fragment thereof, provided that the protein encoded by the nucleic acid sequence exhibits the function of the ABC monoterpenoid transporter and is capable of transporting terpenoids across a membrane in which it is located. In one embodiment, the nucleic acids provided herein encodes a polypeptide containing an amino acid sequence as set out in SEQ ID NO:1, SEQ ID NO:3 or SEQ ID NO:5. In yet another embodiment the nucleic acids provided herein encodes a polypeptide containing an amino acid sequence that is at least 70%, at least 75%, at least 80%, at least 85% identical, at least 90% or at least 95% identical to SEQ ID NO:1, SEQ ID NO:3 or SEQ ID NO:5. Due to the degeneracy of the genetic code wherein more than one codon can encode the same amino acid, multiple DNA sequences can code for the same polypeptide. Such variant DNA sequences can result from genetic drift or artificial manipulation (e.g., occurring during PCR amplification or as the product of deliberate mutagenesis of a native sequence). Thus, among nucleic acids encompassed herein is any nucleic acid capable of encoding a protein derived from the SEQ ID NO:1, SEQ ID NO:3 or SEQ ID NO:5 or variants thereof.

Also provided are one, or more than one ABC terpenoid transporter polypeptides. The one, or more than one ABC terpenoid transporter polypeptides can contain the sequence set forth in SEQ ID NO: 1, SEQ ID NO: 3, SEQ ID NO: 5, active fragments thereof, or sequences having at least about 70-100% sequence similarity thereto, including any percent similarity within these ranges, such as 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence similarity to any of SEQ ID NO: 1, SEQ ID NO: 3 or SEQ ID NO: 5, provided that the protein resulting from the amino acid sequence exhibits the function of the ABC terpenoid transporter and is capable of transporting terpenoids across a membrane in which it is located.

2. ABC Transporter from *Ophiostoma piceae* (Op) and Related Molecules

Provided herein is an ABC Transporter from *Ophiostoma piceae* (Op). As for *G. clavigera*, an ABC transporter that removes toxic compounds from cells is involved in *O. piceae's* tolerance to terpenes, and can be used to improve methods of producing terpenes in cells.

*Ophiostoma piceae* is a wood-staining fungus that grows in the sapwood of conifer logs and lumber. *O. piceae* is a saprobe that is dispersed by generalist bark beetles. This fungal species has been found across Canada, and has been reported in North America, Europe and Asia (Krokene et al. (1998) *Plytopathology,* 88:39-44; Uzunovic et al. (1999) *Can J. Microbiol.,* 45:914-922; and Chung et al. (2006) *Mycologia,* 98:801-814). *O. piceae* is a more superficial sap stain fungus that becomes established in the outer two to three centimeters of sapwood (Seifert, K. Sapstain of commercial lumber by species of *Ophiostoma* and *Ceratocystis*. In *Ceratocystis and Ophiostoma: taxonomy, ecology, and pathogenicity*. Edited by Wingfield M, Seifert K, Webber J. St. Paul, Minn.: APS Press; 1993:141-151; DiGuistini et al. (2007) *FEMS Microbiol. Lett.,* 267:151-158); Fleet et al. (2001) *Holzforschung,* 55:340-346). Species in the *O. piceae* complex have retained the attention of wood industry researchers because they cause stain in processed wood and used to be the most commonly isolated species of sap stain fungi in Canadian saw mills. In contrast to *G. clavigera*, which is specific to pine, *O. piceae* is able to grow not only on pine, but also on wood of other conifers in Canada, including black and white spruce, balsam fir and hemlock. *O. piceae* also acts generally in cut logs and processed lumber. Because members of the *O. piceae* complex members grow poorly on freshly cut pine logs and prefer the dryer environment of lumber, their effects are minimized by keeping logs frozen or saturated with water, or by prompt log processing. Green lumber is protected by kiln drying below 20% moisture content, or by chemical and biological treatments.

Provided herein is one, or more than one, nucleic acid encoding a ABC terpenoid transporter. The one or more nucleic acid encodes an ABC monoterpenoid transporter, for example, OPP_06758 (SEQ ID NO:7), or an active fragment thereof, or sequence identical thereto. For example, the nucleic acid has the sequence set forth in SEQ ID NO: 8, or a portion thereof encoding an active fragment, or sequences substantially similar thereto. In particular examples herein, the nucleic acids provided herein has a sequence substantially as set out in SEQ ID NO:8. In one embodiment, the nucleic acid provided herein is at least 70%, 75%, 80%, 85%, at least 90%, or at least 95% identical to nucleotides set forth as SEQ ID NO:8. As one of skill in the art would appreciate, the sequence of the nucleic acid can be changed, for example, to account for codon preference in a particular host cell. The nucleic acid can be obtained from a fungi such as *Ophiostoma piceae* (Op), provided that the protein encoded by the nucleic acid sequence exhibits the function of the ABC monoterpenoid transporter and is capable of transporting terpenoids across a membrane in which it is located.

Thus, provided herein are nucleic acid sequences encoding for a polypeptide having a sequence that is SEQ ID NO: 7 or sequences substantially identical thereto that has at least 63%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with the ABC terpenoid transporter set forth in SEQ ID NO:7 or an active fragment thereof, provided that the protein encoded by the nucleic acid sequence exhibits the function of the ABC monoterpenoid transporter and is capable of transporting terpenoids across a membrane in which it is located. In one embodiment, the nucleic acids provided herein encodes a polypeptide containing an amino acid sequence as set out in SEQ ID NO:7. In yet another embodiment the nucleic acids provided herein encodes a polypeptide containing an amino acid sequence that is at least 70%, at least 75%, at least 80%, at least 85% identical, at least 90% or at least 95% identical to SEQ ID NO:7. Due to the degeneracy of the genetic code wherein more than one codon can encode the same amino acid, multiple DNA sequences can code for the same polypeptide. Such variant DNA sequences can result from genetic drift or artificial manipulation (e.g., occurring during PCR amplification or as the product of deliberate mutagenesis of a native sequence). Thus, among nucleic acids encompassed herein is any nucleic acid capable of encoding a protein derived from SEQ ID NO:7 or variants thereof.

Also provided are one, or more than one ABC terpenoid transporter polypeptides. The one, or more than one ABC terpenoid transporter polypeptides can contain the sequence set forth in SEQ ID NO: 7, active fragments thereof, or sequences having at least about 70-100% sequence similarity thereto, including any percent similarity within these ranges, such as 71, 72, 73, 74, 75, 76, 77, 78, 79, 80, 81, 82, 83, 84, 85, 86, 87, 88, 89, 90, 91, 92, 93, 94, 95, 96, 97, 98, 99% sequence similarity to any of SEQ ID NO: 7, provided that the protein resulting from the amino acid sequence exhibits the function of the ABC terpenoid transporter and is capable of transporting terpenoids across a membrane in which it is located.

D. METHODS OF PRODUCING OR GENERATING ABC TRANSPORTERS, VECTORS & HOST CELLS

Provided herein are polynucleotides encoding any of the ABC transporters provided herein, or the encoded ABC transporters, such as any set forth in Section C. As described herein, the nucleic acids and encoding polypeptides can be derived from an ophiostomatoid fungi, such as *Grosmannia clavigera* (Gc) or *Ophiostoma piceae* (Op). The polypeptide or the nucleic acid can be used in any of the methods provided herein for improving the production of a terpene. Also provided herein are vectors and hosts containing nucleic acid encoding the ABC transporter and that can be used for producing diterpenoids.

The ABC transporter polypeptides to be used in methods provided herein also can be generated synthetically. Standard reference works setting forth the general principles of peptide synthesis technology and methods known to those of skill in the art include, for example: Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; Sambrook et al., Molecular Cloning: A Laboratory Manual, 3$^{rd}$ ed., Cold Spring Harbor Press, Cold Spring Harbor, N.Y. 2001; and Ausubel et al., Current Protocols in Molecular Biology, Greene Publishing Associates and John Wiley & Sons, NY, 1994.

1. Isolation of Nucleic Acid Encoding an ABC Transporter

The one or more than one polynucleotide sequences encoding the ABC Transporter as provided herein can be prepared by any method known by the person skilled in the art. For example, the polynucleotide sequence encoding an ABC Transporter can be amplified from a cDNA template, by polymerase chain reaction with specific primers. In such an example the codons of the cDNA can be chosen to favor the expression of said protein in the desired expression system. In other examples, nucleic acids encoding any of the ABC Transporters provided herein, can be cloned or isolated using any available methods known in the art for cloning and isolating nucleic acid molecules. Such methods include PCR amplification of nucleic acids and screening of libraries, including nucleic acid hybridization screening. In some examples, methods for amplification of nucleic acids can be used to isolate nucleic acid molecules encoding an polypeptide, including for example, polymerase chain reaction (PCR) methods. A nucleic acid containing material can be used as a starting material from which a ABC Transporter-encoding nucleic acid molecule can be isolated. For example, DNA and mRNA preparations from an ophiostomatoid fungi, including but not limited to *Grosmannia clavigera* (Gc) or *Ophiostoma piceae* (Op), can be used to obtain ABC transporter genes.

Nucleic acid libraries also can be used as a source of starting material. Primers can be designed to amplify an ABC Transporter-encoding molecule, such as a *G. clavigera* or *O. piceae* ABC Transporter-encoding molecule. For example, primers can be designed based on known nucleic acid sequences encoding an ABC transporter, such as a *G.*

*clavigera* or *O. piceae* ABC Transporter. Nucleic acid molecules generated by amplification can be sequenced and confirmed to encode an ABC transporter polypeptide.

Additional nucleotide sequences can be joined to a ABC transporter-encoding nucleic acid molecule, including linker sequences containing restriction endonuclease sites for the purpose of cloning the synthetic gene into a vector, for example, a protein expression vector or a vector designed for the amplification of the core protein coding DNA sequences. Furthermore, additional nucleotide sequences specifying functional DNA elements can be operatively linked to an ABC transporter-encoding nucleic acid molecule. Still further, nucleic acid encoding other moieties or domains also can be included so that the resulting synthase is a fusion protein. For example, nucleic acids encoding other enzymes, such as a FPP, GPP or GGPP synthase, or protein purification tags, such as His or Flag tags.

2. Vectors and Cells

The disclosure also relates, in part, to vectors containing such sequences, transformed cells, cell lines, and transgenic organisms. For recombinant expression of one or more of the ABC transporter polypeptides provided herein, including *G. clavigera* and *O. piceae* ABC transporter polypeptides, the nucleic acid containing all or a portion of the nucleotide sequence encoding the ABC transporter can be inserted into an appropriate expression vector, i.e., a vector that contains the necessary elements for the transcription and translation of the inserted protein coding sequence. Depending upon the expression system used, the necessary transcriptional and translational signals also can be supplied by the native promoter for an ABC transporter gene, and/or their flanking regions. For example, vectors containing a polynucleotide sequence encoding an ABC transporter are provided herein. The vector can be obtained and introduced in a host cell by well-known recombinant DNA and genetic engineering techniques.

The disclosure also provides a prokaryotic or eukaryotic host cell which is modified by a polynucleotide or a vector as provided herein. The host cell can be prokaryotic, such as bacterial, or eukaryotic, such as fungal (e.g., yeast), plant, Archea, insect, amphibian or animal cell. The host cell can contain an ABC transporter vector, a synthetic ABC transporter gene, and/or ABC transporter nucleic acid. The host cell can be any cell that is capable of being transformed by the vector, synthetic gene, and/or nucleic acid. The host cell can also be any cell that is capable of expressing the ABC transporter polypeptide. The host cell can be incubated under conditions that allow expression of the ABC transporter polypeptide.

Any method known to those of skill in the art for the insertion of DNA fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid sequences encoding an ABC transporter polypeptide, or a fragment thereof, can be regulated by a second nucleic acid sequence so that the genes or fragments thereof are expressed in a host transformed with the recombinant DNA molecule(s). For example, expression of the proteins can be controlled by any promoter/enhancer known in the art. In a specific embodiment, the promoter is not native to the genes for an ABC transporter protein. Promoters that can be used include but are not limited to prokaryotic, yeast, mammalian and plant promoters. The type of promoter depends upon the expression system used, described in more detail below.

In a specific embodiment, a vector is used that contains a promoter operably linked to nucleic acids encoding an ABC transporter polypeptide, or a fragment thereof, one or more origins of replication, and optionally, one or more selectable markers (e.g., an antibiotic resistance gene).

3. Expression Systems

ABC transporters, including ABC transporter polypeptides provided herein, can be produced by any methods known in the art for protein production including in vitro and in vivo methods such as, for example, the introduction of nucleic acid molecules encoding the ABC transporter into a host cell or host plant for in vivo production or expression from nucleic acid molecules encoding the ABC transporter in vitro. ABC transporter polypeptides can be expressed in any organism suitable to produce the required amounts and forms of a synthase polypeptide. Expression hosts include prokaryotic and eukaryotic organisms such as *E. coli*, yeast, plants, insect cells, mammalian cells, including human cell lines and transgenic animals. Expression hosts can differ in their protein production levels as well as the types of post-translational modifications that are present on the expressed proteins. The choice of expression host can be made based on these and other factors, such as regulatory and safety considerations, production costs and the need and methods for purification.

Isolated higher eukaryotic cells, such for example cell culture, can also be used, instead of complete organisms, as hosts to carry out the method provided herein in vivo. Suitable eukaryotic cells can be any non-human cell, but are generally plant cells. Representative examples of a plant host cell include for example plants that naturally produce high amounts of terpenes. The plant can be selected from the family of Pinaceae, Funariacea, Solanaceae, Poaceae, Brassicaceae, Fabaceae, Malvaceae, Asteraceae or Lamiaceae. For example, the plant is selected from the genera *Picea* (spruce), *Pinus* (pine), *Abies* (fir), *Physcomitrella*, *Funariaceae*, *Nicotiana*, *Solanum*, *Sorghum*, *Arabidopsis*, *Brassica* (rape), *Medicago* (alfalfa), *Gossypium* (cotton), *Artemisia*, *Salvia* and *Mentha*. Preferably, the plant belongs to the species of *Nicotiana tabacum*, *Nicotiana benthamiana* or *Physcomitrella patens*. Additional plants and plant cells include, for example, citrus, corn, rice, algae, and lemna. In other examples, the eukaryotic cells are yeast cells. Representative examples of a yeast host cell include those from the *Saccharomyces* genus (e.g. *Saccharomyces cerevisiae*) and *Pichia* genus (e.g. *Pichia pastoris*). In some examples, insect cells such as *Drosophila* cells and *lepidopteran* cells are used for the expression of an ABC transporter provided herein. Eukaryotic cells for expression also include mammalian cells lines such as Chinese hamster ovary (CHO) cells or baby hamster kidney (BHK) cells.

Eukaryotic expression hosts also include production in transgenic animals, for example, including production in serum, milk and eggs. There are several methods known in the art for the creation of transgenic host organisms or cells such as plants, fungi, prokaryotes, or cultures of higher eukaryotic cells. Appropriate cloning and expression vectors for use with bacterial, fungal, yeast, plant and mammalian cellular hosts are described, for example, in Pouwels et al., Cloning Vectors: A Laboratory Manual, 1985, Elsevier, New York and Sambrook et al., Molecular Cloning: A Laboratory Manual, $2^{nd}$ edition, 1989, Cold Spring Harbor Laboratory Press. Cloning and expression vectors for higher plants and/or plant cells in particular are available to the skilled person. See for example Schardl et al. (1987) *Gene* 61: 1-11.

Methods for transforming host organisms or cells to harbor transgenic nucleic acids are familiar to the skilled person. For the creation of transgenic plants, for example, current methods include: electroporation of plant protoplasts, liposome-mediated transformation, agrobacterium-mediated transformation, polyethylene-glycol-mediated transformation, particle bombardement, microinjection of plant cells, and transformation using viruses.

Many expression vectors are available and known to those of skill in the art for the expression of an ABC transporter, such as an ABC transporter provided herein. Exemplary of expression vectors are pET expression vectors, such as pET28b(+). The choice of expression vector is influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vectors in the cells.

ABC transporters, including ABC transporter polypeptides, also can be used or expressed as protein fusions. For example, a fusion can be generated to add additional functionality to a polypeptide. Examples of fusion proteins include, but are not limited to, fusions of a signal sequence, a tag such as for localization, e.g. a $his_6$ tag or a myc tag, or a tag for purification, for example, a GST fusion, GFP fusion or CBP fusion, and a sequence for directing protein secretion and/or membrane association.

a. Prokaryotic cells

Prokaryotes, especially *E. coli*, provide a system for producing large amounts of the ABC transporter polypeptides provided herein. Transformation of *E. coli* is a simple and rapid technique well known to those of skill in the art. Representative examples of a bacterial host cell include, but are not limited to, *E. coli* strains such as for example *E. coli* BL21DE3-C41 (Miroux and Walker (1996) *J Mol Biol* 260:289-298). Exemplary expression vectors for transformation of *E. coli* cells, include, for example, the pGEM expression vectors, the pQE expression vectors, and the pET expression vectors (see, U.S. Pat. No. 4,952,496; available from Novagen, Madison, Wis.; see, also literature published by Novagen describing the system). Such plasmids include pET11a, which contains the T7lac promoter, T7 terminator, the inducible *E. coli* lac operator, and the lac repressor gene; pET12a-c, which contains the T7 promoter, T7 terminator, and the *E. coli* ompT secretion signal; and pET15b and pET19b (Novagen, Madison, Wis.), which contain a His-Tag™ leader sequence for use in purification with a His column and a thrombin cleavage site that permits cleavage following purification over the column, the T7-lac promoter region and the T7 terminator; and pET28b (Novagen, Madison, Wis.), which contains a His-Tag™ leader sequence for use in purification with a His column and a thrombin cleavage site that permits cleavage following purification over the column, the T7-lac promoter region and the T7 terminator; and the pJET vectors (Thermo Scientific), such as the pJET1.2 vector which contains a lethal gene which is disrupted by ligation of a DNA insert into the cloning site and a T7 promoter for in vitro transcription.

Expression vectors for *E. coli* can contain inducible promoters that are useful for inducing high levels of protein expression and for expressing proteins that exhibit some toxicity to the host cells. Exemplary prokaryotic promoters include, for example, the β-lactamase promoter (Jay et al., (1981) *Proc. Natl. Acad. Sci. USA* 78:5543) and the tac promoter (DeBoer et al., (1983) *Proc. Natl. Acad Sci. USA* 80:21-25); see also "Useful Proteins from Recombinant Bacteria": in Scientific American 242:79-94 (1980)). Examples of inducible promoters include the lac promoter, the trp promoter, the hybrid tac promoter, the T7 and SP6 RNA promoters and the temperature regulated $\lambda P_L$ promoter.

ABC transporters, including *G. clavigera* and *O. piceae* polypeptides provided herein, can be expressed in the cytoplasmic environment of *E. coli*. The cytoplasm is a reducing environment and for some molecules, this can result in the formation of insoluble inclusion bodies. Reducing agents such as dithiothreitol and β-mercaptoethanol and denaturants (e.g., such as guanidine-HCl and urea) can be used to resolubilize the proteins. An alternative approach is the expression ABC transporter polypeptides in the periplasmic space of bacteria which provides an oxidizing environment and chaperonin-like and disulfide isomerases leading to the production of soluble protein. Typically, a leader sequence is fused to the protein to be expressed which directs the protein to the periplasm. The leader is then removed by signal peptidases inside the periplasm. Examples of periplasmic-targeting leader sequences include the pelB leader from the pectate lyase gene and the leader derived from the alkaline phosphatase gene. In some cases, periplasmic expression allows leakage of the expressed protein into the culture medium. The secretion of proteins allows quick and simple purification from the culture supernatant. Proteins that are not secreted can be obtained from the periplasm by osmotic lysis. Similar to cytoplasmic expression, in some cases proteins can become insoluble and denaturants and reducing agents can be used to facilitate solubilization and refolding. Temperature of induction and growth also can influence expression levels and solubility. Typically, temperatures between 25° C. and 37° C. are used. Mutations also can be used to increase solubility of expressed proteins. Typically, bacteria produce aglycosylated proteins.

b. Yeast cells

Yeast systems, such as, but not limited to, those from the *Saccharomyces* genus (e.g. *Saccharomyces cerevisiae*), *Schizosaccharomyces pombe*, *Yarrowia lipolytica*, *Kluyveromyces lactis*, and *Pichia pastoris* can be used to express the ABC transporters, such as the ABC transporter polypeptides, provided herein. Yeast expression systems also can be used to produce diterpenes whose reactions are catalyzed by the synthases. Yeast can be transformed with episomal replicating vectors or by stable chromosomal integration by homologous recombination. In some examples, inducible promoters are used to regulate gene expression. Exemplary promoter sequences for expression of ABC transporter polypeptides in yeast include, among others, promoters for metallothionine, 3-phosphoglycerate kinase (Hitzeman et al. (1980) *J. Biol. Chem.* 255:2073), or other glycolytic enzymes (Hess et al. (1968) *J. Adv. Enzyme Reg.* 7:149; and Holland et al. (1978) *Biochem.* 17:4900), such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other suitable vectors and promoters for use in yeast expression are further described in Hitzeman, EPA-73,657 or in Fleer et al. (1991) *Gene*, 107:285-195; and van den Berg et al. (1990) *Bio/Technology*, 8:135-139. Another alternative includes, but is not limited to, the glucose-repressible ADH2 promoter described by Russell et al. (*J. Biol. Chem.* 258:2674, 1982) and Beier et al. (*Nature* 300:724, 1982), or a modified ADH1 promoter. Shuttle vectors replicable in yeast and *E. coli* can be constructed by, for example, inserting DNA sequences from pBR322 for selection and replication in *E. coli* (Amp$^r$ gene and origin of replication) into a yeast vector.

Yeast expression vectors can include a selectable marker such as LEU2, TRP1, HIS3, and URA3 for selection and maintenance of the transformed DNA. Proteins expressed in yeast are often soluble and co-expression with chaperonins, such as Bip and protein disulfide isomerase, can improve expression levels and solubility. Additionally, proteins expressed in yeast can be directed for secretion using secretion signal peptide fusions such as the yeast mating type alpha-factor secretion signal from *Saccharomyces cerevisiae* and fusions with yeast cell surface proteins such as the Aga2p mating adhesion receptor or the *Arxula adeninivorans* glucoamylase. A protease cleavage site (e.g., the Kex-2 protease) can be engineered to remove the fused sequences from the polypeptides as they exit the secretion pathway.

c. Plants and Plant Cells

Transgenic plant cells and plants can be used for the expression of ABC transporters, including ABC transporter polypeptides provided herein. Expression constructs are typically transferred to plants using direct DNA transfer such as microprojectile bombardment and PEG-mediated transfer into protoplasts, and with *agrobacterium*-mediated transformation. Expression vectors can include promoter and enhancer sequences, transcriptional termination elements, and translational control elements. Expression vectors and transformation techniques are usually divided between dicot hosts, such as *Arabidopsis* and tobacco, and monocot hosts, such as corn and rice. Examples of plant promoters used for expression include the cauliflower mosaic virus promoter, the nopaline synthase promoter, the ribose bisphosphate carboxylase promoter and the ubiquitin and UBQ3 promoters. Selectable markers such as hygromycin, phosphomannose isomerase and neomycin phosphotransferase are often used to facilitate selection and maintenance of transformed cells. Transformed plant cells can be maintained in culture as cells, aggregates (callus tissue) or regenerated into whole plants. Transgenic plant cells also can include algae engineered to produce proteins (see, for example, Mayfield et al. (2003) *Proc Natl Acad Sci USA* 100:438-442). Transformed plants include, for example, plants selected from the genera *Picea* (spruce), *Pinus* (pine), *Abies* (fir), *Physcomitrella*, *Funariaceae*, *Nicotiana*, *Solanum*, *Sorghum*, *Arabidopsis*, *Medicago* (alfalfa), *Gossypium* (cotton), *Brassica* (rape), *Artemisia*, *Salvia* and *Mentha*. In some examples, the plant belongs to the species of *Nicotiana tabacum*, *Nicotiana benthamiana* or *Physcomitrella patens*, and is transformed with vectors that overexpress an ABC transporter.

d. Insects and Insect Cells

Insects and insect cells, particularly a baculovirus expression system, can be used for expressing ABC transporter, including ABC transporter polypeptides provided herein (see, for example, Muneta et al. (2003) *J. Vet. Med. Sci.* 65(2):219-223). Insect cells and insect larvae, including expression in the haemolymph, express high levels of protein and are capable of most of the post-translational modifications used by higher eukaryotes. Baculoviruses have a restrictive host range which improves the safety and reduces regulatory concerns of eukaryotic expression. Typically, expression vectors use a promoter such as the polyhedrin promoter of baculovirus for high level expression. Commonly used baculovirus systems include baculoviruses such as *Autographa californica* nuclear polyhedrosis virus (AcNPV), and the *Bombyx mori* nuclear polyhedrosis virus (BmNPV) and an insect cell line such as Sf9 derived from *Spodoptera frugiperda*, *Pseudaletia unipuncta* (A7S) and *Danaus plexippus* (DpN1). For high level expression, the nucleotide sequence of the molecule to be expressed is fused immediately downstream of the polyhedrin initiation codon of the virus. Mammalian secretion signals are accurately processed in insect cells and can be used to secrete the expressed protein into the culture medium. In addition, the cell lines *Pseudaletia unipuncta* (A7S) and *Danaus plexippus* (DpN1) produce proteins with glycosylation patterns similar to mammalian cell systems.

An alternative expression system in insect cells is the use of stably transformed cells. Cell lines such as the Schnieder 2 (S2) and Kc cells (*Drosophila melanogaster*) and C7 cells (*Aedes albopictus*) can be used for expression. The *Drosophila* metallothionein promoter can be used to induce high levels of expression in the presence of heavy metal induction with cadmium or copper. Expression vectors are typically maintained by the use of selectable markers such as neomycin and hygromycin.

e. Mammalian Expression

Mammalian expression systems can be used to express ABC transporters, including ABC transporter polypeptides provided herein and also can be used to produce diterpenes whose reactions are catalyzed by the synthases. Expression constructs can be transferred to mammalian cells by viral infection such as adenovirus or by direct DNA transfer such as liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. Such vectors often include transcriptional promoter-enhancers for high level expression, for example the SV40 promoter-enhancer, the human cytomegalovirus (CMV) promoter, and the long terminal repeat of Rous sarcoma virus (RSV). These promoter-enhancers are active in many cell types. Tissue and cell-type promoters and enhancer regions also can be used for expression. Exemplary promoter/enhancer regions include, but are not limited to, those from genes such as elastase I, insulin, immunoglobulin, mouse mammary tumor virus, albumin, alpha-fetoprotein, alpha 1-antitrypsin, beta-globin, myelin basic protein, myosin light chain-2 and gonadotropic releasing hormone gene control. Selectable markers can be used to select for and maintain cells with the expression construct. Examples of selectable marker genes include, but are not limited to, hygromycin B phosphotransferase, adenosine deaminase, xanthine-guanine phosphoribosyl transferase, aminoglycoside phosphotransferase, dihydrofolate reductase and thymidine kinase. Fusion with cell surface signaling molecules such as TCR-ζ and Fc$_e$RI-γ can direct expression of the proteins in an active state on the cell surface.

Many cell lines are available for mammalian expression including mouse, rat human, monkey, and chicken and hamster cells. Exemplary cell lines include, but are not limited to, BHK (i.e. BHK-21 cells), 293-F, CHO, CHO Express (CHOX; Excellgene), Balb/3T3, HeLa, MT2, mouse NSO (non-secreting) and other myeloma cell lines, hybridoma and heterohybridoma cell lines, lymphocytes, fibroblasts, Sp2/0, COS, NIH3T3, HEK293, 293S, 293T, 2B8, and HKB cells. Cell lines also are available adapted to serum-free media which facilitates purification of secreted proteins from the cell culture media. One such example is the serum free EBNA-1 cell line (Pham et al. (2003) *Biotechnol. Bioeng.* 84:332-342).

4. Purification

Also provided is a method of producing the ABC transporter polypeptide. The ABC transporter polypeptide can be purified using standard chromatographic techniques.

The polypeptide to be used when the method is carried out in vitro can be obtained by extraction from any organism expressing it, using standard protein or enzyme extraction technologies. If the host organism is a unicellular organism or cell releasing the provided polypeptide into the culture medium, the polypeptide can simply be collected from the culture medium, for example by centrifugation, optionally followed by washing steps and re-suspension in suitable buffer solutions. If the organism or cell accumulates the polypeptide within its cells, the polypeptide can be obtained by disruption or lysis of the cells and further extraction of the polypeptide from the cell lysate.

Methods for purification of ABC transporters, such as ABC transporter polypeptides, from host cells depend on the chosen host cells and expression systems. For secreted molecules, proteins are generally purified from the culture media after removing the cells. For intracellular expression, cells can be lysed and the proteins purified from the extract. When transgenic organisms such as transgenic plants and animals are used for expression, tissues or organs can be used as starting material to make a lysed cell extract. Additionally, transgenic animal production can include the production of polypeptides in milk or eggs, which can be collected, and if necessary the proteins can be extracted and further purified using standard methods in the art.

ABC transporters, including ABC transporter polypeptides provided herein, can be purified using standard protein purification techniques known in the art including but not limited to, SDS-PAGE, size fraction and size exclusion chromatography, ammonium sulfate precipitation, chelate chromatography and ionic exchange chromatography. Expression constructs also can be engineered to add an affinity tag such as a myc epitope, GST fusion or $His_6$ and affinity purified with myc antibody, glutathione resin, and Ni-resin, respectively, to a protein. Purity can be assessed by any method known in the art including gel electrophoresis and staining and spectrophotometric techniques. The polypeptides, either in an isolated form or together with other proteins, for example in a crude protein extract obtained from cultured cells or microorganisms, can then be suspended in a buffer solution at optimal pH. If adequate, salts, DTT, BSA and other kinds of enzymatic co-factors, can be added in order to optimize enzyme activity.

5. Fusion Proteins

Fusion proteins containing an ABC transporter, including ABC transporter polypeptides, and one or more other polypeptides also are provided. Linkage of a ABC transporter polypeptide with another polypeptide can be effected directly or indirectly via a linker. In one example, linkage can be by chemical linkage, such as via heterobifunctional agents or thiol linkages or other such linkages. Fusion also can be effected by recombinant means. Fusion of an ABC transporter, such as a ABC transporter polypeptide to another polypeptide can be to the N- or C-terminus of the ABC transporter polypeptide.

A fusion protein can be produced by standard recombinant techniques. For example, DNA fragments coding for the different polypeptide sequences can be ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel et al. (eds.) Current Protocols in Molecular Biology, John Wiley & Sons, 1992). Moreover, many expression vectors are commercially available that already encode a fusion moiety (e.g., a GST polypeptide). For example, an ABC transporter polypeptide-encoding nucleic acid can be cloned into such an expression vector such that nucleic acid encoding an ABC transporter is linked in-frame to a polypeptide encoding a protein purification tag, such as a His tag. In another example, a nucleic acid molecule encoding an ABC transporter polypeptide can be linked in-frame to another polypeptide. The ABC transporter polypeptide and additional polypeptide can be linked directly, without a linker, or alternatively, linked indirectly in-frame with a linker.

E. EXEMPLARY USES OF ABC TRANSPORTERS

The ABC transporters provided herein and ABC transporters in general have a variety of applications. In one example, an ABC terpenoid transporter or an active fragment thereof is used to produce a terpenoid resistant cell or a cell that exhibits increased resistance to terpenes. Host cells, particularly yeast host cells, such as those that have been developed for the production of terpenes, that encode an ABC transporter, particularly a heterologous transporter, are provided. By virtue of their increased resistance to terpenes, particularly monoterpenes, such host cells exhibit increased production of terpenes compared to the same cells in the absence of the transporter. In another example, an ABC terpenoid transporter or an active fragment thereof provided herein is a probe to determine the occurrence of, or identity of, a pathogen within an organism of interest.

1. Methods for Microbial Production of Terpenoids

Plant terpenes, which are important in plant defense against pathogens and in the interactions of plants with other organisms (Gershenzon & Dudareva (2007) *Nature Chemical Biology* 3: 408-414), also are employed for metabolic engineering of biofuels and bioproducts in microbial hosts (Bohlmann & Keeling (2008) *Plant Journal* 54: 656-669, Peralta-Yahya et al. (2011) *Nat Commun* 2: 483). Host cells, such as *Saccharomyces cerevisiae*, and other microorganisms are employed or the production of monoterpenes and other terpenoids of plant origin as high-value bioproducts and advanced biofuels (Fischer et al. (2011) *Biotechnol Bioeng* 108: 1883-1892, Kirby & Keasling (2009) *Annual Review of Plant Biology* 60: 335-355). The transporters described as herein are introduced into such host cells resulting in increased terpene production.

Plants often develop specialized anatomical structures for extracellular sequestration of large amounts of low molecular weight terpenoids (Bohlmann & Keeling (2008) *Plant Journal* 54: 656-669). In engineered single cell production systems, the toxicity of monoterpenes and biofuels can limit yield and performance (Dunlop et al. (2011) *Molecular Systems Biology* 7: 487). For producing biofuels with *E. coli*, increased cell survival and improved yield have been obtained by expressing ABC transporters from other bacteria (Dunlop et al. (2011) *Molecular Systems Biology* 7: 487). While *S. cerevisiae* is sometimes preferred over bacteria for producing some terpenoids, expression of native PDR transporters in *S. cerevisiae* (YOR328, YOR153) did not result in increased yields of the monoterpenoids geraniol or linalool, which are potentially relevant for biofuel production (Oswald et al. (2007) *FEMS Yeast Research* 7: 413-421).

The *G. clavigera* GcABC-G1 and the *O. piceae* ABC transporter provided herein are eukaryotic ABC transporters that play a role in enhanced tolerance against monoterpenes. These proteins, when expressed in eukaryotic hosts, such as yeast host cells employed for expression of terpenes, provide improved terpenoid production in *S. cerevisiae* and other systems.

The ABC terpenoid transporter nucleic acid molecules and polypeptides provided herein are used in the production of terpenoid resistant host cells. The ABC terpenoid transporters identified herein, including *G. clavigera* and *O. piceae* ABC transporters, are used to produce cells that are exhibit increased resistance to terpenoids, compared to such cells that do not express them. These cells are produced by introducing nucleic acid encoding the ABC terpenoid transporter, whereby the encoded transporter is expressed to thereby produce a cell that is more resistant to terpenes, particularly monoterpenes. The cell or host cell can be prokaryotic, such as bacterial, but typically is eukaryotic, such as fungal (e.g., yeast), plant, insect, amphibian or animal cell. Fungal cells include, but are not limited to yeast cells. Representative examples of a fungal host cell include, but are not limited to *Saccharomyces cerevisiae* or *Neurospora crassa*. Representative examples of a yeast host cell include those from the *Saccharomyces* genus (e.g. *Saccharomyces cerevisiae*) and *Pichia* genus (e.g. *Pichia pastoris*) (see, e.g., Takahashi et al. (2007) *Biotechnol Bioeng* 97:170-181; Martin et al. (2003) *Nat Biotechnol* 21:796-802; Ignea et al. (2011) *Microb Cell Fact* 10:4; Ro et al. (2006) *Nature* 440:940-943; Bencurova et al. (2003) *Biochimie* 85:413-422; Malissard et al. (2000) *Biochem Biophys Res Commun* 267:169-173). These cells have been engineered to encode terpene synthases and other enzymes for the production of terpenes (see, e.g., U.S. Pat. Nos. 6,531,303, 6,689,593, 7,838,279, 7,842,497, 7,405,057 and 5,824,774, 6,072,045, 6,468,772, 6,495,354, 6,890,752, 6,559,297, 6,645,762, 6,569,656, 7,186,891, 7,442,785, 7,504,057, 8,106,260, 8,192,950, 8,263,362, 8,354,504, published U.S. Pat. Application Nos. 20040249219, 20110189717, 20080178354, 20100151519, 20100151555, 20110318797, 20120196340, 20120246767, International Pat. Publication Nos. WO2011000026, WO2004031376, WO2005056803, WO20060134523, WO2009050816, WO2009101126, WO2009044336, WO2009095366, WO2010067309 and U.S. patent application Ser. No. 13/694,350 and International Pat. Application Ser. No. PCT/CA2012/050837, each of which are incorporated herein by reference). Cells that encode a transporter, such as an ABC transporter, and a synthase and optionally other enzymes, such as P450, for the production of terpenes are provided. These cells are cultured, the terpene is produced, and the terpenes that are produced are optionally isolated. Also provided are methods for producing a cell for improved secretion of terpenoids, by transforming the cell with a vector encoding an ABC terpenoid transporter. Also provided herein are terpenoid resistant cells, such as terpenoid resistant fungal, e.g., yeast, cells. Such terpenoid resistant cells can be used for the production of terpenes and terpenoids, including mono-, sesqui- and di-terpenes/terpenoids, by expression of a mono-, sesqui- and di-terpene synthase in the terpenoid resistant cell. In particular, such terpenoid resistant cells can be used for the production of monoterpenes and monoterpenoids, such as, for example, R-(+)-limonene, 3-carene, α-pinene, β-pinene, verbenol, verbenone, myrcene, ipsdienol, geraniol, linalool, camphene, β-phellandrene, γ-terpinene and α-terpinolene. Exemplary monoterpenoids that can be produced by the terpenoid resistance cells provided herein include R-(+)-limonene, 3-carene, α-pinene and β-pinene. Also provided herein are methods for increasing production of a terpene/terpenoid using the terpenoid resistant cells provided herein. For example, a terpenoid resistant cell provided herein can be transformed with nucleic acid molecule encoding a mono-, sesqui- and di-terpene synthase capable of catalyzing the formation of a terpene/terpenoid from an acyclic pyrophosphate terpene precursor. The cell is then cultured under conditions suitable for the expression of the terpene synthase encoded by the nucleic acid molecule, wherein the terpene synthase catalyzes the formation of a terpene/terpenoid from the acyclic pyrophosphate terpene precursor. In some examples, the terpene/terpenoid that is produced is isolated. Any mono-, sesqui- or di-terpene synthase known to one of skill in the art may be used in the methods provided herein. Exemplary acyclic pyrophosphate terpene precursors include geranyl pyrophosphate (GPP), famesyl pyrophosphate (FPP) and geranyl-geranyl pyrophosphate (GGPP). Yeast expression systems, including yeast host cells that can be transformed with an ABC terpenoid transporter provided herein and that are useful for the production of terpenes and terpenoids are discussed in further detail below.

a. Yeast Expression Systems for the Production of Terpenes/Terpenoids

Yeast systems, such as, but not limited to, those from the *Saccharomyces* genus (e.g. *Saccharomyces cerevisiae*), *Schizosaccharomyces pombe*, *Yarrowia lipolytica*, *Kluyveromyces lactis*, and *Pichia pastoris* can be used to express terpene synthases, including mono-, sesqui- and diterpene synthases, and in turn can be used to produce mono-, sesqui- and diterpenes whose reactions are catalyzed by the terpene synthases. Yeast can be transformed with episomal replicating vectors or by stable chromosomal integration by homologous recombination. In some examples, inducible promoters are used to regulate gene expression. Exemplary promoter sequences for expression of terpene synthases in yeast include, among others, promoters for metallothionine, 3-phosphoglycerate kinase (Hitzeman et al. (1980) *J. Biol. Chem.* 255:2073), or other glycolytic enzymes (Hess et al. (1968) *J. Adv. Enzyme Reg.* 7:149; and Holland et al. (1978) *Biochem.* 17:4900), such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other suitable vectors and promoters for use in yeast expression are further described in Hitzeman, EPA-73,657 or in Fleer et al. (1991) *Gene,* 107:285-195; and van den Berg et al. (1990) *Bio/Technology*, 8:135-139. Another alternative includes, but is not limited to, the glucose-repressible ADH2 promoter described by Russell et al. (*J. Biol. Chem.* 258:2674, 1982) and Beier et al. (*Nature* 300:724, 1982), or a modified ADH1 promoter. Shuttle vectors replicable in yeast and *E. coli* can be constructed by, for example, inserting DNA sequences from pBR322 for selection and replication in *E. coli* (Amp$^r$ gene and origin of replication) into a yeast vector.

Yeast expression vectors can include a selectable marker such as LEU2, TRP1, HIS3, and URA3 for selection and maintenance of the transformed DNA. Proteins expressed in yeast are often soluble and co-expression with chaperonins, such as Bip and protein disulfide isomerase, can improve expression levels and solubility. Additionally, proteins expressed in yeast can be directed for secretion using secretion signal peptide fusions such as the yeast mating type alpha-factor secretion signal from *Saccharomyces cerevisiae* and fusions with yeast cell surface proteins such as the Aga2p mating adhesion receptor or the *Arxula adeninivorans* glucoamylase. A protease cleavage site (e.g., the Kex-2 protease) can be engineered to remove the fused sequences from the polypeptides as they exit the secretion pathway.

Yeast naturally express the required proteins, including GPP, FPP and GGPP synthases for the mevalonate-dependent isoprenoid biosynthetic pathway. Thus, expression of terpene synthases in yeast cells can result in the production of mono-, sesqui- and diterpenes, from GPP, FPP and GGPP, respectively. Exemplary yeast cells for the expression of terpene synthases include yeast modified to express increased levels of GPP, FPP and/or GGPP. For example, yeast cells can be modified to produce less squalene synthase or less active squalene synthase (e.g. erg9 mutants; see e.g. U.S. Pat. Nos. 6,531,303 and 6,689,593). This results in accumulation of FPP in the host cell at higher levels compared to wild type yeast cells, which in turn can result in increased yields of GGPP. In another example, yeast cells can be modified to produce more GPP, FPP or GGPP synthase by introduction of a GPP synthase gene, FPP synthase gene or GGPP synthase gene, such as the GGPP synthases BTS1 from *S. cerevisiae*, crtE from *Erwinia uredovora*, crtE from *Xanthophyllomyces dendrorhous*, al-3 from *Neuspora crassa* or ggs from *Giverella fujiuroi* (see U.S. Pat. No. 7,842,497). In some examples, the native GPP, FPP or GGPP gene in such yeast can be deleted. Other modifications that enable increased production of GPP, FPP and GGPP in yeast include, for example, but are not limited to, modifications that increase production of acetyl CoA, inactivate genes that encode enzymes that use GPP, FPP and GGPP as substrate and overexpress of HMG-CoA reductases, as described in U.S. Pat. No. 7,842,497.

i. Exemplary Cells

Exemplary modified yeast cells for the production of terpenes and terpenoids include, but are not limited to, modified *Saccharomyces cerevisiae* strains YPH499 (MATa, ura3-52, lys2-801, ade2-101, trp1-Δ63, his3-Δ200, leu2-Δ1), WAT11 (MATa, ade2-1, his3-11,-15; leu2-3,-112, ura3-1, canR, cyr+; containing chromosomally integrated *Arabidopsis* NADPH-dependent P450 reductase ATR1; see Pompon et al. (1995) *Toxicol Lett* 82-83:815-822; Ro et al. (2005) *Proc Natl Acad Sci USA* 102:8060-8065), BY4741 (MATa, his3Δ1, 1eu2Δ0, met15Δ0, ura3Δ0; ATCC #201388), CALI5-1 (ura3, leu2, his3, trp1, Δerg9::HIS3, HMG2cat/TRP1::rDNA, dpp1, sue), ALX7-95 (ura3, his3, trp1, Δerg9::HIS3, HMG2cat/TRP1::rDNA, dpp1 sue), ALX11-30 (ura3, trp1, erg9$^{def}$25, HMG2cat/TRP1::rDNA, dpp1, sue), which are known and described in one or more of U.S. Pat. Nos. 6,531,303, 6,689,593, 7,838,279, 7,842,497, 7,405,057 and 5,824,774 and published U.S. Pat. Application Serial Nos. 20040249219, 20110189717 and 2012-0246767 and copending applications PCT/CA2012/050837 and Ser. No. 13/694,350. Such cells can be modified to be terpenoid resistant by introduction of a gene encoding an ABC terpenoid transporter provided herein, by any method known to one of skill in the art or any method described herein.

ii. Culture of Cells

Any of a variety of fermentation methodologies can be used or developed for the production of mono-, sesqui- or diterpenes/terpenoids from terpenoid resistant cells that express the mono-, sesqui- or diterpene synthases. For example, large scale production can be effected by either batch or continuous fermentation. A classical batch fermentation is a closed system where the composition of the medium is set at the beginning of the fermentation and not subject to artificial alterations during the fermentation. Thus, at the beginning of the fermentation the medium is inoculated with the desired microorganism or microorganisms and fermentation is permitted to occur without further addition of nutrients. Typically, the concentration of the carbon source in a batch fermentation is limited, and factors such as pH and oxygen concentration are controlled. In batch systems the metabolite and biomass compositions of the system change constantly up to the time the fermentation is stopped. Within batch cultures cells typically modulate through a static lag phase to a high growth log phase and finally to a stationary phase where growth rate is diminished or halted. If untreated, cells in the stationary phase will eventually die.

A variation on the standard batch system is the Fed-Batch system, which is similar to a typical batch system with the exception that nutrients are added as the fermentation progresses. Fed-Batch systems are useful when catabolite repression tends to inhibit the metabolism of the cells and where it is desirable to have limited amounts of substrate in the medium. Also, the ability to feed nutrients will often result in higher cell densities in Fed-Batch fermentation processes compared to Batch fermentation processes. Factors such as pH, dissolved oxygen, nutrient concentrations, and the partial pressure of waste gases such as CO are generally measured and controlled in Fed-Batch fermentations.

Production of mono-, sesqui- or diterpenes/terpenoids also can be accomplished with continuous fermentation. Continuous fermentation is an open system where a defined fermentation medium is added continuously to a bioreactor and an equal amount of conditioned medium is removed simultaneously for processing. This system generally maintains the cultures at a constant high density where cells are primarily in their log phase of growth. Continuous fermentation allows for modulation of any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the medium turbidity, is kept constant. Continuous systems aim to maintain steady state growth conditions and thus the cell loss due to the medium removal must be balanced against the cell growth rate in the fermentation. Methods of modulating nutrients and growth factors for continuous fermentation processes as well as techniques for maximizing the rate of product formation are well known in the art.

Following cell culture, the cell culture medium then can be harvested to obtain the produced mono-, sesqui- or diterpenes.

iii. Isolation and Assays for Detection and Identification

The mono-, sesqui- or diterpenes/terpenoids produced using the methods above can be isolated and assessed by any method known in the art. In one example, the cell culture medium is extracted with an organic solvent to partition any terpenes or terpenoids produced into the organic layer. Production of mono-, sesqui- or diterpenes can be assessed and/or the mono-, sesqui- or diterpenes isolated from other products using any method known in the art, such as, for example, gas chromatography or column chromatography. For example, the organic layer can be analyzed by GC-MS.

The quantity of mono-, sesqui- or diterpenes produced can be determined by any known standard chromatographic technique useful for separating and analyzing organic compounds. For example, mono-, sesqui- or diterpene production can be assayed by any known chromatographic technique useful for the detection and quantification of hydrocarbons, including, but not limited to, gas chromatography mass spectrometry (GC-MS), gas chromatography using a flame ionization detector (GC-FID), capillary GC-MS, high performance liquid chromatography (HPLC) and column chromatography. Typically, these techniques are carried out in the presence of known internal standards which are used to quantify the amount of the terpenoid produced. For example, terpenoids, including sesquiterpenoids, such as mono-, sesqui- or diterpenoids, can be identified by comparison of retention times and mass spectra to those of authentic standards in gas chromatography with mass spectrometry detection. In other examples, quantification can be achieved by gas chromatography with flame ionization detection based upon calibration curves with known amounts of authentic standards and normalization to the peak area of an internal standard. These chromatographic techniques allow for the identification of any terpene present in the organic layer, including, for example, other terpenoids produced by the mono-, sesqui- or diterpene synthases.

In some examples, kinetics of mono-, sesqui- or diterpene production can be determined by synthase assays in which radioactive isoprenoid substrates, such as $^3$H or $^{14}$C GPP, FPP or GGPP, are used with varying concentrations of synthase. The products are extracted into an organic layer and radioactivity is measured using a liquid scintillation counter. Kinetic constants are determined from direct fits of the Michaelis-Menton equation to the data.

2. Methods for Detecting, Identifying, or Detecting and Identifying a Pathogen

Provided herein are methods for detecting, identifying, or detecting and identifying a pathogen involving obtaining a sample from an organism, or part thereof, by contacting the sample with a probe that specifically binds to a pathogenicity marker containing an ABC terpenoid transporter, and detecting the probe; thereby detecting or identifying a pathogen in an organism. If the pathogenicity marker is a nucleic acid, then the probe can be a nucleic acid or a pair of nucleic acids that can be used to detect the marker using PCR or related techniques, or the probe can be a nucleic acid that exhibits sufficient sequence identify so that the probe can hybridize to the marker under conditions of stringent hybridization. If the pathogenicity marker is a protein, then the probe can be for example an antibody raised against the target protein.

The sample can be obtained from an organism that is infected with a pathogen, or from a culture isolated from a symptomatic or asymptomatic diseased organism. The organism can be for example a pine tree for example but not limited to *Pinus contorta*, *Pinus banksiana*, or *Pinus jeffriei*.

The pathogen can be a fungus for example a fungus associated with an insect for example but not limited to the mountain pine beetle (*Dendroctonus ponderosae*). More specifically the pathogen might be *Grosmannia clavigera* or *Ophiostoma piceae*.

F. EXAMPLES

The following examples are included for illustrative purposes only and are not intended to limit the scope of the invention.

Example 1

G. clavigera Strain kw1407

The wild type *Grosmannia clavigera* (Gc) strain kw1407 (NCBI Taxonomy ID: 655863) is available from the University of Alberta Microfungus Collection and Herbarium, Edmonton, Alberta, Canada (UAMH Catalogue #11150). Also, this strain was deposited at the International Depositary Authority of Canada, National Microbiology Laboratory, Public Health Agency of Canada (1015 Arlington Street, Winnipeg, Manitoba, Canada, R3E 3R2) under Accession number 030212-01 on Feb. 3, 2012. The complete genomic sequence is available as described herein.

*G. clavigera* strain kw1407 was cultured on 1% malt extract agar (MEA, 0.83% Oxoid™ malt extract agar and 0.75% technical agar, pH was adjusted to 5-6) for maintenance or assessing growth rates.

Example 2

ABC Transporters in the G. clavigera Genome

*G. clavigera* ABC transporter genes were identified and annotated as described below.

A. Annotation of GcABC Genes

HMMER3.0 (hmmer.janelia.org) was used to search the Gc genome and ESTs and retrieve gene models containing the conserved ABC protein motif sequences "ABC-transporter (PF00005)", "ABC-2 transporters (PF01061)" and "ABC transporter transmembrane region (PF00664)". The resulting gene model annotations were curated manually, considering alternatively spliced isoforms, exon-intron boundaries and coding starts/stops. Potential pseudo-genes were excluded. The amino acid sequence was used for a Pfam domain search and topology determination (pfam-.sanger.ac.uk/search) for classification.

The *Magnaporthe grisea* ABC transporter collection (Crouzet et al. (2006) *FEBS Lett* 580:1123-1130) was used as a query for TBLASN local searches and to confirm the gene prediction and classification in Gc using CLC DNA main workbench 4.5.1 software (clcbio.com).

B. Results

Thirty-nine (39) ABC transporter genes in the Gc genome have been identified (see, DiGuistini et al. (2011) *Proc Natl Acad Sci USA* 108: 2504-2509, which provides the genomic sequence of the Gc genome). Table 3 below lists the GcABCs, Groups, Genbank IDs, protein length (in amino acids), contig number (genome locations), intron number, predicted topology, function and subcellular locations. All of the proteins contain at least one nucleotide-binding fold (NBF) domain. The gene models were located in 16 contigs. The transporter gene lengths vary from 999 to 5,241 base pairs (bp) and intron numbers vary from zero to 14 per gene. Gc cDNA EST data (Hesse-Orce et al. (2010) *BMC Genomics* 11:536) and RNA-seq transcriptome data (see DiGuistini et al. (2011) *Proc Natl Acad Sci USA* 108: 2504-2509) indicated that 23 (59%) and 37 (95%) of the genes are expressed, respectively (see Table 3).

Using functional domain predictions and TBLASTN searches of other fungal genomes, the GcABC proteins were classified into subfamilies GcABC-A through GcABC-G, following the Human Genome Organization (HUGO) nomenclature. Sequence similarity (Kovalchuk & Driessen (2010) *BMC Genomics* 11:177) was used to further subdivide the transporters of each subfamily into smaller groups. Among the 39 GcABC proteins identified, 24 proteins were full transporters with more than one transmembrane domain (TMD) or NBF, while eight proteins were half transporters with either a TMD-NBF or an NBF-TMD arrangement. The remaining eight proteins had one or two NBFs but lacked TMDs and were considered not to be membrane proteins or not to have a transport function.

The number of *G. clavigera* ABC transporter proteins in each subfamily were compared to those from various closely related fungal species, including the yeast species *S. cerevisiae* and *Yarrowia lipolytica*, the ascomycete rice pathogen *Magnaporthe grisea* and the ascomycete saprophyte *Neurospora crassa*. The results are set forth in Table 4 below. The total number of ABC transporters in each these species is similar, ranging from 30 to 48. Gc has five group V members in the ABC-C and ABC-G subfamilies, while *M. grisea* has two ABC-C group V members and one ABC-G group V member. In contrast to mitochondrial and peroxisome transporters (GcABC-B, GcABC-D), which are highly conserved across these species (70-80% identity), seven out of the ten GcABC-C members share less than 50% amino acid identity with closely related fungal species.

TABLE 3

| GcABCs | Group | Genbank ID (SEQ ID NO) | Length (aa) | Contig No. | Gene introns | Predicted topology | identified activity/function | EST Evidence | RNA-seq Evidence |
|---|---|---|---|---|---|---|---|---|---|
| GcABC-A1 | A | EFX05787.1 (9) | 1661 | 113 | 0 | (TMD-NBF)2 | / | / | Y |
| GcABC-B1* | B-I | EFX02238.1 (10) | 1417 | 156 | 2 | (TMD-NBF)2 | a-pheromone efflux | / | Y |
| GcABC-B2* | B-III | EFW98992.1 (11) | 890 | 97 | 5 | TMD-NBF-TMD | Multidrug resistance | / | / |
| GcABC-B3 | B-IV | EFW99076.1 (12) | 1360 | 89 | 1 | (TMD-NBF)2 | Multidrug resistance | Yes | Yes |
| GcABC-B4* | B-I | EFX05555.1 (13) | 918 | 113 | 1 | TMD-NBF | Mitochondrial precursor transport | Yes | Yes |
| GcABC-B5* | B-II | EFX00542.1 (14) | 758 | 173 | 2 | TMD-NBF | Heavy metal detoxification | Yes | Yes |
| GcABC-B6* | B-III | EFW99428.1 (15) | 997 | 82 | 5 | TMD-NBF | Heavy metal transporter | / | Yes |
| GcABC-B7* | B-III | EFX01489.1 (16) | 1154 | 167 | 0 | TMD-NBF | Multidrug resistance | Yes | Yes |
| GcABC-C1 | C-I | EFX03767.1 (17) | 1747 | 140 | 1 | (TMD-NBF)2 | Bile acid transporter | Yes | Yes |
| GcABC-C2 | C-II | EFX02908.1 (18) | 1718 | 144 | 2 | (TMD-NBF)2 | Bile acid transporter | Yes | Yes |
| GcABC-C3 | C-II | EFW99141.1 (19) | 1513 | 89 | 5 | TMD-TMD-NBF | Bile acid transporter | Yes | Yes |
| GcABC-C4 | C-III | EFX00086.1 (20) | 1602 | 173 | 3 | (TMD-NBF)2 | Bile acid transporter | Yes | Yes |
| GcABC-C5 | C-IV | EFX06644.1 (21) | 1550 | 108 | 0 | (TMD-NBF)2 | Multidrug resistance | / | Yes |
| GcABC-C6 | C-IV | EFX02441.1 (22) | 1462 | 156 | 0 | (TMD-NBF)2 | Multidrug resistance | Yes | Yes |
| GcABC-C7* | C-V | EFX06313.1 (23)/ EFX06672.1 (24) | 1144 | 108 | 14 | (TMD-NBF)2 | Multidrug resistance | / | / |
| GcABC-C8* | C-V | EFX06639.1 (25) | 1317 | 108 | 9 | (TMD-NBF)2 | Multidrug resistance | / | Yes |
| GcABC-C9* | C-V | EFX04947.1 (26) | 1336 | 132 | 2 | (TMD-NBF)2 | Multidrug resistance | / | Yes |
| GcABC-C10* | C-V | EFX03081.1 (27)/ EFX02994.1 (28) | 564 | 144 | 11 | (TMD-NBF)2 | Multidrug resistance | / | Yes |
| GcABC-C11* | C-V | EFX02174.1 (29)/ EFX02266.1 (30) | 1259 | 156 | 1 | (TMD-NBF)2 | Multidrug resistance | Yes | Yes |
| GcABC-C12 | C-VI | EFW99233.1 (31) | 1552 | 89 | 5 | (TMD-NBF)2 | Metal ion transporter | Yes | Yes |
| GcABC-C13* | C-VII | EFX02817.1 (32) | 1488 | 144 | 2 | TMD-(TMD-NBF)2 | Multidrug resistance | Yes | Yes |
| GcABC-D1 | D-1 | EFW99459.1 (33) | 735 | 82 | 1 | TMD-NBF | Fatty acid transport | / | Yes |
| GcABC-D2 | D-2 | EFX00928.1 (34) | 817 | 168 | 2 | TMD-NBF | Fatty acid transport | Yes | Yes |
| GcABC-E1 | E-1 | EFX01682.1 (35) | 609 | 161 | 5 | NBF-NBF | Rnase 1 inhibitor | Yes | Yes |
| GcABC-F1 | F-I | EFX02105.1 (36) | 619 | 156 | 2 | NBF-NBF | Ribosome biogenesis | Yes | |
| GcABC-F2 | F-II | EFX02105.1 (37) | 770 | 167 | 1 | NBF-NBF | Translation initiation regulator | Yes | Yes |

TABLE 3-continued

| GcABCs | Group | Genbank ID (SEQ ID NO) | Length (aa) | Contig No. | Gene introns | Predicted topology | identified activity/function | EST Evidence | RNA-seq Evidence |
|---|---|---|---|---|---|---|---|---|---|
| GcABC-F3 | F-IV | EFX01944.1 (38) | 1122 | 160 | 1 | NBF-NBF | mRNA-nucleus export | Yes | Yes |
| GcABC-F4 | F-V | EFX04290.1 (39) | 1055 | 140 | 1 | NBF-NBF | Elongation factor 3 | Yes | Yes |
| GcABC-G1 | G-I | EFX06115.1 (1) | 1460 | 113 | 5 | (NBF-TMD)2 | Multidrug resistance | / | Yes |
| GcABC-G2 | G-I | EFX00255.1 (2)(3)/ | 1540 | 173 | 1 | (NBF-TMD)2 | Multidrug resistance | Yes | Yes |
| GcABC-G3* | G-I | EFX03218.1 (40) | 1444 | 144 | 4 | (NBF-TMD)2 | Multidrug resistance | Yes | Yes |
| GcABC-G4 | G-V | EFX01574.1 (41) | 1507 | 161 | 1 | (NBF-TMD)2 | Multidrug resistance | / | Yes |
| GcABC-G5* | G-V | EFW98765.1 (42) | 1124 | 97 | 8 | (NBF-TMD)2 | Multidrug resistance | / | Yes |
| GcABC-G6 | G-V | EFX03933.1 (43) | 1374 | 140 | 0 | (NBF-TMD)2 | Multidrug resistance | / | Yes |
| GcABC-G7 | G-V | EFW99599.1 (44) | 1390 | 82 | 1 | (NBF-TMD)2 | Multidrug resistance | / | Yes |
| GcABC-G8 | G-VI | EFX00337.1 (45) | 606 | 173 | 2 | NBF-TMD | Multidrug resistance | Yes | Yes |
| GcABC-G9 | G-VII | EFX05969.1 (46) | 1118 | 113 | 3 | NBF-TMD | / | Yes | Yes |
| GcABC-NC1 | N.C-1 | EFX01444.1 (47) | 33 | 167 | 0 | NBF | / | Yes | Yes |
| GcABC-NC2 | N.C-2 | EFW99237.1 (48) | 646 | 89 | 0 | NBF | / | Yes | Yes |

*Annotation was corrected from the published genome.

TABLE 4

Subfamily distribution of ABC transporter proteins in fungal species

| | G. clavigera | M. grisea* | N. crassa* | Y. lipolytica* | S. cerevisiae* |
|---|---|---|---|---|---|
| ABC-A | 1 | 2 | 1 | 1 | 0 |
| ABC-B (H) | 3 | 12 | 5 | 4 | 1 |
| ABC-B (F) | 4 | 6 | 4 | 2 | 3 |
| ABC-C | 13 | 10 | 9 | 10 | 6 |
| ABC-D | 2 | 2 | 2 | 2 | 2 |
| ABC-E | 1 | 1 | 1 | 1 | 1 |
| ABC-F | 4 | 5 | 4 | 4 | 5 |
| ABC-G (H) | 2 | 2 | 3 | 1 | 2 |
| ABC-G (F) | 7 | 6 | 4 | 5 | 8 |
| N.C | 2 | 2 | 2 | 2 | 2 |
| Total | 39 | 48 | 35 | 32 | 30 |
| Genome size | 30 | 40 | 43 | 32 | 12.07 |
| Transporters/ mb of genome | 1.46 | 1.25 | 0.81 | 1.56 | 2.49 |

The symbols (H), (F) and (N.C) represent full, half, and non classified transporters, respectively.
*Data for other fungi are from the review by Kovalchuk and Diressen (2010) BMC Genomics 11: 177.

Example 3

Expression of GcABC Transporter Genes in Response to Terpenoids

GcABC transporter genes that are up-regulated in response to exposure of Gc to terpenoids were identified by an analysis of Gc genome and transcriptome sequences
A. Methods
To identify the ABC transporters involved in G. clavigera's response to terpenes, RNA-seq expression profiles were compared for all GcABCs grown on 1) a complete medium containing a blend of mono- and diterpenes, and 2) a yeast nitrogen base medium containing monoterpenes as the sole carbon source.

1. Fungal Growth Under Various Conditions

G. clavigera was grown on a complete medium with a blend of mono- and diterpenes (CM+T) for 12 h and 36 h, as described in DiGuistini et al. (2011) Proc Natl Acad Sci USA 108: 2504-2509. The mono- and diterpene blend contained monoterpenoids R-(+)-limonene, 3-carene, α-pinene and β-pinene at a ratio of 5:3:1:1 and 0.01% diterpenes (abietic acid, dehydroabietic acid and isopimaric acid). Monoterpenes included R-(+)-limonene ((R)-(+)-Limonene 90%, Sigma cat #62122), 3-carene (3-carene 90%, Sigma, cat #115576), α-pinene ((±)-2-pinene 98%, Sigma cat #147524), β-pinene ((1S)-(−)-β-Pinene 99%, Sigma, cat #112089). All of the monoterpenes used were highly volatile and insoluble. Diterpenes included Abietic acid 90-95% (Orchid Cellmark, cat #R002); Dehydroabietic acid 99% (Orchid Cellmark, cat #R001) and Isopimaric acid 99% (Orchid Cellmark cat #R004). G. clavigera grown on complete medium, without any mono- or diterpenes, was used as a control.

Mono- and diterpene treatments were performed on glass petri dishes with the mono- and diterpenes applied to filter paper that was placed in the cover of the petri dish, which was sealed by Duraseal film. Specifically, plugs of actively growing G. clavigera fungal cultures on MEA were transferred into the center of glass petri dishes containing yeast nitrogen base-complete medium (YNB-CM; 0.17% YNB without amino acids, 1.5% granulated agar, 1% maltose, 0.1% PHP, and 0.3% asparagine). Two (2×4 cm) strips of filter paper were placed inside the lid of the plate and 200 μL of individual mono- or diterpenes or a mixture of monoterpenes (MT) were added onto the filter paper. The glass plates were sealed with DuraSeal™ film (Laboratory Sealing Film, VWR, cat #89031-573) and incubated at ~22° C. in a sealed glass container for 7 days or until the mycelium reached the edge of the plates. Colony diameters were measured daily.

2. Fungal Growth Using Monoterpenes as Carbon Sources

Fungal spores were incubated for 3 days on 1% malt extract agar (MEA) overlaid with cellophane (Amersham Biosciences, cat #80611781), then the young mycelia were treated with a mixture of monoterpenes (200 μL) for 3-4 days before being transferred onto yeast nitrogen base (YNB) medium with a mixture of monoterpenes (MT) as sole carbon source (YNB+MT; 6.7% YNB without amino acids, but with ammonium sulphate) in glass plates. The synthetic monoterpenoid blend contained R-(+)-limonene, 3-carene, α-pinene and β-pinene at a ratio of 5:3:1:1. If necessary monoterpenes were re-supplied biweekly until the mycelia covered at least half of the media surface (3-4 weeks). RNA-seq analysis was performed after 10 days. *G. clavigera* grown on YNB+1% mannose as the sole carbon source was used as a control.

3. RNA-seq Analysis

Ten μg of RNA was isolated from each sample and were paired-end sequenced on an Illumina GAIIx. Sequence filtering, trimming, mapping to the reference genome and RNA-seq analyses were conducted on CLC Genome Workbench v4, as described in DiGuistini et al. (*Proc Natl Acad Sci USA* 108: 2504-2509 (2011)). For each RNA-seq library, samples were collected from 3 biological replicates, DNA was extracted separately and the samples were pooled for paired-end sequencing on an Illumina GAIIx.

Five RNA-seq data sets were analyzed. Two were generated previously in previous work (see, DiGuistini et al. (2011) *Proc Natl Acad Sci USA* 108: 2504-2509); the third was generated for *G. clavigera* growing on YNB with a mixture of monoterpenes as the sole carbon source. Results were normalized to a *G. clavigera* sample grown on mannose (YNB+1% mannose) as a carbon source. Results for *G. clavigera* grown in the presence of mono- and di-terpenes were normalized to a *G. clavigera* sample grown on complete medium.

B. Results

FIG. 3A shows GcABC transporter genes whose transcripts were significantly up-regulated under at least one of the tested conditions. Up-regulation indicates a P-value<0.05 for differential abundance and a fold change of at least 1.5× relative to the non-treated control (for CM+T) or the control grown on mannose (for YNB+MT). As shown in FIG. 3A, for *G. clavigera* grown in CM+T, six (6) GcABC transporter genes were up-regulated at 12 h, while eleven (11) were up-regulated at 36 h. For *G. clavigera* grown with monoterpenes as the sole carbon source (YNB+MT), ten (10) GcABCs were up-regulated. Five (5) GcABCs were up-regulated under all three conditions. Two (2) GcABCs belonged to the ABC-G-group I transporters, namely GcABC-G1 and GcABC-G2, and three (GcABC-F1, GcABC-F2, GcABC-F3) belonged to the ABC-F subfamily, whose members are not considered to be true transporters due to the absence of a TMD (Kovalchuk and Diressen (2010) *BMC Genomics* 11:177). Three (3) GcABCs were up-regulated only on the more restrictive YNB+MT medium, in which monoterpenes were the only available carbon source. These include a PDR (GcABC-G3), a vacuolar transporter (GcABC-B5) and a peroxisome transporter (GcABC-D1) that could be involved in fatty acid metabolism.

Example 4

Differential Gene Expression of GcABC-G1

GcABC-G1 was the most strongly up-regulated of the 39 GcABCs. Its transcript abundance relative to controls increased at least 100-fold under all three conditions, and transcripts were almost 1,500-fold more abundant in YNB+ MT than in YNB+mannose, which was used as a control (see FIG. 3A). These results were validated by reverse-transcription PCR (RT-qPCR) analysis of *G. clavigera* grown on either complete media+mono- and diterpenes (CM+T) for up to 72 hr or yeast nitrogen base+monoterpenoids (YNB+ MT) for 18 days. Fungal growth and terpene treatment experiments were performed as described in Example 3 above.

Differential gene expression was validated by RT-qPCR. Fungal mycelium samples were removed at 0, 6, 12, 36, 48 and 72 hrs from complete medium with mono- and diterpenes (CM+T) and 7, 10, 14, 18 days from YNB medium with a mixture of monoterpenes as sole carbon (YNB+MT). Extraction of total RNA, cDNA synthesis and qPCR were performed as described by Hesse-Orce et al. (2010). Briefly, trizol (Invitrogen, Mississauga, ON) extractions were used to purify RNA for quantitative real-time PCR (qPCR) with the following modifications: (1) centrifugations were performed at 4° C. and (2) 1-bromo-3-chloro-propane (BCP) was substituted for chloroform. DNaseI (Fisher Scientific, Ottawa, ON) treatment of the Trizol extracted RNA ensured adequate removal of all genomic DNA contamination. cDNA was produced from 5 mg of total RNA using Superscript II (Invitrogen, Mississauga, ON) and oligo (dT)12-18 following the manufacturer's protocol. qPCR was performed on a Stratagene M3000P (La Jolla, Calif.) and data analysis was performed within SAS (Statistical Analysis Systems, Cary, N.C.). PCR reactions were composed of forward and reverse primers, each at 300 or 600 nM (optimum primer concentration was determined using a dilution curve), 1xiQ supermix premix (Bio-Rad, Mississauga, ON) and 50 ng of *G. clavigera* cDNA in a total volume of 25 mL. Cycling parameters for qPCR were 95° C. for 10 min, followed by 40 cycles of 95° C. for 10 s, 62° C. for 30 s, 72° C. for 30 s and an observation step of 82° C. for 18 s, followed by a melting point analysis. Three biological and technical replicates were used for each time point. Data collection and statistical analysis were performed on the Bio-Rad CFX96 real-time PCR detection system (Roche, Quebec, CA). mRNA abundance was normalized using β-tubulin, a housekeeping gene.

As shown in FIG. 3B, GcABC-G1 showed increased transcript levels throughout fungal growth on CM+T compared to non-treated control (complete medium). The increase was up to 115-fold after 6 h, reached a peak of 648-fold at 12 h, and was still above 50-fold after 72 h growth. GcABC-G1 also showed increased transcript levels (more than 100-fold) throughout fungal growth on YNB+ MT compared to YNB+mannose (see FIG. 3C).

GcABC-G1 was not induced by other stress treatments (e.g. oxidative, osmotic, nitrogen starvation, high temperature, and lodgepole pine phloem extract). The genome and RNA-seq resources that was created for *G. clavigera* indicated that its response to host-specific metabolites differed for phloem phenolic extracts (lodgepole pine phloem methanol extract (LPPE)) containing defensive phenolic chemicals, sugars and other metabolites, and synthetic terpenoids (Hesse-Orce et al. (2010) *BMC Genomics* 11:536; DiGuistini et al. (2011) *Proc Natl Acad Sci USA* 108: 2504-2509). Twelve hours after a treatment, RNA degradation was substantial for exposure to terpenoids, but was minimal for treatments with LPPE, or oxidative, osmotic, temperature and nitrogen stresses.

Example 5

Generation of an *G. clavigera* abc-g1 Gene Knockout Mutant

To further functionally characterize GcABC-G1, a Gc PDR ABC transporter that was highly induced (>100 fold change) on the transcriptome level by monoterpenes, a gene deletion (knockout) mutant was generated using an *Agrobacterium*-mediated gene deletion procedure (Wang et al. (2010) *Curr Genet* 56:297-307). *Agrobacterium* GV3101, a laboratory stock, was used to transform *G. clavigera*. The whole gene open reading frame (ORF) encoding GcABC-G1 in *G. clavigera* was replaced with the selective gene marker hygromycin B (hph). Gene replacement (deletion) was verified by PCR amplification of adjacent regions, target region and selective marker gene, and copy numbers were determined by southern blot. The *G. clavigera* GcABC-G1 deletion mutant was designated mutant Δgcabc-g1.

Example 6

Effect of GcABC-G1 on *G. clavigera* Fungal Sensitivity to Terpenes

To compare the response of wildtype *G. clavigera* (WT) and the *G. clavigera* Δgcabc-g1 mutant to a mixture of monoterpenes, the strains were grown on MEA and treated with individual monoterpenes, a mixture of monoterpenes or individual diterpenes. Growth rates and colony morphologies were examined.

A. Growth of *G. clavigera* WT and Mutant Δgcabc-g1 in the Presence of Monoterpenes Colony morphologies and growth rates were examined for *G. clavigera* WT and mutant Δgcabc-g1 grown on malt extract agar (MEA) in the presence and absence of 200 μL of a mixture of monoterpenes as described in Example 3.A.1. above. Fungal growth rates were calculated (mm/day). The results are shown in FIGS. 4A and 4B. Mycelium growth rates were also determined in the presence or absence of 200 μL of individual monoterpenes, including R-(+)-limonene, 3-carene, α-pinene and β-pinene, or 200 μL of a mixture of monoterpenes (R-(+)-limonene, 3-carene, α-pinene and β-pinene at a ratio of 5:3:1:1). Fungal spores were incubated for 3 days on MEA overlaid with cellophane (Amersham Biosciences, cat #80611781); then the young mycelia were treated with individual monoterpenes or a mixture of monoterpenes (200 μL) for 3-4 days before being transferred onto YNB. In YNB, monoterpenes were provided on filter paper as described in Example 3.A.1. and if necessary were re-supplied biweekly until the mycelia covered at least half of the media surface (3-4 weeks). Colony diameters were measured daily. Fungal growth rates were calculated (mm/day). Results were calculated as the average of 5 replicates and standard deviation was calculated.

As indicated in FIGS. 4A and 4B, deletion of GcABC-G1 increases fungal sensitivity to monoterpenes. On malt extract agar (MEA), colony morphologies and growth rates were similar for *G. clavigera* WT and mutant Δgcabc-g1 (see FIG. 4A). In the presence of a mixture of monoterpenes, the mutant Δgcabc-g1 is more sensitive than *G. clavigera* WT, as shown by the decreased growth and a change in colony morphology.

In the presence of individual monoterpenes the growth of *G. clavigera* WT was delayed by 1 day for 3-carene, (+)-limonene and the mixture of monoterpenes (MT) but not for α-pinene. In contrast, the mutant Δgcabc-g1 showed longer growth delays for all monoterpenes tested: 1 day for α-pinene; 2 days for 3-carene, (+)-limonene and MT; and up to 3 days for (−)-β-pinene. Fungal growth rates in the linear phase that followed such delays were calculated. FIG. 4B shows that the growth rates of mutant Δgcabc-g1 and *G. clavigera* WT were similar in the presence of α-pinene (~7 mm/day) and only slightly different with 3-carene (~5 to 6 mm/day). The growth rates of the mutant Δgcabc-g1 were 52% and 60% lower than *G. clavigera* WT on (+)-limonene and (−)-β-pinene, respectively. Student t-test indicated significant difference between *G. clavigera* WT and mutant Δgcabc-g1 on (+)-limonene, 3-carene, (−)-β-pinene and MT ($p<0.01$), but not on control and α-pinene. These results indicate that GcABC-G1 supports the growth of *G. clavigera* in the presence of certain monoterpenes.

Figure 8:
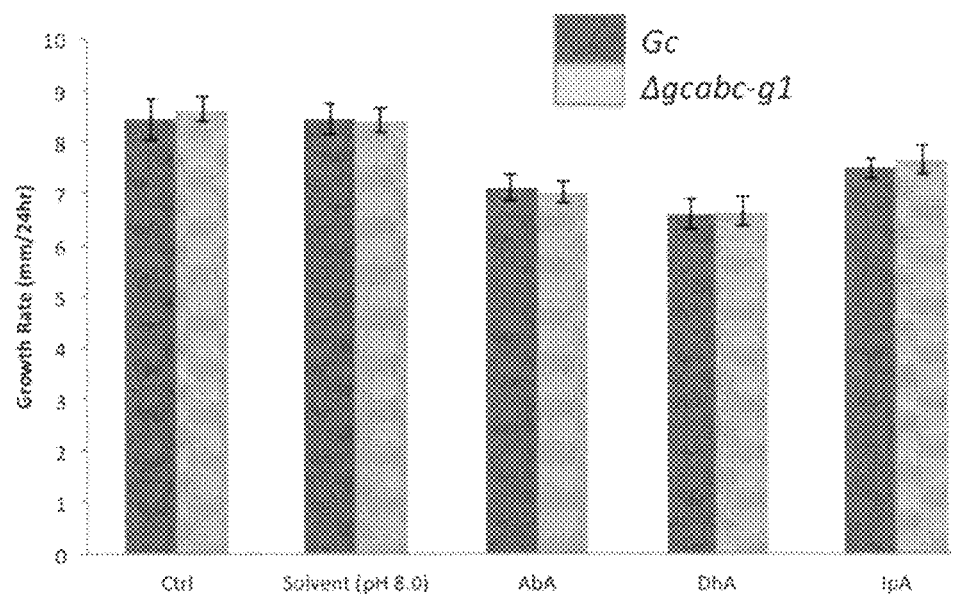
FIG. 8 shows individual diterpenes in MEA inhibited the growth of *G. clavigera* and mutant Δgcabc-g1 at similar rates. Results are the average of three replicates. Error bar represents standard deviation. Ctrl: Control; Aba: 0.1% abietic acid; Dha: 0.1% dehydroabietic acid; Ipa: 0.1% isopimaric acid.

B. Growth of *G. clavigera* WT and Mutant Δgcabc-g1 in the Presence of Diterpenes Growth rates were examined for *G. clavigera* WT and the mutant Δgcabc-g1 grown on MEA in the presence or absence of 200 μL of abietic acid, dehydroabietic acid and isopimaric acid as described in Example 3.A.2. Each diterpene was dissolved in a basic NaOH solution before being added into the MEA medium; the final pH of the medium was ~8.0. Growth rates were calculated daily (mm/day). The results are shown in FIG. 8, which indicates growth rate in mm/24 hr for the average of three replicates. Error bar represents standard deviation.

As shown in FIG. 8, in contrast to the effects of the monoterpenes, individual diterpenoids abietic acid (AbA), dehydroabietic acid (DhA) and isopimaric acid (IpA) only slightly inhibited growth for *G. clavigera* WT and mutant Δgcabc-g1, without significant differences between *G. clavigera* WT and mutant Δgcabc-g1.

Example 7

Effect of GcABC-G1 on *G. clavigera* Asexual Spore Germination in the Presence of Monoterpenes To further assess GcABC-G1's role in the *G. clavigera* response to monoterpenes, the effects of monoterpenes on asexual spore germination in Gc and Δgcabc-g1 were compared.

A. Fungal Spore Germination and Survival

*G. clavigera* WT or mutant Δgcabc-g1 fungal spores were collected from 7-14 day old cultures grown on MEA (0.83% Oxoid™ malt extract agar and 0.75% technical agar, pH was adjusted to 5-6). Mycelium debris was removed by filtration (BD Falcon Cell Strainers; cat #08-771-1). Spore concentrations were determined using a haemocytometer and further diluted to ~2 spores/μL. 100 μL of the spore suspension was spread on MEA in glass plates. For monoterpene treatment, two (2×4 cm) strips of filter paper were placed inside the lid of the plate and 200 μL of a mixture of monoterpenes were added onto the filter paper. For diterpene treatment, 100 μL of the spore suspension was spread on MEA containing 0.01% of a mixture of diterpenes (abietic acid, dehydroabietic acid and isopimaric acid). The glass plates were sealed with DuraSeal™ film (Laboratory Sealing Film, VWR, cat #89031-573) and incubated at ~22° C. in a sealed glass container. The germinated spores were counted daily; at day 6 the monoterpenes were removed and the MEA plates were further incubated for 4 days to assess the survival of the spores.

B. Results

For *G. clavigera*, germination was not inhibited by α-pinene or 3-carene, and only partially reduced by (+)-limonene and (−)-β-pinene (~70%) (see FIG. 4C, which shows the average of 5 replicates, with error bars indicating standard deviations). For the mutant Δgcabc-g1, α-pinene reduced spore germination by only 30%. 3-carene, (+)-limonene, and (−)-β-pinene completely prevent spore germination. When these monoterpenes were removed after 6 days of incubation and incubation was continued, 90% of the mutant Δgcabc-g1 spores had been killed. Student t-test indicated significant difference between *G. clavigera* WT and mutant Δgcabc-g1 for all the monoterpenes (p<0.01), but not on control MEA.

Example 8

Growth of *G. claivgera* or Mutant Δgcabc-g1 on Monoterpene Carbon Sources

It was previously reported that *G. clavigera* was able to grow on YNB with various monoterpenes as the sole carbon source (see, DiGuistini et al. (2011) *Proc Natl Acad Sci USA* 108: 2504-2509, FIG. 1). In this example, various monoterpenes were assessed for their ability to support growth of the *G. clavigera* wildtype stain and the Δgcabc-g1 mutant.

Experiments were performed as described in Example 3.A.2. Growth of wildtype *G. clavigera* and the mutant Δgcabc-g1 was determined utilizing yeast nitrogen base (YNB)+either 10 μL or 200 μL of (+)-limonene, α-pinene or β-pinene. Growth was determined after 4 weeks. Monoterpenes were re-supplied every 2 weeks. Growth on YNB alone was used as a negative control. Growth on YNB+1% mannose was used as a positive control.

Wildtype *G. clavigera* grew on YNB with 200 μL of (+)-limonene or 1% mannose as a sole carbon source. In contrast, *G. clavigera* was not able to utilize α-pinene or β-pinene as a sole carbon source. The mutant Δgcabc-g1 was killed by 200 μL (+)-limonene, while at 10 μL (+)-limonene the mutant survived, but did not grow.

While the *G. clavigera* WT grows on minimal medium with monoterpenoids as the sole carbon source, the abc-g1 mutant cannot grow or survive under the same conditions (see FIG. 1). At very low monoterpenoid concentrations the mutant survives. These results reveal two adaptive mechanisms for survival of *G. clavigera* in the presence of host monoterpenoids; 1) *G. clavigera* can use monoterpenoids as a carbon source; 2) GcABC-G1 can function as a monoterpenoid transporter removing potentially toxic monoterpenoids and their derivatives.

Example 9

Effect of GcABC-G1 on Sensitivity of *G. clavigera* to Other PDR Substrates

Based on sequence similarity and domain topology (see Tables 3 and 4), GcABC-G1 belongs to the pleiotropic drug resistance (PDR) group of transporters, members of which are able to excrete a wide range of chemicals (Rogers et al. (2001) *J Mol Microbiol Biotechnol* 3: 207-214, de Waard et al. (2006) *Pest Manag Sci* 62: 195-207). To establish whether GcABC-G1 affects the tolerance of *G. clavigera* to compounds other than monoterpenes, the growth rate of *G. clavigera* WT and the mutant Δgcabc-g1 on other potential PDR substrates including azoles (propiconazole and tebuconazole), antibiotics (cycloheximide, erythromycin), flavonoids (fisetin, quercetin), simple phenolics (benzoic acid, salicylic acid, vanillic acid, gentisic acid), and phytoalexins (catechin, resveratrol, and taxifolin) was assessed. Chemicals were selected based on the literature for PDR transporters, and concentrations affecting *G. clavigera* growth rates were determined experimentally by gradient tests.

A. Fungal Growth in the Presence of Potential PDR Substrates

PDR substrates were added directly to MEA media after autoclaving. The optimal concentration of each chemical was determined by gradient tests. The final concentrations of the PDR substrates were: 2 μM for azoles (propiconazole, Sigma cat #45642 and tebuconazole, Sigma, cat #32013), 50 μM for flavonoids (quercetin, Sigma, cat #Q4951 and fisetin Sigma, cat #F4043), 500 μM for antibiotics (cycloheximide, Sigma, cat #C7698 and erythromycin, VWR, cat #CA100218-996), 7.5 μM for phenolic compounds (benzoic acid, Sigma, cat #12349, salicylic acid, Sigma, cat #S7401, vanillic acid, Sigma, cat #94770 and gentisic acid, Sigma, cat #149357) and 50 μM for phytoalexins (catechin, Sigma, cat #C1251, resveratrol, Sigma, cat #R5010 and taxifolin, Sigma, cat #T4512).

*G. clavigera* WT or mutant Δgcabc-g1 fungal cultures were cultured on 1% MEA (0.83% Oxoid™ malt extract agar and 0.75% technical agar, pH was adjusted to 5-6). Plugs of actively growing *G. clavigera* WT or mutant Δgcabc-g1 fungal cultures were transferred into the center of glass petri dishes containing PDR supplemented MEA media. The glass plates were sealed with DuraSeal™ film (Laboratory Sealing Film, VWR, cat #89031-573) and incubated at ~22° C. in a sealed glass container for 7 days or until the mycelium reached the edge of the plates. Colony diameters were measured daily.

B. Results

On MEA, none of the tested antibiotics, flavonoids and phytoalexins affects the growth of either *G. clavigera* WT or the mutant Δgcabc-g1. Azoles and phenolics inhibit fungal growth, but there are no differences in inhibition of growth between *G. clavigera* WT and the mutant Δgcabc-g1. These results show that GcABC-G1 is specific for monoterpenoids.

Example 10

Heterologous GcABC-G1 Expression Enhances Survival of *S. cerevisiae* in the Presence of Monoterpenes GcABC-G1 was heterologously expressed in *Saccharomyces cerevisiae* to further assess the role of GcABC-G1 in monoterpene tolerance and to demonstrate its use in heterologous host cells. The protein was expressed and monoterpene resistance was determined.

A. Heterologous Expression of GcABC-G1 in *S. cerevisiae*.

To further support the results showing that the GcABC-G1 transporter provides monoterpenoid resistance, the GcABC-G1 gene was cloned and expressed in *S. cerevisiae* under the control of the GAL1 promoter, which was induced in a synthetic galactose (SG) medium. *S. cerevisiae* (Sc) BY4741(MATa his3Δ1 leu2Δ0 met15Δ0 ura3Δ0) and plasmid pESC-URA (Stratagene, Gene Bank accession NO. AF063585) were used for heterologous expression. Yeast wild type (WT) and transformants were maintained on yeast extract peptone dextrose (YPD; complete medium: 1% yeast extract, 2% peptone, 2% glucose, 1.5% agar). Gene cloning and plasmid manipulation were carried out in *Escherichia coli* DH5α and Top10 following standard procedures.

The full-length cDNA enoding GcABC-G1 (SEQ ID NO:2) was amplified and cloned into the yeast expression vector pESC-URA under the control of the GAL1 promoter, using conventional digestion/ligation methods (HindIII and BamHI). Yeast were also transformed with the empty vector pESC-URA that was used as a control. Expression of GcABC-G1 was confirmed by PCR and reverse transcription-PCR (RT-PCR). The transformation of yeast was carried out following the short protocol kit from Sigma (cat #Yeast 1). Integration of GcABC-G1 into the yeast genome was confirmed using PCR and expression of GcABC-G1 was confirmed by RT-PCR.

B. Monoterpenoid Sensitivity

To test yeast sensitivity to monoterpenoids, S. cerevisiae cells were grown for 40 hrs in synthetic-galactose liquid medium with galactose (SG; induction medium; 0.67% YNB without amino acid, 2% galactose, 0.13% Yeast synthetic drop-out medium supplements without uracil, 1.5% agar; pH was adjusted to 6.0-6.5) to induce gene expression. Induced cells were serially diluted and spotted on the SG agar medium. Four filter paper discs (0.5 cm each) placed in the centre of the plate were loaded with 100 µL synthetic monoterpenoid blend to provide a saturated environment. The chemical sensitivity was determined based on the presence or absence of colonies onto the plate after 1 week incubation at 28° C. with and without monoterpenoids.

Figure 2:
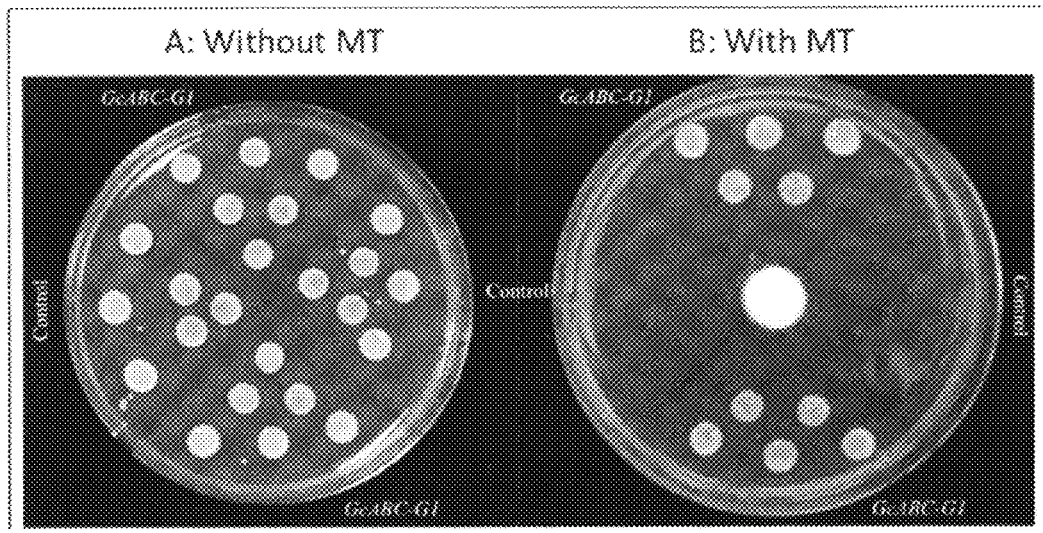
FIG. 2 shows *S. cerevisiae* gained resistance to the synthetic monoterpenoid blend upon receiving GcABC-G1 but not the empty vector (control).

S. cerevisiae transformed with the vector only (Sc-V) or with the vector containing the GcABC-G1 (Sc-ABC), grew at similar rates on yeast extract-peptone-dextrose (YPD) and SG media. When both transformed strains were serially diluted, spotted on SG media, and treated with the synthetic monoterpenoid blend, only the transformant containing the GcABC-G1 gene grew after 1 week incubation (see FIG. 2). The transformant containing only the vector did not grow under these conditions.

C. Yeast Spot Test

Yeast cells were inoculated into SG broth and incubated at 28° C. for overnight at a shaking speed of 250 rpm. The overnight culture was diluted to an OD600 of 0.1 and spotted on SG glass plates (~$10^5$/spot). Four filter paper discs (0.5 cm each) were placed in the centre of the plate and were loaded with 60 µL mixture or individual monoterpenes to provide a saturated environment. The plates were sealed with DuraSeal™ film and incubated facing up at 28° C. until colonies showed up.

Figure 6:
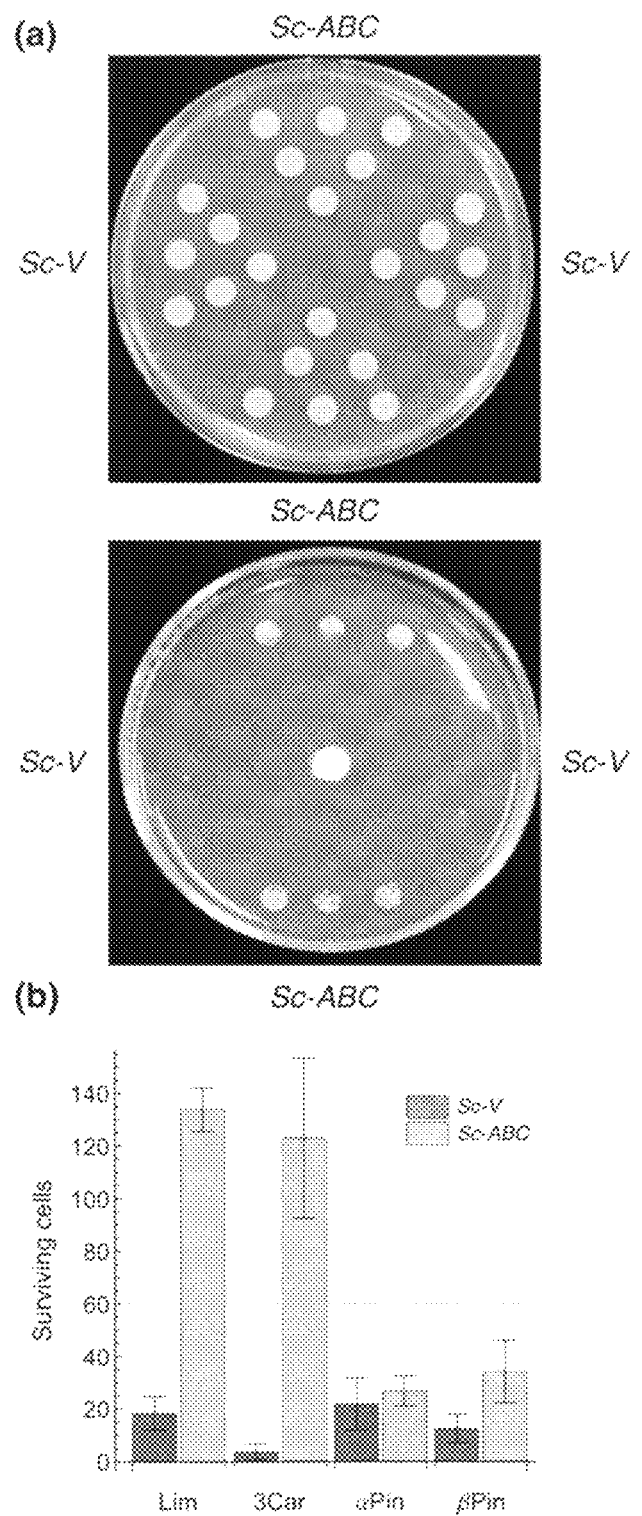
FIG. 6 shows GcABC-G1 conferred monoterpene tolerance to *S. cerevisiae* (Sc).

When Sc-V and Sc-ABC were spotted onto SG plates and treated with 60 µL of a mixture of monoterpenes, only Sc-ABC had grown after 7 days of incubation (FIG. 6A). Monoterpene treatments with more than 60 µL per plate killed all yeast cells. These tests demonstrate that Sc-V and Sc-ABC are more sensitive to monoterpenes than the pine pathogen G. clavigera.

D. Yeast Cell Survival

The survival of Sc-V and Sc-ABC with individual monoterpenes was shown using a dilution plate assay. Overnight yeast cultures grown in SG broth were diluted to an OD600 of 0.2 and further grown to an OD600 of 0.4 at 28° C. The yeast cells were diluted to an appropriate density that was spread on SG media in Petri dishes glass ($10^5$ per petri dish). The yeast cells were treated for one hour with a specific monoterpene (5 µL) diluted in 245 µL ethanol; the solution was applied on five small filter papers placed inside the lid and the glass plates were sealed with DuraSeal film. After one-hour incubation, the chemical was removed and plates were further incubated for 4 days at 28° C. The numbers of surviving cells with and without monoterpene treatments were counted.

When the yeast GcABC-G1 transformant was treated with individual monoterpenoids, β-pinene had the strongest inhibition effect while (+)-limonene had the least inhibitory effect. When $10^5$ yeast cells were spread on SG plates and incubated with 5 µL of individual monoterpene for 3 days, neither Sc-V nor Sc-ABC survived. When the duration of monoterpene treatments was reduced to one hour, a sufficient number of Sc-V and Sc-ABC cells survived to allow for comparative analyses (see FIG. 6B). Under conditions of one-hour treatment with 3-carene, approximately 30-times more Sc-ABC cells survived than Sc-V; for (+)-limonene and (−)-β-pinene, approximately 7 and 3 times more Sc-ABC cells survived than Sc-V. In contrast, with α-pinene, the numbers of surviving cells were low and not significantly different for Sc-V and Sc-ABC (FIG. 6B). Student t-test indicated significant differences between S. cerevisiae and Sc-ABC for all the monoterpenes (p<0.01) except for α-pinene. These results show that the heterologous expression of GcABC-G1 in S. cerevisiae improves the survival of yeast cells in the presence of some monoterpenes.

Two independent lines of experiments, gene knockout in Gc and heterologous expression in yeast (Saccharomyces cerevisiae), demonstrated that GcABC-G1 confers resistance to pine monoterpenes. Taken together, the results obtained in independent experiments with Gc and Sc demonstrate a role for GcABC-G1 in tolerating (+)-limonene, 3-carene and (−)-β-pinene, while effects varied for α-pinene depending on the experimental system (Table 5).

TABLE 5

Summary of GcABC-G1-dependent differences in effects of specific monoterpenes on Gc asexual spores and transformed Sc cells

| Monoterpenes | Observation (A) Gc spore survival | Observation (B) Transformed Sc survival | Comparison of observation (A) and (B) |
|---|---|---|---|
| (+)-Limonene | + | +++ | Consistent |
| 3-carene | +++ | +++ | Consistent |
| α-pinene | + | Δ | — |
| (−)-β-pinene | + | +++ | Consistent |

+++: Difference between with and without GcABC-G1 is more than 50%, P-value < 0.01
+: Difference between with and without GcABC-G1 is less than 50%, P-value < 0.01
Δ: no significant difference between with and without GcABC-G1

Example 11

GcABC-G1 Occupies a Unique Position in the Phylogeny of PDR Transporters

Figure 9:
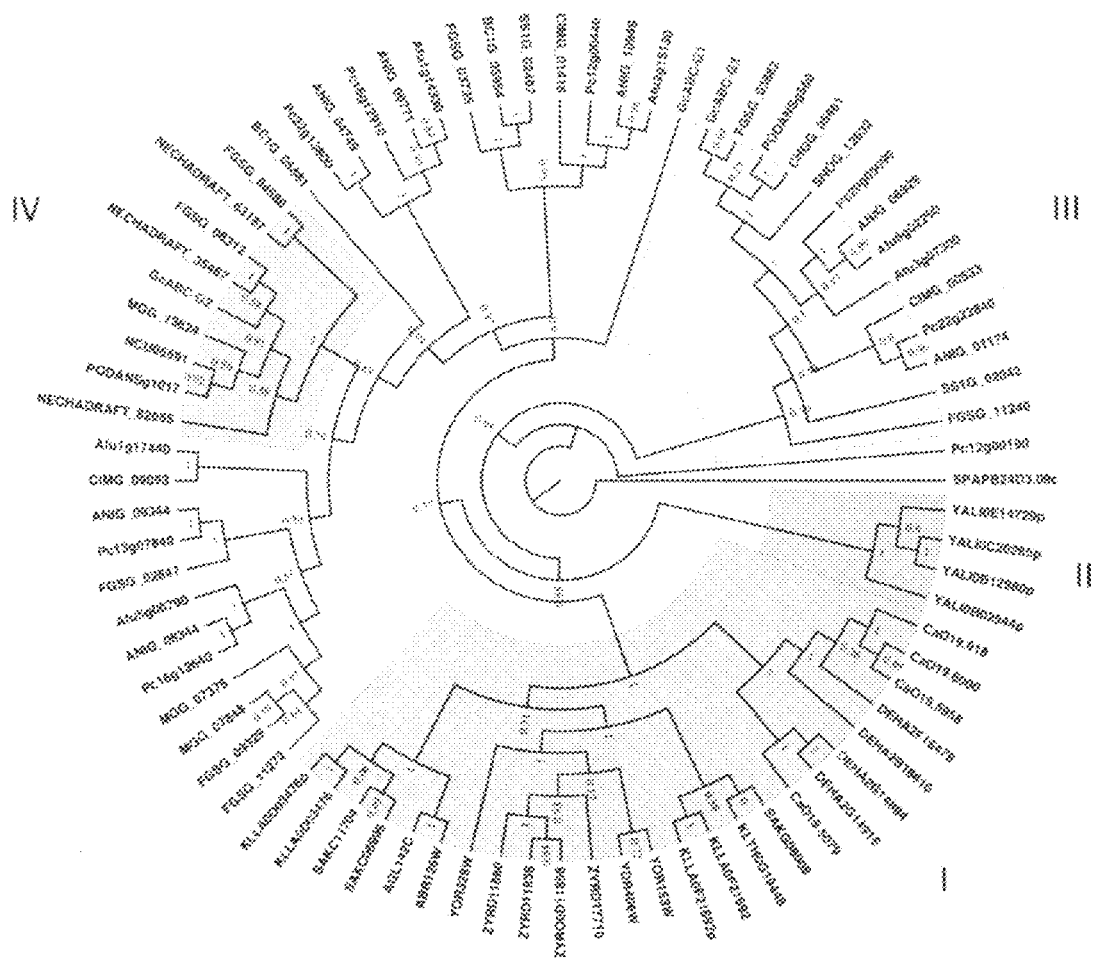
FIG. 9 shows a maximum likelihood phylogenetic tree of ABC-G group I transporters from 23 Ascomycota species. The species are listed in Table 6. Some specific clades are highlighted. I and II: Yeast-specific clades, with II showing only *Yarrowia lipolytica*; III: Eurotiomycetes-Sordariomycetes clade; IV: Sordariomycetes-specific clade.

G. clavigera has three ABC-G-group I transporters. Maximum likelihood (ML) phylogenetic analyses of the predicted amino acid sequences for these three proteins (GcABC-G1, G2, G3) with sequences for 80 ABC-G-group I transporters from 23 ascomycete species (Table 6), resolved four distinct clades. The four included two clades that appear to be yeast-specific, one of which contains only the yeast Yarrowia, and two Eurotiomycete-Sordariomycete clades (see FIG. 9). GcABC-G3 was placed in a Eurotiomycete-Sordariomycete clade showing an orthologous relationship with Gibberella zeae (FGSG_03882). GcABC-G2 was placed in a Sordariomycete specific sub-clade, which includes several transporters that have been reported as pathogenicity factors (e.g. M. grisea MGG13624) or exporters of plant defense chemicals (Nectria haematococca NECHADRAFT_63187) in plant pathogens. Whether GcABC-G2 has comparable functionality for Gc remains to be confirmed. In contrast, GcABC-G1 was placed outside of these four clades, and was separated from other sequences included in our ML analysis.

Phylogenetic analysis and tests with a suite of substrates for PDR transporters (antibiotics, azoles, phenolics, phytoalexins, Example 9) on the wild type (WT) and abc-g1 mutant Gc reveal that GcABC-G1 is specific for monoterpenoids.

TABLE 6

List of species and proteins used for the phylogenetic analysis of the Ascomycota ABC-G group I transporters

| Species | GENE Bank ID | Class |
|---|---|---|
| Ashbya gossypii | ABR126W, AGL142C | Saccharomycetales |
| Candida albicans | CaO19.5079, CaO19.5958, CaO19.6000, CaO19.918 | Saccharomycetales |
| Debaryomyces hansenii | DEHA2B16610, DEHA2F16478, DEHA2G14894, DEHA2G14916 | Saccharomycetales |
| Kluyveromyces lactis | KLLA0D03476, KLLA0D03476p, KLLA0F21692, KLLA0F21692p, KLTH0G19448 | Saccharomycetales |
| Saccharomyces cerevisiae | YDR406W, YOR153W, YOR328W | Saccharomycetales |
| Saccharomyces kluyveri | SAKC06996, SAKC11704, SAKG08008 | Saccharomycetales |
| Schizosaccharomyces pombe | SPAPB24D3.09c | Saccharomycetales |
| Yarrowia lipolytica | YALI0B02544p, YALI0B12980p, YALI0C20265p, YALI0E14729p | Saccharomycetales |
| Zygosaccharomyces rouxii | ZYRD11836, ZYRD11880, ZYRD17710, ZYRO0D11858 | Saccharomycetales |
| Coccidioides immitis | CIMG_00533, CIMG_01418, CIMG_09093), | Eurotiomycetes |
| Aspergillus fumigatus | Afu1g14330, Afu1g17440, Afu2g15130, Afu3g07300, Afu5g00790, Afu5g02260 | Eurotiomycetes |
| Aspergillus nidulans | ANIG_00771, ANIG_01174, ANIG_04749, ANIG_08344, ANIG_08928, ANIG_09344, ANIG_10949 | Eurotiomycetes |
| Penicillium chrysogenum | Pc12g00190, Pc12g00440, Pc13g07840, Pc16g12640, Pc16g12910, Pc20g05090, Pc22g13800, Pc22g22840 | Eurotiomycetes |
| Phaeosphaeria nodorum | SNOG_12632 | Eurotiomycetes |
| Chaetomium globosum | CHGG_05461 | |
| Gibberella zeae | FGSG_02847, FGSG_03735, FGSG_03882, FGSG_04580, FGSG_08312, FGSG_09329, FGSG_11240, FGSG_11272 | Sordariomycetes |
| Grosmannia clavigera | GcABC-G1, GcABC-G2, GcABC-G3 | Sordariomycetes |
| Magnaporthe grisea | MGG_07375, MGG_07848, MGG_13624 | Sordariomycetes |
| Neurospora crassa | NCU05591 | Sordariomycetes |
| Nectria Haematococca | NECHADRAFT_63187, NECHADRAFT_82005, NECHADRAFT_35467 | Sordariomycetes |
| Podospora anserina | PODANSg560, PODANSg1017 | Sordariomycetes |
| Sclerotinia sclerotiorum | SS1G_02042, SS1G_02407 | Leotiomycetes |
| Botrytis cinerea | BC1G_05881, BC1G_05954 | Leotiomycetes | type 2489 and NcABC-1 mutant 11238 (Δncu05591) were obtained from Fungal Genetic Stock Centre (FGSC), Kansas City, Mo. The *N. crassa* 2489 and ABC-G1 mutant 11238, deletion mutant of NCU05591 were incubated on the same MEA plates and treated by 200 μL or 10 μL mixture of monoterpenes (20 times less then applied on *G. clavigera*). Plates were incubated at 22° C. for 48 hours.

Example 12

Monoterpene Tolerance in *Neurospora crassa*

To show that, GcABC-G1 is a specialized PDR transporter that allows *G. clavigera* to colonize a monoterpenoid-rich host environment, monoterpene tolerance experiments were performed using *N. crassa*, a saprophyte that does not colonize terpenoid-rich conifer trees, and its ABC-G1 (NCU05591) deletion mutant. The *Neurospora crassa* wild type 2489 and NcABC-1 mutant 11238 (Δncu05591) were obtained from Fungal Genetic Stock Centre (FGSC), Kansas City, Mo.

On MEA, *N. crassa* was highly sensitive to monoterpenes, and was killed by the same amount of monoterpenes applied on *G. clavigera* (200 μL). The two strains grew similarly when no monoterpenes were applied. When the mixture of monoterpene was reduced to 10 μL/plate, both *N. crassa* and its ABC-G1 mutant were strongly inhibited but grew at similar low rates. Finally, consistent with *N. crassa* being adapted to different niches from *G. clavigera*, *N. crassa* and its mutant were found to be more tolerant to azoles than *G. clavigera*.

Example 13

Comparing the Monoterpene Response Transcriptomes of G. clavigera and the Δgcabc-g1 Mutant GcABC-G1 plays a critical role in G. clavigera's tolerance to certain monoterpenes. To assess broader effects of the deletion of GcABC-G1 in the Gc's response to monoterpenes, mRNA libraries of G. clavigera and the Δgcabc-g1 mutant grown for 12 h on MEA, with and without a mixture of monoterpenes ((+)-limonene, 3-carene, α-pinene and (−)-β-pinene at a ratio of 5:3:1:1), were sequenced. Gene expression was normalized to the non-treated controls. Up-regulated and down-regulated genes are defined as having at least 1.5-fold change relative to the control.

In response to monoterpenes, RNA-seq analyses in the Δgcabc-g1 mutant identified transcripts for 1,312 genes as significantly up-regulated and 3,495 as down-regulated, while in G. clavigera 961 genes were up-regulated and 2,501 genes were down-regulated (P-value<0.05). G. clavigera and the Δgcabc-g1 mutant shared 846 up-regulated genes (88% of the total up-regulated in G. clavigera; 64% of the total up-regulated in the Δgcabc-g1 mutant), and 2,230 down-regulated genes (also 88% of the total down-regulated in G. clavigera; 64% of the total down-regulated in the Δgcabc-g1 mutant). These data show that monoterpene exposure resulted in substantial changes in the G. clavigera transcriptome, and that a large number of genes were differentially induced between G. clavigera and the Δgcabc-g1 mutant.

Using KEGG and InterProScan, it was determined that the 466 genes that were up-regulated only in the transcriptome of the mutant were mainly involved in metabolism (e.g. carbohydrate/lipid metabolism, macromolecular biosynthesis), genetic information processing (transcription, protein/RNA folding, sorting and degradation, DNA replication and repair), environmental information processing (transportation and signal transduction) and stress responses (see Table 7 below).

TABLE 7

Functional groups of genes up-regulated in the Δgcabc-g1 library

| Functional Grouping | Percentage |
| --- | --- |
| Metabolism | 29% |
| Transportation | 17% |
| Transcriptional regulation | 15% |
| Folding, sorting and degradation | 13% |
| Cell growth and development | 9% |
| Signal transduction | 9% |
| DNA replication and repair | 4% |
| Stress response | 4% |

Further, in the Δgcabc-g1 mutant, ten ABC transporters showed expression changes; nine of them were up-regulated more highly in the mutant than in G. clavigera (P-value<0.05, Table 8). Genes that were up-regulated in G. clavigera and the Δgcabc-g1 mutant included an acetyl-CoA-acyltransferase, an alcohol dehydrogenase and a fatty acid activator that could be involved in degrading hydrophobic compounds. These genes were also up-regulated when G. clavigera was grown on YNB with monoterpenes as the sole carbon source. Also observed were two clusters with co-expressed genes in G. clavigera that are involved in the detoxification and utilization of terpenoids through the fatty acid beta-oxidation pathway.

TABLE 8

Comparison of selected GcABC transporter genes showing transcript abundance differences in Gc and Δgcabc-g1

| GENE ID | Identified Activity/function | Transcript abundance fold change** | |
| --- | --- | --- | --- |
| | | Gc | Δgcabc-g1 |
| GcABC-G1 | Multidrug resistance | 594* | 0 |
| GcABC-G2 | Multidrug resistance | 1.05 | 1.56* |
| GcABC-G9 | Multidrug resistance | −1.1 | 2.24* |
| GcABC-C8 | Multidrug resistance | 34.96* | 3.95 |
| GcABC-C12 | Metal ion transport | 1.17 | 2* |
| GcABC-C11 | Multidrug resistance | 2.64 | 7.39* |
| GcABC-C3 | Bile acid transport | 1.73 | 5.7* |
| GcABC-B5 | Mitochondrial precursor transporter | 4.43* | 10.39* |
| GcABC-B3 | Multi drug resistance | 2.37 | 6.19* |
| GcABC-D2 | Peroxisome transporter | 1.40 | 2.05* |
| GcABC-D1 | Peroxisome transporter | 2.07 | 4.44* |

**The abundance was normalized to each strain's non-treatment control
*Indicate significant values with p-value < 0.05

Example 14

Pathogenicity and Detection of GcABC-G1 Transcripts in Lodgepole Pine Inoculated with G. clavigera or its GcABC-G1 Mutant (Δgcabc-g1)

A. Inoculation of Young Lodgepole Pine Trees with Gc or its GcABC-G1 Mutant

Five-year old lodgepole pine trees were grown in the University of British Columbia greenhouse and maintained as described previously for other conifer saplings (Miller et al., (2005) Plant Physiol 137:369-382). Trees were inoculated at six points along the stem with plugs of actively growing fungal mycelium on MEA medium. Circular bark plugs were removed from the outer stem tissue using a 5 mm diameter metal cork borer. Inoculations were done on opposite sides of the stem at locations that were approximately 5 cm, 10 cm and 15 cm above the base of the stem. Fungal inoculums of 5 mm diameter circular MEA/mycelium plugs were inserted into each circular bark hole and a bark plug placed on top to close the hole. The inoculated stem section was sealed with Parafilm® M and an outer layer of duct tape (see, e.g., Wang et al., (2010) Curr Genet 56:297-307). For control treatments, MEA plugs without fungal mycelium were used. Symptoms, i.e. wilting, and discoloration of needles and growing shoot tips, were recorded weekly for four weeks. At 4 weeks after inoculation the stems were harvested, and needles, branches and outer bark tissue were removed. Discoloration of the inner stem tissue was recorded, and fungi (i.e., G. clavigera or its mutant) were re-isolated from the phloem and the inner stem. Replicate experiments were carried out in April 2011, and May and June 2012. For each replicate, 7 trees were used for the control, and 11 trees were inoculated with either G. clavigera or the deletion mutant.

B. Results

Figure 3:
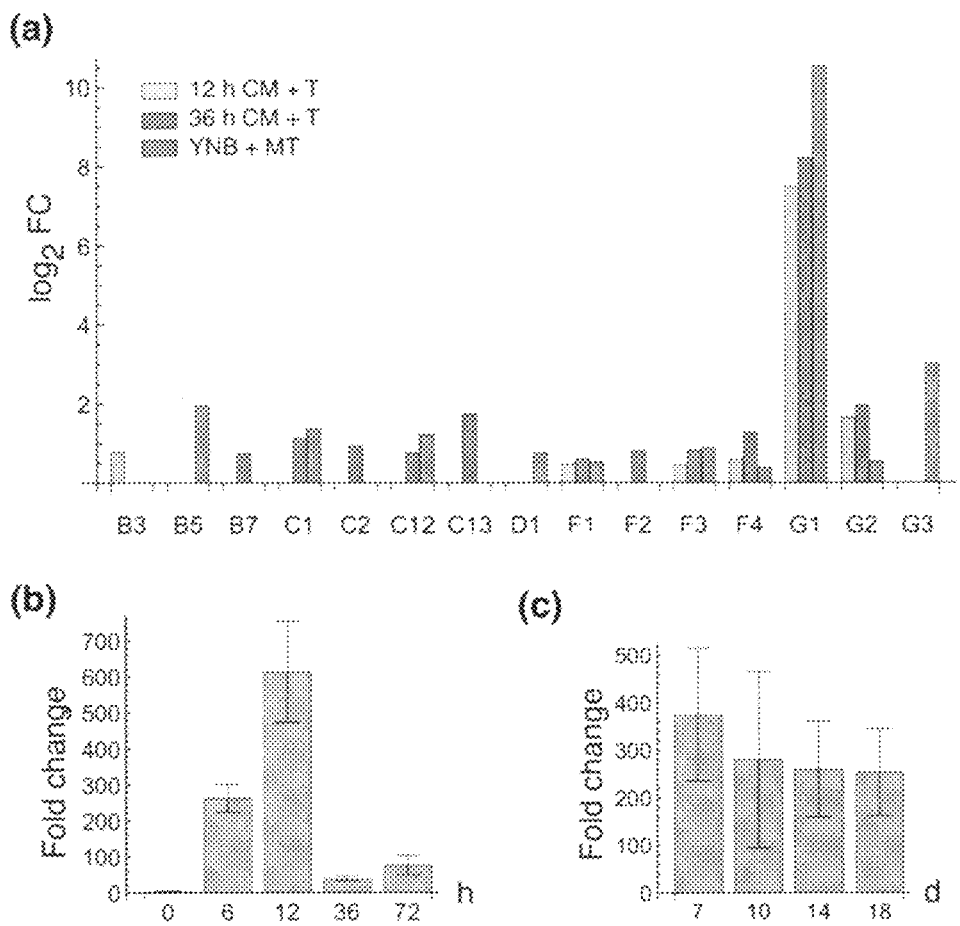
FIG. 3 shows transcript abundance of selected GcABC transporter genes for terpenoid treatments.
Figure 4:
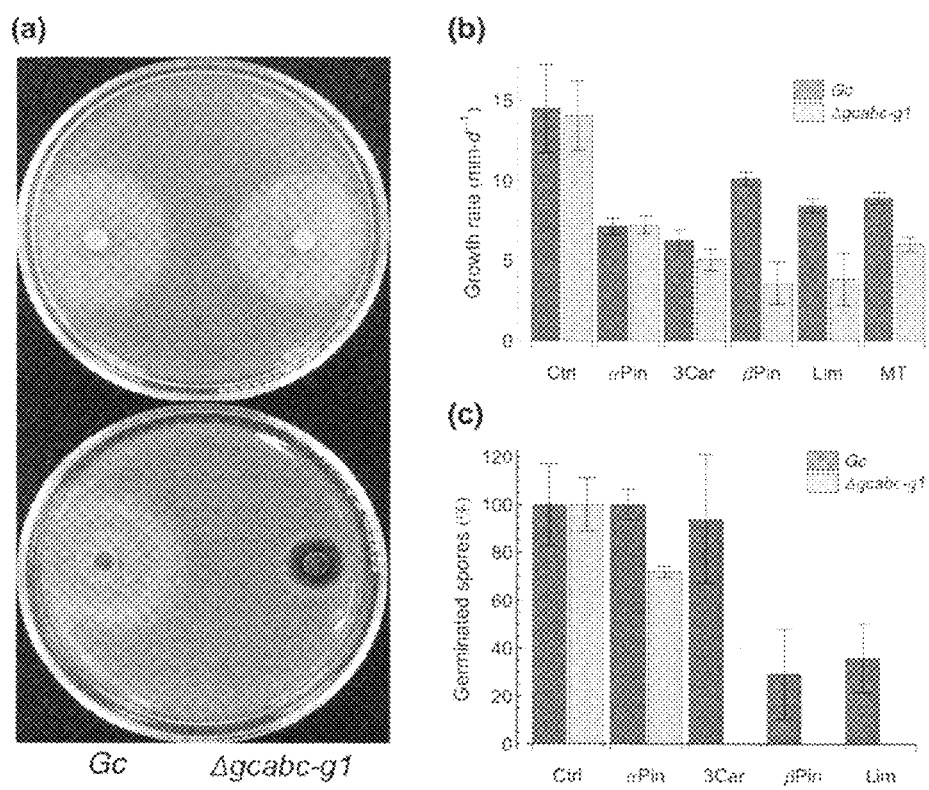
FIG. 4 shows effects of monoterpenes on the growth of wildtype *G. clavigera* and mutant Δgcabc-g1 on MEA.
Figure 10:
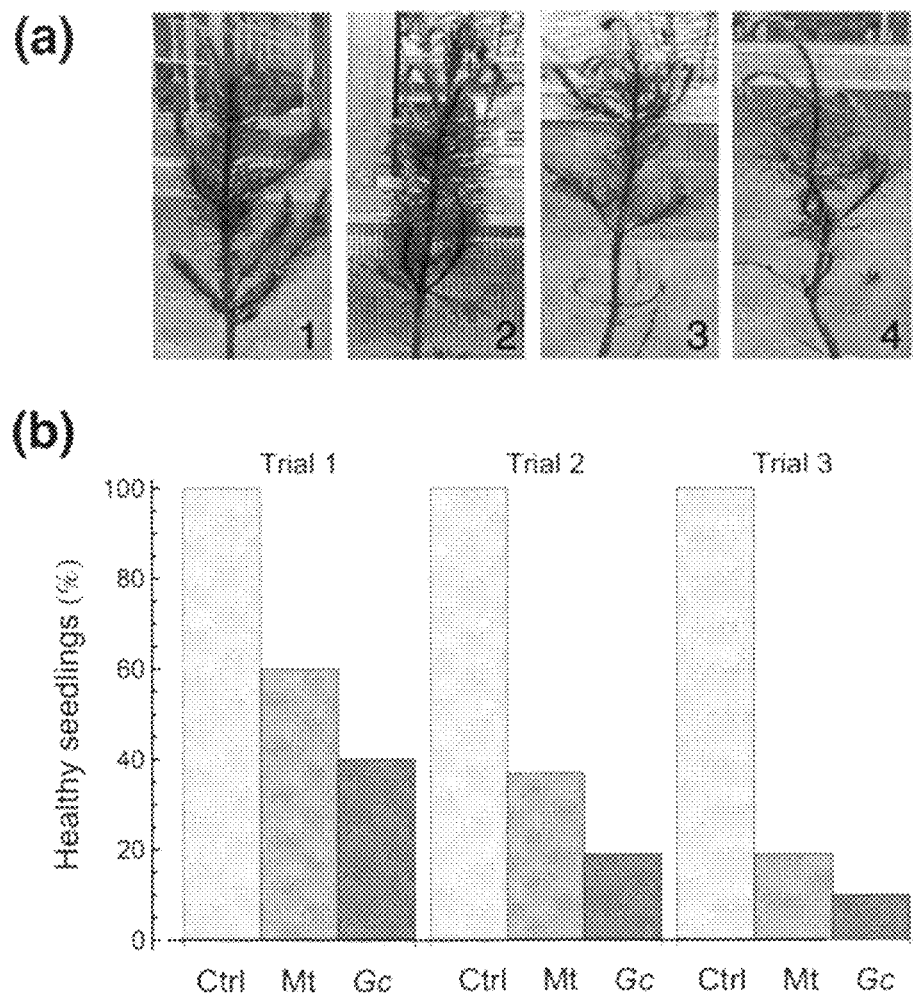
FIG. 10 shows pathogenicity tests with young lodgepole pine inoculated with *G. clavigera* and the Δgcabc-g1 mutant.

To show the effect of the deletion of the GcABC-G1 gene on the development of symptoms in lodgepole pine, greenhouse inoculations were performed on stems of young lodgepole pines with G. clavigera, the Δgcabc-g1 mutant, or controls without fungus (FIG. 10). Two weeks after inoculation, several trees inoculated with G. clavigera showed early symptoms of infection, i.e. wilting of growing shoots and browning of needles (FIG. 10a-2); similar symptoms were observed two to three days later in the pines inoculated with the Δgcabc-g1 mutant. During the third and fourth week severe symptoms developed on branches and growing shoots for G. clavigera and the Δgcabc-g1 mutant (FIG. 10a-3). During the fourth week, all of the needles of several trees had become completely brown, and growing shoots had severely wilted (FIG. 10a-4). Although the numbers of trees that appeared healthy (FIG. 10a-1) was low for both treatments after four weeks, trees treated with the Δgcabc-g1 mutant showed a 10 to 20% higher survival rate in all three experiments compared to trees inoculated with G. clavigera (FIG. 10b). For both fungi, the typical blue/black discoloration in the stem cross section of the young pine trees that is associated with fungal growth and melanin production was measured. After four weeks, higher numbers of stem cross-sections with dark stains were observed for G. clavigera (81%) than for the Δgcabc-g1 mutant (21%). G. clavigera and the Δgcabc-g1 mutant were re-isolated from stem cross-sections and from inner bark, but not from the controls inoculated with MEA agar plugs, confirming that the symptoms were due to fungal growth and not from wounding.

Figure 11:
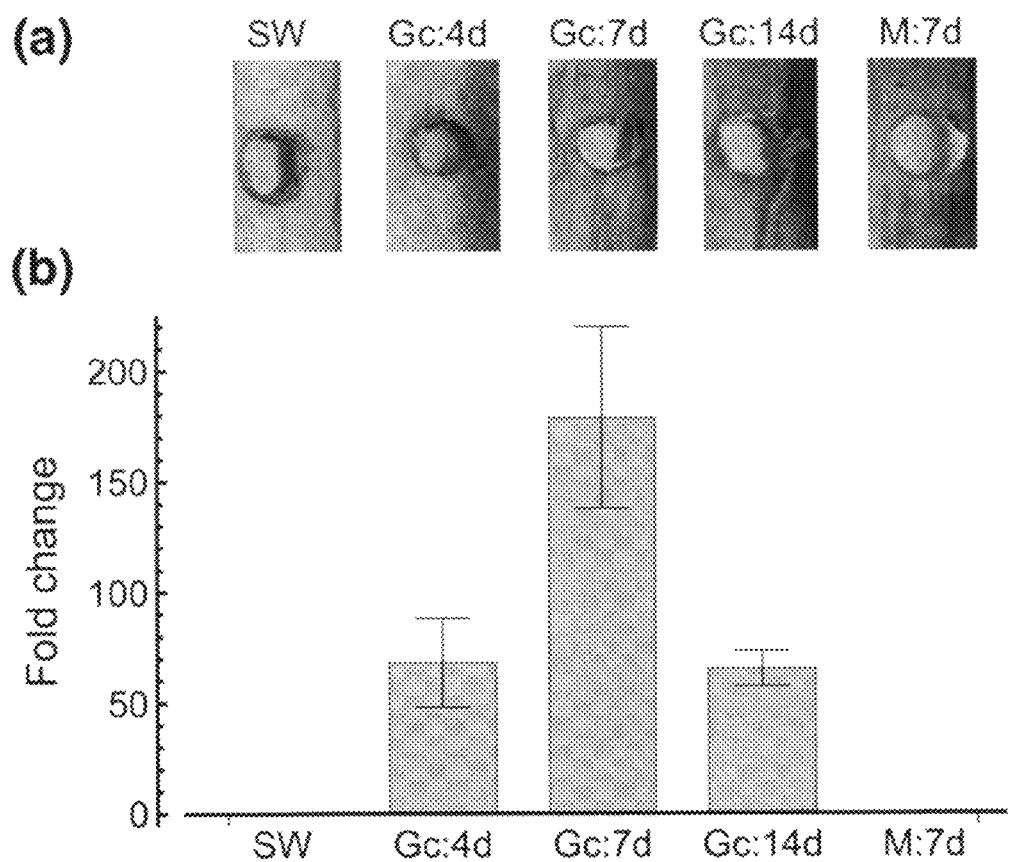
FIG. 11 shows the relative abundance of the fungal GcABC-G1 transcript in the phloem of young lodgepole pine trees inoculated with Gc or the GcABC-G1 mutant (Δgcabc-g1) for 4, 7, and 14 days.

To show that the GcABC-G1 gene was expressed in G. clavigera upon inoculation of trees its transcript levels were measured in stem tissues inoculated with G. clavigera or the Δgcabc-g1 mutant as well as in the controls treated with MEA plugs only. No GcABC-G1 gene transcripts were detected in the pine tissue treated with the Δgcabc-g1 mutant or in the controls. In trees inoculated with G. clavigera, GcABC-G1 transcripts clearly were detectable at four, seven and 14 days after inoculation. Since transcript abundance was normalized to fungal β-tubulin transcripts, a temporal profile of increased relative abundance of the GcABC-G1 transcript with a maximum 178-fold change at 7 days relative to G. clavigera grown on MEA was detected (FIG. 11). The observed induction of GcABC-G1 gene transcripts when G. clavigera grows in pine host tissue further demonstrate the role of this gene in the pine-G. clavigera interaction in vivo.

Example 15

Ophiostoma piceae

The O. piceae strain was isolated from Pinus contorta lumber (Uzunovic et al. (1999) Can J Microbiol 45(11):914-922) and is available from the University of Alberta Microfungus Collection and Herbarium, Edmonton, Alberta, Canada (UAMH Catalogue #11346). For growth and maintenance, spores or plugs of fungal mycelium were inoculated and grown at room temperature on plates of MEA (1.6% Oxoid™ malt extract agar and 1.5% technical agar, pH 5-6).

To assess the growth of O. piceae in anaerobic conditions, a freshly grown plug of hyphae was placed on an MEA plate, the plate was sealed in a BBL GasPak Pouch (Becton Dickinson, N.J. USA) following the manufacturer's instructions.

Example 16

Ophiostoma Piceae Genome Sequencing and Assembly

A. Genome Sequencing

DNA was extracted from fungal hyphae grown on MEA using methods described by Haridas and Gantt (FEMS Microbiol Lett 308(1):29-34 (2010)). Illumina® HiSeq® sequencing was done at the BC Genome Sciences Centre in Vancouver, Canada and 454 SEQUENCING® was done at the Plate-forme d'Analyses Génomiques at Laval University in Québec, Canada.

B. Genome Assembly

The genome was assembled using ABySS v1.3.0 (Simpson et al. (2009) Genome Res 19(6):1117-1123) with a kmer size of 60. In order to efficiently use the 454 reads for scaffolding, a minimum contig size (1000) and read pairs for building scaffolds (2) (SCAFFOLD_OPTIONS='-s1000-n2') were used. The assembly was scrubbed and gaps closed with Anchor (v0.3.0; bcgsc.ca/platform/bioinfo/software/anchor). When Abyss is unable to find overlaps between contigs where paired end data suggests that the contigs should overlap, it joins the contigs with a single lowercase 'n'. Such overlaps were resolved using transcriptome assembly (described below) or by finding small overlaps at the ends of the contigs using exonerate v2.2.0 (Slater and Birney (2005) BMC Bioinformatics 6:31).

C. Results

Reads obtained from two sequencing technologies, Illumina® HiSeq® 2000, which generated 100 nt reads, and 454 Titanium, which generated longer reads (Table 9), were assembled using ABySS (Simpson et al. (2009) Genome Res 19(6):1117-1123). Libraries with three different insert sizes provided the assembler with a range of read pair distances for efficient scaffolding of the assembled contigs. The Illumina® short insert libraries provided the coverage depth (>100x) necessary for efficient assembly and initial scaffolding. Sequences from the 454 large insert size library supported long-range scaffolding; to efficiently use this relatively high confidence but low coverage data, the default scaffolding parameters of ABySS were modified. After the initial assembly, Anchor (bcgsc.ca/platform/bioinfo/software/anchor) was used to map reads to the assembly to correct gap estimates, extend assembly into gaps by local reassembly (using ABySS) and correct indels caused by incorrect assembly.

TABLE 9

Sequencing strategy for O. piceae genome

| Sequencing Technology | Read length (nt) | Insert length (nt) | Read pairs (Millions) |
|---|---|---|---|
| Illumina ® HiSeq ® | 100 | 200 | 87.8 |
| Illumina ® HiSeq ® | 100 | 700 | 32.2 |
| 454 Titanium ® | 318 (median) | 8000 | 0.3 |

Assembly by ABySS, followed by two iterations of Anchor, produced a genome assembly that contains 244 scaffolds that were at least 1,000 bp long. It contains 335 false gaps represented by a single lowercase 'n'. Of these, 219 were resolved by mapping Trinity-assembled RNA-seq transcripts to the genome using exonerate est2genome (Slater and Birney (2005) BMC Bioinformatics 6:31). The remaining 116 gaps were resolved using exonerate to find small overlaps (<5 bp) at the ends of contigs that are joined by an 'n'. 187 scaffolds and contigs smaller than 10,000 bp (including gaps) that represented 1% of the assembly because they contained no genes or t-RNAs were removed from the final assembly. The corrected 33 Mbp genome assembly contains 47 scaffolds. One percent of the genome contains 342 gaps (N's). Half of the genome was in nine scaffolds that had an N50 of approximately 1.45 Mbp, while 90% was represented in 27 scaffolds that had an N90 of approximately 0.38 Mbp. Using CEGMA (Parra et al. (2007) Bioinformatics 23(9):1061-1067), complete copies of 233 of 248 conserved eukaryotic genes and partial copies of an additional five were identified, which suggests that the assembly represents 94%-96% of the O. piceae gene space (Grabherr et al. (2011) Nat Biotechnol 29(7):644-652).

The genome characteristics of O. piceae and three other ascomycetes also found on wood products, namely G. clavigera (Gc) (DiGuistini et al. (2011) Proc Natl Acad Sci USA 108(6):2504-2509), Neurospora crassa (Nc) (Galagan et al. (2003) Nature 422(6934):859-868) and Trichoderma reesei (Tr) (Martinez et al. (2008) Nat Biotechnol 26(5): 553-560), are summarized in Table 10. The sequences are deposited in NCBI gene bank as assembly and annotations, Project NO. PRJNA182071

TABLE 10

Characteristics of the O. piceae (Op) genome assembly and annotation and a comparison with other related genomes

|  | Op | Gc[a] | Nc (10)[b] | Tr[c] |
| --- | --- | --- | --- | --- |
| Genome size (Mbp) | 32.8 | 30 | 41 | 33.5 |
| Number of scaffolds | 47 | 289 | 7[d] | 87 |
| N50 (Mbp) | 1.45 | 2 | 1.56 | 1.12 |
| Number of ungapped contigs | 388 | 478 | 956 | 231 |
| Genome GC content (%) | 52.8 | 53.4 | 48.25 | 52.7 |
| Non-coding genome (%) | 54 | 54.28 | 56 |  |
| Number of genes | 8,919 | 8,312 | 9,733 | 9,129 |
| Median CDS length (bp) | 1,401 | 1,350 | 1,673 | 1,299 |
| Exon GC content (%) | 59.7 | 60.4 |  | 57.8 |

[a]G. clavigera (Gc);
[b]Neurospora crassa Sequencing 943 Project, Broad Institute of Harvard and MIT (NC10).
[c]Trichoderma reesei (Tr).
[d]Chromosome numbers.

Example 17

Ophiostoma Piceae Transcriptome Assembly

RNA-seq was performed on eight RNA samples extracted from the mycelia of O. piceae hyphae grown under various conditions. Fungal hyphae were grown on MEA for three days and transferred to either complete medium (CM; 0.17% yeast nitrogen base without amino acids, 1.5% granulated agar, 1% maltose, 0.1% potassium hydrogen phthalate and 0.3% asparagine) with or without a terpene blend or yeast nitrogen base with carbon sources (YNB; 0.67% yeast nitrogen base without amino acid and 1.5% agar with carbon sources) as set forth in Table 11 below. Carbon sources included mannose, triglycerides, containing 80% olive oil and 20% fatty acids, and oleic acid. The terpene blend was a mixture of monoterpenes and diterpenes including monoterpenes R-(+)-limonene, 3-carene, α-pinene and β-pinene at a ratio of 5:3:1:1 and diterpenes abietic (Sigma, Oakville, ON), dehydroabietic, levopimaric, isopimaric and pimaric acids (Orchid-Helix Biotech, Vancouver, BC) in a 2:1:1:1:1 ratio, as described by Lah et al. (Fungal Genet Biol (2013) 50:72-81). For growth on sawdust, spores were inoculated and germinated on 1% MEA (Difco) for 2 days, and then transferred to sawdust plates (15% lodgepole pine sawdust, mixed with 2% granulated agar) overlaid with cellophane for one week. All treatment times were calculated from the initial transfer of actively growing hyphae onto the appropriate medium.

TABLE 11

Growth conditions for RNA-seq analysis

| Medium | Carbon source or treatment | Duration |
| --- | --- | --- |
| CM | No treatment | 14 h |
| CM | No treatment | 40 h |
| CM | 200 µL Terpene blend | 14 h |
| CM | 200 µL Terpene blend | 40 h |
| YNB | Mannose (1% v/v) | 5 days |
| YNB | *TG: Olive Oil (1% v/v) | 5 days |
| YNB | Oleic acid (0.5% v/v) | 5 days |
| Sawdust | No treatment | 1 week |

*TG: triglyceride: olive oil 80% + Fatty acids 20%

Multiplexed sequencing in three lanes was done using the Illumina® HiSeq® platform to obtain 100 bp paired end reads from 250 bp fragments. Reads were analyzed using fastqc (bioinformatics.babraham.ac.uk/projects/fastqc/) and showed read bias and in the first few bases of the reads and poor quality in the last few. Reads with minimum quality scores less than 20 were removed and the first six and last four bases of all reads were trimmed using prinseq (Schmieder and Edwards (2011) Bioinformatics 27(6):863-864). Processed RNA-seq reads were assembled using Trinity (Grabherr et al. (2011) Nat Biotechnol 29(7):644-652) using the jaccard_clip option to minimize fusion transcripts. The best protein coding transcripts were identified using the included scripts and aligned back to the assembled genome using exonerate v2.2.0 est2genome (Slater and Birney (2005) BMC Bioinformatics 6:31).

Example 18

Ophiostoma Piceae Genome Features and Annotation

A. Methods

Maker annotation pipeline (v2.26) was used for genome annotation (Holt and Yandell (2011) BMC Bioinformatics 12:491). In addition to the trinity assembled best candidates (see Example 17 above), two additional sources of evidence were used. The first was transcripts predicted by the Core Eukaryotic Genes Mapping Approach (Parra et al. (2007) Bioinformatics 23(9):1061-1067), (CEGMA) and the second was coding sequences of transcripts assembled by cufflinks (Trapnell et al. (2012) Nat Protocol 7(3):562-578) from RNA-seq reads mapped to the assembled genome. Within the Maker framework, SNAP v2006-07-28 (Korf (2004) BMC Bioinformatics 5:59) was trained using the Trinity assembled transcripts, gene models of Magnaporthe grisea for Augustus (v2.5.5) (Stanke and Waack (2003) Bioinformatics 19 Suppl 2:ii215-225) and an hmm file for Genemark-ES (v2.3) (Ter-Hovhannisyan et al. (2008) Genome Res 18(12):1979-1990) using an independent run. The UniProtKB/Swiss-Prot (release 2012_01) fasta file was provided as protein homology evidence and pred_flank was set to 50 to minimize fusion transcripts. Predicted genes smaller than 100 amino acids were removed unless they were at least 80 amino acids long and had transcript, protein or CEGMA evidence. Selected gene models were manually curated. Functional identification of predicted genes was done using Blast2go (v2.5.1) (Conesa et al. (2005) Bioinformatics 21(18):3674-3676). tRNA's were identified using tRNAscan-SE (v1.3.1) (Pavesi et al. (1994) Nucleic Acids Res 22(7):1247-1256). Relative synonymous codon usage (RSCU) was calculated using a local installation of the graphical codon usage analyser (McInerney (1998) Bioinformatics 14(4):372-373). Secretome predictions were made with TargetP (Emanuelsson et al. (2000) *J Mol Biol* 300(4): 1005-1016) and Phobius (Kall et al. (2007) *Nucleic Acids Res* 35(Web Server issue):W429-432). A protein was considered to be secreted if either TargetP or Phobius suggested that it was secreted and this result was not in conflict with the other. Identification of secondary metabolism genes and clusters was done using the Secondary Metabolite Unique Regions Finder (SMURF) (Khaldi et al. (2010) *Fungal Genet Biol* 47(9):736-741).

B. Results

Within the annotated genome of *O. piceae*, genes and gene families were identified for secondary metabolite processing, cytochrome P450 and ABC transporters. Also identified were homologous *O. piceae* and *G. clavigera* proteins based on reciprocal best BLAST hits. In addition, the MAT idiomorph that is responsible for the mating type of the sequenced strain was further characterized.

1. Genes and Gene Families

Maker annotation pipeline (v2.26) results predict 8,919 proteins within the acceptance criteria, of which 8,723 are at least 100 amino acids long. Almost 65% (5,786) of the predicted proteins encoded by the gene models have a known Pfam domain. Some of the major gene families in *O. piceae* are shown in Table 12. About a third of the predicted genes (3,026) have only one exon and only 1,283 transcripts are encoded by four or more exons. In this compact genome, genes, not including their upstream and downstream untranslated regions (UTRs) represent 45% of the assembly. Almost a quarter (1,984) of the predicted gene coding sequences (CDS) are within 500 bp of their respective neighbouring CDS, and almost half (4349) are within 1,000 bp of its neighbour. This analysis predicts that 778 CDSs encode secreted proteins.

TABLE 12

Some major gene families in *O. piceae* (Op) and a comparison with other fungal species

| Gene Family | Op | Gc* | Nc* | Tr* |
|---|---|---|---|---|
| MFS transporters | 289 | 227 | 161 | 236 |
| ABC transporters | 34 | 40 | 36 | 48 |
| ATPases | 308 | 349 | 356 | 352 |
| NAD binding proteins | 258 | 254 | 211 | 301 |
| FAD binding proteins | 130 | 146 | 122 | 144 |
| Cytochrome P450s | 45 | 54 | 43 | 73 |
| Methyltransferases | 112 | 159 | 126 | 125 |
| Transcription factors | 115 | 133 | 106 | 218 |
| Glycoside hydrolases | 140 | 126 | 168 | 170 |
| Glycosyl transferases | 63 | 64 | 76 | 79 |

*G. clavigera (Gc); Neurospora crassa (Nc); and Trichoderma reesei (Tr)

2. Comparison with the Proteome of *G. clavigera*

Figure 12:
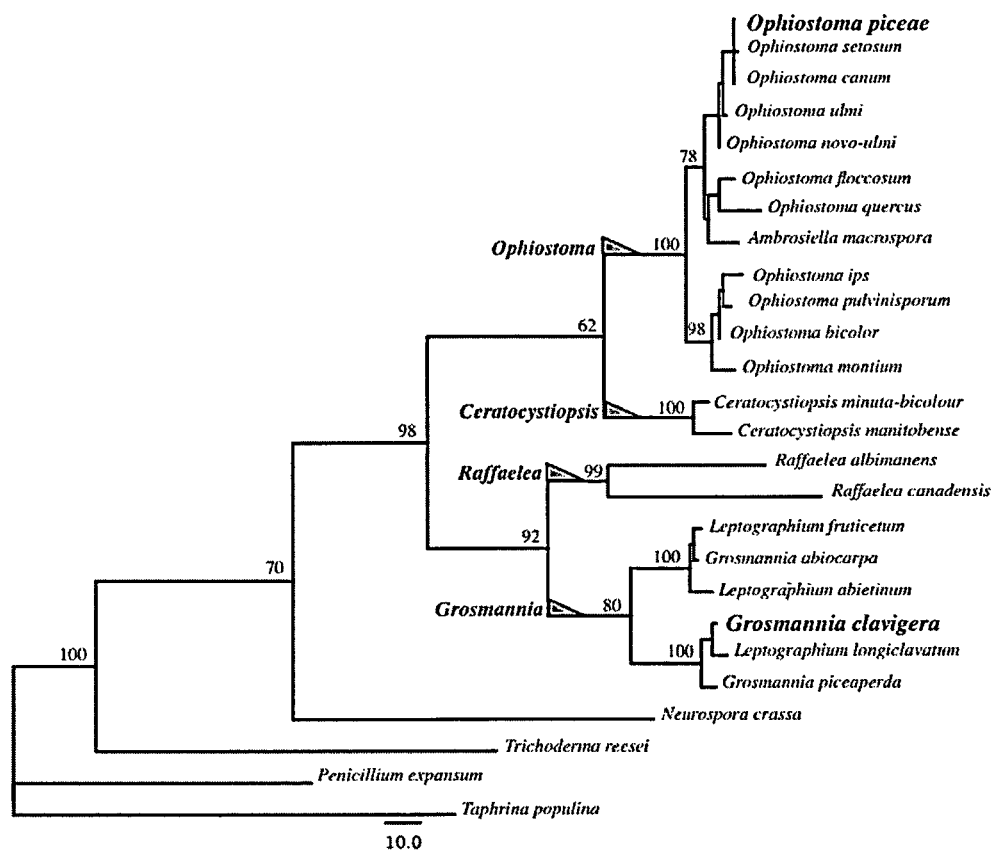
FIG. 12 shows a phylogenetic tree based on the ITSs of rDNA places *O. piceae* within the Pezizomycotina. While *O. piceae* and *G. clavigera* colonize pine sapwood, *O. piceae* is more closely related to the Dutch elm pathogen *O. novo-ulmi* than to *G. clavigera*, which is a pathogen that can grow deeply in the sapwood and can kill pine trees.

Although *O. piceae* and *G. clavigera* share hosts, cause sap-stain in pine, and are in sister clades in the Ophiostomatales (Massoumi et al. (2009) *Mycol Res* 113(Pt 8):822-835) (see FIG. 12), their genomes show no large-scale synteny. A BLAST comparison of the two predicted proteomes shows that 5,450 proteins were reciprocal best hits. These include most of the major metabolic functions. The *O. piceae* proteins with no significant homolog in the *G. clavigera* genome were overrepresented by protein kinases (Gene Ontology (GO) Database GO:0004672), sequence specific DNA binding RNA polymerase II transcription factors (GO:0000981) and zinc ion binding proteins (GO: 0008270). In addition, proteins involved in transmembrane transport (GO:0055085) are also significantly overrepresented in this group of 3,469 proteins. Over 40% (1,397) of the *O. piceae* proteins with no evident homologs in *G. clavigera* are proteins of unknown function (predicted or hypothetical proteins). None of the six carboxylic ester hydrolases (GO:0052689) in the *O. piceae* genome has a homolog in the *G. clavigera* genome.

3. Genes Involved in Producing Secondary Metabolites

A search was performed for genes that involved in producing secondary metabolites (SMs). Such genes are typically organized as contiguous genomic clusters and can be identified by tools like SMURF (Secondary Metabolite Unique Regions Finder; Khaldi et al. (2010) *Fungal Genet Biol* 47(9):736-741), which uses hidden Markov models that consider genomic context and domain content. The first step in fungal SM biosynthesis typically is catalyzed by 'backbone' genes like nonribosomal peptide synthases (NRPSs), polyketide synthases (PKSs), hybrid NRPS-PKS enzymes, prenyltransferases and terpene cyclases (Khaldi et al. (2010) *Fungal Genet Biol* 47(9):736-741). SMURF, which does not identify clusters containing terpene cyclases, identified thirteen backbone genes in nine SM clusters in *O. piceae*, and nineteen genes in fourteen clusters in *G. clavigera*.

Melanin is a secondary metabolite that is produced by *O. piceae* and related species, but, as in *O. piceae*, the genes responsible for its production do not always occur in a cluster. Melanin is synthesized through the 1,8-dihydroxynaphthalene (DHN) pathway (Butler and Day (1998) *Can J Microbiol* 44(12):1115-1136). In *O. piceae*, a number of genes were identified that were similar to genes that have major roles in the DHN pathway in *Ophiostoma*, *Grosmannia* and *Ceratocystis* species (DiGuistini et al. (2007) *FEMS Microbiol Lett* 267(2):151-158, Wang and Breuil (2002) *Molecular Genetics and Genomics* 267(5):557-563, Loppnau et al. (2004) *Fungal Genet Biol* 41(1):33-41). These genes include a PKS (OPP_00823), two reductases (OPP_02710, OPP_00820) and a scytalone dehydratase (OPP_07153). PKSs catalyze the elongation of five ketide subunits and the cyclization of these units to form the base ring of naphthalene. The first reductase (OPP_02710) converts 1,3,6,8-hydroxynaphthalene to scytalone, while the second (OPP_00820) transforms scytalone to vermelone.

4. MAT Idiomorph

*O. piceae* is a heterothallic species. As such it requires two individuals with different mating types for sexual reproduction and production of fertile fruiting bodies. Genome annotation identified *O. piceae*'s MAT1-2 idiomorph (OPP_06680). A truncated MAT1-1 gene was next to the MAT1-2 gene, as in *Grosmannia* and related species (Di-Guistini et al. (2011) *Proc Natl Acad Sci USA* 108(6):2504-2509; Brasier, C. The genetic system as a fungal taxonomic tool: gene flow, molecular variation and sibling species in the "*Ophiostoma piceae-Ophiostoma ulmi*" complex and its taxonomic and ecological significance. In *Ceratocystis* and *Ophiostoma*: taxonomy, ecology, and pathogenicity. Edited by Wingfield M, Seifert K, Webber J. St. Paul, Minn.: APS Press; 1993:77-92). Perithecia of *O. piceae* have been successfully produced by mating UAMH-11346 with AU 131-2; this reveals that AU 131-2 has the MAT1-1 idiomorph.

Example 19

*Ophiostoma Piceae* Gene Expression Patterns

To identify genes that required or important for the saprophyte *O. piceae* to grow in the presence of the nutrients and defense chemicals that are characteristic of its natural pine sapwood substrate, gene expression was determined for the fungus growing on solid agar media supplemented with simple carbon sources (i.e. sugars and lipids), pine sawdust, or pine terpenes (see Example 17).

A. RNA-seq Analysis

Quality trimmed RNA-seq reads were aligned to the *O. piceae* genome using Bowtie (v0.12.7), TopHat (v2.0.4) and Cufflinks (v2.0.2) as described by Trapnell et al. (*Nat Protocol* (2012) 7(3):562-578). Because mapping the RNA-seq reads to the genome without providing fixed gene models resulted in an unacceptable number of predicted fusion transcripts, reads were mapped using the curated gene models predicted by the Maker pipeline.

Mapping the RNA-seq reads to the predicted gene models identified 7,157 genes that had an abundance of at least 10 FPKM (fragments per kilobase of exon per million fragments mapped) in any of the conditions tested. To select genes that are highly differentially regulated under different growth conditions, a gene was required to have an FPKM abundance that was at least ten times higher in a specific condition, or a related set of conditions, than in all other growth conditions. This approach identified 677 genes whose transcripts are differentially abundant in at least one growth condition, and 173 genes whose transcripts are differentially abundant in only one condition. By manually comparing the set of 173 genes to functional information in the Gene Ontology database (geneontology.org) and to reference metabolic pathways KEGG (genome.jp), pathways were identified that are involved in the response of *O. piceae* to the growth conditions tested. Support for these pathways was added by manually identifying genes from the 677-gene set whose transcripts, while up-regulated, did not pass the stringent 10-fold filter used to identify the set of 173 genes.

In addition, alternative transcript splicing across the range of growth conditions used for this study was assessed. To assess how important alternative splicing and transcripts were, TopHat and Cufflinks were used to map the RNA-seq reads to the genome assembly using the techniques described by Trapnell et al. (*Nat Protocol* (2012) 7(3):562-578). The results indicated that approximately 150 alternative transcripts were expressed; however, all of these appeared to be false positives. The dominant cause of these false positive predictions was that closely spaced genes with overlapping UTRs were misassembled as single contigs, and differential regulation of such genes under different growth conditions appeared as alterative isoforms. In other cases, mapping errors produced false gene calls and alternative isoforms. Splicing appeared not to be an important factor under these conditions.

B. Growth on a Simple Carbon Source

Mannose is a simple monomeric epimer of glucose and can be readily utilized as a carbon source by *O. piceae*. Five genes were identified whose expression was at least ten times higher with mannose than in any other conditions tested. These included two transporters, one oxidoreductase and two hypothetical proteins. The data indicates that mannose uptake involves two transporters (OPP_03031, OPP_05665), and a simple isomerisation/epimerization reaction by an oxidoreductase (OPP_00733) converts it into glucose. The function of two remaining up-regulated genes (OPP_02416, OPP_07274) is unknown.

*O. piceae* was grown on triglycerides and fatty acids, which are important lipid compounds in lodgepole pine sapwood, and are a major source of carbon for *O. piceae* (Gao et al. (1994) *Material and Organismen* 28:105-118). Because most sources of triglycerides contain a small proportion of fatty acids, it was not surprising that most of the 129 genes whose transcripts were differentially abundant between these conditions were highly up-regulated in both of the conditions. Of the 25 up-regulated genes that were significantly induced only in these two conditions, 18 were predicted to produce secreted proteins. The differentially up-regulated genes included no fungal lipases, which are necessary for the hydrolysis of triglycerides. Twenty-three of the 25 up-regulated genes were predicted to be involved in the breakdown of carbohydrates and sugars; these included eight genes coding for secreted proteins in the glycoside hydrolase family and four genes for secreted proteins involved in carbohydrate and starch binding. A transcription factor (OPP_02429) was identified that showed significant up-regulation in the presence of triglycerides and oleic acid.

One of the genes differentially expressed between olive oil and oleic acid was a cytochrome P450 (OPP_02426) with a significantly higher expression with triglyceride than with fatty acid. Like its *G. clavigera* homolog (CMQ_5365; CYP630B18) and homologs in several other species including *Fusarium graminearum, Aspergillus niger, A. fumigates* and others, this gene is in close proximity to genes encoding a myo-inositol transporter, ARCA-like protein and a cytochrome P450 reductase (Lau et al. (*Fungal Genet Biol* (2012) dx.doi.org/10.1016/j.fgb.2012.10.002).

C. Growth on Pine Sapwood, a Natural Substrate for *O. piceae*

Figure 13:
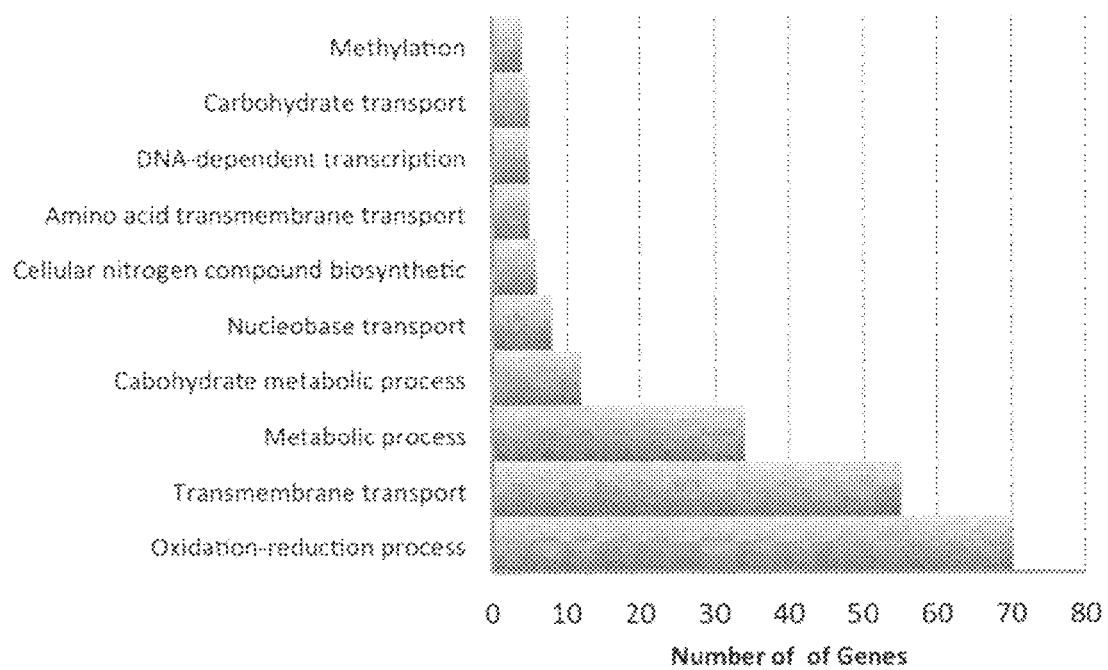
FIG. 13 shows the functional classification of up-regulated genes of *O. piceae* grown on sawdust using Blast2go.

Of the treatments used in the growth study, sawdust obtained by grinding pine sapwood was the closest to the natural substrate. It contains a variety of carbon sources including mannose, triglycerides and fatty acids. In this growth condition, 366 genes were up-regulated, 91 of which were up-regulated only in the presence of sawdust. The subset of 91 genes was overrepresented in GO terms for transport (GO:0005215, GO:0006810; p<0.0001) (FIG. 13), which could reflect the complexity of the nutrient sources used by *O. piceae*. The up-regulated transporters included several allantoate, urea, hexose, iron and sugar transporters, and other major facilitator superfamily (MFS) transporters. As well, oxidoreductase genes that encode proteins (e.g. P450s, dehydrogenase) involved in the modification of aromatic compounds, including phenolics, were highly up-regulated (FIG. 13).

Among the 91 genes up-regulated on sawdust, 32 were found in 8 genomic clusters (four to seven genes each), and, thus, may be co-regulated (see Table 13). Three of the clusters contain the fungal specific transcription factor, $Zn_2cys$, which could be involved in primary and secondary metabolisms and drug resistance (MacPherson et al. (2006) *Microbiology and Molecular Biology Reviews* 70(3):583-604). Four of the clusters contain at least one gene encoding a secreted protein like salicylate dehydroxylase, NAD-dependant epimerase, alpha-mannosyltransferanse and FAD-binding protein. An additional 22 genes that were up-regulated with sawdust were also up-regulated with triglyceride and oleic acid. This set of 113 genes (i.e. the 91 and the 22) was overrepresented in GO terms for secreted proteins (GO:0005576; p<0.001) and those involved in carbohydrate metabolism (GO:0005975, GO:0030246; p<0.001).

One of the above up-regulated genomic clusters contains genes (OPP_08732 to OPP_08738) that are involved in metabolizing quinic acid. The cluster contains seven genes that include a quinate permease, two regulatory genes, one acting as an activator and the other as a repressor, and the four genes of the quinate/shikamate catabolic pathway (Asch et al. (1991) *Mol Gen Genet* 230(3):337-344, Giles et al. *J Hered* 82(1):1-7). The latter four catabolic genes (OPP_08735 to OPP_08738) reveal that *O. piceae* uses quinic acid in wood as a carbon source. While this gene cluster is reported in many fungi, this gene cluster was not identified in G. clavigera. To confirm that O. piceae can use the quinate pathway while G. clavigera cannot, it was observed that the former, but not the latter, grows on YNB media with quinic acid as the sole carbon source. Finally, a secreted lipase (OPP_00605) with a predicted triglycerides degradation activity was identified; its abundance relative to the control mannose was at least 50-fold.

TABLE 13

Gene clusters up-regulated in sawdust

| Gene IDs | Identified Activity/Function | Secreted | Log$_2$ (FC) |
|---|---|---|---|
| Cluster 1 | | | |
| OPP_08738 | Inositol monophosphatase | No | 3.98 |
| OPP_08737 | Catabolic 3-dehydroquinase | No | 5.78 |
| OPP_08736 | 3-dehydroshikimate dehydratase | No | 7.20 |
| OPP_08735 | Quinate dehydrogenase | No | 5.65 |
| Cluster 2 | | | |
| OPP_06948 | Allantoate permease | No | 8.05 |
| OPP_06946 | Sarcosine oxidase | No | 5.97 |
| OPP_06944 | Fungal-specific transcription factor domain protein | No | 4.50 |
| OPP_06943 | Oxoglutarate 3-dioxygenase | No | 8.75 |
| Cluster 3 | | | |
| OPP_07708 | Sugar transporter | No | 6.06 |
| OPP_07707 | Salicylate hydroxylase (salicylate 1-monooxygenase) | Yes | 7.75 |
| OPP_07706 | NAD dependent epimerase | Yes | 3.62 |
| OPP_07705 | Arylacetamide deacetylases | No | 4.69 |
| Cluster 4 | | | |
| OPP_08830 | Amidohydrolase family protein | No | 8.98 |
| OPP_08829 | Aldehyde dehydrogenase | No | 7.04 |
| OPP_08827 | FAD binding domain protein | Yes | 6.25 |
| OPP_08826 | Retinol dehydrogenase 13 | No | 7.78 |
| OPP_08825 | Cytochrome p450 | No | 9.25 |
| OPP_08824 | General alpha-glucoside permease | No | 7.98 |
| Cluster 5 | | | |
| OPP_07998 | Xaa-pro dipeptidase | No | 3.34 |
| OPP_07997 | Major facilitator superfamily transporter | No | 4.21 |
| OPP_07996 | Hexose transporter | No | 5.56 |
| OPP_07995 | Thymine dioxygenase | No | 4.95 |
| Cluster 6 | | | |
| OPP_01495 | N-carbamoyl-1-amino acid hydrolases | No | 9.85 |
| OPP_01494 | Gal4-like transcription factor | No | 6.74 |
| OPP_01493 | Class ii aldolase adducing domain-containing protein | No | 9.97 |
| OPP_01491 | Isoflavone reductase family protein | Yes | 6.49 |
| Cluster 7 | | | |
| OPP_05544 | Hypothetical protein | No | 10.82 |
| OPP_05543 | Alpha- -manosyltransferase | Yes | 8.083 |
| OPP_05542 | Ethanolamine utilization protein | No | 7.16 |
| OPP_05541 | C6 zinc finger domain containing protein | No | 4.99 |
| OPP_05540 | Alpha- -manosyltransferase | No | 8.78 |
| Cluster 8 | | | |
| OPP_02428 | Myo-inositol transporter | No | 7.42 |
| OPP_02427 | Area-like protein | No | 3.81 |
| OPP_02426 | Benzoate 4-monooxygenase cytochrome p450 | No | 4.45 |
| OPP_02425 | NADPH-cytochrome p450 reductase | No | 5.12 |
| OPP_02424 | NAD binding rossman fold | No | 4.02 |

Example 20

*Ophiostoma Piceae* Tolerance of Pine Tree Defense Chemicals

A. Growth on Monoterpenes

Fungal hyphae were grown on malt extract agar (MEA) for three days and transferred to yeast nitrogen base with monoterpenes as the sole nitrogen source (YNB+MT; 0.67% yeast nitrogen base without amino acid and 1.5% agar with a mixture of monoterpenes). The mixture of monoterpenes contained R-(+)-limonene, 3-carene, α-pinene and β-pinene at a ratio of 5:3:1:1. Colony diameters were measured daily. After one month of incubation under a mixture of monoterpenes, the inoculums were transferred from yeast nitrogen base+monoterpenes (YNB+MT) to MEA and colony diameters were measured daily.

The results show that *O. piceae* does not grow when a mixture of monoterpenes were the only carbon source (YNB+MT). After a month of incubation under a mixture of monoterpenes, the inoculums resumed normal growth when they were transferred from YNB+MT to MEA. Thus, *O. piceae* is able to tolerate very high levels of monoterpenes.

B. Growth on MEA Treated with a Mixture of Monoterpenes

Fresh fungal mycelia were used as starting material and grown on malt extract agar (MEA) treated with 50, 100, 200 µL of a mixture of monoterpenes (MT; R-(+)-limonene, 3-carene, α-pinene and β-pinene at a ratio of 5:3:1:1), respectively. Colony diameters were measured daily. The growth rates were calculated as mm/day at linear stage. Results are average of 3 replicates and standard deviations were calculated.

Figure 5:
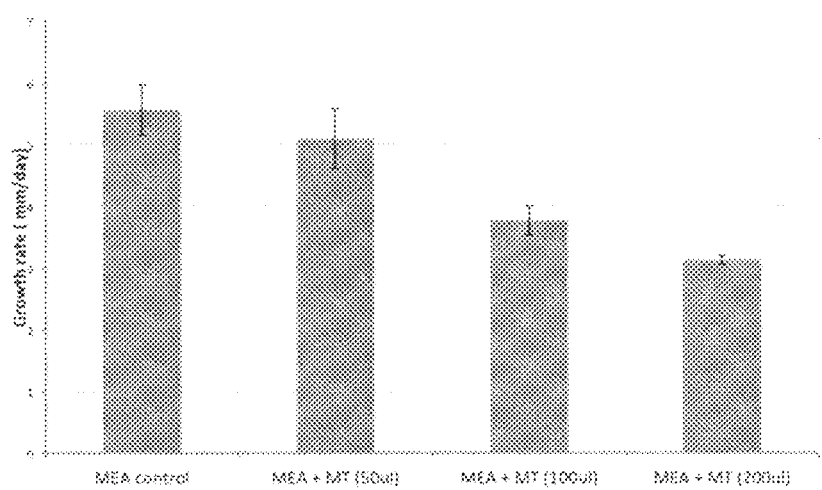
FIG. 5 shows the growth of *O. piceae* on malt extract agar (MEA) treated with various volumes of mixed monoterpenes (MT). Results are average of 3 replicates; error bars are standard deviations. MT: R-(+)-limonene, 3-carene, α-pinene and β-pinene at a ratio of 5:3:1:1.

When the fungus was inoculated on MEA and treated with different amounts of MT, the growth rate was only significantly affected when at least 100 µL/plate (~0.7 g/L) of MT were added (see FIG. 5). For all MT treatments the mycelium was more aerial and fluffy, while the asexual reproduction structures (i.e. formation of synemata) were highly inhibited.

C. RNA-seq Analysis for Terpene Tolerance

In order to identify genes involved in terpene tolerance, *O. piceae* was grown on complete medium (CM) and treated it with a mixture of terpenes as previously described for *G. clavigera* (DiGuistini et al. (2011) *Proc Natl Acad Sci USA* 108(6):2504-2509, Wang et al. *New Phytologist* (2013) 197:617-630). The experiments were performed as described in Example 17 and Table 11 above for complete medium. RNA-seq was performed as described in Example 18.

Gene expression patterns of *O. piceae* after 14 h and 40 h treatments were compared with those of the untreated CM plates at the same time points. At 14 h, most (261) of the 295 differentially regulated genes were down-regulated. No pathways were identified that were up-regulated while carbohydrate metabolism (GO:0005975) was significantly down-regulated (p<0.001). After 40 h in the presence of terpenes, about half (126) of the 264 differentially regulated genes were up-regulated. While carbohydrate metabolism continues to be down-regulated at this time point, several transporters were significantly up-regulated. In *G. clavigera*, which is able to utilize terpenes as a carbon source, more than 250 genes show a 2-fold or greater up-regulation at 12 h and 36 h in the presence of terpenes (see DiGuistini et al. (2011) *Proc Natl Acad Sci USA* 108(6):2504-2509). Of the 34 *O. piceae* genes that were up regulated at 14 h, only 26 had homologs in *G. clavigera*. Of these, nine were up-regulated at 12 h in *G. clavigera*. Similarly, of the 126 *O.* piceae genes up-regulated at 40 h, 75 had *G. clavigera* homologs of which twenty were up-regulated at 36 h.

Twenty-six (26) *O. piceae* genes were identified that are up-regulated only in the presence of terpenes, at one or both time points, of which 18 had *G. clavigera* homologs. The most highly up regulated gene encoded an ABC transporter. Terpene tolerance in *G. clavigera* is mediated by an ABC transporter (CMQ_4184; GcABC-G1; see, Wang et al. *New Phytologist* (2013) 197:617-630). The homolog of GcABC1-G1 in *O. piceae* (OPP_06758) was highly induced in the presence of terpenes. Approximately 1,500 bp upstream of the ABC transporter is a transcription factor whose expression, like that of the transporter, was up-regulated only in the presence of terpenes.

Figure 7:
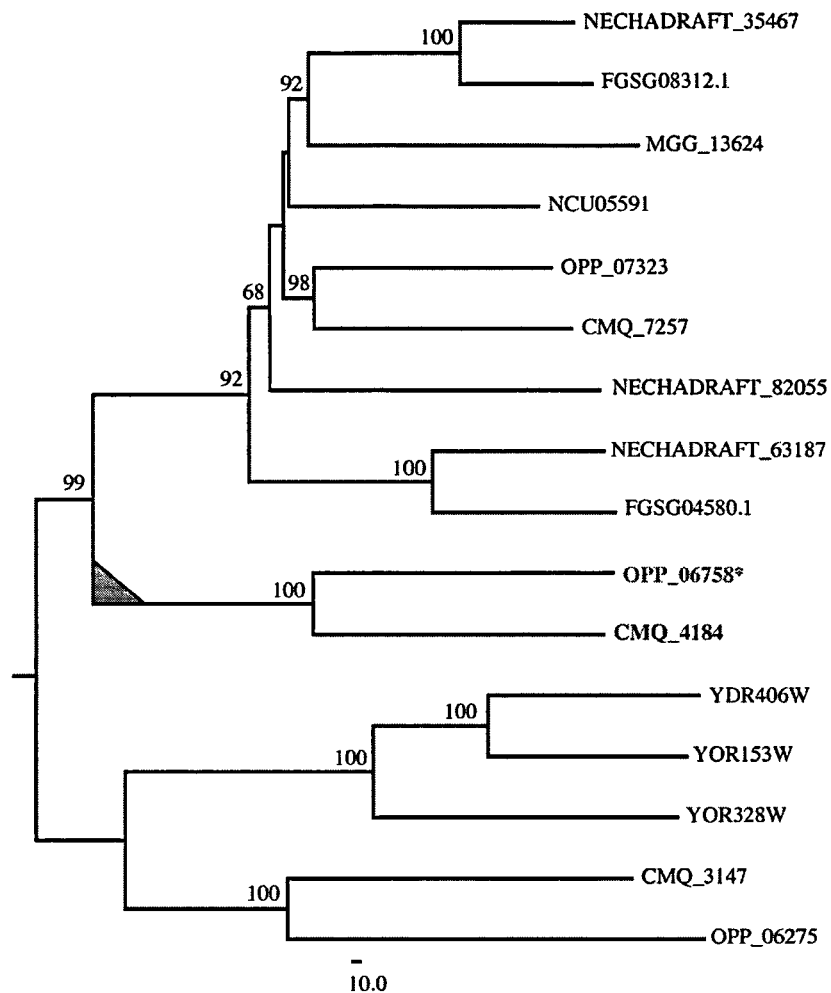
FIG. 7 shows a phylogenetic tree of ABC-G group I transporters in *O. piceae* (OPP_06758; SEQ ID NO:7) and *G. clavigera* (CMQ_4184; SEQ ID NO:1). Included are other two addition from *O. piceae* (OPP_06275 (SEQ ID NO:49), OPP_07323(SEQ ID NO:50)), other *G. clavigera* (CMQ_3147 (SEQ ID NO:6) and CMQ_7257(SEQ ID NO:5)) and a subset of ascomycete species, including *Saccharomyces cerevisiae* (YOR328W (PDR10; Genbank CAA99649.1), YOR153W (PDR5, Genbank P33302.1), YDR406W (PDR15; Genbank DAA12248.1)); Pyrenomycetes like *Gibberella zea* (FGSG04580 (Genbank XP_384756.1), FGSG08312 (Genbank XP_388488.1)), *Nectria Haematococca* (NECHADRAFT_63187 (Genbank EEU42708.1), NECHADRAFT_35467 (Genbank EEU46754.1), NECHADRAFT_82055 (Genbank EEU39655.1)), *Neurospora crassa* (NCU05591; Genbank EAA31317.1) and *Magnaporthe grisea* (MGG_13624; Genbank EHA51203.1).

A phylogenetic tree of ABC transporters from a subset of the fungal species analyzed in an ABC transporter phylogeny (see, Wang et al. (*New Phytologist* (2013) 197:617-630) places the *O. piceae* OPP_06758 and the *G. clavigera* CMQ 4184 (GcABC-G1) transporters in the same clade. This clade appears to be unique to these two fungal species (see FIG. 7).

Since modifications will be apparent to those of skill in this art, it is intended that this invention be limited only by the scope of the appended claims.

The invention claimed is:

1. A cell comprising an ABC terpenoid transporter wherein:
the cell is a eukaryotic cell, with the proviso that, if the cell is a human cell, it is an isolated cell;
the ABC terpenoid transporter is an ascomycete ophiostomatoid fungal ABC monoterpenoid transporter that is heterologous to the cell and comprises an amino acid sequence as set forth in SEQ ID NO:1 or 7, and
wherein the ABC terpenoid transporter is capable of transporting a monoterpenoid across a membrane of the cell.

2. The cell of claim 1, wherein the ABC monoterpenoid transporter is encoded by a nucleic acid molecule as set forth in SEQ ID NO:2 or 8 that transports a monoterpenoid across a membrane of the cell.

3. The cell of claim 1, wherein the ABC transporter is an ascomycete ophiostomatoid fungal ABC monoterpenoid transporter that is an *Ophiostoma piceae* or *Grosmannia clavigera* ABC transporter.

4. The cell of claim 1, wherein said cell is a fungal cell.

5. The cell of claim 1, wherein the cell further comprises a nucleic acid encoding a terpene synthase, wherein the terpene synthase is heterologous to the cell, and catalyzes production of a monoterpene.

6. The cell of claim 1, wherein the cell is more resistant to a monoterpene than a cell of the same species that does not express the ABC terpenoid transporter.

7. The cell of claim 5, further comprising a cytochrome P450 enzyme.

8. The cell of claim 5, wherein the cell is a non-human cell.

9. The cell of claim 5, wherein the cell is a fungal, plant, insect, amphibian or animal cell.

10. The cell of claim 9, wherein the cell is a fungal cell.

11. The cell of claim 9, wherein the cell is a yeast cell.

12. The cell of claim 9 that is a cell identified as YPH499, WAT11, BY4741, CALI5-1, ALX7-95 and ALX11-30, wherein the cell is modified to encode the ABC transporter and the terpene synthase.

13. The cell of claim 5, wherein the ABC transporter is an ascomycete ophiostomatoid fungal ABC monoterpenoid transporter that is an *Ophiostoma piceae* or *Grosmannia clavigera* ABC transporter.

14. The cell of claim 5, wherein the terpene synthase is selected from the group consisting of: a limonene synthase, 3-carene synthase, α-pinene synthase, β-pinene synthase, geraniol synthase and linalool synthase.

15. The cell of claim 7, wherein the P450 enzyme catalyzes hydroxylation, oxidation, demethylation, methylation or monooxygenation of the monoterpene.

16. A method for producing a terpenoid, comprising:
culturing the cell of claim 5, wherein the cell produces a monoterpene; and optionally isolating the monoterpene.

17. A method for producing a terpenoid, comprising:
culturing the cell of claim 5 under conditions whereby the terpene synthase encoded by the nucleic acid molecule is expressed, wherein the terpene synthase catalyzes the formation of the monoterpene from an acyclic pyrophosphate terpene precursor; and,
optionally isolating the monoterpene.

18. The method of claim 17, wherein the cell is a fungal cell.

19. The method of claim 18, wherein the fungal cell is a yeast cell.

20. The method of claim 16, wherein the cell produces an acyclic pyrophosphate precursor.

21. The method of claim 20, wherein the acyclic pyrophosphate terpene precursor is geranyl pyrophosphate (GPP), farnesyl pyrophosphate (FPP) or geranyl-geranyl pyrophosphate (GGPP).

22. The method of claim 21, wherein the acyclic pyrophosphate precursor is GPP.

23. The method of claim 16, wherein the monoterpene is selected from the group consisting of: R-(+)-limonene, 3-carene, α-pinene, β-pinene, geraniol and linalool.

24. The cell of claim 7, wherein said cell is a fungal, plant, insect, amphibian or animal cell.

25. The cell of claim 7, wherein the ABC transporter is an *Ophiostoma piceae* or *Grosmannia clavigera* ABC transporter.

26. The cell of claim 7, wherein said cell is a fungal cell.

27. A vector comprising a nucleic acid molecule, wherein the nucleic acid molecule encodes an ascomycete ophiostomatoid fungal ABC monoterpenoid transporter polypeptide that comprises an amino add sequence as set forth in SEQ ID NO: 1 or 7, wherein the ABC monoterpenoid transporter transports a monoterpenoid across a membrane of a microbial cell.

28. The vector of claim 27, wherein said vector is a yeast expression vector.

29. A cell comprising the vector of claim 27, wherein said vector is heterologous to the cell.

30. The cell of claim 29, wherein said cell is a prokaryotic or eukaryotic host cell.

31. The cell of claim 29, wherein the cell is a bacterial, fungal, plant, insect, amphibian or animal cell.

32. The cell of claim 29, wherein said cell is an *E. coli* or a yeast cell.

33. The cell of claim 29, wherein said cell is a fungal cell.

34. The cell of claim 33, wherein the fungal cell is a yeast cell.

35. The cell of claim 29, wherein the cell produces geranyl pyrophosphate (GPP).

36. The cell of claim 35, wherein the cell is transformed with one or more nucleic acids that result in production of GPP.

37. An isolated nucleic acid molecule encoding an ABC terpenoid transporter, wherein the ABC terpenoid transporter is an ascomycete ophiostomatoid fungal ABC monoterpenoid transporter that comprises an amino acid sequence as set forth in SEQ ID NO: 1 or 7;
wherein the ABC terpenoid transporter transports a monoterpenoid across a membrane of a microbial cell; and
wherein the nucleic acid molecule is cDNA.

38. The isolated nucleic acid molecule of claim 37, wherein the ABC terpenoid transporter is an *Ophiostoma piceae* or *Grosmannia clavigera* ABC transporter.

39. The isolated nucleic acid molecule of claim 37, wherein the microbial cell is a yeast cell.

40. The isolated nucleic acid molecule of claim 37, comprising the the nucleotide sequence as set forth in SEQ ID NO:2 or 8.

41. A method for increasing production of a monoterpenoid in a host cell, comprising:
introducing the heterologous nucleic acid molecule encoding the ABC terpenoid transporter of claim 37 into the cell, wherein the cell produces a monoterpenoid product;
and culturing the cell under conditions, whereby the ABC terpenoid transporter transports a monoterpenoid across the membrane of the cell thereby increasing the production of a monoterpenoid in the host cell.

42. The method of claim 41, wherein the method further comprises introducing a nucleic acid molecule encoding a terpene synthase into the cell, wherein the cell is cultured under conditions suitable for the expression of the terpene synthase, wherein the terpene synthase catalyzes the formation of a monoterpenoid from and acyclic pyrophosphate terpene precursor; and,
optionally isolating the monoterpenoid.

43. The method of claim 41, wherein the cell is a yeast cell.

44. The method of claim 41, wherein the cell produces an acyclic pyrophosphate precursor.

45. The method of claim 41, wherein the monoterpene is selected from the group consisting of: R-(+)-limonene, 3-carene, α-pinene, β-pinene, geraniol and linalool.

46. The vector of claim 27, wherein the nucleic acid molecule comprises the sequence as set forth in SEQ ID NO:2 or 8.

* * * * *